US009045520B2

(12) United States Patent
Chun et al.

(10) Patent No.: US 9,045,520 B2
(45) Date of Patent: Jun. 2, 2015

(54) SYNTHESIS OF PURINE NUCLEOSIDES

(75) Inventors: Byoung-Kwon Chun, Robbinsville, NJ (US); Jinfa Du, New Hope, PA (US); Suguna Rachakonda, Twinsburg, OH (US); Bruce Ross, Plainsboro, NJ (US); Michael Joseph Sofia, Doylestown, PA (US); Ganapati Reddy Pamulapati, Plainsboro, NJ (US); Wonsuk Chang, Princeton, NJ (US); Hai-Ren Zhang, Ellicott City, MD (US); Dhanpalan Nagarathnam, Bethany, CT (US)

(73) Assignee: GILEAD PHARMASSET LLC, Foster City, CA (US)

( * ) Notice: Subject to any disclaimer, the term of this patent is extended or adjusted under 35 U.S.C. 154(b) by 268 days.

(21) Appl. No.: 13/491,437

(22) Filed: Jun. 7, 2012

(65) Prior Publication Data

US 2012/0316327 A1 Dec. 13, 2012

Related U.S. Application Data

(62) Division of application No. 12/645,821, filed on Dec. 23, 2009, now Pat. No. 8,716,263.

(60) Provisional application No. 61/140,317, filed on Dec. 23, 2008.

(51) Int. Cl.
| C07H 1/00 | (2006.01) |
| C07H 5/02 | (2006.01) |
| C07H 15/04 | (2006.01) |
| C07H 19/20 | (2006.01) |
| C07H 19/167 | (2006.01) |
| C07H 19/213 | (2006.01) |

(52) U.S. Cl.
CPC .................. *C07H 19/20* (2013.01); *C07H 1/00* (2013.01); *C07H 15/04* (2013.01); *C07H 5/02* (2013.01); *C07H 19/167* (2013.01); *C07H 19/213* (2013.01)

(58) Field of Classification Search
None
See application file for complete search history.

(56) References Cited

U.S. PATENT DOCUMENTS

| 2,512,572 | A | 6/1950 | Smith, Jr. |
| 2,563,707 | A | 8/1951 | Cosulich |
| 3,053,865 | A | 9/1962 | Taub et al. |
| 3,097,137 | A | 7/1963 | Beer et al. |
| 3,104,246 | A | 9/1963 | Amiard et al. |
| 3,480,613 | A | 11/1969 | Walton |
| 3,524,844 | A | 8/1970 | Keller-Juslen et al. |
| 3,590,028 | A | 6/1971 | Arcamone et al. |
| 3,798,209 | A | 3/1974 | Witkowski et al. |
| 3,849,397 | A | 11/1974 | Robins |
| 3,852,267 | A | 12/1974 | Meyer |
| 3,888,843 | A | 6/1975 | Mizuno et al. |
| 3,923,785 | A | 12/1975 | Ryder et al. |
| 3,929,992 | A | 12/1975 | Sehgal et al. |
| 3,991,045 | A | 11/1976 | Ishida et al. |
| 3,994,974 | A | 11/1976 | Murakami et al. |
| 4,046,878 | A | 9/1977 | Patelli et al. |
| 4,058,519 | A | 11/1977 | Arcamone et al. |
| 4,107,423 | A | 8/1978 | Arcamone et al. |
| RE29,835 | E | 11/1978 | Witkowski et al. |
| 4,197,249 | A | 4/1980 | Murdock et al. |
| 4,199,574 | A | 4/1980 | Schaeffer |
| 4,203,898 | A | 5/1980 | Cullinan et al. |
| 4,210,745 | A | 7/1980 | Montgomery |
| 4,303,785 | A | 12/1981 | Umezawa et al. |
| 4,307,100 | A | 12/1981 | Langlois et al. |
| 4,323,573 | A | 4/1982 | Schaeffer |
| 4,355,032 | A | 10/1982 | Verheyden et al. |
| 4,418,068 | A | 11/1983 | Jones |
| 4,572,912 | A | 2/1986 | Yoshioka et al. |
| 4,604,463 | A | 8/1986 | Miyasaka et al. |
| 4,673,668 | A | 6/1987 | Ishizumi et al. |
| 4,724,232 | A | 2/1988 | Rideout et al. |
| 4,753,935 | A | 6/1988 | Nelson et al. |
| 4,760,137 | A | 7/1988 | Robins et al. |
| 4,797,285 | A | 1/1989 | Barenholz et al. |
| 4,808,614 | A | 2/1989 | Hertel |
| 4,808,716 | A | 2/1989 | Holy et al. |
| 4,814,470 | A | 3/1989 | Colin et al. |
| 4,814,477 | A | 3/1989 | Wijnberg et al. |
| 4,861,870 | A | 8/1989 | Oppico et al. |
| 4,880,784 | A | 11/1989 | Robins et al. |
| 4,918,179 | A | 4/1990 | Watanabe et al. |
| 4,923,986 | A | 5/1990 | Murakata et al. |
| 4,957,924 | A | 9/1990 | Beauchamp |
| 5,004,758 | A | 4/1991 | Boehm et al. |
| 5,013,556 | A | 5/1991 | Woodle et al. |
| 5,026,687 | A | 6/1991 | Yarchoan et al. |
| 5,034,394 | A | 7/1991 | Daluge |
| 5,041,246 | A | 8/1991 | Garrison |
| 5,075,445 | A | 12/1991 | Jarvest et al. |

(Continued)

FOREIGN PATENT DOCUMENTS

| BE | 799805 | 11/1973 |
| BE | 842930 | 10/1976 |

(Continued)

OTHER PUBLICATIONS

U.S. Appl. No. 60/392,350, filed Jun. 28, 2002, Storer.
U.S. Appl. No. 60/392,351, filed Jun. 28, 2002, Gosselin.
Abraham et al., "Synthesis and Biological Activity of Aromatic Amino Acid Phosphoramidates of 5-Fluoro-2'-deoxyuridine and 1-β-Arabinofuranosylcytosine: Evidence of Phosphoramidase Activity" Journal of Medicinal Chemistry, 1996, 39, 4569-4575.
Abraham et al., "Synthesis, Biological Activity and Decomposition Studies of Amino Acid Phosphomonoester Amidates of Acyclovir" Nucleosides, Nucleotides and Nucleic Acids, 1997, 16(10), 2079.
Adelfinskaya, et al., Nucleic Acids Research, 35(15):5060-5072 (2007).

(Continued)

*Primary Examiner* — Traviss C McIntosh, III

(57) ABSTRACT

A process for preparing phosphoramidate prodrugs or cyclic phosphate prodrugs of nucleoside derivatives, which is a compound, its stereoisomers, salts (acid or basic addition salts), hydrates, solvates, or crystalline forms thereof.

4 Claims, 3 Drawing Sheets

(56) References Cited

U.S. PATENT DOCUMENTS

| | | |
|---|---|---|
| 5,077,056 A | 12/1991 | Bally et al. |
| 5,077,057 A | 12/1991 | Szoka, Jr. |
| 5,091,188 A | 2/1992 | Haynes |
| 5,104,888 A | 4/1992 | Yoshioka et al. |
| 5,118,820 A | 6/1992 | Hertel |
| 5,130,421 A | 7/1992 | Starrett, Jr. et al. |
| 5,137,918 A | 8/1992 | Weiershausen et al. |
| 5,145,684 A | 9/1992 | Liversidge et al. |
| 5,149,794 A | 9/1992 | Yatvin et al. |
| 5,154,930 A | 10/1992 | Popescu et al. |
| 5,157,027 A | 10/1992 | Biller et al. |
| 5,192,549 A | 3/1993 | Barenolz et al. |
| 5,194,654 A | 3/1993 | Hostetler et al. |
| 5,196,438 A | 3/1993 | Martin et al. |
| 5,206,244 A | 4/1993 | Zahler et al. |
| 5,213,804 A | 5/1993 | Martin et al. |
| 5,223,263 A | 6/1993 | Hostetler et al. |
| 5,225,212 A | 7/1993 | Martin et al. |
| 5,246,937 A | 9/1993 | Harnden et al. |
| 5,256,641 A | 10/1993 | Yatvin et al. |
| 5,256,798 A | 10/1993 | Chou |
| 5,277,914 A | 1/1994 | Szoka, Jr. |
| 5,316,771 A | 5/1994 | Barenholz et al. |
| 5,372,808 A | 12/1994 | Blatt et al. |
| 5,376,380 A | 12/1994 | Kikuchi et al. |
| 5,405,598 A | 4/1995 | Schinazi et al. |
| 5,411,947 A | 5/1995 | Hostetler et al. |
| 5,420,266 A | 5/1995 | Britton et al. |
| 5,426,183 A | 6/1995 | Kjell |
| 5,453,499 A | 9/1995 | Chou |
| 5,462,724 A | 10/1995 | Schinazi et al. |
| 5,463,092 A | 10/1995 | Hostetler et al. |
| 5,484,926 A | 1/1996 | Dressman et al. |
| 5,494,911 A | 2/1996 | Bartlett et al. |
| 5,496,546 A | 3/1996 | Wang et al. |
| 5,538,865 A | 7/1996 | Reyes et al. |
| 5,538,975 A | 7/1996 | Dionne |
| 5,543,389 A | 8/1996 | Yatvin et al. |
| 5,543,390 A | 8/1996 | Yatvin et al. |
| 5,543,391 A | 8/1996 | Yatvin et al. |
| 5,549,910 A | 8/1996 | Szoka, Jr. |
| 5,554,728 A | 9/1996 | Basava et al. |
| 5,567,434 A | 10/1996 | Szoka, Jr. |
| 5,610,054 A | 3/1997 | Draper |
| 5,620,985 A | 4/1997 | Jacquesy et al. |
| 5,633,358 A | 5/1997 | Gruetzke et al. |
| 5,633,388 A | 5/1997 | Diana et al. |
| 5,635,517 A | 6/1997 | Muller et al. |
| 5,676,942 A | 10/1997 | Testa et al. |
| 5,695,784 A | 12/1997 | Pollinger et al. |
| 5,703,058 A | 12/1997 | Schinazi et al. |
| 5,711,944 A | 1/1998 | Gilbert et al. |
| 5,719,147 A | 2/1998 | Dorn et al. |
| 5,725,859 A | 3/1998 | Omer |
| 5,736,155 A | 4/1998 | Bally et al. |
| 5,738,845 A | 4/1998 | Imakawa |
| 5,738,846 A | 4/1998 | Greenwald et al. |
| 5,747,646 A | 5/1998 | Hakimi et al. |
| 5,767,097 A | 6/1998 | Tam |
| 5,792,834 A | 8/1998 | Hakimi et al. |
| 5,827,533 A | 10/1998 | Needham |
| 5,830,455 A | 11/1998 | Valtuena et al. |
| 5,830,905 A | 11/1998 | Diana et al. |
| 5,834,594 A | 11/1998 | Hakimi et al. |
| 5,837,257 A | 11/1998 | Tsai et al. |
| 5,846,964 A | 12/1998 | Ozeki |
| 5,849,696 A | 12/1998 | Chretien et al. |
| 5,852,195 A | 12/1998 | Romines et al. |
| 5,869,253 A | 2/1999 | Draper |
| 5,882,679 A | 3/1999 | Needham |
| 5,891,468 A | 4/1999 | Martin et al. |
| 5,891,874 A | 4/1999 | Colacino et al. |
| 5,905,070 A | 5/1999 | Schinazi et al. |
| 5,908,621 A | 6/1999 | Glue et al. |
| 5,922,757 A | 7/1999 | Chojkier |
| 5,925,643 A | 7/1999 | Chu |
| 5,928,636 A | 7/1999 | Alber et al. |
| 5,942,223 A | 8/1999 | Bazer et al. |
| 5,980,884 A | 11/1999 | Blatt et al. |
| 5,990,276 A | 11/1999 | Zhang et al. |
| 6,004,933 A | 12/1999 | Spruce et al. |
| 6,034,134 A | 3/2000 | Gold et al. |
| 6,043,077 A | 3/2000 | Barber et al. |
| 6,056,961 A | 5/2000 | Lavie et al. |
| 6,060,080 A | 5/2000 | Kikuchi et al. |
| 6,090,932 A | 7/2000 | McGee et al. |
| 6,130,326 A | 10/2000 | Ramasamy et al. |
| 6,132,763 A | 10/2000 | Fisher |
| 6,143,321 A | 11/2000 | Needham et al. |
| 6,156,501 A | 12/2000 | McGall et al. |
| 6,174,905 B1 | 1/2001 | Suzuki et al. |
| 6,180,134 B1 | 1/2001 | Zalipsky et al. |
| 6,200,598 B1 | 3/2001 | Needham |
| 6,214,375 B1 | 4/2001 | Modi |
| 6,224,903 B1 | 5/2001 | Martin et al. |
| 6,232,300 B1 | 5/2001 | Schinazi et al. |
| 6,239,159 B1 | 5/2001 | Brown et al. |
| 6,267,985 B1 | 7/2001 | Chen et al. |
| 6,294,192 B1 | 9/2001 | Patel et al. |
| 6,296,870 B1 | 10/2001 | Needham et al. |
| 6,320,078 B1 | 11/2001 | Suzuki et al. |
| 6,348,587 B1 | 2/2002 | Schinazi |
| 6,372,883 B1 | 4/2002 | Attwood et al. |
| 6,383,471 B1 | 5/2002 | Chen et al. |
| 6,391,859 B1 | 5/2002 | Schinazi et al. |
| 6,395,300 B1 | 5/2002 | Straub et al. |
| 6,410,531 B1 | 6/2002 | Llinas-Brunet et al. |
| 6,420,380 B2 | 7/2002 | Llinas-Brunet et al. |
| 6,455,513 B1 | 9/2002 | McGuigan |
| 6,455,690 B1 | 9/2002 | Tam et al. |
| 6,475,985 B1 | 11/2002 | Wagner |
| 6,479,463 B1 | 11/2002 | Wang et al. |
| 6,495,677 B1 | 12/2002 | Ramasamy et al. |
| 6,509,320 B1 | 1/2003 | Wang et al. |
| 6,534,523 B1 | 3/2003 | Llinas-Brunet et al. |
| 6,552,183 B1 | 4/2003 | Ramasamy et al. |
| 6,552,197 B2 | 4/2003 | Kamihara et al. |
| 6,555,677 B2 | 4/2003 | Petrillo et al. |
| 6,569,463 B2 | 5/2003 | Patel et al. |
| 6,573,248 B2 | 6/2003 | Ramasamy et al. |
| 6,620,325 B2 | 9/2003 | Fuenfschilling et al. |
| 6,635,278 B1 | 10/2003 | Dahl et al. |
| 6,642,206 B2 | 11/2003 | Ramasamy et al. |
| 6,645,528 B1 | 11/2003 | Straub et al. |
| 6,653,455 B1 | 11/2003 | Johdo et al. |
| 6,660,721 B2 | 12/2003 | Devos et al. |
| 6,677,314 B2 | 1/2004 | Klecker et al. |
| 6,677,315 B2 | 1/2004 | Klecker et al. |
| 6,680,068 B2 | 1/2004 | Campbell et al. |
| 6,680,303 B2 | 1/2004 | Schinazi et al. |
| 6,682,715 B2 | 1/2004 | Klecker et al. |
| 6,683,045 B2 | 1/2004 | Klecker et al. |
| 6,703,374 B1 | 3/2004 | Klecker et al. |
| 6,726,925 B1 | 4/2004 | Needham |
| 6,753,309 B2 | 6/2004 | Klecker et al. |
| 6,777,395 B2 | 8/2004 | Bhat et al. |
| 6,784,166 B2 | 8/2004 | Devos et al. |
| 6,787,305 B1 | 9/2004 | Li et al. |
| 6,787,526 B1 | 9/2004 | Bryant et al. |
| 6,812,219 B2 | 11/2004 | LaColla |
| 6,815,542 B2 | 11/2004 | Hong et al. |
| 6,846,810 B2 | 1/2005 | Martin |
| 6,897,201 B2 | 5/2005 | Boyer et al. |
| 6,908,924 B2 | 6/2005 | Watanabe et al. |
| 6,911,424 B2 | 6/2005 | Schinazi |
| 6,914,054 B2 | 7/2005 | Sommadossi et al. |
| 6,923,988 B2 | 8/2005 | Patel et al. |
| 6,932,983 B1 | 8/2005 | Straub et al. |
| 6,962,991 B2 | 11/2005 | Dempcy et al. |
| 6,977,257 B2 | 12/2005 | Parab et al. |
| 7,018,985 B1 | 3/2006 | Boyer et al. |
| 7,018,989 B2 | 3/2006 | McGuigan et al. |
| 7,060,294 B2 | 6/2006 | Batra et al. |
| 7,060,689 B2 | 6/2006 | Goins et al. |

(56) References Cited

U.S. PATENT DOCUMENTS

| | | |
|---|---|---|
| 7,070,801 B2 | 7/2006 | Yamazaki et al. |
| 7,081,449 B2 | 7/2006 | Pietrzkowski et al. |
| 7,105,493 B2 | 9/2006 | Sommadossi et al. |
| 7,105,499 B2 | 9/2006 | Carroll et al. |
| 7,125,855 B2 | 10/2006 | Bhat |
| 7,148,206 B2 | 12/2006 | Sommadossi et al. |
| 7,163,929 B2 | 1/2007 | Sommadossi et al. |
| 7,202,224 B2 | 4/2007 | Eldrup |
| 7,217,523 B2 | 5/2007 | Wagner |
| 7,265,152 B2 | 9/2007 | Saha et al. |
| 7,268,119 B2 | 9/2007 | Cook |
| 7,307,065 B2 | 12/2007 | Schinazi |
| 7,323,453 B2 | 1/2008 | Olsen |
| 7,365,057 B2 | 4/2008 | LaColla |
| 7,378,402 B2 | 5/2008 | Martin et al. |
| 7,390,791 B2 | 6/2008 | Becker |
| 7,429,572 B2 | 9/2008 | Clark |
| 7,462,608 B2 | 12/2008 | Chen et al. |
| 7,601,820 B2 | 10/2009 | Wang |
| 7,608,597 B2 | 10/2009 | Sommadossi |
| 7,608,600 B2 | 10/2009 | Storer |
| 7,635,689 B2 | 12/2009 | LaColla |
| 7,705,281 B2 | 4/2010 | Kawasaki |
| 7,754,699 B2 | 7/2010 | Chun |
| 7,879,815 B2 | 2/2011 | MacCoss |
| 7,964,560 B2 | 6/2011 | Wang et al. |
| 7,964,580 B2 | 6/2011 | Sofia |
| 8,173,621 B2 | 5/2012 | Du et al. |
| 8,334,270 B2 | 12/2012 | Sofia |
| 8,351,428 B2 | 1/2013 | Kim |
| 8,492,539 B2 | 7/2013 | Chun |
| 8,551,973 B2 | 10/2013 | Bao |
| 8,563,530 B2 | 10/2013 | Chang |
| 2001/0034440 A1 | 10/2001 | Shepard |
| 2002/0058635 A1 | 5/2002 | Averett |
| 2002/0142050 A1 | 10/2002 | Straub et al. |
| 2002/0198173 A1 | 12/2002 | Schinazi et al. |
| 2003/0050229 A1 | 3/2003 | Sommadossi et al. |
| 2003/0060400 A1 | 3/2003 | LaColla et al. |
| 2003/0120071 A1 | 6/2003 | McGuigan et al. |
| 2003/0144502 A1 | 7/2003 | Pietrzkowski et al. |
| 2003/0153744 A1 | 8/2003 | Mekouar et al. |
| 2003/0187018 A1 | 10/2003 | Llinas-Brunet et al. |
| 2004/0006007 A1 | 1/2004 | Gosselin et al. |
| 2004/0014108 A1 | 1/2004 | Eldrup et al. |
| 2004/0023240 A1 | 2/2004 | Marliere et al. |
| 2004/0023901 A1 | 2/2004 | Cook et al. |
| 2004/0059104 A1 | 3/2004 | Cook et al. |
| 2004/0063622 A1 | 4/2004 | Sommadossi et al. |
| 2004/0067901 A1 | 4/2004 | Bhat et al. |
| 2004/0072788 A1 | 4/2004 | Bhat et al. |
| 2004/0097461 A1 | 5/2004 | Sommadossi et al. |
| 2004/0097462 A1 | 5/2004 | Sommadossi et al. |
| 2004/0101535 A1 | 5/2004 | Sommadossi et al. |
| 2004/0102414 A1 | 5/2004 | Sommadossi et al. |
| 2004/0110717 A1 | 6/2004 | Carroll et al. |
| 2004/0167140 A1 | 8/2004 | Schinazi et al. |
| 2004/0191824 A1 | 9/2004 | Dempcy et al. |
| 2004/0214844 A1 | 10/2004 | Otto et al. |
| 2004/0224917 A1 | 11/2004 | Dahl et al. |
| 2004/0229839 A1 | 11/2004 | Babu et al. |
| 2004/0229840 A1 | 11/2004 | Bhat |
| 2004/0248892 A1 | 12/2004 | Wang |
| 2004/0254141 A1 | 12/2004 | Schinazi et al. |
| 2004/0259934 A1 | 12/2004 | Olsen et al. |
| 2004/0265969 A1 | 12/2004 | Li et al. |
| 2004/0266996 A1 | 12/2004 | Rabi |
| 2005/0009737 A1 | 1/2005 | Clark |
| 2005/0020825 A1 | 1/2005 | Storer |
| 2005/0026853 A1 | 2/2005 | Mekouar et al. |
| 2005/0031588 A1 | 2/2005 | Sommadossi et al. |
| 2005/0048116 A1 | 3/2005 | Straub et al. |
| 2005/0058710 A1 | 3/2005 | Straub et al. |
| 2005/0075309 A1 | 4/2005 | Storer et al. |
| 2005/0080034 A1 | 4/2005 | Standring et al. |
| 2005/0090660 A1 | 4/2005 | Watanabe et al. |
| 2005/0124532 A1 | 6/2005 | Sommadossi et al. |
| 2005/0130931 A1 | 6/2005 | Boyer et al. |
| 2005/0137161 A1 | 6/2005 | Sommadossi et al. |
| 2005/0142532 A1 | 6/2005 | Poo et al. |
| 2005/0148534 A1 | 7/2005 | Castellino et al. |
| 2005/0154056 A1 | 7/2005 | Yang |
| 2005/0164960 A1 | 7/2005 | Olsen et al. |
| 2005/0190931 A1 | 9/2005 | Hsieh |
| 2005/0215513 A1 | 9/2005 | Boojamra et al. |
| 2005/0227947 A1 | 10/2005 | Chen et al. |
| 2005/0261237 A1 | 11/2005 | Boojamra et al. |
| 2005/0267018 A1 | 12/2005 | Blatt |
| 2006/0003951 A1 | 1/2006 | Mekouar et al. |
| 2006/0014689 A1 | 1/2006 | Vesely |
| 2006/0014943 A1 | 1/2006 | Dempcy et al. |
| 2006/0034937 A1 | 2/2006 | Patel |
| 2006/0035866 A1 | 2/2006 | Cannizzaro et al. |
| 2006/0040890 A1 | 2/2006 | Martin |
| 2006/0040927 A1 | 2/2006 | Blake |
| 2006/0040944 A1 | 2/2006 | Gosselin et al. |
| 2006/0057196 A1 | 3/2006 | Hussain et al. |
| 2006/0079478 A1 | 4/2006 | Boojamra et al. |
| 2006/0110727 A9 | 5/2006 | McGall et al. |
| 2006/0122146 A1 | 6/2006 | Chun et al. |
| 2006/0122154 A1 | 6/2006 | Olsen et al. |
| 2006/0142238 A1 | 6/2006 | McGuigan |
| 2006/0144502 A1 | 7/2006 | Weder |
| 2006/0165655 A1 | 7/2006 | Babu et al. |
| 2006/0188570 A1 | 8/2006 | Batra et al. |
| 2006/0194749 A1 | 8/2006 | Keicher |
| 2006/0199783 A1 | 9/2006 | Wang |
| 2006/0241064 A1 | 10/2006 | Roberts |
| 2006/0252715 A1 | 11/2006 | Keicher |
| 2006/0276511 A1 | 12/2006 | Serrano-Wu et al. |
| 2006/0293306 A1 | 12/2006 | Beaulieu |
| 2007/0015905 A1 | 1/2007 | LaColla et al. |
| 2007/0026073 A1 | 2/2007 | Doney |
| 2007/0037735 A1 | 2/2007 | Gosselin et al. |
| 2007/0037773 A1 | 2/2007 | Sommadossi et al. |
| 2007/0042939 A1 | 2/2007 | LaColla et al. |
| 2007/0042988 A1 | 2/2007 | Klumpp |
| 2007/0042990 A1 | 2/2007 | Gosselin et al. |
| 2007/0049754 A1 | 3/2007 | Boojamra |
| 2007/0059360 A1 | 3/2007 | Jaiswal et al. |
| 2007/0060498 A1 | 3/2007 | Gosselin et al. |
| 2007/0060541 A1 | 3/2007 | Gosselin et al. |
| 2007/0077295 A1 | 4/2007 | Dahl et al. |
| 2007/0087960 A1 | 4/2007 | Storer et al. |
| 2007/0099902 A1 | 5/2007 | Dahl et al. |
| 2007/0197463 A1 | 8/2007 | Chun |
| 2007/0225249 A1 | 9/2007 | Shi |
| 2007/0265222 A1 | 11/2007 | MacCoss |
| 2007/0275912 A1 | 11/2007 | Bhat |
| 2007/0275947 A1 | 11/2007 | Bergstrom |
| 2008/0014228 A1 | 1/2008 | Darmuzey et al. |
| 2008/0070861 A1 | 3/2008 | Clark |
| 2008/0139802 A1 | 6/2008 | Axt et al. |
| 2008/0253995 A1 | 10/2008 | Clark |
| 2008/0261913 A1 | 10/2008 | Sommadossi et al. |
| 2008/0286230 A1 | 11/2008 | Sommadossi et al. |
| 2008/0300200 A1 | 12/2008 | Babu et al. |
| 2009/0004135 A1 | 1/2009 | Clark |
| 2009/0036666 A1 | 2/2009 | Clark |
| 2009/0137521 A1 | 5/2009 | Hamilton |
| 2009/0169504 A1 | 7/2009 | Sommadossi et al. |
| 2009/0176732 A1 | 7/2009 | Beigelman |
| 2009/0233879 A1 | 9/2009 | Reddy |
| 2009/0280084 A1 | 11/2009 | Schinazi |
| 2009/0306007 A1 | 12/2009 | Wagner |
| 2009/0317361 A1 | 12/2009 | Cho et al. |
| 2010/0016251 A1 | 1/2010 | Sofia |
| 2010/0016252 A1 | 1/2010 | Keana et al. |
| 2010/0021425 A1 | 1/2010 | Butler et al. |
| 2010/0022468 A1 | 1/2010 | Meppen |
| 2010/0029008 A1 | 2/2010 | Rojas Stutz |
| 2010/0035835 A1 | 2/2010 | Narjes |
| 2010/0048917 A1 | 2/2010 | Wang |
| 2010/0056770 A1 | 3/2010 | Axt |

(56) References Cited

U.S. PATENT DOCUMENTS

| | | |
|---|---|---|
| 2010/0081628 A1 | 4/2010 | Du |
| 2010/0137576 A1 | 6/2010 | Stec |
| 2010/0152128 A1 | 6/2010 | Attenni |
| 2010/0173863 A1 | 7/2010 | Schinazi |
| 2010/0227801 A1 | 9/2010 | Hopkins |
| 2010/0234316 A1 | 9/2010 | MacCoss et al. |
| 2010/0234584 A1 | 9/2010 | Chang |
| 2010/0256098 A1 | 10/2010 | Appella et al. |
| 2010/0279973 A1 | 11/2010 | Chun |
| 2010/0286083 A1 | 11/2010 | Bao et al. |
| 2010/0298257 A1 | 11/2010 | Ross et al. |
| 2010/0316594 A1 | 12/2010 | Sommadossi |
| 2011/0015146 A1 | 1/2011 | Sofia |
| 2011/0038833 A1 | 2/2011 | Clark |
| 2011/0070194 A1 | 3/2011 | Cho et al. |
| 2011/0124592 A1 | 5/2011 | McGuigan |
| 2011/0245484 A1 | 10/2011 | Ross et al. |
| 2011/0251152 A1 | 10/2011 | Ross et al. |
| 2011/0257121 A1 | 10/2011 | Chang et al. |
| 2011/0257122 A1 | 10/2011 | Sofia |
| 2011/0286962 A1 | 11/2011 | Sommadossi et al. |
| 2011/0293563 A1 | 12/2011 | Butler et al. |
| 2012/0142626 A1 | 6/2012 | Du |
| 2012/0254824 A1 | 10/2012 | Bansod |
| 2013/0029929 A1 | 1/2013 | Sofia |

FOREIGN PATENT DOCUMENTS

| | | |
|---|---|---|
| BE | 898506 | 4/1984 |
| CA | 956939 | 10/1974 |
| CA | 995608 | 8/1976 |
| CN | 1079473 | 12/1993 |
| CN | 101108870 | 1/2008 |
| DE | 2426304 | 1/1975 |
| DE | 2510866 | 10/1975 |
| DE | 2517596 | 10/1975 |
| DE | 2539963 | 3/1976 |
| DE | 2835661 | 3/1979 |
| DE | 19914474 | 10/1999 |
| EP | 0014853 | 9/1980 |
| EP | 0062503 | 10/1982 |
| EP | 0107486 | 5/1984 |
| EP | 0173059 | 3/1986 |
| EP | 0180276 | 5/1986 |
| EP | 0184162 | 6/1986 |
| EP | 0206459 | 12/1986 |
| EP | 0206497 | 12/1986 |
| EP | 0219829 | 4/1987 |
| EP | 0242851 | 10/1987 |
| EP | 0253738 | 1/1988 |
| EP | 0321122 | 6/1989 |
| EP | 0349242 | 1/1990 |
| EP | 0350287 | 1/1990 |
| EP | 0432695 | 6/1991 |
| EP | 0495432 | 7/1992 |
| EP | 0503537 | 9/1992 |
| EP | 0524579 | 1/1993 |
| EP | 0737686 | 10/1996 |
| EP | 1828217 | 9/2007 |
| EP | 1881001 | 1/2008 |
| EP | 2097430 | 9/2009 |
| EP | 2124555 | 12/2009 |
| EP | 2207786 | 7/2010 |
| FR | 2707988 | 1/1995 |
| GB | 768821 | 2/1957 |
| GB | 985598 | 3/1965 |
| GB | 1209654 | 10/1970 |
| GB | 2004293 | 3/1973 |
| GB | 1449708 | 9/1976 |
| GB | 2133005 | 7/1984 |
| GB | 2136425 | 9/1984 |
| JP | 47016483 | 10/1972 |
| JP | 58219196 | 12/1983 |
| JP | 5238939 | 9/1993 |
| JP | 6019790 | 1/1994 |
| JP | 2002504558 | 2/2002 |
| SU | 508076 | 10/1976 |
| WO | WO 88/07045 | 9/1988 |
| WO | WO 89/02733 | 4/1989 |
| WO | WO 90/00555 | 1/1990 |
| WO | WO 91/16920 | 11/1991 |
| WO | WO 91/17159 | 11/1991 |
| WO | WO 91/17748 | 11/1991 |
| WO | WO 91/18914 | 12/1991 |
| WO | WO 91/19721 | 12/1991 |
| WO | WO 92/10497 | 6/1992 |
| WO | WO 92/14743 | 9/1992 |
| WO | WO 93/00910 | 1/1993 |
| WO | WO 94/09010 | 4/1994 |
| WO | WO 94/26273 | 11/1994 |
| WO | WO 95/09843 | 4/1995 |
| WO | WO 95/13090 | 5/1995 |
| WO | WO 95/16679 | 6/1995 |
| WO | WO 95/24185 | 9/1995 |
| WO | WO 95/30670 | 11/1995 |
| WO | WO 96/15132 | 5/1996 |
| WO | WO 96/32403 | 10/1996 |
| WO | WO 97/12033 | 4/1997 |
| WO | WO 97/36554 | 10/1997 |
| WO | WO 97/42949 | 11/1997 |
| WO | WO 98/09964 | 3/1998 |
| WO | WO 98/13344 | 4/1998 |
| WO | WO 98/16184 | 4/1998 |
| WO | WO 98/17679 | 4/1998 |
| WO | WO 98/22496 | 5/1998 |
| WO | WO 98/54185 | 12/1998 |
| WO | WO 99/07734 | 2/1999 |
| WO | WO 99/15194 | 4/1999 |
| WO | WO 99/32139 | 7/1999 |
| WO | WO 99/32140 | 7/1999 |
| WO | WO 99/43691 | 9/1999 |
| WO | WO 99/59621 | 11/1999 |
| WO | WO 99/64016 | 12/1999 |
| WO | WO 00/06529 | 2/2000 |
| WO | WO 00/09531 | 2/2000 |
| WO | WO 00/24355 | 5/2000 |
| WO | WO 00/32153 | 6/2000 |
| WO | WO 00/37110 | 6/2000 |
| WO | WO 01/09121 | 2/2001 |
| WO | WO 01/32153 | 5/2001 |
| WO | WO 01/60315 | 8/2001 |
| WO | WO 01/79246 | 10/2001 |
| WO | WO 01/81359 | 11/2001 |
| WO | WO 01/90121 | 11/2001 |
| WO | WO 01/91737 | 12/2001 |
| WO | WO 01/92282 | 12/2001 |
| WO | WO 01/96353 | 12/2001 |
| WO | WO 02/08187 | 1/2002 |
| WO | WO 02/08198 | 1/2002 |
| WO | WO 02/08251 | 1/2002 |
| WO | WO 02/08256 | 1/2002 |
| WO | WO 02/18404 | 3/2002 |
| WO | WO 02/32414 | 4/2002 |
| WO | WO 02/32920 | 4/2002 |
| WO | WO 02/42172 | 5/2002 |
| WO | WO 02/48116 | 6/2002 |
| WO | WO 02/48157 | 6/2002 |
| WO | WO 02/48165 | 6/2002 |
| WO | WO 02/48172 | 6/2002 |
| WO | WO 02/49165 | 6/2002 |
| WO | WO 02/057287 | 7/2002 |
| WO | WO 02/057425 | 7/2002 |
| WO | WO 02/060926 | 8/2002 |
| WO | WO 02/100415 | 12/2002 |
| WO | WO 03/000713 | 1/2003 |
| WO | WO 03/006490 | 1/2003 |
| WO | WO 03/010141 | 2/2003 |
| WO | WO 03/011877 | 2/2003 |
| WO | WO 03/024461 | 3/2003 |
| WO | WO 03/026589 | 4/2003 |
| WO | WO 03/037895 | 5/2003 |
| WO | WO 03/051899 | 6/2003 |
| WO | WO 03/053989 | 7/2003 |

(56) References Cited

FOREIGN PATENT DOCUMENTS

| | | |
|---|---|---|
| WO | WO 03/061576 | 7/2003 |
| WO | WO 03/062256 | 7/2003 |
| WO | WO 03/064456 | 8/2003 |
| WO | WO 03/066885 | 8/2003 |
| WO | WO 03/068244 | 8/2003 |
| WO | WO 03/101993 | 12/2003 |
| WO | WO 03/104250 | 12/2003 |
| WO | WO 03/105770 | 12/2003 |
| WO | WO 03/106477 | 12/2003 |
| WO | WO 2004/000858 | 12/2003 |
| WO | WO 2004/002422 | 1/2004 |
| WO | WO 2004/002940 | 1/2004 |
| WO | WO 2004/002944 | 1/2004 |
| WO | WO 2004/002977 | 1/2004 |
| WO | WO 2004/002999 | 1/2004 |
| WO | WO 2004/003000 | 1/2004 |
| WO | WO 2004/003138 | 1/2004 |
| WO | WO 2004/007512 | 1/2004 |
| WO | WO 2004/009020 | 1/2004 |
| WO | WO 2004/009610 | 1/2004 |
| WO | WO 2004/011478 | 2/2004 |
| WO | WO 2004/014313 | 2/2004 |
| WO | WO 2004/014852 | 2/2004 |
| WO | WO 2004/035571 | 4/2004 |
| WO | WO 2004/041201 | 5/2004 |
| WO | WO 2004/046331 | 6/2004 |
| WO | WO 2004/052905 | 6/2004 |
| WO | WO 2004/058792 | 7/2004 |
| WO | WO 2004/065367 | 8/2004 |
| WO | WO 2004/080466 | 9/2004 |
| WO | WO 2004/094452 | 11/2004 |
| WO | WO 2004/096234 | 11/2004 |
| WO | WO 2004/096235 | 11/2004 |
| WO | WO 2004/096286 | 11/2004 |
| WO | WO 2004/106356 | 12/2004 |
| WO | WO 2005/000864 | 1/2005 |
| WO | WO 2005/002626 | 1/2005 |
| WO | WO 2005/003147 | 1/2005 |
| WO | WO 2005/007810 | 1/2005 |
| WO | WO 2005/008877 | 1/2005 |
| WO | WO 2005/009418 | 2/2005 |
| WO | WO 2005/012327 | 2/2005 |
| WO | WO 2005/020884 | 3/2005 |
| WO | WO 2005/021568 | 3/2005 |
| WO | WO 2005/028502 | 3/2005 |
| WO | WO 2005/037214 | 4/2005 |
| WO | WO 2005042556 A1 | 5/2005 |
| WO | WO 2005/067900 | 7/2005 |
| WO | WO 2005/072361 | 8/2005 |
| WO | WO 2005/082144 | 9/2005 |
| WO | WO 2005/087788 | 9/2005 |
| WO | WO 2005/095403 | 10/2005 |
| WO | WO 2005/103045 | 11/2005 |
| WO | WO 2005/123087 | 12/2005 |
| WO | WO 2006/000922 | 1/2006 |
| WO | WO 2006/012078 | 2/2006 |
| WO | WO 2006/012440 | 2/2006 |
| WO | WO2006/012440 * | 2/2006 |
| WO | WO 2006/029081 | 3/2006 |
| WO | WO 2006/031725 | 3/2006 |
| WO | WO 2006/035061 | 4/2006 |
| WO | WO 2006/037028 | 4/2006 |
| WO | WO 2006/050161 | 5/2006 |
| WO | WO 2006/061576 | 6/2006 |
| WO | WO 2006/063149 | 6/2006 |
| WO | WO 2006/063717 | 6/2006 |
| WO | WO 2006/065335 | 6/2006 |
| WO | WO 2006/094347 | 9/2006 |
| WO | WO 2006/100310 | 9/2006 |
| WO | WO 2006/100439 | 9/2006 |
| WO | WO 2006/119347 | 11/2006 |
| WO | WO 2006/120251 | 11/2006 |
| WO | WO 2006/120252 | 11/2006 |
| WO | WO 2006/121820 | 11/2006 |
| WO | WO 2007/002191 | 1/2007 |
| WO | WO 2007/002602 | 1/2007 |
| WO | WO 2007/014920 | 2/2007 |
| WO | WO 2007/014921 | 2/2007 |
| WO | WO 2007/014922 | 2/2007 |
| WO | WO 2007/014925 | 2/2007 |
| WO | WO 2007/014926 | 2/2007 |
| WO | WO 2007/015824 | 2/2007 |
| WO | WO 2007/020193 | 2/2007 |
| WO | WO 2007/027248 | 3/2007 |
| WO | WO 2007/038507 | 4/2007 |
| WO | WO 2007/039142 | 4/2007 |
| WO | WO 2007/039145 | 4/2007 |
| WO | WO 2007/065829 | 6/2007 |
| WO | WO 2007/069923 | 6/2007 |
| WO | WO 2007/070556 | 6/2007 |
| WO | WO 2007/076034 | 7/2007 |
| WO | WO 2007/088148 | 8/2007 |
| WO | WO 2007/092000 | 8/2007 |
| WO | WO 2007/093901 | 8/2007 |
| WO | WO 2007/095269 | 8/2007 |
| WO | WO 2008/010921 | 1/2008 |
| WO | WO 2008/024843 | 2/2008 |
| WO | WO 2008/045419 | 4/2008 |
| WO | WO 2008/048128 | 4/2008 |
| WO | WO 2008/062206 | 5/2008 |
| WO | WO 2008/079206 | 7/2008 |
| WO | WO 2008/082601 | 7/2008 |
| WO | WO 2008/085508 | 7/2008 |
| WO | WO 2008/121634 | 10/2008 |
| WO | WO 2008/142055 | 11/2008 |
| WO | WO 2009/009951 | 1/2009 |
| WO | WO 2009/029844 | 3/2009 |
| WO | WO 2009/052287 | 4/2009 |
| WO | WO 2009/067409 | 5/2009 |
| WO | WO 2009/115893 | 9/2009 |
| WO | WO 2009/120878 | 10/2009 |
| WO | WO 2009/129120 | 10/2009 |
| WO | WO 2009/132123 | 10/2009 |
| WO | WO 2009/152095 | 12/2009 |
| WO | WO 2009152095 | 12/2009 |
| WO | WO 2010/042834 | 4/2010 |
| WO | WO 2010/075517 | 7/2010 |
| WO | WO 2010/075549 | 7/2010 |
| WO | WO 2010/075554 | 7/2010 |
| WO | WO 2010/080878 | 7/2010 |
| WO | WO 2010/081082 | 7/2010 |
| WO | WO 2010075554 | 7/2010 |
| WO | WO 2010/130726 | 11/2010 |
| WO | WO 2010/135569 | 11/2010 |
| WO | WO 2011/035231 | 3/2011 |
| WO | WO 2011/123668 | 10/2011 |
| ZA | 66/7585 | 6/1968 |
| ZA | 68/2378 | 12/1968 |

OTHER PUBLICATIONS

Andrews, R.C. et al., "Asymmetric Total Synthesis of (-)-Podophyllotoxin," J. Am. Chem. Soc., vol. 110, No. 23, pp. 7854-7858 (1988).

Aquaro et al., Antimicrobial Agents and Chemotherapy (2000) 1: 173-177.

Arcamone, F. et al., "Adriamycin, 14-Hydroxydaunomycin, a New Antitumor Antobiotic from S. peucetius var. caesius," Biotechnology and Bioengineering, vol. XI, pp. 1101-1110 (1969).

Arcamone, F. et al., "Synthesis and antitumor activity of new daunorubicin and adriamycin analogues," Experientia, vol. 34, No. 10, pp. 1255-1257 (1978).

Arcamone, F. et al., "Synthesis and Antitumor Properties of New Glycosides of Daunomycinone and Adriamycinone," Journal of Medicinal Chemistry, vol. 18, No. 7, pp. 703-707 (1975).

Arnold, A.M. et al., "Etoposide: A New Anti-Cancer Agent," The Lancet, vol. 318, Issue 8252, pp. 912-915 (1981).

Ashton, W.T. et al., "Activation by Thymidine Kinase and Potent Antiherpetic Activity of 2'-Nor-2'Deoxyguanosine (2'NDG)," Biochemical and Biophysical Research Communications, vol. 108, No. 4, pp. 1716-1721 (1982).

Asif, G. et al., "Pharmacokinetics of the Antiviral Agent β-D-2'-Deoxy-2'-Fluoro-2'-C-Methylcytidine in Rhesus Monkeys," Antimicrobial Agents and Chemotherapy, vol. 51, No. 8, pp. 2877-2882 (2007).

(56) References Cited

OTHER PUBLICATIONS

Babu BR, et al. 2'-Spiro ribo- and arabinonucleosides: synthesis, molecular modelling and incorporation into oligodeoxynucleotides. Org Biomol Chem. Oct. 21, 2003; 1(20):3514-26.
Baker, D.C. et al., "Studies Related to the Total Synthesis of Pentostatin. Approaches to the Synthesis of (8R)-3,6,7,8-Tetrahydroimidazo-[4,5-d][1,3]diazepin-8-ol and N-3 Alkyl Congeners (1a)," J. Heterocyclic Chem., vol. 20, pp. 629-634 (1983).
Balzarini J. et al., "Mechanism of anti-HIV action of masked alaninyl d4T-MP derivatives," Proc. Nall. Acad. Sci. USA, vol. 93, pp. 7295-7299 (1996).
Barnett, C.J. et al., "Structure-Activity Relationships of Dimeric Catharanthus Alkaloids. 1. Deacetylvinblastine Amide (Vindesine) Sulfate," Journal of Medicinal Chemistry, vol. 21, No. 1, pp. 88-96 (1978).
Bartenschlager, J. Virol., 1993, 67, 3835-3844.
Bartenschlager, J. Virol., 1994, 68, 5045-5055.
Baschang et al., Angewandte Chemie, 85:1, 44-45, 1973.
Baschang et al. "New derivatives of thymidine 3',5'-cyclophosphate," Angewandte chemie, 1973, 71-72.
Battaglia, A.M. et al., "Combination Therapy with Interferon and Ribavirin in the Treatment of Chronic Hepatitis C Infection," The Annals of Pharmacotherapy, vol. 34, No. 4, pp. 487-494 (2000).
Bauta, W.E. et al., "A New Process for Antineoplastic Agent Clofarabine," Organic Process Research & Development, vol. 8, No. 6, pp. 889-896 (2004).
Beach, J. W. et al., "Synthesis of Enantiomerically Pure (2'R,5'S)-(-)-1-[2-(Hydroxymethyl)oxathiolan-5-yl]cytosine as a Potent Antiviral Agent against Hepatitis B Virus (HBV) and Human Immunodeficiency Virus (HIV)," J. Org. Chem, vol. 57, No. 8, pp. 2217-2219 (1992).
Beaulieu, Current Opinion in Investigational Drugs, 2004, 5, 838-850.
Behrens, EMBO, 1996, 15, 12-22.
Ben-Hattar, J. et al., "Facile Synthesis of Base-Labile 2'-Deoxyribonucleosides: An Improved Synthesis of 2'-Deoxy-5-Aza-Cytidine," Nucleosides & Nucleotides, vol. 6, Nos. 1 & 2, pp. 393-394 (1987).
Berenguer, M. et al., "Hepatitis C Virus in the Transplant Setting," Antiviral Therapy 3 (Supplement 3), pp. 126-136 (1998).
Beres et al. J. Med Chem., 1986, vol. 29(4) 494-499.
Beres et al., J. Med. Chem., 1986, 29, 1243-1249.
Berman, J.D. et al., "Activity of Purine Analogs against *Leishmania donovani* In Vivo," Antimicrobial Agents and Chemotherapy, vol. 31, No. 1, pp. 111-113 (1987).
Bhat, B. et al., "Synthesis and Pharmacokinetic Properties of Nucleoside Analogues as Possible Inhibitors of HGV RNA Replication," Antiviral Research, Abstract No. 120, vol. 57, No. 3, p. A75 (2003).
Brands, K.M.J. et al., "Efficient Synthesis of NK1 Receptor Antagonist Aprepitant Using a Crystallization-Induced Diastereoselective Transformation," J. Am. Chem. Soc., vol. 125, pp. 2129-2135 (2003).
Brazhnikova, M.G. et al., "Physical and Chemical Characteristics and Structure of Carminomycin, A New Antitumor Antibiotic," The Journal of Antibiotics, vol. XXVII, No. 4, pp. 254-259 (1974).
Broeders et al., Can J. Chem., 1993, 71, 855-863.
Broeders et al., Journal of American Chemical Society, 1990, vol. 112, 7475-7482.
Brox, L.W. et al., "Studies on the Growth Inhibition and Metabolism of 2'-Deoxy-2'-ftuorocytidine in Cultured Human Lymphoblasts," Cancer Research, vol. 34, pp. 1838-1842 (1974).
Bush, E.J. et al., "Asymmetric Total Synthesis of (-)-Podophyllotoxin," J. Chem. Soc., Chem. Commun., pp. 1200-1201 (1993).
Byrn S.R. et al., "Hydrates and Solvates," Solid-Slate Chemistry of Drugs, Chapter 11, pp. 233-247 (2nd ed. 1999).
Byrn et al. Pharmaceutical Research (1995) 12(7) 945-954.
Cahard, D. et al., "Aryloxy Phosphoramidate Triesters as Pro-Tides," Mini-Reviews in Medicinal Chemistry, vol. 4, No. 4, pp. 371-381 (2004).
Calisher, J. Gen. Virol, 1989, 70, 37-43.
Carrol, Infectious Disorders-Drug Targets, 2006, 6, 17-29.
CAS Registry No. 1157-33-1 Dated Nov. 16, 1984.
CAS Registry No. 117309-87-2 Dated Nov. 5, 1988.
CAS Registry No. 117309-88-3 Dated Nov. 5, 1988.
CAS Registry No. 117309-89-4 Dated Nov. 5, 1988.
CAS Registry No. 117309-90-7 Dated Nov. 5, 1988.
CAS Registry No. 117309-91-8 Dated Nov. 5, 1988.
CAS Registry No. 117309-92-9 Dated Nov. 5, 1988.
CAS Registry No. 117309-93-0 Dated Nov. 5, 1988.
CAS Registry No. 117309-94-1 Dated Nov. 5, 1988.
CAS Registry No. 13117-60-7 Dated Nov. 16, 1984.
CAS Registry No. 13440-33-0 Dated Nov. 16, 1984.
CAS Registry No. 15718-49-7 Dated Nov. 16, 1984.
CAS Registry No. 16719-36-1 Dated Nov. 16, 1984.
CAS Registry No. 30275-80-0 Dated Nov. 16, 1984.
CAS Registry No. 32115-08-5 Dated Nov. 16, 1984.
CAS Registry No. 33116-16-4 Dated Nov. 16, 1984.
CAS Registry No. 33904-28-8 Dated Nov. 16, 1984.
CAS Registry No. 3616-08-8 Dated Nov. 16, 1984.
CAS Registry No. 37839-81-9 Dated Nov. 16, 1984.
CAS Registry No. 4004-57-3 Dated Nov. 16, 1984.
CAS Registry No. 40245-60-1 Dated Nov. 16, 1984.
CAS Registry No. 40732-48-7 Dated Nov. 16, 1984.
CAS Registry No. 51821-84-2 Dated Nov. 16, 1984.
CAS Registry No. 52134-59-5 Dated Nov. 16, 1984.
CAS Registry No. 53303-84-7 Dated Nov. 16, 1984.
CAS Registry No. 54532-48-8 Dated Nov. 16, 1984.
CAS Registry No. 54925-33-6 Dated Nov. 16, 1984.
CAS Registry No. 55726-99-3 Dated Nov. 16, 1984.
CAS Registry No. 56632-58-7 Dated Nov. 16, 1984.
CAS Registry No. 59668-85-8 Dated Nov. 16, 1984.
CAS Registry No. 60-92-4 Dated Nov. 16, 1984.
CAS Registry No. 61866-09-9 Dated Nov. 16, 1984.
CAS Registry No. 62190-71-0 Dated Nov. 16, 1984.
CAS Registry No. 7665-99-8 Dated Nov. 16, 1984.
CAS Registry No. 93839-95-3 Dated Aug. 24, 1985.
CAS Registry No. 93919-42-7 Dated Aug. 31, 1985.
CAS Registry No. 99606-22-1 Dated Jan. 4, 1986.
CAS Registry No. 99606-25-4 Dated Jan. 4, 1986.
CAS Registry No. 99641-46-0 Dated Jan. 12, 1986.
CAS Registry No. 99641-47-1 Dated Jan. 12, 1986.
CAS Registry No. 99641-48-2 Dated Jan. 12, 1986.
CAS Registry No. 99641-50-6 Dated Jan. 12, 1986.
Chan, E. et al., "Total Synthesis of (8R)-3-(2-Deoxy-β-D-erythropenlofuranosyl)-3,6,7,8-letrahydroimidazo[4,5-d][1,3] diazepin-8-ol (Pentostatin), the Potent Inhibitor of Adenosine Deaminase," J. Org. Chem., vol. 47, No. 18, pp. 3457-3464 (1982).
Chang et al., "Amino Acid Phosphoramidate Monoesters of 3'-Azido-3'-deoxythymidine: Relationship between Antiviral Potency and Intracellular Metabolism" Journal of Medicinal Chemistry, 2001, 44, 223-231.
Chang, et al. ACS Medicinal Chemistry Letters (2011), 2(2), 130-135.
Chapman et al., Nucleotides, Nucleosides and Nucleic Acids (2001) 20(4-7): 621-628.
Chapman et al., Nucleotides, Nucleosides and Nucleic Acids (2001) 20(4-7): 1085-1090.
Chawla et al., CRIPS, 5(1): 9-12 (2004).
Chen et al., "In Vivo Pharmacokinetics and Metabolism of Anti-Human Immunodeficiency Virus Agent D4t-5'-[p-Bromophenyl Methoxyalaninyl Phosphate] (Sampidine) in Mice" Drug Metabolism and Disposition, 2001, 29(7), 1035-1041.
Chen et al., "Metabolism of Stavudine-5'-[P-Bromophenyl Methoxyalaninyl Phosphate], Stampidine, in Mice, Dogs, and Cats" Drug Metabolism and Disposition, 2002, 30(12) 1523-1531.
Chou T-F. et al., "31P NMR and Genetic Analysis Establish hinT as the Only *Escherchia coli* Purine Nucleoside Phosphoramidase and as Essential for Growth under High Salt Conditions," J. Biol. Chem., vol. 280, No. 15, pp. 15356-15361 (2005).
Chou, T-F. et al., "Evidence that Human Histidine Triad Nucleotide Binding Protein 3 (HinI3) is a Distinct Branch of the Histidine Triad (HIT) Superfamily," J. Mol. Biol., vol. 373, pp. 978-989 (2007).

(56) References Cited

OTHER PUBLICATIONS

Chou, T-F et al., "Phosphoramidale Pronucleolides: A Comparison of the Phosphoramidase Substrate Specificity of Human and *Escherichia coli* Histidine Triad Nucleotide Binding Proteins," Molecular Pharmaceutics, vol. 4, No. 2, pp. 208-217 (2007).

Chou, T.S. et al., "Stereospecific Synthesis of 2-Deoxy-2,2-difluororibonolactone and Its Use in the Preparation of 2'- Deoxy-2',2'-difluoro-β-D-ribofuranosyl Pyrimidine Nucleosides: The Key Role of Selective Crystallization," Synthesis, pp. 565-570 (1992).

Christensen, L.F. et al., "Synthesis and Biological Activity of Selected 2,6-Disubstituted-(2-Deoxy-α-and-β-D-erythro-pentofuranosyl)purines," J. Med. Chem., vol. 15, No. 7, pp. 735-739 (1972).

Chu, C.K. et al., "An Efficient Total Synthesis of 3'-Azido-3'-Deoxythymidine (AZT) and 3'-Azido-2',3'-Dideoxyuridine (AZDDU, CS-87) From D-Mannitol," Tetrahedron Letters, vol. 29, No. 42, pp. 5349-5352 (1988).

Chu, M. et al., "Structure of Sch 68631: A New Hepatitis C Virus Proteinase Inhibitor from *Streptomyces* sp.," Tetrahedron Letters, vol. 37, No. 40, pp. 7229-7232 (1996).

Chu, M., et al., "Isolation and Structure of SCH 351633: A Novel Hepatitis C Virus (HGV) NS3 Protease Inhibitor from the Fungus Penicillium Griseofulvum," Bioorganic & Medicinal Chemistry Letters, vol. 9, pp. 1949-1952 (1999).

Cihlar et al., "Design and Profiling of GS-9148, a Novel Nucleotide Analog Active against Nucleoside-Resistant Variants of Human Immunodeficiency Virus Type 1, and Its Orally Bioavailable Phosphonoamidate Prodrug, GS-9131" Antimicrobial Agents and Chemotherapy, 2008, 52(2), 655-665.

Clark, J. et al., "Design, Synthesis, and Antiviral Activity of 2'-Deoxy-2'-ftuoro-2'-C-methyleytidine, a Potent Inhibitor of Hepatitis C Virus Replication," Journal of Medicinal Chemistry, vol. 48, No. 17, pp. 5504-5508 (2005).

Clutterbuck, PW. et al., "CLXXI. Studies in the Biochemistry of Micro-Organisms," Biochem. J., vol. 26, pp. 1441-1458 (1932).

Clutterbuck, PW. et al., "LXXXVI. Studies in the Biochemistry of Micro-Organisms," Biochem. J., vol. 27, pp. 654-667 (1933).

Congiatu et al., "Molecular Modeling Studies on the Binding of Some Protides to the Putative Human Phosphoramidase Hintl" Nucleosides, Nucleotides and Nucleic Acids, 2007, 26(8), 1121-1124.

Congiatu et al., "Naphthyl Phosphoramidate Derivatives of BVdU as Potential Anticancer Agents: Design, Synthesis and Biological Evaluation" Nucleosides, Nucleotides, and Nucleic Acids, 2005, 24(5-7), 485-489.

Cosulich, D.B. et al., "Analogs of Pteroylglutamic Acid. I. N10-Alkylpteroic Acid and Derivatives," J. Am. Chem. Soc., vol. 70, pp. 1922-1926 (1948).

Crimmins, M.T. et al., "An Efficient Asymmetric Approach to Carbocyclic Nucleosides: Asymmetric Synthesis of 1592U89, a Potent Inhibitor of HIV Reverse Transcriptase," J. Org. Chem., vol. 61, No. 13, pp. 4192-4193 (1996).

Curley et al., "Synthesis and anti-HIV evaluation of some phosphoramidate derivatives of AZT: studies on the effect of chain elongation on biological activity" Antiviral research, 1990, 14, 345-356.

D'Cruz et al., "Stampidine: a selective oculo-genital microbicide" Journal of Antimicrobial Chemotherapy, 2005, 56, 10-19.

Davis, G.L., "Current Therapy for Chronic Hepatitis C," Gastroenterology, vol. 118, No. 2, pp. S104-S114 (2000).

De Lombaert, S. et al., "N-Phosphonomethyl Dipeptides and Their Phosphonate Prodrugs, a New Generation of Neutral Endopeptidase (NEP, EC 3.4.24.11) Inhibitors," J. Med. Chem., vol. 37, No. 4, pp. 498-511 (1994).

Di Marco, A. et al., "'Daunomycin', a New Antibiotic of the Rhodomycin Group," Nature, vol. 201, pp. 706-707 (1964).

Drontle et al., "Designing a Pronucleotide Stratagem: Lessons from Amino Acid Phosphoramidates of Anticancer and Antiviral Pyrimidines" MiniReviews in Medicinal Chemistry, 2004, 4, 409-419.

Eckart, Biochem. Biophys. Res. Comm. 1993, 192, 399-406.

Edmundson, R.S. et al., "Cyclic Organophosphorus Compounds. Part 23. Configurational Assignments in the 4-Phenyl-1,3,2-dioxaphosphorinane Series. X-Ray Molecular Structure of cis-2-Benzylamino-4-phenyl-1,3,2A5-dioxaphosphorinane Series. X-Ray Molecular Structure of cis-2-Benzylamino-4-phenyl-1,3,2-dioxaphosphorinane 2-Oxide," J. Chem. Research (S), pp. 122-123 (1989).

Egron et al., "S-Acyl-2-thioethyl Phosphoramidate Diester Derivatives as Mononucleotide Prodrugs" Journal of Medicinal Chemistry, 2003, 46, 4564-4571.

Eisenberg et al., Nucleosides, Nucleotides & Nucleic Acids (2001) 20(4-7): 1091-1098.

Eldrup, A.B. et al., "Structure Activity Relationship of 2' Modified Nucleosides for Inhibition of Hepatitis C Virus," Antiviral Research, Abstract No. 119, vol. 57, No. 3, p. A75 (2003).

Eldrup, A.B. et al., "Structure-Activity Relationship of Heterobase-Modified 2'-C-Methyl Ribonucleosides as Inhibitors of Hepatitis C Virus RNA Replication," J. Med. Chem., vol. 47, No. 21, pp. 5284-5297 (2004).

Eldrup, A.B. et al., "Structure-Activity Relationship of Purine Ribonucleosides for Inhibition of Hepatitis C Virus RNA-Dependent RNA Polymerase," J. Med. Chem., vol. 47, No. 9, pp. 2283-2295 (2004).

Engels et al., Chem. Ber., 110:6, 2019-2027, 1977.

Erion, M.D., "Prodrugs for Liver-targeted Drug Delivery," Biotechnology: Pharmaceutical Aspects, vol. V, pp. 541-572 (2007).

Evans, CA et al., "Divergent Asymmetric Syntheses of Dioxolane Nucleoside Analogues," Tetrahedron: Asymmetry, vol. 4, No. 11, pp. 2319-2322 (1993).

Fahy, J. et al., "Vinca Alkaloids in Superacidic Media: A Method for Creating a New Family of Antitumor Derivatives," J. Am. Chem. Soc., vol. 119, No. 36, pp. 8576-8577 (1997).

Failla, J. Virol., 1994, 68, 3753-3760.

Farquhar, D. et al., "Synthesis and Biological Evaluation of 9-[5'-(2-Oxo-1,3,2-oxazaphosphorinan-2-yl)-β-D-arabinosyl] adenine and 9-[5'-(2-Oxo-1,3,2-dioxaphosphorinan-2-yl)-β-D-arabinosyl]adenine: Potential Neutral Precursors of 9-[β-D-Arabinofuranosyl] 5'-Monophosphate," J. Med. Chem., vol. 28, No. 9, pp. 1358-1361 (1985).

Farquhar, D. et al., "Synthesis and Biological Evaluation of Neutral Derivatives of 5-Fluoro-2'deoxyuridine 5'-Phosphate," J. Med. Chem., vol. 26, No. 8, pp. 1153-1158 (1983).

Fields Virology, Editors: Fields, B. N., Knipe, D. M., and Howley, P. M., Lippincott—Raven Publishers, Philadelphia, PA, 1996, Chapter 31, 931-959.

Fors, K.S. et al., "A Convergent, Scalable Synthesis of HIV Protease Inhibitor PNU-140690," J. Org. Chem., vol. 63, No. 21, pp. 7348-7356 (1998).

Freed, J.J. et al., "Evidence for Acyloxymethyl Esters of Pyrimidine 5'-Deoxyribonucleotides as Extracellular Sources of Active 5'-Deoxyribonucleotides in Cultured Cells," Biochemical Pharmacology, vol. 38, No. 19, pp. 3193-3198 (1989).

Fretz, H. et al., "Rapamycin and FK506 Binding Proteins (Immunophilins)," J. Am. Chem. Soc., vol. 113, pp. 1409-1411 (1991).

Fukukawa, K. et al., "Synthesis of Bredinin From 5-Aminoimidazole-4-Carboxamide-Ribofuranoside (AICA-Riboside)," Chem. Pharm. Bull., vol. 32, No. 4, pp. 1644-1646 (1984).

Gauze, G.F. et al., "Production of Antitumor Antibiotic Carminomycin by *Actinomadura carminata* Sp. Nov.," pp. 675-678 (1973).

Gensler, W.J. et al., "Synthesis of Podophyllotoxin," J. Am. Chem. Soc., vol. 84, pp. 1748-1749 (1962).

Gillespie, et al., Phosphorus, Sulfur, and Silicon, 122:205-208 (1997).

Glinski, RP. et al., "Nucleotide Synthesis. IV. Phosphorylated 3'-Amino-3'-deoxythymidine and 5'-Amino-5'-Deoxythymidine and Derivatives," J. Org. Chem., vol. 38, No. 25, pp. 4299-4305 (1973).

Goekjian, Journal of Organic Chemistry, 1999, 64 (12) 4238-4246.

Gorbalenya et al., Nature, 1988, 333, 22.

Gorbalenya, Nucleic Acid Res., 1989, 17, 3889-3897.

(56) References Cited

OTHER PUBLICATIONS

Goris, N. et al., 2'-C-Methylcytidine as potent and selective inhibitor of the replication of foot-and-mouth disease virus, Antiviral Research, vol. 73, pp. 161-168 (2007).
Gorman, M. et al., "Vinca Alkaloids III. Characterization of Leurosine and Vincaleukoblastine, New Alkaloids From Vinca Rosea Linn," J. Am. Chem. Soc., vol. 81, pp. 4754-4755 (1959).
Gorman, M. et al., "Vinca Alkaloids. IV. Structural Features of Leurosine and Vincaleukoblastine, Representatives of a New Type of Indole-Indoline Alkaloids," J. Am. Chem. Soc., vol. 81, pp. 4745-4746 (1959).
Grakoui, J. Virol. 1993, 67, 2832-2843.
Grakoui, Proc. Natl. Acad Sci. USA 1993, 90, 10583-10587.
Griffith, Annual Reports in Medicinal Chemistry, 2004, 39, 223-237.
Gromova et al., Biochem. Biophys. Acta, 1971, 240, 1-11.
Gunic et al., Biorganic and Medicinal Chemistry Letters, 2007, vol. 17, 2452-2455.
Gunic Bioorg. & Med. Chem.Letters, 2007, vol. 17, No. 9, pp. 2456-2458.
Hale, J.J. et al., "Structural Optimization Affording 2-(R)-(1-(R)-3,5-Bis(trifluoromethyl)phenylethoxy)-3-(S)-(4-ftuoro) phenyl-4-{3-oxo-1,2,4-triazol-5-yl)methylmorpholine, a Potent, Orally Active, Long-Acting Morpholine Acetal Human NK-1 Receptor Antagonist," J. Med. Chem., vol. 41, No. 23, pp. 4607-4614 (1998).
Haleblian, J. Pharm. Sci. 64(8): 1269-1288 (1975).
Halstead, Rev. Infect. Dis., 1984, 6, 251-264.
Halstead, Science, 1988, 239, 476-481.
Harris et al., Antiviral Chemistry & Chemotherapy, 2002, 12, 293-300.
Hannah, J. et al., "Carba-acyclonucleoside Antiherpetic Agents," J. Heterocyclic Chem., vol. 26, pp. 1261-1271 (1989).
Harnden, M.R. et al., "Synthesis and Antiviral Activity of 9-[4-Hydroxy-3-(hydroxymethyl)but-1-yl]purines," J. Med. Chem., vol. 30, No. 9, pp. 1636-1642 (1987).
Hayashi, M. et al., "Studies on Bredinin. III. Chemical Synthesis of Bredinin (A Novel Imidazole Nucleoside)," Chem. Pharm. Bull., vol. 23, No. 1, pp. 245-246 (1975).
Hecker, S. J. et al., "Prodrugs of Phosphates and Phosphonates," J. Med. Chem., vol. 51, No. 8, pp. 2328-2345 (2008).
Hernandez, Journal of Organic Chemistry, 2004, 69 (24), 8437-8444.
Hertel, L.W. et al., "Synthesis of 2-Deoxy-2,2-difluoro-D-ribose and 2-Deoxy-2,2-difluoro-D-ribofuranosyl Nucleosides," J. Org. Chem., vol. 53, No. 11, pp. 2406-2409 (1988).
Hijikata, J. Virol. 1993, 67, 4665-4675.
Holton, R.A. et al., "First Total Synthesis of Taxol. 1. Functionalization of the B Ring," J. Am. Chem. Soc., vol. 116, pp. 1597-1598 (1994).
Holton, R.A. et al., "First Total Synthesis of Taxol. 2. Completion of the C and D Rings," J. Am. Chem. Soc., vol. 116, pp. 1599-1600 (1994).
Holy, A. et al., "Synthesis of 9-(2-Phosphonylmethoxyethyl)Adenine and Related Compounds," Collection Czechoslovak Chem. Comm., vol. 52, pp. 2801-2809 (1987).
Holy, A. et al., "Synthesis of Enantiomeric N-(2-Phosphonomethoxypropyl) Derivatives of Purine and Pyrimidine Bases. II. The Synthon Approach," Collect. Czech. Chem. Commun., vol. 60, pp. 1390-1409 (1995).
Hooz et al., Can. J. Chem., 1968, 46, 86-87.
Horowitz, J.P. et al., "Nucleosides. IX. The Formation of 2',3'-Unsaturated Pyrimidine Nucleosides via a Novel β-Elimination Reaction," J. Org. Chem., vol. 31, pp. 205-211 (1966).
Horowitz, J.P. et al., "Nucleosides. V. The Monomesylates of 1-(2'-Deoxy-β-D-lyxofuranosyl)thymine," J. Org. Chem., vol. 29, pp. 2076-2078 (1964).
Horowitz, J.P. et al., "Nucleosides. XI. 2',3'-Dideoxycytidine," J. Org. Chem., vol. 32, pp. 817-818 (1967).
Hostetler, K.Y. et al., "Greatly Enhanced Inhibition of Human Immunodeficiency Virus Type 1 Replication in GEM and HT4-6C Cells by 3'-Deoxythymidine Diphosphate Dimyristoylglycerol, a Lipid Prodrug of 3'-Deoxythymidine," Antimicrobial Agents and Chemotherapy, vol. 36, No. 9, pp. 2025-2029 (1992).
Hostetler, K.Y. et al., "Synthesis and Antiretroviral Activity of Phospholipid Analogs of Azidothymidine and Other Antiviral Nucleosides," The Journal of Biological Chemistry, vol. 265, No. 11, pp. 6112-6117 (1990).
Howes et al. Nucleosides, Nucleotides and Nucleic Acids (2003) 22(5): 687-689.
Humber, D.C. et al., "Expeditious Preparation of (−)-2'-Deoxy-3'-Thiacytidine (3TC)," Tetrahedron Lellers, vol. 33, No. 32, pp. 4625-4628 (1992).
Hunston, R.N. et al., "Synthesis and Biological Properties of Some Cyclic Phosphotriesters Derived from 2'-Deoxy-5-fluorouridine," vol. 27, No. 4, pp. 440-444 (1984).
Ikehara, M. et al., "A New Type of 'Cyclonucleoside' Derived from 2-Chloro-8-mercapto-9- -D-xylofuranosyladenine," J. Am. Chem. Soc., vol. 85, pp. 2344-2345 (1963).
Ikehara, M. et al., "Studies of Nucleosides and Nucleotides. XXIV. Purine Cyclonucleosides. I. 8,2'-Cyclonucleoside Derived from 2-Chloro-8-mercapto-9- -D-xylofuranosyladenine," J. Am. Chem. Soc., vol. 87, No. 3, pp. 606-610. (1965).
International Preliminary Examination Report of PCT/EP2006/069060 mailed Nov. 5, 2008.
International Preliminary Examination Report of PCT/US2004/012472 issued Dec. 1, 2005.
International Preliminary Examination Report of PCT/US2005/025916 issued Jan. 23, 2007.
International Preliminary Examination Report of PCT/US2005/032406 issued Mar. 10, 2009.
International Preliminary Examination Report of PCT/US2008/058183 issued Apr. 7, 2010.
International Preliminary Examination Report of PCT/US2009/069420 issued May 18, 2012.
International Preliminary Examination Report of PCT/US2011/030762 issued Oct. 2, 2012.
International Search Report of PCT/US2005/25916 mailed Jun. 15, 2006.
International Search Report of PCT/EP2006/069060 mailed Jan. 30, 2007.
International Search Report of PCT/US2004/012472 mailed Dec. 30, 2004.
International Search Report of PCT/US2005/032406 mailed May 8, 2008.
International Search Report of PCT/US2008/058183 mailed Mar. 31, 2010.
International Search Report of PCT/US2009/046619 mailed Sep. 23, 2010.
International Search Report of PCT/US2010/035641 mailed Sep. 28, 2010.
International Search Report of PCT/US2011/062643 mailed May 10, 2012.
International Search Report of PCT/US2011/030767 mailed Oct. 2, 2012.
International Search Report of PCT/US2009/069420 mailed May 8, 2012.
International Search Report of PCT/US2011/030762 mailed Mar. 2, 2012.
International Search Report and Written Opinion mailed May 10, 2010—International Application No. PCT/US2009/069475.
International Preliminary Report mailed Jul. 7, 2011 (issued Jun. 29, 2011)—International Application No. PCT/US2009/069475.
Invitation to Pay Additional Fees & Partial International Search Report of PCT/US2010/035641 mailed Jul. 23, 2010.
Ishii et al., Heptology, 1999, 29:1227-1235.
Iyer et al., "Synthesis, in Vitro Anti-Breast Cancer Activity, and Intracellular Decomposition of Amino Acid Methyl Ester and Alkyl Amide Phosphoramidate Monoesters of 3'-Azido-3'-deoxythymidine (AZT)" Journal of Medicinal Chemistry 2000, 43, 2266-2274.
Jantzen et al., "Prodrugs," Modern Pharmaceutics, Banker, G.S. et al. eds., Marcel Dekker, Inc., p. 596 (3rd ed.).

(56) References Cited

OTHER PUBLICATIONS

Jenkins, S.R. et al., "Branched-Chain Sugar Nucleosides. IV. 2'-C-Methyladenosine," J. Org. Chem., vol. 33, No. 6, pp. 2490-2494 (1968).

Jeong, L.S. et al., "Asymmetric Synthesis and Biological Evaluation of β-L-(2R,5R)-and α-L-(2R,5R)-1,3-Oxathiolane- Pyrimidine and -Purine Nucleosides as Potential Anti-HIV Agents," J. Med. Chem., vol. 36, No. 2, pp. 181-195 (1993).

Jin and Paterson, Arch. Biochem. Biophys., 1995, 323,47-53.

J.K. Guillory, Polymorphism in Pharmaceutical Solids (1999); pp. 183-226; H.G. Brittain (Ed.); Marcel Dekker, Inc. (New York).

Jones, G.D. et al., "Antiestrogens. 2. Structure-Activity Studies in a Series of 3-Aroyl-2-arylbenzo[b]thiophene Derivatives Leading to [6-Hydroxy-2-( 4-hydroxypheny)benzo[b ]thien-3-yl][4-[2-(1-piperidinyl)ethoxy]-phenyl]methanone Hydrochloride (LY156758), a Remarkably Effective Estrogen Antagonist with Only Minimal Intrinsic Estrogenicity," J. Med. Chem., vol. 27, No. 8, pp. 1057-1066 (1984).

Jones, R.J. et al., "Minireview: Nucleotide Prodrugs," Antiviral Research, vol. 27, pp. 1-17 (1995).

Jones, T.K. et al., "Total Synthesis of the Immunosuppressant (-)-FK-506," J. Am. Chem. Soc., vol. 111, No. 3, pp. 1157-1159 (1989).

Juodka et al., J. Carbohydrates, Nucleosides, Nucleotides, 1979, 6(4), 333-357.

Juodka et al., J. Carbohydrates, Nucleosides, Nucleotides, 1981, 8(1), 19-39.

Juodka et al., J. Carbohydrates, Nucleosides, Nucleotides, 1981, 8(6), 519-535.

Kahl, R., "The Liver," Toxicology, Marquardt et al. eds., Chapter 13, pp. 273-296 (1999).

Kaneko, T. et al., "Total Synthesis of (±) Podophyllotoxin," Tetrahedron Letters, vol. 28, No. 5, pp. 517-520 (1987).

Kazimierczuk, Z. et al., "Synthesis of 2'-Deoxytubercidin, 2'-Deoxyadenosine, and Related 2'-Deoxynucleosides via a Novel Direct Stereospecific Sodium Salt Glycosylation Procedure," J. Am. Chem. Soc., vol. 106, No. 21, pp. 6379-6382 (1984).

Khamnei, S. et al., "Neighboring Group Catalysis in the Design of Nucleotide Prodrugs," Journal of Medicinal Chemistry, vol. 39, No. 20, pp. 4109-4115 (1996).

Kim et al., "Monitoring the Intracellular Metabolism of Nucleoside Phosphoramidate Pronucleotides by 31PNMR" Nucleosides, Nucleotides and Nucleic Acid, 2004, 23(1) 483-493.

Kim et al., Biochem. Biophys. Res. Comm., 1995, 215, 160-166.

Kingsbury, W.D. et al., "Synthesis of Water-Soluble (Aminoalkyl)camptothecin Analogues: Inhibition of Topoisomerase I and Antitumor Activity," J. Med. Chem., vol. 34, No. 1, pp. 98-107 (1991).

Kino, T. et al., "FK-506, A Novel Immunosuppressant Isolated From a *Streptomyces*," The Journal of Antibiotics, vol. XL, No. 9, pp. 1249-1255 (1987).

Knaggs, M.H. et al., "A QSAR Study Investigating the Effect of L-Alanine Ester Variation on the Anti-HIV Activity of Some Phosphoramidate Derivatives of d4T," Bioorganic & Medicinal Chemistry Letters, vol. 10, No. 18, pp. 2075-2078 (2000).

Koonin et al., V.V., Crir. Rev. Biochem. Molec. Biol. 1993, 28, 375-430.

Kotra, L.P., "Structure-Activity Relationships of 2'-Deoxy-2',2'-difluoro-L-erythro-pentofuranosyl Nucleosides," J. Med. Chem., vol. 40, pp. 3635-3644, (1997).

Krapcho, A.P. et al., "6,9-Bis[(aminoalkyl)amino]benzo[g]isoquinoline-5,10-diones. A Novel Class of Chromophore-Modified Antitumor Anthracene-9,10-diones: Synthesis and Antitumor Evaluations," J. Med. Chem., vol. 37, No. 6, pp. 828-837 (1994).

Kryuchkov, A.A. et al., "Influence of Solvent on the Strength of Cyclic Oxygen-Containing Phosphorus Acids," Bulletin of the Academy of Sciences of the USSR, vol. 36, No. 6, Part 1, pp. 1145-1148 (1987).

Kucera, LS. et al., "Novel Membrane-Interactive Ether Lipid Analogs That Inhibit Infectious HIV-1 Production and Induce Defective Virus Formation," AIDS Research and Human Retroviruses, vol. 6, No. 4, pp. 491-501 (1990).

Lackey et al., Biochemical Pharmacology, 2001, 61, 179-189.

Lee et al., Antimicrobial Agents and Chemotherapy, 2005, 49(5), 1898-1906.

Lehsten, D.M. et al., "An Improved Procedure for the Synthesis of Nucleoside Phosphoramidates," Org. Proc. Res. & Dev., vol. 6, pp. 819-822 (2002).

Li, N.S. et al., "Synthesis of the Phosphoramidite Derivative of 2'-Deoxy-2'-C- -methylcytidine," J. Org. Chem., vol. 68, No. 17, pp. 6799-6802 (2003).

Lin, T-S. et al., "Synthesis and Antiviral Activity of Various 3'-Azido,3'-Amino,2',3'-Unsaturated, and 2',3'-Dideoxy Analogues of Pyrimidine Deoxyribonucleosides against Retroviruses," J. Med. Chem., vol. 30, No. 2, pp. 440-444 (1987).

Lohmann, J. Virol., 1997, 71, 8416-8428.

Lohmann, et al., Virology, 1998, 249: 108-118.

Lopez Aparicio et al., "Branched-Chain Sugars, Part VII, Synthesis of Saccharinic Acid Derivatives" Carbohydrate Research, 129, 99-109, 1984.

Ma et al., J. Biol. Chem. (2007) 282(41): 29812-29820.

Mangatal, L. et al., "Application of the Vicinal Oxyamination Reaction with Asymmetric Induction to the Hemisynthesis of Taxol and Analogues," Tetrahedron, vol. 45, No. 13, pp. 4177-4190 (1989).

March, J., Aliphatic Nucleophilic Substitution, Advanced Organic Chemistry, Chapter 10, pp. 348-357, John Wiley.

Martin, J.C. et al., "9-[(1,3-Dihydroxy-2-proposy)methyl]guanine: A New Potent and Selective Antiherpes Agent," J. Med. Chem., vol. 26, No. 5, pp. 759-761 (1983).

Marumoto, R. et al., "One-Step Halogenation at the 2'-Position of Uridine, and Related Reactions of Cytidine and N4-Acetylcytidine," Chem. Pharm. Bull., vol. 22, No. 1, pp. 128-134 (1974).

Matsumoto, H. et al., "A Convenient Synthesis of 9-(2-Hydroxyethoxymethyl)guanine (Acyclovir) and Related Compounds," Chem. Pharm. Bull., vol. 36, No. 3, pp. 1153-1157 (1988).

McGuigan, et al., "Application of Phosphoramidate Pronucleotides Technology to Abacavir Leads to a Significant Enhancement of Antiviral Potency" Journal of Medicinal Chemistry, 2005, 48, 3504-3515.

McGuigan, et al., "Application of Phosphoramidate ProTide Technology Significantly Improves Antiviral Potency of Carbocyclic Adenosine Derivatives" Journal of Medicinal Chemistry, 2006, 49, 7215-7226.

McGuigan, et al., "Aryl phosphate derivatives of AZT retain activity against HIV1 in cell lines which are resistant to the action of AZT" Antiviral Research, 1992, 17, 311-321.

McGuigan, et al., "Synthesis and anti-HIV activity of some novel chain-extended phosphoramidate derivatives of d4T (stavudine): esterase hydrolysis as a rapid predictive test for antiviral potency" Antiviral Chemistry and Chemotherapy, 1998, 9, 109-115.

McGuigan, et al., "Synthesis and evaluation of some novel phosphoramidate derivatives of 3'-azido-3'-deoxythymidine (AZT) as anti-HIV compounds" Antiviral Chemistry and Chemotherapy, 1990, 1(2), 107-113.

McGuigan, C. et al., "Aryl Phosphoramidate Derivatives of d4T Have Improved Anti-HIV Efficacy in Tissue Culture and May Act by the Generation of a Novel Intracellular Metabolite," J. Med. Chem., vol. No. 8, pp. 1748-1753 (1996).

McGuigan, C. et al., "Design, synthesis and evaluation of a novel double pro-drug: INX-08189. A new clinical candidate for hepatitis C virus", Bioorg. Med. Chem. Lett., vol. 20, pp. 4850-4854 (2010).

McGuigan, C. et al., "Phosphoramidate ProTides of 2'-C-Methylguanosine as Highly Potent Inhibitors of Hepatitis C Virus. Study of Their in Vitro and in Vivo Properties," J. Med. Chem., vol. 53, No. 13, pp. 4949-4957 (2010).

McGuigan et al., Antiviral Chemistry and Chemotherapy (1998) 9: 473-479.

McGuigan et al. Biorg. Med. Chem. (2005) 13: 3219-3227.

McIntee et al., "Probing the Mechanism of Action and Decomposition of Amino Acid Phosphomonoester Amidates of Antiviral Nucleoside Prodrugs" Journal of Medicinal Chemistry, 1997, 3323-3331.

(56) References Cited

OTHER PUBLICATIONS

McIntee et al., Biorg. & Med. Chem. Lett., 2001, 11, 2803-2805.
Mehellou, Y. et al., "Aryloxy Phosphoramidate Triesters: a Technology for Delivering Monophosphorylated Nucleosides and Sugars into Cells," ChemMedChem, vol. 4, pp. 1779-1791 (2009).
Meier, C. et al., "Cyclic Saligenyl Phosphotriesters of 2',3'-Dideoxy-2',3'-didehydrothymidine (d4T)—A New Pro-Nucleotide Approach," Bioorganic & Medicinal Chemistry Letters, vol. 7, No. 2, pp. 99-104 (1997).
Meyers et al., Advances in Virus Research, 1996, 47, 53-118.
Mitchell, A.G. et al., "Bioreversible Protection for the Phospho Group: Bioactivation of the Di(4-acyloxybenzyl) and Mono(4-acyloxybenzyl) Phosphoesters of Methylphosphonate and Phosphonoacetate," J. Chem. Soc. Perkin Trans., pp. 2345-2353 (1992).
Mizuno, K. et al., "Studies on Bredinin. I Isolation, Characterization and Biological Properties," The Journal of Antibiotics, vol. XXVII, No. 10, pp. 775-782 (1974).
Moening, Adv. Vir. Res. 1992, 41, 53-98.
Monath, New Eng. J. Med, 1988, 319, 641-643.
Moncrief, J.W. et al., "Structures of Leurocristine (Vincristine) and Vincaleukoblastine. X-Ray Analysis of Leurocristine Methiodide," J. Am. Chem. Soc., vol. 87, No. 21, pp. 4963-4964 (1965).
Montgomery, JA et al., "An Improved Procedure for the Preparation of 9-D-Arabinofuranosyl 1-2-fluoroadenine," J. Heterocyclic Chem., vol. 16, pp. 157-160 (1979).
Montgomery, JA et al., "Nucleosides of 2-Fluoroadenine," J. Med. Chem., vol. 12, pp. 498-504 (1969).
Montgomery, JA et al., "Synthesis and Biologic Activity of 2'-Flouro-2-halo Derivatives of 9-B-D-Arabinofuranosyladenine," J. Med. Chem., vol. 35, No. 2, pp. 397-401 (1992).
Morissette, SL et al., "High-throughput crystallization: polymorphs, salts, co-crystals and solvates of pharmaceutical solids," Advanced Drug Delivery Reviews, vol. 56, pp. 275-300 (2004).
Murakami et al., Antiviral Chemistry & Chemotherapy (2007) 51(2): 503-509.
Murakami et al., Antimicrobial Agents and Chemotherapy (2008) 52(2): 458-464.
Murdock, K.C. et al., "Antitumor Agents. 1. 1,4-Bis[(aminoalkyl)amino]-9, 10-anthracenediones," J. Med. Chem., vol. 22, No. 9, pp. 1024-1030 (1979).
Neidlein, R. et al., "Mild Preparation of 1-Benzyloxyiminoalkylphosphonic Dichlorides: Application to the Synthesis of Cyclic Phosphonic Diesters and Cyclic Monoester Amides," Heterocycles, vol. 35, No. 2, pp. 1185-1203 (1993).
Nelson et al., J. Am. Chem. Soc., 109:13, 4058-4064, 1987.
Neuss, N. et al., "Vinca Alkaloids. XXL The Structures of the Oncolytic Alkaloids Vinblastine (VLB) and Vincristine (VCR)," J. Am. Chem. Soc., vol. 86, pp. 1440-1442 (1964).
NI, Current Opinion in Drug Discovery and Development, 2004, 7, 446-459.
Nicolaou, K.C. et al., "Total synthesis of taxol," Nature, vol. 367, pp. 630-634 (1994).
Nifantyev, E.E. et al., "Synthesis and Structure of Some Stable Phospholane-Phospholanes," Phosphorus, Sulfur, and Silicon, vol. 113, pp. 1-13 (1996).
Noble, R.L. et al., "Role of Chance Observations in Chemotherapy: Vinca Rosea," Annals New York Academy of Sciences, vol. 76, pp. 882-894.
Novak Collection of Czechoslovak Chemical Communications, vol. 39, 869-882, 1974.
Novak Collection of Czechoslovak Chemical Communications, vol. 36, 3670-3677, 1971.
Office Actions issued and Responses submitted in U.S. Appl. No. 10/828,753.
Office Actions issued and Responses submitted in U.S. Appl. No. 11/225,425.
Office Actions issued and Responses submitted in U.S. Appl. No. 11/353,597.
Office Actions issued and Responses submitted in U.S. Appl. No. 11/635,898.
Office Actions issued and Responses submitted in U.S. Appl. No. 11/845,218.
Office Actions issued and Responses submitted in U.S. Appl. No. 12/053,015.
Office Actions issued and Responses submitted in U.S. Appl. No. 12/142,554.
Office Actions issued and Responses submitted in U.S. Appl. No. 12/131,868.
Office Actions issued and Responses submitted in U.S. Appl. No. 12/553,483.
Office Actions issued and Responses submitted in U.S. Appl. No. 12/240,342.
Office Actions issued and Responses submitted in U.S. Appl. No. 12/479,075.
Office Actions issued and Responses submitted in U.S. Appl. No. 12/645,710.
Office Actions issued and Responses submitted in U.S. Appl. No. 12/645,765.
Office Actions issued and Responses submitted in U.S. Appl. No. 12/654,821.
Office Actions issued and Responses submitted in U.S. Appl. No. 13/076,718.
Ogilvie, K.K. et al., "Biologically active acyclonucleoside analogues. II. The synthesis of 9-[[2-hydroxy-1-(hydroxymethyl)ethoxy]methyl]guanine (BIOLF-62)," Can. J. Chem., vol. 60, pp. 3005-3010 (1982).
Oishi, Tetrahedron Letters, 1993, 34 (22), 3573-3576.
Oliveto, E.P. et al., "16-Alkylated Corticoids. III. 16β-Methyl-9α-Fluoroprednisolone 21-Acetate," J. Am. Chem. Soc., vol. 80, pp. 6687-6688 (1958).
Olsen, D.B. et al., "2'-Modified Nucleoside Analogs as Inhibitors of Hepatitis C RNA Replication," Program and Abstracts of Sixteenth InI'l Conf. on Antiviral Research, Abstract No. 121, vol. 57, No. 3, p. A76 (2003).
Otto, M.J., "Evaluation of nucleoside analogs in the hepatitis C virus replicon system," Framing the Knowledge of Therapeutics for Viral Hepatitis, Schmazi and Schiff, eds., pp. 247-261 (2006).
Oxford, A. E. et al., "CXCIX. Studies in the Biochemistry of Micro-Organisms," BioChem. J., vol. 27, pp. 1473-1478 (1933).
Pandit, U.K. et al., "A New Class of Nucleoside Analogues. Synthesis of N1-Pyrimidinyl- and N9-Puriny1-4'-Hydroxy-3-(Hydroxymethyl) Butanes," Synthetic Communications, vol. 2, No. 6, pp. 345-351 (1972).
Parkes, K.E.B. et al., "Studies toward the Large-Scale Synthesis of the HIV Proteinase Inhibitor Ro 31-8959," J. Org. Chem., vol. 59, No. 13, pp. 3656-3664 (1994).
Partial International Search Report mailed Mar. 5, 2010—International Application No. PCT/US2009/069475.
Penco, S., "Antitumour Anthracyclines: New Developments," Process Biochemistry, vol. 15, No. 5, pp. 12-17 (1980).
Perrone et al., "First Example of Phosphoramidate Approach Applied to a 4'Substituted Purine Nucleoside (4'-Azidoadenosine): Conversion of an Inactive Nucleoside to a Submicromolar Compound versus Hepatitis C Virus" Journal of Medicinal Chemistry, 2007, 50, 5463-5470.
Perrone et al., J. Med. Chem. (2007) 50(8): 1840-1849.
Piantadosi, C. et al., "Synthesis and Evaluation of Novel Ether Lipid Nucleoside Conjugates for Anti-HIV-1 Activity," J. Med. Chem., vol. 34, No. 4, pp. 1408-1414 (1991).
Pierra, C., "Synthesis and Pharmacokinetics of Valopicitabine (NM283), an Efficient Prodrug of the Potent Anti-HCV Agent 2'-C-Methylcytidine," J. Med. Chem. 2006, 49(22):6614-6620.
Pogam et al., "No Evidence of R7128 Drug Resistance After Up to 4 Weeks Treatment of GT1, 2 and 3 Hepatitis C Virus Infected Individuals", from 44th Annual Meeting of European Association for the Study of the Liver (EASL), Copenhagen, Denmark Apr. 22-Apr. 26, 2009.
Ray et al., Antimicrobial Agents and Chemotherapy, 2008, 52(2), 648-654.
Reddy, et al. Journal of Organic Chemistry (2011), 76(10), 3782-3790.

(56) References Cited

OTHER PUBLICATIONS

Remy et al., J. Org. Chem., 1962, 27, 2491-2500.
Response filed Oct. 25, 2010 at the EPO for European patent application No. EP08732818.3.
Remiszewski, S.W. et al., "N-Hydroxy-3-phenyl-2-propenamides as Novel Inhibitors of Human Histone Deacetylase with in Vivo Antitumor Activity: Discovery of (2E)-N-Hydroxy-3-[4-[[(2-hydroxyethyl)[2-(1 H-indol-3-yl)ethyl]amino] methyl]-phenyl]-2-propenamide (NVP-LAQ824)," J. Med. Chem., vol. 46, No. 21, pp. 4609-4624 (2003).
Rosenberg, I. et al., "Phosphonylmethoxyalkyl and Phosphonylalkyl Derivatives of Adenine," Collection Czechoslovak Chem. Commun., vol. 53, pp. 2753-2777 (1988).
Ross, et al. Journal of Organic Chemistry (2011), 76(20), 8311-8319.
Rouhi, A.M. et al., "The Right Stuff," Chemical & Engineering News, vol. 81, No. 8, pp. 32-35 (2003).
Saboulard et al., "Characterization of the Activation Pathway of Phosphoramidate Triester Prodrugs of Stavudine and Zidovudine" American Society for Pharmacology and Experimental Therapeutics, 1999, 56, 693-704.
Sawada, S. et al., "Synthesis and Antitumor Activity of 20(S)-Camptothecin Derivatives: A-Ring Modified and 7,10-Disubstituted Camptothecins," Chem. Pharm. Bull., vol. 39, No. 12, pp. 3183-3188 (1991).
Sawada, S. et al., "Synthesis and Antitumor Activity of 20(S)-Camptothecin Derivatives: Carbamate-Linked, Water-Soluble Derivatives of 7-Ethyl-10-hydroxycamptothecin," Chem. Pharm. Bull., vol. 39, No. 6, pp. 1446-1454 (1991).
Schultz et al., "Prodrugs of Biologically Active Phosphate Esters" Bioorganic and Medicinal Chemistry, 2003, 11, 885-898.
Schultze, L.M. et al., "Practical Synthesis of the anti-HIV Drug, PMPA," Tetrahedron Letters, vol. 39, pp. 1853-1856 (1998).
Seeger, D.R. et al., "Analogs of Pteroylglutamic Acid. III. 4-Amino Derivatives," J. Am. Chem. Soc., vol. 71, pp. 1753-1758 (1949).
Seeger, D.R. et al., "Antagonist for Pteroylglutamic Acid," J. Am. Chem. Soc., p. 2567 (1947).
Selected Prosecution Documents for U.S. Appl. No. 12/131,868: (1) Jun. 2, 2008 Preliminary Amendment; (2) Nov. 16, 2010 Restriction/Election Requirement; (3) Dec. 14, 2010 Response; (4) Mar. 3, 2011 Office Action; (5) May 27, 2011 Amendment; (6) Aug. 16, 2011 Office Action; (7) Sep. 20, 2011.
Selected Prosecution Documents for U.S. Appl. No. 12/142,536: (1) Jun. 19, 2008 Preliminary Amendment; (2) Oct. 2, 2009 Office Action; (3) Mar. 31, 2010 Amendment; (4) Jul. 8, 2010 Office Action; (5) Oct. 8, 2010 Amendment; (6) Oct. 8, 2010 Declaration; (7) Nov. 26, 2010 Advisory Action; (8) May 17, 2011 Response.
Selected Prosecution Documents from U.S. Appl. No. 12/142,536: (1) Jun. 19, 2008 Amendment; (2) Oct. 2, 2009 Office Action; (3) Mar. 31, 2010 Amendment; (4) Jul. 8, 2010 Office Action; (5) Dec. 6, 2010 Response; and (6) Dec. 6, 2010 Declaration.
Selected Prosecution Documents from U.S. Appl. No. 12/479,075: (1) Original Claims and (2) Jun. 14, 2011 Office Action.
Shannahoff, D.H. et al., "2,2'-Anhydropyrimidine Nucleosides. Novel Syntheses and Reactions," J. Org. Chem., vol. 38, No. 3, pp. 593-598 (1973).
Shih, Y.E. et al., "Preparation and Structures of 2-Dimethylamino-4-phenyl-1,3,2-dioxaphosphorinane-2-oxides," Bull. Inst. Chem. Academia Sinica, No. 41, pp. 9-16 (1994).
Showalter, H.D.H. et al., "Adenosine Deaminase Inhibitors. Synthesis and Biological Evaluation of (±)-3,6,7,8-Tetrahydro-3-[(92-hydroxyethoxy)methyl]imidazo[4,5-d][1,3]diazepin-8-ol and Some Selected C-5 Homologues of Pentostatin," J. Med. Chem., vol. 26, No. 10, pp. 1478-1482 (1983).
Siccardi et al., "Stereospecific chemical and enzymatic stability of phosphoramidate triester prodrugs of d4T in vitro" European Journal of Pharmaceutical Sciences, 2004, 22, 25-31.
Siccardi et al., "Stereoselective and Concentration-Dependent Polarized Epithelial Permeability of a Series of Phosphoramidate Triester Prodrugs of d4T: An in Vitro Study in Caco-2 and Madin-Darby Canine Kidney Cell Monolayers" The Journal of Pharmacology and Experimental Therapeutics, 2003, 307(3), 1112-1119.
Siddiqui et al., "Design and Synthesis of Lipophilic Phosphoramidate d4T-MP Prodrugs Expressing High Potency Against HIV in Cell Culture: Structural Determinants for in Vitro Activity and QSAR" Journal of Medicinal Chemistry, 1999, 42, 4122-4128.
Siddiqui et al., "Enhancing the Aqueous Solubility of d4T-based Phosphoramidate Prodrugs" Bioorganic and Medicinal Chemistry Letters, 2000, 10, 381-384.
Smirnov et al., FEBS Letters, 1975, 51(1), 211-214.
Smith, D.B. et al., "Design, synthesis, and antiviral properties of 4'-substituted ribonucleosides as inhibitors of hepatitis C virus replication: The discovery of R1479," Bioorganic & Medicinal Chemistry Letters, vol. 17, pp. 2570-2576 (2007).
Smith, D.B. et al., "The Design, Synthesis, and Antiviral Activity of 4'-Azidocytidine Analogues against Hepatitis C Virus Replication: The Discovery of 4'-Azidoarabinocytidine," J. Med. Chem., vol. 52, No. 1, pp. 219-223 (2009).
Smith, D.B. et al., "The Design, Synthesis, and Antiviral Activity of Monofluoro and Difluoro Analogues of 4'- Azidocytidine Against Hepatitis C Virus Replication: The Discovery of 4'-Azido-2'-deoxy-2'- fluorocytidine and 4'-Azido-2'-dideoxy-2',2'-difluorocytidine," J. Med. Chem., vol. 52, No. 9, pp. 2971-2978 (2009).
Sofia, et al, ".beta. -D-2'-Deoxy-2'-fluoro-2'-C-methyluridine Phosphoramidates: Potent and Selective Inhibitors of HCV RNA Replication", 2nd International Workshop on HCV, Poster #7, 2007.
Sofia, et al., ".beta.-D2'-Deoxy-2'-C-methyluridine Phosphoramidates: Potent and Selective Inhibitors of HCV RNA Replication", Postser # P-259, presented at the 14.sup.th International Symposium on Hepatitis C Virus and Related Viruses, Glasgow, Scotland, UK, Sep. 9-13, 2007.
Sofia, et al., "R7128, A Potent and Selective Nucleoside Inhibitor of HCV NS5B Polymerase: An Overview of Clinical Efficacy and Progress Toward Second Generation Inhibitors", From HCV Drug Discovery 2008, Chicago, IL, Apr. 28, 2008.
Sofia, ".beta.-D-2'-Deoxy-2'-fluoro-2'-C-methyluridine Phosphoramidates: Potent and Selective Inhibitors of HCV RNA Replication", 2nd International Workshop on HCV—Resistance and New Compounds, Oct. 31, 2007.
Sofia, "Discovery of PSI-352938 and PSI-353661: Purine Nucleotide Prodrugs for the treatment of HCV", First Disclosure Symposium, ACS 240th National Meeting, Boston, MA, Aug. 2010.
Song et al., "Pharmacokinetics of Amino Acid Phosphoramidate Monoesters of Zidovudine in Rats" Antimicrobial Agents and Chemotherapy, 2002, 46(5), 1357-1363.
Sorbera, LA et al., "SDZ-RAD," Drugs of the Future, vol. 24, No. 1, pp. 22-29 (1999).
Starrett, Jr., J.E. et al., "Synthesis, Oral Bioavailability Determination, and in Vitro Evaluation of Prodrugs of the Antiviral Agent 9-[2-(Phosphonomethoxy)ethyl]adenine (PMEA)," Journal of Medicinal Chemistry, vol. 37, No. 12, pp. 1857-1864 (1994).
Stella, V.J., "Prodrugs as Therapeutics," Expert Opinion Ther. Patents, vol. 14, No. 3, pp. 277-280 (2004).
Strassmaier, T., Karpen, J.W., "Novel N7- and N1-substituted cGMP Derivatives are Potent Activators of Cyclic Nucleotide-gated Channels," Journal of Medicinal Chemistry,(2007) 50(17):4186-94.
Stuyver "Inhibition of hepatitis C replicon RNA synthesis by β-D-2'-deoxy-2'-fluoro-2'-C-methlcytidine: a specific inhibitor of hepatitis C virus replication," Antiviral Chemistry & Chemotherapy 2006, 17:79-87, 2006.
Stuyver L.J. et al., "Dynamics of Subgenomic Hepatitis C Virus Replicon RNA Levels in Huh-7 Cells after Exposure to Nucleoside Antimetabolites," Journal of Virology, vol. 77, No. 19, pp. 10689-10694 (2003).
Stuyver L.J. et al., "Ribonucleoside Analogue That Blocks Replication of Bovine Viral Diarrhea and Hepatitis C Viruses in Culture," Antimicrobial Agents and Chemotherapy, vol. 47, No. 1, pp. 244-254 (2003).
Stuyver et al., Antiviral Chemistry & Chemotherapy (2004) 48(2): 651-654.

(56) References Cited

OTHER PUBLICATIONS

Xiao-Ling, et al. "Study on the Chirality of Sulfur in Ethyl (2S, 3R,4R)-4,5-O-Isopropylidene-2,3-sulfinyl-2,3,4,5-tetrahydroxy-pentanoate", Acta Chimica Sinica, 1997, vol. 55, 600-604.
Xiao-Ling, et al., "The Synthesis of (2S,3R)-Sphingosine from D-Mannitol", Acta Chimica Sinica, 1996, vol. 54, 826-832.
Supplemental European Search Report of European patent appln No. EP 05775359.2 dated Sep. 15, 2010.
Tan, Nature Rev. Drug Discov., 2002, 1, 867-881.
Taub, D. et al., "16β-Methyl Cortical Steroids," J. Am. Chem. Soc., p. 4435 (1958).
Taub, D. et al., "16β-Methyl Cortical Steroids," J. Am. Chem. Soc., vol. 82, pp. 4012-4026 (1960).
Tomei, J. Virol., 1993, 67, 4017-4026.
Turner, S.R. et al., "Tipranavir (PNU-140690): A Potent, Orally Bioavailable Nonpeptidic HIV Protease Inhibitor of the 5,6-Dihydro-4-hydroxy-2-pyrone Sulfonamide Class," J. Med. Chem., vol. 41, No. 18, pp. 3467-3476 (1998).
Uckun et al., "In Vivo Pharmacokinetics and Toxicity Profile of the Anti-HIV Agent Stampidine in Dogs and Feline Immunodeficiency Virus-infected Cats" Arzneim.-Forsch./Drug Research 2006, 56(2a), 176-192.
Umezawa, H. et al., "Tetrahydropyranyl Derivatives of Daunomycin and Adriamycin," The Journal of Antibiotics, vol. XXXII, No. 10, pp. 1082-1084 (1979).
U.S. Appl. No. 12/142,536—Pending Claims as of Mar. 31, 2010.
U.S. Appl. No. 12/479,075 Amendment filed Dec. 14, 2011.
U.S. Appl. No. 12/645,765—Originally filed claims.
U.S. Appl. No. 12/645,710—Originally filed claims.
U.S. Appl. No. 13/076,718—Originally filed claims.
Valette G. et al., "Decomposition Pathways and in Vitro HIV Inhibitory Effects of lsoddA Pronucleotides: Toward a Rational Approach for Intracellular Delivery of Nucleoside 5'-Monophosphates," J. Med. Chem., vol. 39, No. 10, pp. 1981-1990 (1996).
Venkatachalam et al., "Synthesis and metabolism of naphthyl substituted phosphoramidate derivatives of stavudine" Bioorganic and Medicinal Chemistry, 2006, 14, 5161-5177.
Venkatachalam et al., Rational Drug Design of Multifunctional Phosphoramidate Substituted Nucleoside Analogs Current Pharmaceutical Design, 2004, 10 (15), 1713-1726.
Venner, H., "Synthese der len natürlichen entsprechenden 2-Desoxy-Nucleoside des Adenins, Guanins and Hypoxanthins," Ber., pp. 140-149 (1960).
Wagner et al., "Antiviral Nucleoside Drug Delivery via Amino Acid Phosphoramidates', Nucleosides, Nucleotides and Nucleic Acids" Nucleosides, Nucleotides and nucleic Acids, 1999, 18(4), 913-918.
Walker, Exp. Opin. Investigational Drugs, 2003, 12, 1269-1280.
Walton, E. et al., "Branched-Chain Sugar Nucleosides. A New Type of Biologically Active Nucleoside," J. Am. Chem. Soc., vol. 88, No. 19, pp. 4524-4525 (1966).
Wani, M.C. et al., "Plant Antitumor Agents. 23. Synthesis and Anti leukemic Activity of Camptothecin Analogues," J. Med. Chem., vol. 29, No. 11, pp. 2358-2363 (1986).
Wani, M.C. et al., "Plant Antitumor Agents. VI. The Isolation and Structure of Taxol, a Novel Antileukemic and Antitumor Agent from *Taxus brevifolia*," J. Am. Chem. Soc., vol. 93, No. 9, pp. 2325-2327 (1971).
Warrener et al., J. Virol. 1995, 69, 1720-1726.
Webb II., R.R. et al., "Synthesis of 2',3'-Dideoxyinosine," Nucleosides & Nucleotides, vol. 7, No. 2, pp. 147-153 (1988).
Wiskerchen et al.,, Virology, 1991, 184, 341-350.
Wittine, K. et al., "The novel phosphoramidate derivatives of NSAID 3-hydroxypropylamides: Synthesis, cytostatic and antiviral activity evaluations," European J. Med. Chem., vol. 44, pp. 143-151 (2009).
Wolff, M.E., "Some Considerations for Prodrug Design," Burger's Medicinal Chemistry and Drug Discovery, vol. 1, pp. 975-977 (5th ed. 1995).
Wolff, "Burger's Medicinal Chemistry, 5ed, Part 1", John Wiley & Sons, 1995, pp. 975-977.
Woo, P.W.K. et al., "A Novel Adenosine and Ara-A Deaminase Inhibitor, (R)-3-(2-Deoxy-β-D-erythro-pento-furanosyl)-3,6,7,8-tetrahydroimidazo[4,5-d] [1,3] diazepin-8-ol," J. Heterocyclic Chem., vol. 11, pp. 641-643 (1974).
Written Opinion of PCT/EP2006/069060 mailed Jan. 30, 2007.
Written Opinion of PCT/US2004/012472 mailed Dec. 30, 2004.
Written Opinion of PCT/US2005/025916 mailed Jun. 15, 2006.
Written Opinion of PCT/US2005/032406 mailed May 8, 2008.
Written Opinion of PCT/US2008/058183 mailed Mar. 31, 2010.
Written Opinion of PCT/US2010/035641 mailed Sep. 28, 2010.
Written Opinion of PCT/US2009/069420 mailed May 8, 2012.
Written Opinion of PCT/US2011/030762 mailed Mar. 2, 2012.
Wu et al., "Synthesis and Biological Activity of a Gemcitabine Phosphoramidate Prodrug" Journal of Medicinal Chemistry, 2007, 50, 3743-3746.
Wu, Current Drug Targets—Infectious Disorders, 2003, 3, 207-219.
Xu et al., J. Virol., 1997, 71:5312-5322.
Yoshioka, T. et al., "Studies on Hindered Phenols and Analogues. 1. Hypolipidemic and Hypoglycemic Agents with Ability to Inhibit Lipid Peroxidation," J. Med. Chem., vol. 32, No. 2, pp. 421-428 (1989).
Yuan, Biochem. Biophys. Res. Comm. 1997, 232, 231-235.
Yuodka et al., translated from Bioorganicheskaya Khimiya, 1976, 2(11), 1513-1519.
Zee-Cheng, R.K.Y. et al., "Antineoplastic Agents. Structure-Activity Relationship Study of Bis(substituted aminoalkylamino)anthraquinones," J. Med. Chem., vol. 21, No. 3, pp. 291-294 (1978).
Zhong, J. Virol., 1998, 72, 9365-9369.
Zhu, T. et al., "Design and synthesis of HGV agents with sequential triple inhibitory potentials," Bioorg. Med. Chem. Lett., vol. 20, pp. 5212-5216 (2010).
Zon, G., "Cyclophosphamide Analogues," Progress in Medicinal Chemistry, vol. 19, pp. 205-246 (1982).
(4aR,6R,7R,7aS)-6-[6-amino-2-(trifluoromethyl)purin-9-yl]-2-hydroxy-2-oxo-4a,6,7,7a-tetrahydro-4H-furo[3,2-d][1,3,2]dioxaphosphinin-7-ol (Jun. 11, 2006).
Sodium;(4aR,6R,7R,7aS)-6-[6-amino-2-(trifluoromethyl)purin-9-yl]-2-oxido-2-oxo-4a,6,7,7a-tetrahydro-4H-furo[3,2-d][1,3,2]dioxaphosphinin-7-ol (May 2, 2008).
Sodium;(4aR,6R,7R,7aS)-6-(6-aminopurin-9-yl)-2-oxido-2-oxo-4a,6,7,7a-tetrahydro-4H-furo[3,2-d][1,3,2]dioxaphosphinin-7-ol (May 2, 2008).
N-[9-[(4aR,6R,7R,7aS)-2,7-dihydroxy-2-oxo-4a,6,7,7a-tetrahydro-4H-furo[3,2-d][1,3,2]dioxaphosphinin-6-yl]purin-6-yl]benzamide (Sep. 8, 2005).
(4aR,6R,7R,7aS)-6-(4-aminopyrrolo[2,3-d]pyrimidin-7-yl)-2-hydroxy-2-oxo-4a,6,7,7a-tetrahydro-4H-furo[3,2-d][1,3,2]dioxaphosphinin-7-ol (Aug. 8, 2005).

* cited by examiner

SYNTHESIS OF PURINE NUCLEOSIDES

PRIORITY CLAIM

This application is a divisional of U.S. patent application Ser. No. 12/645,821, filed Dec. 23, 2009, which claims priority under 35 U.S.C. §119(e) to U.S. Provisional Application No. 61/140,317, filed Dec. 23, 2008, the disclosure of which is hereby incorporated by reference in its entirety.

BACKGROUND

Hepatitis C virus (HCV) infection is a major health problem that leads to chronic liver disease, such as cirrhosis and hepatocellular carcinoma, in a substantial number of infected individuals, estimated to be 2-15% of the world's population. There are an estimated 4.5 million infected people in the United States alone, according to the U.S. Center for Disease Control. According to the World Health Organization, there are more than 200 million infected individuals worldwide, with at least 3 to 4 million people being infected each year. Once infected, about 20% of people clear the virus, but the rest can harbor HCV the rest of their lives. Ten to twenty percent of chronically infected individuals eventually develop liver-destroying cirrhosis or cancer. The viral disease is transmitted parenterally by contaminated blood and blood products, contaminated needles, or sexually and vertically from infected mothers or carrier mothers to their offspring. Current treatments for HCV infection, which are restricted to immunotherapy with recombinant interferon-α alone or in combination with the nucleoside analog ribavirin, are of limited clinical benefit. Moreover, there is no established vaccine for HCV. Consequently, there is an urgent need for improved therapeutic agents that effectively combat chronic HCV infection.

Purine phosphoramidates have been shown to be potent inhibitors of the HCV virus (U.S. patent application Ser. No. 12/053,015, see also WO 2008/121634). However, preparation of these compounds has been made difficult due to poor yields associated with the coupling of the ribose sugar to the purine base and because of poor C-1' beta-stereoselectivity associated with the ribose to purine base coupling step.

Generally, there are two ways to prepare a nucleoside analogue. The first way follows a linear synthetic sequence in which the target nucleoside is prepared from an appropriate nucleoside. In this approach, usually there is less concern about stereoselective chemistry as most if not all of the stereocenters are set. However, the synthesis can be lengthy if extensive modification of the sugar is required.

An alternative approach toward the synthesis of novel nucleosides utilizes a convergent synthesis where a sugar portion is separately modified and later coupled with an appropriate silylated base (Vorbrueggen et al., J. Org. Chem. 1976, 41, 2084). In the case of ribose derivatives in which there is a 2-α-O-acyl group present, the desired β stereochemistry at the 1'-position is secured by neighboring group participation in the presence of a Lewis acid such as $SnCl_4$ or TMSOTf. However, if the sugar has no 2-α-O-acyl group as for 2-deoxy nucleoside, the Vorbrueggen conditions would be expected to generate an isomeric mixture which is then often difficult to separate. A common way to avoid this stereochemical problem is to employ an α-halosugar so that an $S_N2$ type coupling with a salt of a purine base or a silylated pyrimidine base would generate the desired β isomer enriched mixture (Kazimierczuk, Z. et al. J. Am. Chem. Soc. 1984, 106, 6379-6382; Chun, B. K. et al J. Org. Chem., 2000, 65, 685-693; Zhong, M. et al. J. Org. Chem. 2006, 71, 7773-7779). However, the main problem of this approach from a process chemistry point of view is that, in many cases, it is difficult to obtain the desired reactive α-halosugar in a good yield without any difficult purification steps. There are many literature and patent examples of reacting salts of purine bases with α-halosugars.

Another possible way to do an $S_N2$ type coupling is enzymatic glycosylation in which the sugar-1-α-O-phosphate is coupled with purine base using either isolated enzymes or whole cells. The phosphate intermediate can be generated enzymatically from another nucleoside containing the desired sugar. This coupled reaction is called transglycosylation. This conversion is highly stereospecific. Unfortunately, natural enzymes only work with a limited number of modified sugars. For custom sugars, existing enzymes from a range of microorganisms need to be screened for activity or through extensive research there is a possibility that a mutated enzyme can be selected and produced though genetic engineering (Komatsu, H. et al Tetrahedron Lett. 2003, 44, 2899-2901; Okuyama, K. et al. Biosci. Biotechnol. Biochem. 2003, 67(5), 989-995). 2'-Fluorinated nucleosides are difficult to enzymatically glycosylate but it has been accomplished using specialized natural enzymes (Krenitsky et al., J. Med. Chem. 1993, 36, 119-12) or with proprietary genetically engineered enzymes (Metkinen Chemistry, Kuusisto, Finland). There is no literature report of using enzymatic glycosylation for the 2'-fluoro-2'-C-methyl sugar. If it were possible, it would be necessary to start with 2'-fluoro-2'-C-methyluridine for transglycosylation or the 1-O-α-phosphate of the sugar for glycosylation. The cost of the synthesis of these starting materials approaches the cost of the final purines made chemically by the proposed route.

A final alternative method to couple a sugar with a purine base is through the use of Mitsunobu chemistry. This approach uses a condensing reagent such as N,N-dicyclohexylcarbodiimide (DCC) and triphenylphosphine. Although this reaction accepts a wide variety of substrates, yields are typically lower and there is no stereoselectivity. Purification of the product from the Mitsunubo reagents and by-products is often challenging as well.

2'-deoxy-2'-fluoro-2'-C-methyl purine nucleosides and their corresponding nucleotide phosphoramidates belong to the 2'-deoxy nucleoside category since there is no directing α-acyloxy group in 2'-position. A close derivative of the purine analogs was first prepared using the linear nucleoside route in a less than 5% overall yield due to the complexity of forming the 2' quaternary center. The lowest yielding step, fluorination, was done late in the sequence. This route was unsuitable for large scale synthesis (Clark, J. L. et al. Bioorg. Med. Chem. Lett. 2006, 16, 1712-1715).

SUMMARY OF THE INVENTION

Disclosed is compound I or salts thereof or compound II or salts thereof:

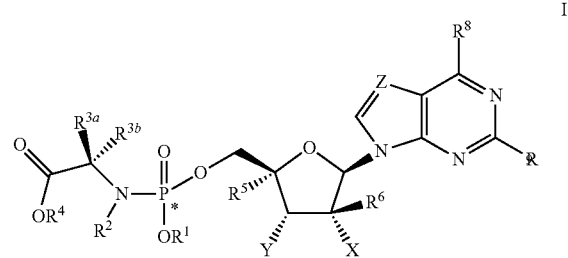

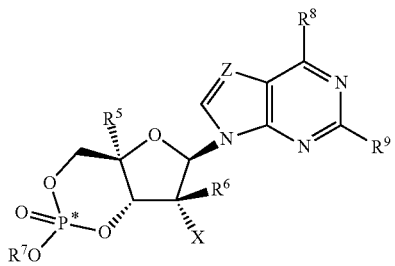

II wherein
(a) $R^1$ is hydrogen, n-alkyl; branched alkyl; cycloalkyl; or aryl, which includes, but is not limited to, phenyl or naphthyl, where phenyl or naphthyl are optionally substituted with at least one of $C_{1-6}$ alkyl, $C_{2-6}$ alkenyl, $C_{2-6}$ alkynyl, $C_{1-6}$ alkoxy, F, Cl, Br, I, nitro, cyano, $C_{1-6}$ haloalkyl, —N$(R^{1'})_2$, $C_{1-6}$ acylamino, —NHSO$_2C_{1-6}$ alkyl, —SO$_2$N$(R^{1'})_2$, COR$^{1''}$, and —SO$_2C_{1-6}$ alkyl; ($R^{1'}$ is independently hydrogen or alkyl, which includes, but is not limited to, $C_{1-20}$ alkyl, $C_{1-10}$ alkyl, or $C_{1-6}$ alkyl, $R^{1''}$ is —OR' or —N$(R^{1'})_2$);

(b) $R^2$ is hydrogen, $C_{1-10}$ alkyl, or $R^{3a}$ or $R^{3b}$ and $R^2$ together are $(CH_2)_n$ so as to form a cyclic ring that includes the adjoining N and C atoms, where n is 2 to 4;

(c) $R^{3a}$ and $R^{3b}$ are
(i) independently selected from hydrogen, $C_{1-10}$ alkyl, cycloalkyl, —$(CH_2)_c(NR^{3'})_2$, $C_{1-6}$ hydroxyalkyl, —CH$_2$SH, —$(CH_2)_2$S(O)$_d$Me, —$(CH_2)_3$NHC(=NH)NH$_2$, (1H-indol-3-yl)methyl, (1H-imidazol-4-yl)methyl, —$(CH_2)_e$COR$^{3''}$, aryl and aryl $C_{1-3}$ alkyl, said aryl groups optionally substituted with a group selected from hydroxyl, $C_{1-10}$ alkyl, $C_{1-6}$ alkoxy, halogen, nitro and cyano;
(ii) $R^{3a}$ and $R^{3b}$ both are $C_{1-6}$ alkyl;
(iii) $R^{3a}$ and $R^{3b}$ together are $(CH_2)_f$ so as to form a spiro ring;
(iv) $R^{3a}$ is hydrogen and $R^{3b}$ and $R^2$ together are $(CH_2)_n$ so as to form a cyclic ring that includes the adjoining N and C atoms
(v) $R^{3b}$ is hydrogen and $R^{3a}$ and $R^2$ together are $(CH_2)_n$ so as to form a cyclic ring that includes the adjoining N and C atoms, where c is 1 to 6, d is 0 to 2, e is 0 to 3, f is 2 to 5, n is 2 to 4, and where $R^{3'}$ is independently hydrogen or $C_{1-6}$ alkyl and $R^{3''}$ is —OR' or —N$(R^{3'})_2$);
(vi) $R^{3a}$ is H and $R^{3b}$ is H, CH$_3$, CH$_2$CH$_3$, CH(CH$_3$)$_2$, CH$_2$CH(CH$_3$)$_2$, CH(CH$_3$)CH$_2$CH$_3$, CH$_2$Ph, CH$_2$-indol-3-yl, —CH$_2$CH$_2$SCH$_3$, CH$_2$CO$_2$H, CH$_2$C(O)NH$_2$, CH$_2$CH$_2$COOH, CH$_2$CH$_2$C(O)NH$_2$, CH$_2$CH$_2$CH$_2$CH$_2$NH$_2$, —CH$_2$CH$_2$CH$_2$NHC(NH)NH$_2$, CH$_2$-imidazol-4-yl, CH$_2$OH, CH(OH)CH$_3$, CH$_2$((4'-OH)-Ph), CH$_2$SH, or lower cycloalkyl; or
(vii) $R^{3a}$ is CH$_3$, —CH$_2$CH$_3$, CH(CH$_3$)$_2$, CH$_2$CH(CH$_3$)$_2$, CH(CH$_3$)CH$_2$CH$_3$, CH$_2$Ph, CH$_2$-indol-3-yl, —CH$_2$CH$_2$SCH$_3$, CH$_2$CO$_2$H, CH$_2$C(O)NH$_2$, CH$_2$CH$_2$COOH, CH$_2$CH$_2$C(O)NH$_2$, CH$_2$CH$_2$CH$_2$CH$_2$NH$_2$, —CH$_2$CH$_2$CH$_2$NHC(NH)NH$_2$, CH$_2$-imidazol-4-yl, CH$_2$OH, CH(OH)CH$_3$, CH$_2$((4'-OH)-Ph), CH$_2$SH, or lower cycloalkyl and $R^{3b}$ is H, where $R^{3'}$ is independently hydrogen or alkyl, which includes, but is not limited to, $C_{1-20}$ alkyl, $C_{1-10}$ alkyl, or $C_{1-6}$ alkyl, $R^{3''}$ is —OR' or —N$(R^{3'})_2$);

(d) $R^4$ is hydrogen, $C_{1-10}$ alkyl, $C_{1-10}$ alkyl optionally substituted with a lower alkyl, alkoxy, di(lower alkyl)-amino, or halogen, $C_{1-10}$ haloalkyl, $C_{3-10}$ cycloalkyl, cycloalkyl alkyl, cycloheteroalkyl, aminoacyl, aryl, such as phenyl, heteroaryl, such as, pyridinyl, substituted aryl, or substituted heteroaryl;

(e) $R^5$ is H, a lower alkyl, CN, vinyl, O-(lower alkyl), hydroxyl lower alkyl, i.e., —$(CH_2)_p$OH, where p is 1-6, including hydroxylmethyl (CH$_2$OH), CH$_2$F, N$_3$, CH$_2$CN, CH$_2$NH$_2$, CH$_2$NHCH$_3$, CH$_2$N(CH$_3$)$_2$, alkyne (optionally substituted), or halogen, including F, Cl, Br, or I;

(f) $R^6$ is H, CH$_3$, CH$_2$F, CHF$_2$, CF$_3$, F, CN, vinyl, or ethynyl;

(g) $R^7$ is hydrogen, n-alkyl, branched alkyl, cycloalkyl, alkaryl, or aryl, which includes, but is not limited to, phenyl or naphthyl, where phenyl or naphthyl are optionally substituted with at least one of H, F, Cl, Br, I, OH, OR$^{7'}$, SH, SR$^{7'}$, NH$_2$, NHR$^{7'}$, NR$^{7'}_2$, lower alkyl of $C_1$-$C_6$, halogenated (F, Cl, Br, I) lower alkyl of $C_1$-$C_6$, halogenated (F, Cl, Br, I) lower alkenyl of $C_2$-$C_6$, lower alkynyl of $C_2$-$C_6$, such as C≡CH, halogenated (F, Cl, Br, I) lower alkynyl of $C_2$-$C_6$, lower alkoxy of $C_1$-$C_6$, halogenated (F, Cl, Br, I) lower alkoxy of $C_1$-$C_6$, CO$_2$H, CO$_2$R$^{7'}$, CONH$_2$, CONHR$^{7'}$, CONR$^{7'}_2$, CH=CHCO$_2$H, or CH=CHCO$_2$R$^{7'}$ wherein R$^{7'}$ is an optionally substituted alkyl, cycloalkyl, alkenyl, alkynyl, or alkoxyalkyl, which includes, but is not limited to, $C_{1-10}$ alkyl, $C_{3-7}$ cycloalkyl, $C_{2-10}$ alkenyl, $C_{2-10}$ alkynyl, and $C_{1-10}$ alkoxyalkyl, (h) X is H, OH, OMe, halogen, CN, NH$_2$, or N$_3$;
(i) Y is OH;
(j) Z is N or CR$^{10}$;
(k) $R^8$ and $R^9$ are independently H, F, Cl, Br, I, OH, OR', SH, SR', NH$_2$, NHR', NR'$_2$, nitrogen heterocycle, lower alkyl of $C_1$-$C_6$, halogenated (F, Cl, Br, I) lower alkyl of $C_1$-$C_6$, lower alkenyl of $C_2$-$C_6$, halogenated (F, Cl, Br, I) lower alkenyl of $C_2$-$C_6$, lower alkynyl of $C_2$-$C_6$ such as C≡CH, halogenated (F, Cl, Br, I) lower alkynyl of $C_2$-$C_6$, lower alkoxy of $C_1$-$C_6$, halogenated (F, Cl, Br, I) lower alkoxy of $C_1$-$C_6$, CO$_2$H, CO$_2$R', CONH$_2$, CONHR', CONR'$_2$, CH=CHCO$_2$H, or CH=CHCO$_2$R',
and (l) $R^{10}$ is H, halogen (including F, Cl, Br, I), OH, OR', SH, SR', NH$_2$, NHR', NR'$_2$, NO$_2$ lower alkyl of $C_1$-$C_6$, halogenated (F, Cl, Br, I) lower alkyl of $C_1$-$C_6$, lower alkenyl of $C_2$-$C_6$, halogenated (F, Cl, Br, I) lower alkenyl of $C_2$-$C_6$, lower alkynyl of $C_2$-$C_6$, halogenated (F, Cl, Br, I) lower alkynyl of $C_2$-$C_6$, lower alkoxy of $C_1$-$C_6$, halogenated (F, Cl, Br, I) lower alkoxy of $C_1$-$C_6$, CO$_2$H, CO$_2$R', CONH$_2$, CONHR', CONR'$_2$, CH=CHCO$_2$H, or CH=CHCO$_2$R';

wherein R' is an optionally substituted alkyl, which includes, but is not limited to, an optionally substituted $C_{1-20}$ alkyl, an optionally substituted $C_{1-10}$ alkyl, an optionally substituted lower alkyl; an optionally substituted cycloalkyl; an alkaryl; an optionally substituted alkynyl of $C_2$-$C_6$; an optionally substituted lower alkenyl of $C_2$-$C_6$, or optionally substituted acyl, which includes but is not limited to C(O) alkyl, C(O)($C_{1-20}$ alkyl), C(O)($C_{1-10}$ alkyl), or a C(O)(lower alkyl).

Also disclosed is a process for preparing compound I or compound II, as defined above, wherein said process comprises:

(a) stereoselective reduction of a protected ribonolactone III using a hydride reducing agent

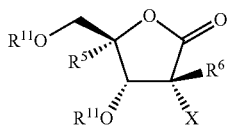

III to provide a beta-lactol derivative IV; and

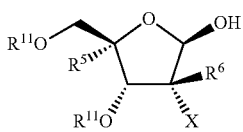

IV (b) stereoselective conversion of the lactol derivative using a reagent to obtain an anomeric alpha-derivative V

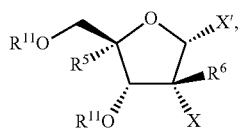

V wherein $R^5$, $R^6$, and X have the meanings as defined above, X' is a leaving group and $R^{11}$ is a protecting group.

DEFINITIONS

Figure 1:
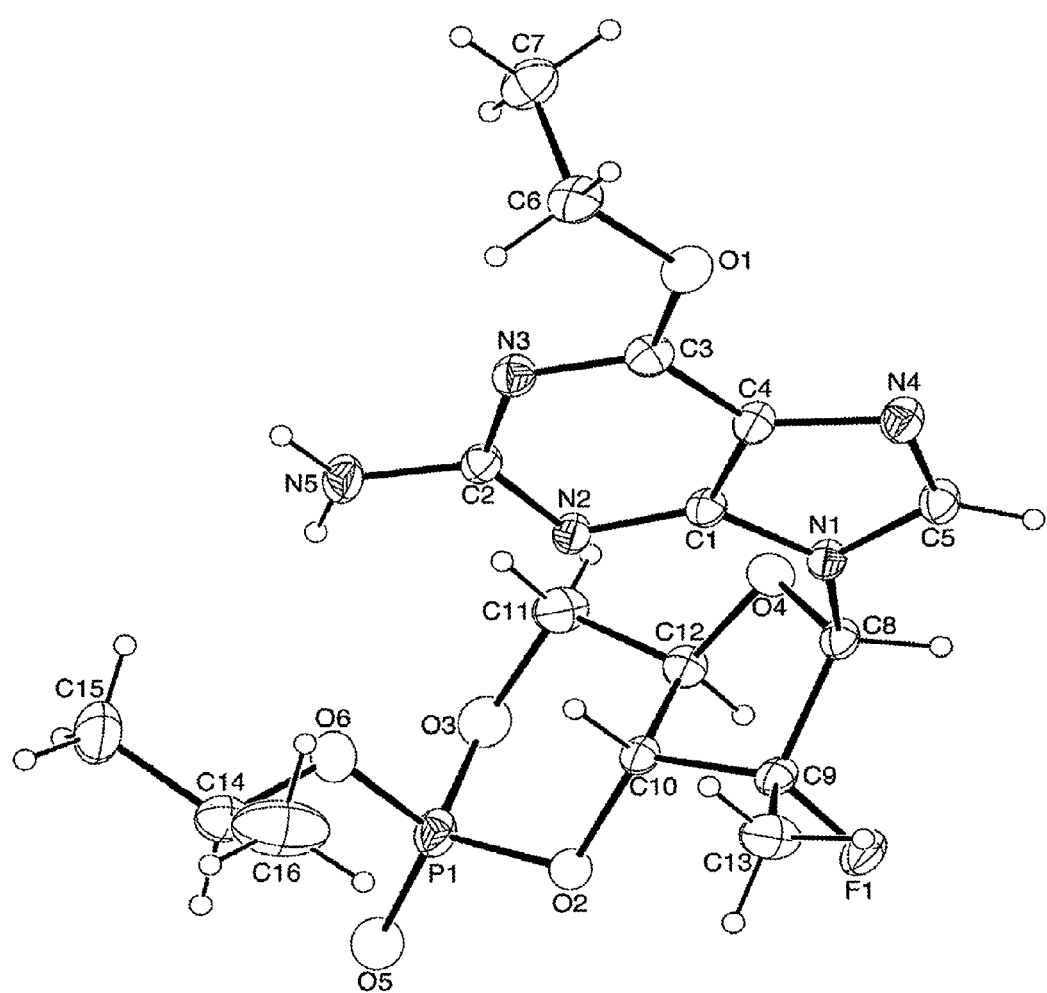
FIG. 1. X-Ray Crystal Structure (ORTEP drawing with 30% probability thermal ellipsoids) for $R_P$-17.

The phrase "a" or "an" entity as used herein refers to one or more of that entity; for example, a compound refers to one or more compounds or at least one compound. As such, the terms "a" (or "an"), "one or more", and "at least one" can be used interchangeably herein.

The phrase "as defined herein above" or "as defined above" with respect to the substituents refers to the first definition provided in the Summary of the Invention or if no definitions there, then the DEFINITIONS, if none there, the meaning understood by one of ordinary skill.

The terms "optional" or "optionally" as used herein means that a subsequently described event or circumstance may but need not occur, and that the description includes instances where the event or circumstance occurs and instances in which it does not. For example, "optional bond" means that the bond may or may not be present, and that the description includes single, double, or triple bonds.

The term "about" (also represented by ~) means that the recited numerical value is part of a range that varies within standard experimental error.

The term "halo," as used herein, includes chloro, bromo, iodo and fluoro.

The term "independently" is used herein to indicate that a variable is applied in any one instance without regard to the presence or absence of a variable having that same or a different definition within the same compound. Thus, in a compound in which R appears twice and is defined as "independently carbon or nitrogen", both R's can be carbon, both R's can be nitrogen, or one R' can be carbon and the other nitrogen.

The term "purified," as described herein, refers to the purity of a given compound. For example, a compound is "purified" when the given compound is a major component of the composition, i.e., at least 50% w/w pure. Thus, "purified" embraces at least 50% w/w purity, at least 60% w/w purity, at least 70% purity, at least 80% purity, at least 85% purity, at least 90% purity, at least 92% purity, at least 94% purity, at least 96% purity, at least 97% purity, at least 98% purity, and at least 99% purity.

The term "tautomerism" and "tautomers" have their accepted plain meanings

The term "P*" means that the phosphorus atom is chiral and that it has a corresponding Cahn-Ingold-Prelog designation of "R" or "S" which have their accepted plain meanings. It is contemplated that the phosphoramidate nucleoside I and the cyclic phosphate nucleotide II can exist as a mixture of diastereomers due to the chirality at phosphorus. Applicants contemplate use of the mixture of diastereomers and/or the resolved diastereomers. In some instances, an asterisk does not appear next to the phosphoroamidate or cyclic phosphate phosphorus atom. In these instances, it is understood that the phosphorus atom is chiral and that one of ordinary skill understands this to be so unless the substituents bound to the phosphorus exclude the possibility of chirality at phosphorus, such as in $P(O)Cl_3$.

Also contemplated are isotopically-enriched analogs of compounds I and II. The term "isotopically-enriched" means that at least one atom of compounds I and II is enriched with a particular isotope, such as, for example, $^2H$, $^3H$, $^{13}C$, $^{15}N$, $^{32}P$, etc. The term "deuterated analogs" means a compound described herein or its salts thereof, whereby a hydrogen atom is enriched with its $^2H$-isotope, i.e., deuterium (D). Deuterium substitution can be partial or complete. Partial deuterium substitution means that at least one hydrogen is substituted by at least one deuterium. For instance, for a compound 11, one of ordinary skill can contemplate at least the following partial deuterated analogs (where "$d_n$" represents n-number of deuterium atoms, such as, for an isopropyl group n=1-7, while for a phenyl group, n=1-5). Although the methyl groups depicted below are shown as being completely deuterated, one will recognize that partial-deuterated variations are also possible, such as, —$CDH_2$ and —$CD_2H$.

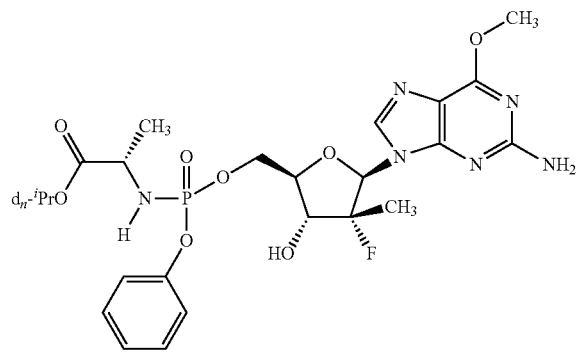

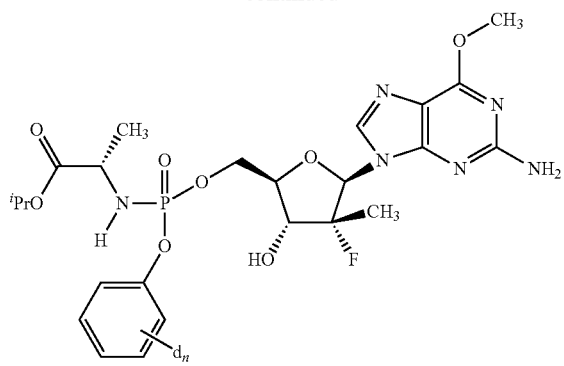

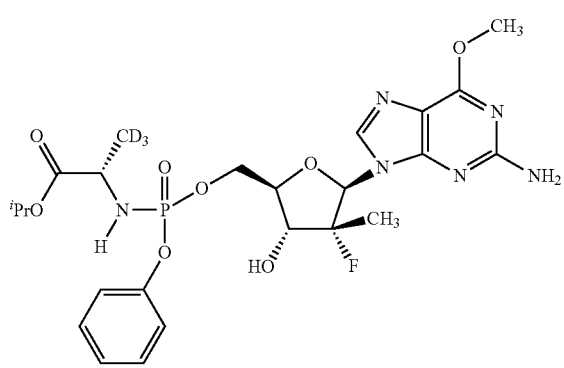

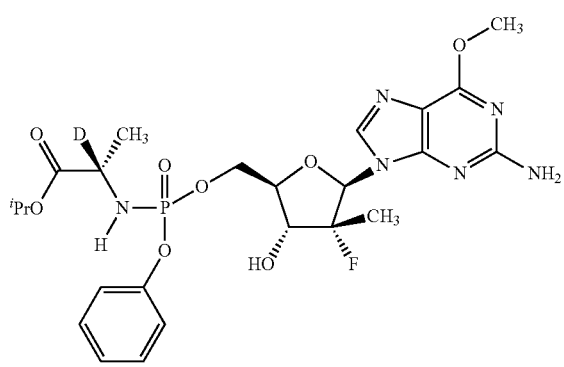

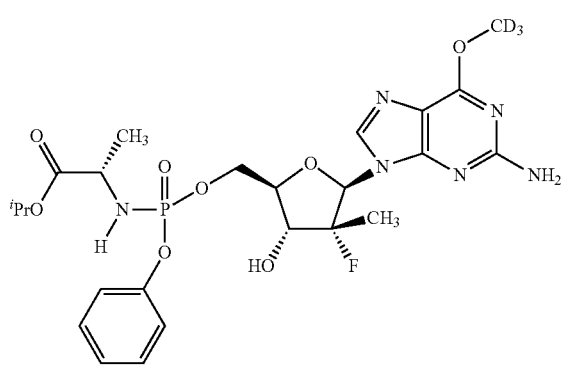

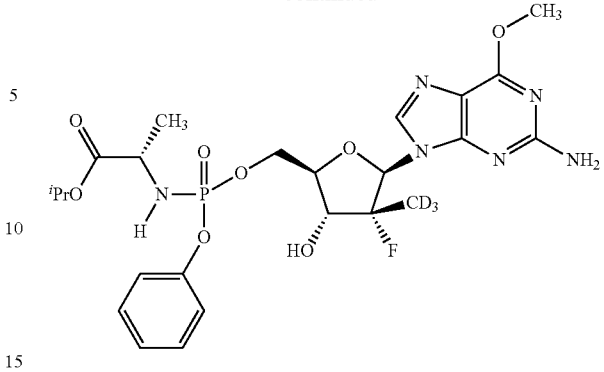

These are but a few deuterated analogs that are synthetically accessible by procedures and reagents that are known to one of ordinary skill.

The term "alkenyl" refers to an unsubstituted hydrocarbon chain radical having from 2 to 10 carbon atoms having one or two olefinic double bonds, preferably one olefinic double bond. The term "$C_{2-N}$ alkenyl" refers to an alkenyl comprising 2 to N carbon atoms, where N is an integer having the following values: 3, 4, 5, 6, 7, 8, 9, or 10. The term "$C_{2-10}$ alkenyl" refers to an alkenyl comprising 2 to 10 carbon atoms. The term "$C_{2-4}$ alkenyl" refers to an alkenyl comprising 2 to 4 carbon atoms. Examples include, but are not limited to, vinyl, 1-propenyl, 2-propenyl (allyl) or 2-butenyl (crotyl).

The term "halogenated alkenyl" refers to an alkenyl comprising at least one of F, Cl, Br, and I.

The term "alkyl" refers to an unbranched or branched chain, saturated, monovalent hydrocarbon residue containing 1 to 30 carbon atoms. The term "$C_{1-M}$ alkyl" refers to an alkyl comprising 1 to M carbon atoms, where M is an integer having the following values: 2, 3, 4, 5, 6, 7, 8, 9, 10, 11, 12, 13, 14, 15, 16, 17, 18, 19, 20, 21, 22, 23, 24, 25, 26, 27, 28, 29, or 30. The term "$C_{1-4}$ alkyl" refers to an alkyl containing 1 to 4 carbon atoms. The term "lower alkyl" denotes a straight or branched chain hydrocarbon residue comprising 1 to 6 carbon atoms, which is also designated by the expression "$C_{1-6}$-alkyl." "$C_{1-20}$ alkyl" as used herein refers to an alkyl comprising 1 to 20 carbon atoms. "$C_{1-10}$ alkyl" as used herein refers to an alkyl comprising 1 to 10 carbons. Examples of alkyl groups include, but are not limited to, methyl, ethyl, propyl, i-propyl, n-butyl, i-butyl, t-butyl, pentyl, isopentyl, neopentyl, hexyl, heptyl, octyl, nonyl, decyl, etc. Examples of lower alkyl groups include, but are not limited to, methyl, ethyl, propyl, i-propyl, n-butyl, i-butyl, t-butyl, pentyl, isopentyl, neopentyl, hexyl, etc. The term (ar)alkyl or (heteroaryl)alkyl indicate the alkyl group is optionally substituted by an aryl or a heteroaryl group respectively.

The term "halogenated alkyl" (or "haloalkyl") refers to an unbranched or branched chain alkyl comprising at least one of F, Cl, Br, and I. The term "$C_{1-M}$ haloalkyl" refers to an alkyl comprising 1 to M carbon atoms that comprises at least one of F, Cl, Br, and I, where M is an integer having the following values: 2, 3, 4, 5, 6, 7, 8, 9, 10, 11, 12, 13, 14, 15, 16, 17, 18, 19, 20, 21, 22, 23, 24, 25, 26, 27, 28, 29, or 30. "$C_{1-3}$ haloalkyl" refers to a haloalkyl comprising 1 to 3 carbons and at least one of F, Cl, Br, and I. The term "halogenated lower alkyl" (or "lower haloalkyl") refers to a haloalkyl comprising 1 to 6 carbon atoms and at least one of F, Cl, Br, and I. Examples include, but are not limited to, fluoromethyl, chloromethyl, bromomethyl, iodomethyl, difluoromethyl, dichloromethyl, dibromomethyl, diiodomethyl, trifluoromethyl, trichloromethyl, tribromomethyl, triiodomethyl, 1-fluoroethyl, 1-chloroethyl, 1-bromoethyl, 1-iodoethyl, 2-fluoroethyl, 2-chloroethyl, 2-bromoethyl, 2-iodoethyl, 2,2-difluoroethyl, 2,2-dichloroethyl, 2,2-dibromomethyl, 2-2-diiodomethyl, 3-fluoropropyl, 3-chloropropyl, 3-bromopropyl, 2,2,2-trifluoroethyl or 1,1,2,2,2-pentafluoroethyl.

The term "alkynyl" refers to an unbranched or branched hydrocarbon chain radical having from 2 to 10 carbon atoms, preferably 2 to 5 carbon atoms, and having one triple bond. The term "$C_{2-N}$ alkynyl" refers to an alkynyl comprising 2 to N carbon atoms, where N is an integer having the following values: 3, 4, 5, 6, 7, 8, 9, or 10. The term "C $C_{2-4}$ alkynyl" refers to an alkynyl comprising 2 to 4 carbon atoms. The term "$C_{2-10}$ alkynyl" refers to an alkynyl comprising 2 to 10 carbons. Examples include, but are limited to, ethynyl (i.e., —C≡CH), 1-propynyl, 2-propynyl, 1-butynyl, 2-butynyl or 3-butynyl.

The term "halogenated alkynyl" refers to an unbranched or branched hydrocarbon chain radical having from 2 to 10 carbon atoms, preferably 2 to 5 carbon atoms, and having one triple bond and at least one of F, Cl, Br, and I.

The term "alkoxy" refers to an —O-alkyl group, an —O-cycloalkyl group, an —O-lower cycloalkyl, wherein alkyl, cycloalkyl, and lower cycloalkyl are as defined above. Examples of —O-alkyl groups include, but are not limited to, methoxy, ethoxy, n-propyloxy, i-propyloxy, n-butyloxy, i-butyloxy, t-butyloxy. "Lower alkoxy" as used herein denotes an alkoxy group with a "lower alkyl" group as previously defined. "$C_{1-10}$ alkoxy" refers to an —O-alkyl wherein alkyl is $C_{1-10}$. Examples of —O-cycloalkyl groups include, but are not limited to, —O-c-propyl, —O-c-butyl, —O-c-pentyl, and —O-c-hexyl.

The term "halogenated alkoxy" refers to an —O-alkyl group in which the alkyl group comprises at least one of F, Cl, Br, and I.

The term "halogenated lower alkoxy" refers to an —O-(lower alkyl) group in which the lower alkyl group comprises at least one of F, Cl, Br, and I.

The term "cycloalkyl" refers to an unsubstituted or substituted carbocycle, in which the carbocycle contains 3 to 10 carbon atoms; preferably 3 to 8 carbon atoms; more preferably 3 to 6 carbon atoms (i.e., lower cycloalkyls). Examples of cycloalkyl groups include, but are not limited to, cyclopropyl, 2-methyl-cyclopropyl, cyclobutyl, cyclopentyl, cycloheptyl, or cyclooctyl. The term "$C_{3-7}$ cycloalkyl" as used herein refers to a cycloalkyl comprising 3 to 7 carbons in the carbocyclic ring. The term "lower cycloalkyl" refers to $C_{3-6}$ cycloalkyl rings, which include, but are not limited to, cyclopropyl ($^c$Pr), 2-methyl-cyclopropyl, etc., cyclobutyl ($^c$Bu), 2-methyl-cyclobutyl, 3-methyl-cyclobutyl, etc., cyclopentyl ($^c$Pn), 2-methyl-cyclopentyl, 3-methyl-cyclopentyl, 4-methyl-cyclopentyl, etc., cyclohexyl ($^c$Hx), etc.

The term "cycloalkyl alkyl" refers to an additionally unsubstituted or substituted alkyl substituted by a lower cycloalkyl. Examples of cycloalkyl alkyls include, but are not limited to, any one of methyl, ethyl, propyl, i-propyl, n-butyl, i-butyl, t-butyl or pentyl, isopentyl, neopentyl, hexyl, heptyl, and octyl that is substituted with cyclopropyl, 2-methyl-cyclopropyl, cyclobutyl, cyclopentyl, and cyclohexyl.

The term "cycloheteroalkyl" refers to an unsubstituted or substituted heterocycle, in which the heterocycle contains 2 to 9 carbon atoms; preferably 2 to 7 carbon atoms; more preferably 2 to 5 carbon atoms. Examples of cycloheteroalkyls include, but are not limited to, aziridin-2-yl, N—$C_{1-3}$-alkyl-aziridin-2-yl, azetidinyl, N—$C_{1-3}$-alkyl-azetidin-m'-yl, pyrrolidin-m'-yl, N—$C_{1-3}$-alkyl-pyrrolidin-m'-yl, piperidin-m'-yl, and N—$C_{1-3}$-alkyl-piperidin-m'-yl, where m' is 2, 3, or 4 depending on the cycloheteroalkyl. Specific examples of N—$C_{1-3}$-alkyl-cycloheteroalkyls include, but are not limited to, N-methyl-aziridin-2-yl, N-methyl-azetidin-3-yl, N-methyl-pyrrolidin-3-yl, N-methyl-pyrrolidin-4-yl, N-methyl-piperidin-2-yl, N-methyl-piperidin-3-yl, and N-methyl-piperidin-4-yl. In the instance of $R^4$, the point of attachment between the cycloheteroalkyl ring carbon and the oxygen occurs at any one of m'.

The term "acyl" refers to a substituent containing a carbonyl moiety and a non-carbonyl moiety. The carbonyl moiety contains a double-bond between the carbonyl carbon and a heteroatom, where the heteroatom is selected from among O, N and S. When the heteroatom is N, the N is substituted by a lower alkyl. The non-carbonyl moiety is selected from straight, branched, and cyclic alkyl, which includes, but is not limited to, a straight, branched, or cyclic $C_{1-20}$ alkyl, $C_{1-10}$ alkyl, or lower alkyl; alkoxyalkyl, including methoxymethyl; aralkyl, including benzyl; aryloxyalkyl, such as phenoxymethyl; or aryl, including phenyl optionally substituted with halogen (F, Cl, Br, I), hydroxyl, $C_1$ to $C_4$ alkyl, or $C_1$ to $C_4$ alkoxy, sulfonate esters, such as alkyl or aralkyl sulphonyl, including methanesulfonyl, the mono, di or triphosphate ester, trityl or monomethoxytrityl, substituted benzyl, trialkylsilyl (e.g. dimethyl-t-butylsilyl) or diphenylmethylsilyl. When at least one aryl group is present in the non-carbonyl moiety, it is preferred that the aryl group comprises a phenyl group.

The term "lower acyl" refers to an acyl group in which the non-carbonyl moiety is lower alkyl.

The term "aryl," as used herein, and unless otherwise specified, refers to substituted or unsubstituted phenyl (Ph), biphenyl, or naphthyl, preferably the term aryl refers to substituted or unsubstituted phenyl. The aryl group can be substituted with one or more moieties selected from among hydroxyl, F, Cl, Br, I, amino, alkylamino, arylamino, alkoxy, aryloxy, nitro, cyano, sulfonic acid, sulfate, phosphonic acid, phosphate, and phosphonate, either unprotected, or protected as necessary, as known to those skilled in the art, for example, as taught in T. W. Greene and P. G. M. Wuts, "Protective Groups in Organic Synthesis," 3rd ed., John Wiley & Sons, 1999.

The terms "alkaryl" or "alkylaryl" refer to an alkyl group with an aryl substituent, such as benzyl. The terms "lower alkaryl" or "lower alkylaryl" refer to a lower alkyl group with an aryl substituent, such as benzyl. The terms "aralkyl" or "arylalkyl" refer to an aryl group with an alkyl substituent.

The term "di(lower alkyl)amino-lower alkyl" refers to a lower alkyl substituted by an amino group that is itself substituted by two lower alkyl groups. Examples include, but are not limited to, $(CH_3)_2NCH_2$, $(CH_3)_2NCH_2CH_2$, $(CH_3)_2NCH_2CH_2CH_2$, etc. The examples above show lower alkyls substituted at the terminus carbon atom with an N,N-dimethyl-amino substituent. These are intended as examples only and are not intended to limit the meaning of the term "di(lower alkyl)amino-lower alkyl" so as to require the same. It is contemplated that the lower alkyl chain can be substituted with an N,N-di(lower alkyl)-amino at any point along the chain, e.g., $CH_3CH(N-(lower\ alkyl)_2)CH_2CH_2$.

The term "heterocycle" refers to an unsubstituted or substituted heterocycle containing carbon, hydrogen, and at least one of N, O, and S, where the C and N can be trivalent or tetravalent, i.e., $sp^2$- or $sp^3$-hybridized. Examples of heterocycles include, but are not limited to, aziridine, azetidine, pyrrolidine, piperidine, imidazole, oxazole, piperazine, etc. The term "nitrogen heterocycle" as used for $R^8$ and $R^9$ represents a heterocycle containing a nitrogen where the nitrogen is the point of attachment to the purine. Examples of a nitrogen heterocycle, as used for $R^8$ or $R^9$, include, but are not limited to, —N(—$CH_2CH_2$—) (aziridin-1-yl), —N(—

CH$_2$CH$_2$CH$_2$—) (azetidin-1-yl), —N(—CH$_2$CH$_2$CH$_2$CH$_2$—) (pyrrolidin-1-yl), etc. In the instance of piperazine, as related to R$^{10}$ for NR'$_2$, the corresponding opposite nitrogen atom of the piperazinyl is substituted by a lower alkyl represented by the following structure:

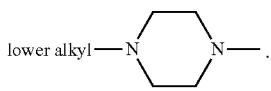

Preferably, the opposite nitrogen of the piperazinyl is substituted by a methyl group.

The term "amino acid" includes naturally occurring and synthetic α, β γ or δ amino acids, and includes but is not limited to, amino acids found in proteins, i.e. glycine, alanine, valine, leucine, isoleucine, methionine, phenylalanine, tryptophan, proline, serine, threonine, cysteine, tyrosine, asparagine, glutamine, aspartate, glutamate, lysine, arginine and histidine. In a preferred embodiment, the amino acid is in the L-configuration. Alternatively, the amino acid can be a derivative of alanyl, valinyl, leucinyl, isoleucinyl, prolinyl, phenylalaninyl, tryptophanyl, methioninyl, glycinyl, serinyl, threoninyl, cysteinyl, tyrosinyl, asparaginyl, glutaminyl, aspartoyl, glutaroyl, lysinyl, argininyl, histidinyl, β-alanyl, β-valinyl, β-leucinyl, β-isoleucinyl, β-prolinyl, β-phenylalaninyl, β-tryptophanyl, β-methioninyl, β-glycinyl, β-serinyl, β-threoninyl, β-cysteinyl, β-tyrosinyl, β-asparaginyl, β-glutaminyl, β-aspartoyl, β-glutaroyl, β-lysinyl, β-argininyl or β-histidinyl. When the term amino acid is used, it is considered to be a specific and independent disclosure of each of the esters of α, β γ or δ glycine, alanine, valine, leucine, isoleucine, methionine, phenylalanine, tryptophan, proline, serine, threonine, cysteine, tyrosine, asparagine, glutamine, aspartate, glutamate, lysine, arginine and histidine in the D and L-configurations.

The term "aminoacyl" includes unsubstituted, N-monosubstituted, and N,N-disubstituted derivatives of naturally occurring and synthetic α, β γ or δ amino acyls, where the amino acyls are derived from amino acids. The amino-nitrogen can be substituted or unsubstituted. When the amino-nitrogen is substituted, the nitrogen is either mono- or di-substituted, where the substituent bound to the amino-nitrogen is a lower alkyl or an alkaryl.

The terms "alkylamino" or "arylamino" refer to an amino group that has one or two alkyl or aryl substituents, respectively.

The term "protected," as used herein and unless otherwise defined, refers to a group that is added to an oxygen, nitrogen, or phosphorus atom to prevent its further reaction or for other purposes. A wide variety of oxygen and nitrogen protecting groups are known to those skilled in the art of organic synthesis. Non-limiting examples include: C(O)-alkyl, C(O)Ph, C(O)aryl, CH$_3$, CH$_2$-alkyl, CH$_2$-alkenyl, CH$_2$Ph, CH$_2$-aryl, CH$_2$O-alkyl, CH$_2$O-aryl, SO$_2$-alkyl, SO$_2$-aryl, tert-butyldimethylsilyl, tert-butyldiphenylsilyl, and 1,3-(1,1,3,3-tetraisopropyldisiloxanylidene).

The term "purine" or "pyrimidine" base includes, but is not limited to, adenine, N$^6$-alkylpurines, N$^6$-acylpurines (wherein acyl is C(O)(alkyl, aryl, alkylaryl, or arylalkyl), N$^6$-benzylpurine, N$^6$-halopurine, N$^6$-vinylpurine, N$^6$-acetylenic purine, N$^6$-acyl purine, N$^6$-hydroxyalkyl purine, N$^6$-alkylaminopurine, N$^6$-thioalkyl purine, N$^2$-alkylpurines, N$^2$-alkyl-6-thiopurines, thymine, cytosine, 5-fluorocytosine, 5-methylcytosine, 6-azapyrimidine, including 6-azacytosine, 2- and/or 4-mercaptopyrmidine, uracil, 5-halouracil, including 5-fluorouracil, C$^5$-alkylpyrimidines, C$^5$-benzylpyrimidines, C$^5$-halopyrimidines, C$^5$-vinylpyrimidine, C$^5$-acetylenic pyrimidine, C$^5$-acyl pyrimidine, C$^5$-hydroxyalkyl purine, C$^5$-amidopyrimidine, C$^5$-cyanopyrimidine, C$^5$-iodopyrimidine, C$^6$-Iodo-pyrimidine, C$^5$-Br-vinyl pyrimidine, C$^6$-Br-vinyl pyrimidine, C$^5$-nitropyrimidine, C$^5$-amino-pyrimidine, N$^2$-alkylpurines, N$^2$-alkyl-6-thiopurines, 5-azacytidinyl, 5-azauracilyl, triazolopyridinyl, imidazolopyridinyl, pyrrolopyrimidinyl, and pyrazolopyrimidinyl. Purine bases include, but are not limited to, guanine, adenine, hypoxanthine, 2,6-diaminopurine, and 6-chloropurine. Functional oxygen and nitrogen groups on the base can be protected as necessary or desired. Suitable protecting groups are well known to those skilled in the art, and include trimethylsilyl, dimethylhexylsilyl, t-butyldimethylsilyl, and t-butyldiphenylsilyl, trityl, alkyl groups, and acyl groups such as acetyl and propionyl, methanesulfonyl, and p-toluenesulfonyl.

The term "protecting group" refers to a chemical group which exhibits the following characteristics. The group must react selectively in good yield to give a protected substrate that is stable to the projected reactions; and the protective group must be selectively removable in good yield by readily available, preferably nontoxic reagents that do not attack the functional group(s) generated in such projected reactions (see Protective Groups in Organic Synthesis, 3$^{rd}$ ed. T. W. Greene and P. G. M. Wuts, John Wiley & Sons, New York, N.Y., 1999). Examples of protecting groups include, but are not limited to: benzoyl, substituted benzoyl, acetyl, phenyl-substituted benzoyl, trityl, DMT (4,4'-dimethoxytrityl), MMT (4-monomethoxytrityl), pixyl (9-phenylxanthen-9-yl)group, thiopixyl (9-phenylthioxanthen-9-yl). The substituted benzoyl groups can be partially substituted or fully substituted. For instance, one of ordinary skill would recognize that the 2-, 3-, 4-, 5-, and 6-positions of the benzoyl ring can be substituted with either hydrogen (an unsubstituted position) or another substituent (a substituted position), such as the substituents contemplated above and throughout the present disclosure. Examples of substituted benzoyl groups include, but are not limited to: 2-halo-benzoyl, 3-halo-benzoyl, 4-halo-benzoyl; 2,4-dihalo-benzoyl, 3,4-dihalo-benzoyl, and 3,5-dihalo-benzoyl; 2-(C$_{1-6}$-alkyl)-benzoyl, 3-(C$_{1-6}$-alkyl)-benzoyl, and 4-(C$_{1-6}$-alkyl)-benzoyl; 2,4-(diC$_{1-6}$-alkyl)-benzoyl, 3,4-(diC$_{1-6}$-alkyl)-benzoyl, and 3,5-(diC$_{1-6}$-alkyl)-benzoyl; 2-nitro-benzoyl, 3-nitro-benzoyl, 4-nitro-benzoyl; 2,4-(dinitro)-benzoyl, 3,4-(dinitro)-benzoyl, and 3,5-(dinitro)-benzoyl, etc.

The term "leaving group", (see also "Lv") as used herein, has the same meaning to the skilled artisan (Advanced Organic Chemistry: reactions, mechanisms and structure—Fourth Edition by Jerry March, John Wiley and Sons Ed.; 1992 pages 351-357) and represents a group which is part of and attached to a substrate molecule; in a reaction where the substrate molecule undergoes a displacement reaction (with for example a nucleophile), the leaving group is then displaced. Examples of leaving groups include, but are not limited to: halogen (F, Cl, Br, and I), preferably Cl, Br, or I; tosylate, mesylate, triflate, acetate, etc.

The term "hydride reducing agent", as used herein, has the meaning of at least one compound capable of reducing the carbonyl (C=O) group of the lactone to a hydroxy group (C—OH). Hydride reducing agents include, but are not limited to: ($^t$BuO)$_3$AlH, sodium (bis(2-methoxyethoxy)(2,2,2-trifluoro-ethoxy)aluminum hydride, Red-Al (sodium bis(2-methoxyethoxy)aluminum hydride), sodium borohydride, lithium aluminum hydride, diborane, borane-tetrahydrofuran complex, borane-dimethylsulfide complex, aluminum triisopropoxide, boron triacetoxy hydride, alcohol dehydrogenase enzymes, (−)- or (+)-diisopinocampheylchloroborane, lithium (2,3-Dimethyl-2-butyl)-t-butoxyborohydride, Diisobutylaluminum 2,6-Di-t-butyl-4-methylphenoxide. Preferably, the hydride reducing agent is ($^t$BuO)$_3$AlH or sodium (bis(2-methoxyethoxy)(2,2,2-trifluoro-ethoxy)aluminum hydride.

The term "reagent" standing alone, as used herein, has the meaning of at least one compound capable of reacting with the lactol derivative by introducing a leaving group at the anomeric carbon atom. The at least one compound includes, but is not limited to, Ph$_3$P/CBr$_4$, Ph$_3$P/CHBr$_3$, Ph$_3$P/CHBr$_3$/imidazole, Ph$_3$P/Br$_2$, Ph$_3$P/Br$_2$/imidazole, N-bromosuccinimide/Ph$_3$P, HBr in acetic acid, PBr$_3$/DMF, PBr$_3$/sodium bicarbonate, PBr$_3$/imidazole, PBr$_5$/DMF, PBr$_5$/sodium bicarbonate, PBr$_5$/imidazole, N-chlorosuccinimide/Ph$_3$P, POBr$_3$/imidazole, POCl$_3$/imidazole, SOCl$_2$, SO$_2$Cl$_2$, N-chlorosuccinimide, Ph$_3$P/CCl$_4$, HCl (g)/ether, acid chlorides and anhydrides such as acetyl chloride, acetic anhydride, benzoyl chloride, benzoic anhydride, triflic anhydride and trichloroacetonitrile/DBU. Other trivalent phosphorus compounds may be used in place of triphenylphosphine, such as triphenyl phosphite and (4-dimethylaminophenyl)diphenylphosphine.

The term "basic reagent", as used herein, means a compound that is capable of abstracting a proton from an acidic reagent, such as a purine base, whereby the "acidic" functional group of the purine base includes the N—H of the fused imidazole ring. Examples of basic reagents include, but are not limited to, a (lower alk)oxide ((lower alkyl)OM) in combination with an alcoholic solvent, where (lower alk)oxides include, but are not limited to, MeO$^−$, EtO$^−$, $^n$PrO$^−$, $^i$PrO$^−$, $^t$BuO$^−$, $^i$AmO- (iso-amyloxide), etc., and where M is an alkali metal cation, such as Li$^+$, Na$^+$, K$^+$, etc. Alcoholic solvents include (lower alkyl)OH, such as, for example, MeOH, EtOH, $^n$PrOH, $^i$PrOH, $^t$BuOH, $^i$AmOH, etc. Non-alkoxy bases can also be used such as sodium hydride, sodium hexamethyldisilazane, lithium hexamethyldisilazane, lithium diisopropylamide, calcium hydride, sodium carbonate, potassium carbonate, cesium carbonate, DBU, and DBN.

The term "nucleophilic reagent", as used herein, means a compound that contains a radical that is capable of replacing another radical, e.g., by way of a nucleophilic-substitution reaction. An example of a nucleophilic reagent includes, but is not limited to, a (lower alk)oxide ((lower alkyl)OM) in combination with an alcoholic solvent, where (lower alk) oxides include, but are not limited to, MeO$^−$, EtO$^−$, $^n$PrO$^−$, $^i$PrO$^−$, $^t$BuO$^−$, etc., and where M is an alkali metal cation, such as Li$^+$, Na$^+$, K$^+$, etc. Alcoholic solvents include (lower alkyl) OH, such as, for example, MeOH, EtOH, $^n$PrOH, $^i$PrOH, $^t$BuOH, etc. Another example of a nucleophilic reagent includes, but is not limited to, an (aralkyl)oxide in combination with an aralkanol solvent, such as, for example, BnONa/BnOH, where "Bn" represents a benzyl radical (C$_6$H$_5$CH$_2$—). Another example of a nucleophilic reagent includes, but is not limited to, an unsubstituted or substituted heterocycle containing carbon, hydrogen, and at least one of N, O, and S, where the C and N can be trivalent or tetravalent, i.e., sp$^2$- or sp$^3$-hybridized in the presence of a basic reagent or lower alkyl amine, such as triethylamine or diisopropyl ethyl amine, etc. Specific examples of heterocycles include (see also a preceding paragraph), but are not limited to, aziridine, azetidine, pyrrolidine, piperidine, imidazole, oxazole, piperazine, etc. Thus, any one of aziridine, azetidine, pyrrolidine, piperidine, imidazole, oxazole, piperazine can be used in combination with triethylamine or diisopropyl ethyl amine, etc. Yet another example of a nucleophilic reagents includes primary and secondary amines, which includes, but is not limited to, H$_2$NR' or HNR'$_2$, wherein R' is an optionally substituted alkyl, which includes, but is not limited to, an optionally substituted C$_{1-20}$ alkyl, an optionally substituted C$_{1-10}$ alkyl, an optionally substituted lower alkyl; or an optionally substituted cycloalkyl. The term "nucleophilic reagent" also provides for functional groups, which when introduced at the 6 position of the purine moiety, are capable of being coverted to a hydroxy group. The term "a group capable of being converted to OH," as used in the process described herein, means a substituent comprised of —OZ, where —OZ is converted to —OH on exposure to certain chemical reagents. Z includes, but is not limited to, an unsubstituted or substituted benzyl, such as, benzyl or p-methoxybenzyl; a silyl, such as, trimethylsilyl-, t-butyl-diphenylsilyl-, t-butyl-dimethylsilyl, etc.; and an unsubstituted or substituted allyl, such as, —CH$_2$CH═CH$_2$.

The term P(III)-reagent as used in the process described herein means a chemical reagent whereby the phosphorus atom has a +3-oxidation state. Examples of such P(III)-reagents include, but are not limited to, P(Lv)$_3$, R$^7$OP(Lv)$_2$, R$^7$OP(Lv)(N(C$_{1-6}$ alkyl)$_2$), R$^7$OP[N(C$_{1-6}$ alkyl)$_2$]$_2$, and mixtures thereof, where Lv is a leaving group, R$^7$ and C$_{1-6}$ alkyl are defined herein.

The term activator reagent as used in the process described herein means a compound that promotes the reaction involving a P(III)-reagent. Examples of activators include, but are not limited to, 1H-tetrazole, 5-ethylthiotetrazole, imidazolium triflate, and 4,5-dicyano-imidazole, as well as those disclosed in U.S. Pat. No. 6,274,725.

The term P(V)-reagent as used in the process described herein means a P(III)-reagent having an additional oxo (P═O, depicted also as —P(O)—) substituent, whereby the phosphorus atom has a +5-oxidation state. Examples of such P(V)-reagents include, but are not limited to, P(O)(Lv)$_3$, R$^7$OP(O)(Lv)$_2$, R$^7$OP(O)(Lv)(N(C$_{1-6}$ alkyl)$_2$), R$^7$OP(O)[N(C$_{1-6}$ alkyl)$_2$]$_2$, and mixtures thereof, where Lv is a leaving group, R$^7$ and C$_{1-6}$ alkyl are defined herein.

The term oxidizing agent as used in the process described herein means a chemical reagent that increases the oxidation state of an atom, i.e., an oxidizing agent promotes "oxidizing" or "oxidation." In a particular embodiment, the atom that is oxidized is phosphorus, as in a phosphite derivative of II. Examples of oxidizing agents include, but are not limited to, hydrogen peroxide, hydroperoxides, peroxides, peracids, iodine, and mixtures thereof. Hydrogen peroxide can be used in the presence of a solvent, such as acetonitrile, as disclosed in Cvetovich, R. J. Organic Process Research & Development, Article ASAP, Publication Date (Web): May 11, 2009. Hydroperoxides, ROOH, include peroxides in which R is an alkyl or an aryl and salts thereof, which include, but is not limited to t-butylperoxide ($^t$BuOOH). Peroxides include alkyl, aryl, or mixed alkyl/aryl peroxides and salts thereof. Peracids include alkyl and aryl peracids, which include, but are not limited to, m-chloroperoxybenzoic acid (mCPBA). Use of an elemental halogent, such as, bromine (Br$_2$), chlorine (Cl$_2$), or iodine (I$_2$), can be done in the presence of water and other components, such as, pyridine, tetrahydrofuran, and water. Alternatively, an aqueous Cl$_2$ solution in the presence of TEMPO is contemplated as well.

The expression "equilibrating the phosphite derivative of II" as used herein refers to a process where a composition comprising the two isomers (cis and trans) of the phosphite derivative of II is allowed to equilibrate, as depicted in the following equation.

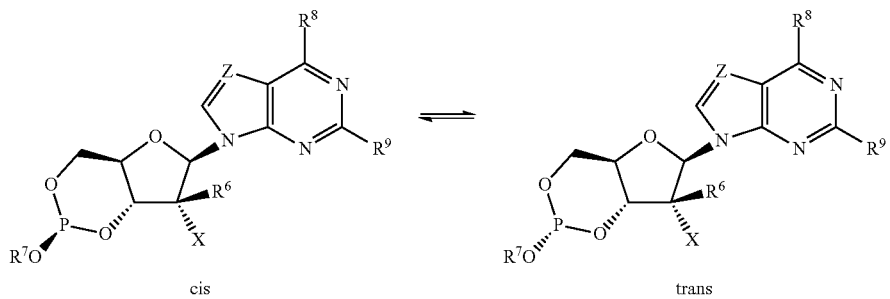

cis ⇌ trans

The terms cis and trans refer to the spatial position of the —OR$^7$ substituent relative to the spatial position of the nucleobase on the furanose ring system. One of ordinary skill will recognize that the equilibrium position, i.e., the ratio of cis-to-trans, may be influenced by solvent, temperature, etc. and that the conditions to obtain a certain equilibrium position can be determined experimentally, such experimental techniques include, but are not limited to, $^1$H- or $^{31}$P-NMR spectroscopy.

The term amine reagent as used herein means a composition containing at least one compound comprising nitrogen in its protonated or unprotonated form. One of ordinary skill will understand that this term embraces ammonia, mono-, and di-substituted alkyl amines, such as methyl amine, di-isopropyl amine, cyclopentyl-amine, as well as heterocyclic compounds that include, but are not limited to, pyrrolidine, piperidine, morpholine, etc., imidazole, N—($C_{1-6}$ alkyl)-imidazole, such as, N-methyl-imidazole, pyrazole, N—($C_{1-6}$ alkyl)-pyrazole, such as, N-methyl-pyrazole, triazole, N—($C_{1-6}$ alkyl)-triazole, such as N-methyl-triazole, tetrazole, N—($C_{1-6}$ alkyl)-tetrazole, such as N-methyl-tetrazole, oxazole, etc. Additional examples of heterocyclic amines are disclosed in T. L. Gilchrist, Heterocyclic Chemistry, 1985, Longman Scientific & Technical, which is hereby incorporated by reference.

The terms "purine" or "derivatized purine", as used in the process described herein, means, in addition to the compounds specifically disclosed in a preceding paragraph, a precursor compound of the "Base" of the compounds represented by the structures of formula I and formula II.

The term "salts thereof" includes acid or basic additions salts, as well as pharmaceutically acceptable salts. The phrase "pharmaceutically acceptable salt" means a salt that is pharmaceutically acceptable and that possesses the desired pharmacological activity of the parent compound. Such salts include, but are not limited to: (1) acid addition salts, formed with inorganic acids such as hydrochloric acid, hydrobromic acid, sulfuric acid, nitric acid, phosphoric acid, and the like; or formed with organic acids such as glycolic acid, pyruvic acid, lactic acid, malonic acid, malic acid, maleic acid, fumaric acid, tartaric acid, citric acid, 3-(4-hydroxybenzoyl) benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, lauryl sulfuric acid, gluconic acid, glutamic acid, salicylic acid, muconic acid, and the like or (2) basic addition salts formed with the conjugate bases of any of the inorganic acids listed above, wherein the conjugate bases comprise a cationic component selected from among Na$^+$, K$^+$, Mg$^{2+}$, Ca$^{2+}$, NH$_g$R'''$_{4-g}{}^+$, in which R''' is a $C_{1-3}$ alkyl and g is a number selected from among 0, 1, 2, 3, or 4. It should be understood that all references to pharmaceutically acceptable salts include solvent addition forms (solvates) or crystal forms (polymorphs) as defined herein, of the same acid addition salt.

The term "preparation" or "dosage form" is intended to include both solid and liquid formulations of the active compound and one skilled in the art will appreciate that an active ingredient can exist in different preparations depending on the desired dose and pharmacokinetic parameters.

The term "excipient" as used herein refers to a compound that is used to prepare a pharmaceutical composition, and is generally safe, non-toxic and neither biologically nor otherwise undesirable, and includes excipients that are acceptable for veterinary use as well as human pharmaceutical use.

The term "crystalline" refers to a situation where a solid sample of compound I or II has crystalline characteristics when determined by X-ray powder diffraction or a single crystal X-ray technique.

The term "crystal-like" refers to a situation where a solid sample of compound I or II has crystalline characteristics when determined by one means, e.g., visually or by optical or polarizing microscopy, but does not have crystalline characteristics when determined by another means, e.g., x-ray powder diffraction. Methods of visually determining the crystallinity of a solid sample by visual or by optical or by polarizing microscopy are disclosed in USP <695> and <776>, both of which are incorporated by reference. A solid sample of compound I or II that is "crystal-like" may be crystalline under certain conditions but may become non-crystalline when subjected to other conditions.

The term "amorphous" refers to a situation where a solid sample of compound I or II is neither crystalline nor crystal-like.

The term "co-crystallates" include co-crystallates of compound I or II in combination with salts, which embraces pharmaceutically acceptable salts.

The term "substantially anhydrous" means that a substance contains at most 10% by weight of water, preferably at most 1% by weight of water, more preferably at most 0.5% by weight of water, and most preferably at most 0.1% by weight of water.

A (lattice or adsorbed) solvent (designated in some instances by the symbol 5) or anti-solvent includes at least one of a $C_1$ to $C_8$ alcohol, a $C_2$ to $C_8$ ether, a $C_3$ to $C_7$ ketone, a $C_3$ to $C_7$ ester, a $C_1$ to $C_2$ chlorocarbon, a $C_5$ to $C_{12}$ saturated hydrocarbon, and a $C_6$ to $C_{12}$ aromatic hydrocarbon.

DETAILED DESCRIPTION OF THE INVENTION

Disclosed is compound I or salts thereof or compound II or salts thereof:

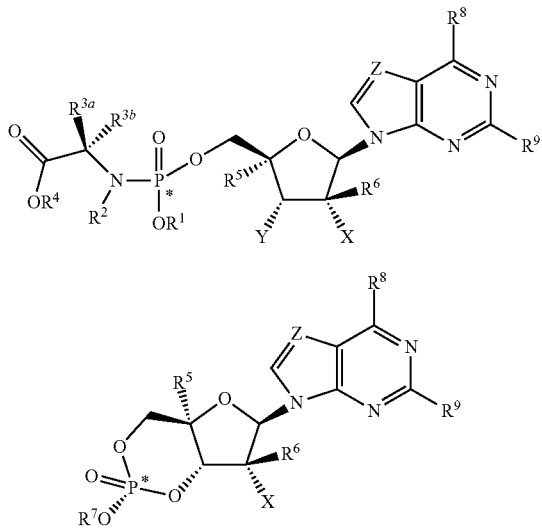

wherein (a) $R^1$ is hydrogen, n-alkyl; branched alkyl; cycloalkyl; or aryl, which includes, but is not limited to, phenyl or naphthyl, where phenyl or naphthyl are optionally substituted with at least one of $C_{1-6}$ alkyl, $C_{2-6}$ alkenyl, $C_{2-6}$ alkynyl, $C_{1-6}$ alkoxy, F, Cl, Br, I, nitro, cyano, $C_{1-6}$ haloalkyl, —N($R^{1'}$)$_2$, $C_{1-6}$ acylamino, —NHSO$_2$$C_{1-6}$ alkyl, —SO$_2$N($R^{1'}$)$_2$, COR$^{1'''}$, and —SO$_2$$C_{1-6}$ alkyl; ($R^{1'}$ is independently hydrogen or alkyl, which includes, but is not limited to, $C_{1-20}$ alkyl, $C_{1-10}$ alkyl, or $C_{1-6}$ alkyl, $R^{1'''}$ is —OR' or —N($R^{1'}$)$_2$);

(b) $R^2$ is hydrogen, $C_{1-10}$ alkyl, or $R^{3a}$ or $R^{3b}$ and $R^2$ together are $(CH_2)_n$ so as to form a cyclic ring that includes the adjoining N and C atoms, where n is 2 to 4;

(c) $R^{3a}$ and $R^{3b}$ are (i) independently selected from hydrogen, $C_{1-10}$ alkyl, cycloalkyl, —(CH$_2$)$_c$(NR$^{3'}$)$_2$, $C_{1-6}$ hydroxyalkyl, —CH$_2$SH, —(CH$_2$)$_2$S(O)$_d$Me, —(CH$_2$)$_3$NHC(═NH)NH$_2$, (1H-indol-3-yl)methyl, (1H-imidazol-4-yl)methyl, —(CH$_2$)$_e$COR$^{3''}$, aryl and aryl $C_{1-3}$ alkyl, said aryl groups optionally substituted with a group selected from hydroxyl, $C_{1-10}$ alkyl, $C_{1-6}$ alkoxy, halogen, nitro and cyano;

(ii) $R^{3a}$ and $R^{3b}$ both are $C_{1-6}$ alkyl;

(iii) $R^{3a}$ and $R^{3b}$ together are $(CH_2)_f$ so as to form a spiro ring;

(iv) $R^{3a}$ is hydrogen and $R^{3b}$ and $R^2$ together are $(CH_2)_n$ so as to form a cyclic ring that includes the adjoining N and C atoms (v) $R^{3b}$ is hydrogen and $R^{3a}$ and $R^2$ together are $(CH_2)_n$ so as to form a cyclic ring that includes the adjoining N and C atoms, where c is 1 to 6, d is 0 to 2, e is 0 to 3, f is 2 to 5, n is 2 to 4, and where $R^{3'}$ is independently hydrogen or $C_{1-6}$ alkyl and $R^{3''}$ is —OR' or —N($R^{3'}$)$_2$);

(vi) $R^{3a}$ is H and $R^{3b}$ is H, CH$_3$, CH$_2$CH$_3$, CH(CH$_3$)$_2$, CH$_2$CH(CH$_3$)$_2$, CH(CH$_3$)CH$_2$CH$_3$, CH$_2$Ph, CH$_2$-indol-3-yl, —CH$_2$CH$_2$SCH$_3$, CH$_2$CO$_2$H, CH$_2$C(O)NH$_2$, CH$_2$CH$_2$COOH, CH$_2$CH$_2$C(O)NH$_2$, CH$_2$CH$_2$CH$_2$CH$_2$NH$_2$, —CH$_2$CH$_2$CH$_2$NHC(NH)NH$_2$, CH$_2$-imidazol-4-yl, CH$_2$OH, CH(OH)CH$_3$, CH$_2$((4'-OH)-Ph), CH$_2$SH, or lower cycloalkyl; or (vii) $R^{3a}$ is CH$_3$, —CH$_2$CH$_3$, CH(CH$_3$)$_2$, CH$_2$CH(CH$_3$)$_2$, CH(CH$_3$)CH$_2$CH$_3$, CH$_2$Ph, CH$_2$-indol-3-yl, —CH$_2$CH$_2$SCH$_3$, CH$_2$CO$_2$H, CH$_2$C(O)NH$_2$, CH$_2$CH$_2$COOH, CH$_2$CH$_2$C(O)NH$_2$, CH$_2$CH$_2$CH$_2$CH$_2$NH$_2$, —CH$_2$CH$_2$CH$_2$NHC(NH)NH$_2$, CH$_2$-imidazol-4-yl, CH$_2$OH, CH(OH)CH$_3$, CH$_2$((4'-OH)-Ph), CH$_2$SH, or lower cycloalkyl and $R^{3b}$ is H, where $R^{3'}$ is independently hydrogen or alkyl, which includes, but is not limited to, $C_{1-20}$ alkyl, $C_{1-10}$ alkyl, or $C_{1-6}$ alkyl, $R^{3''}$ is —OR' or —N($R^{3'}$)$_2$);

(d) $R^4$ is hydrogen, $C_{1-10}$ alkyl, $C_{1-10}$ alkyl optionally substituted with a lower alkyl, alkoxy, di(lower alkyl)-amino, or halogen, $C_{1-10}$ haloalkyl, $C_{3-10}$ cycloalkyl, cycloalkyl alkyl, cycloheteroalkyl, aminoacyl, aryl, such as phenyl, heteroaryl, such as, pyridinyl, substituted aryl, or substituted heteroaryl;

(e) $R^5$ is H, a lower alkyl, CN, vinyl, O-(lower alkyl), hydroxyl lower alkyl, i.e., —(CH$_2$)$_p$OH, where p is 1-6, including hydroxyl methyl (CH$_2$OH), CH$_2$F, N$_3$, CH$_2$CN, CH$_2$NH$_2$, CH$_2$NHCH$_3$, CH$_2$N(CH$_3$)$_2$, alkyne (optionally substituted), or halogen, including F, Cl, Br, or I;

(f) $R^6$ is H, CH$_3$, CH$_2$F, CHF$_2$, CF$_3$, F, CN, vinyl, or ethynyl;

(g) $R^7$ is hydrogen, n-alkyl, branched alkyl, cycloalkyl, alkaryl, or aryl, which includes, but is not limited to, phenyl or naphthyl, where phenyl or naphthyl are optionally substituted with at least one of H, F, Cl, Br, I, OH, OR$^{7'}$, SH, SR$^{7'}$, NH$_2$, NHR$^{7'}$, NR$^{7'}{}_2$, lower alkyl of $C_1$-$C_6$, halogenated (F, Cl, Br, I) lower alkyl of $C_1$-$C_6$, halogenated (F, Cl, Br, I) lower alkenyl of $C_2$-$C_6$, lower alkynyl of $C_2$-$C_6$, such as C≡CH, halogenated (F, Cl, Br, I) lower alkynyl of $C_2$-$C_6$, lower alkoxy of $C_1$-$C_6$, halogenated (F, Cl, Br, I) lower alkoxy of $C_1$-$C_6$, CO$_2$H, CO$_2$R$^{7'}$, CONH$_2$, CONHR$^{7'}$, CONR$^{7'}{}_2$, CH═CHCO$_2$H, or CH═CHCO$_2$R$^{7'}$ wherein R$^{7'}$ is an optionally substituted alkyl, cycloalkyl, alkenyl, alkynyl, or alkoxyalkyl, which includes, but is not limited to, $C_{1-10}$ alkyl, $C_{3-7}$ cycloalkyl, $C_{2-10}$ alkenyl, $C_{2-10}$ alkynyl, and $C_{1-10}$ alkoxyalkyl, (h) X is H, OH, OMe, halogen, CN, NH$_2$, or N$_3$;

(i) Y is OH;

(j) Z is N or CR$^{10}$;

(k) $R^8$ and $R^9$ are independently H, F, Cl, Br, I, OH, OR', SH, SR', NH$_2$, NHR', NR'$_2$, nitrogen heterocycle, lower alkyl of $C_1$-$C_6$, halogenated (F, Cl, Br, I) lower alkyl of $C_1$-$C_6$, lower alkenyl of $C_2$-$C_6$, halogenated (F, Cl, Br, I) lower alkenyl of $C_2$-$C_6$, lower alkynyl of $C_2$-$C_6$ such as C≡CH, halogenated (F, Cl, Br, I) lower alkynyl of $C_2$-$C_6$, lower alkoxy of $C_1$-$C_6$, halogenated (F, Cl, Br, I) lower alkoxy of $C_1$-$C_6$, CO$_2$H, CO$_2$R', CONH$_2$, CONHR', CONR'$_2$, CH═CHCO$_2$H, or CH═CHCO$_2$R', and (l) $R^{10}$ is H, halogen (including F, Cl, Br, I), OH, OR', SH, SR', NH$_2$, NHR', NR'$_2$, NO$_2$ lower alkyl of $C_1$-$C_6$, halogenated (F, Cl, Br, I) lower alkyl of $C_1$-$C_6$, lower alkenyl of $C_2$-$C_6$, halogenated (F, Cl, Br, I) lower alkenyl of $C_2$-$C_6$, lower alkynyl of $C_2$-$C_6$, halogenated (F, Cl, Br, I) lower alkynyl of $C_2$-$C_6$, lower alkoxy of $C_1$-$C_6$, halogenated (F, Cl, Br, I) lower alkoxy of $C_1$-$C_6$, CO$_2$H, CO$_2$R', CONH$_2$, CONHR', CONR'$_2$, CH═CHCO$_2$H, or CH═CHCO$_2$R';

wherein R' is an optionally substituted alkyl, which includes, but is not limited to, an optionally substituted $C_{1-20}$ alkyl, an optionally substituted $C_{1-10}$ alkyl, an optionally substituted lower alkyl; an optionally substituted cycloalkyl; an alkaryl; an optionally substituted alkynyl of $C_2$-$C_6$; an optionally substituted lower alkenyl of $C_2$-$C_6$, or optionally substituted acyl, which includes but is not limited to C(O) alkyl, C(O)($C_{1-20}$ alkyl), C(O)($C_{1-10}$ alkyl), or a C(O)(lower alkyl).

Also disclosed is a process for preparing compound I or compound II, as defined above, wherein said process comprises:

(a) stereoselective reduction of a protected ribonolactone III using a hydride reducing agent

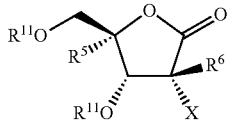

to provide a beta-lactol derivative IV; and

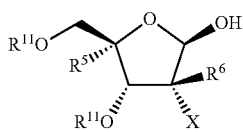

(b) stereoselective conversion of the lactol derivative using a reagent to obtain an anomeric alpha-derivative V

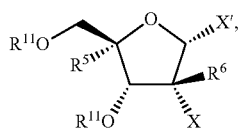

wherein $R^5$, $R^6$, and X have their meanings as described above, X' is a leaving group, and $R^{11}$ is a protecting group.

A first embodiment is directed to compound I, wherein (a) $R^1$ is hydrogen, n-alkyl; branched alkyl; cycloalkyl; or aryl, which includes, but is not limited to, phenyl or naphthyl, where phenyl or naphthyl are optionally substituted with at least one of $C_{1-6}$ alkyl, $C_{2-6}$ alkenyl, $C_{2-6}$ alkynyl, $C_{1-6}$ alkoxy, F, Cl, Br, I, nitro, cyano, $C_{1-6}$ haloalkyl, $-N(R^{1'})_2$, $C_{1-6}$ acylamino, $-NHSO_2C_{1-6}$ alkyl, $-SO_2N(R^{1'})_2$, $COR^{1''}$, and $-SO_2C_{1-6}$ alkyl; ($R^{1'}$ is independently hydrogen or alkyl, which includes, but is not limited to, $C_{1-20}$ alkyl, $C_{1-10}$ alkyl, or $C_{1-6}$ alkyl, $R^{1''}$ is $-OR'$ or $-N(R^{1'})_2$);

(b) $R^2$ is hydrogen or $CH_3$;

(c) $R^{3a}$ and $R^{3b}$ are
(i) independently selected from hydrogen, $C_{1-10}$ alkyl, cycloalkyl, $-(CH_2)_c(NR^{3'})_2$, $C_{1-6}$ hydroxyalkyl, $-CH_2SH$, $-(CH_2)_2S(O)_dMe$, $-(CH_2)_3NHC(=NH)NH_2$, (1H-indol-3-yl)methyl, (1H-imidazol-4-yl)methyl, $-(CH_2)_eCOR^{3'''}$, aryl and aryl $C_{1-3}$ alkyl, said aryl groups optionally substituted with a group selected from hydroxyl, $C_{1-10}$ alkyl, $C_{1-6}$ alkoxy, halogen, nitro and cyano; (ii) $R^{3a}$ and $R^{3b}$ both are $C_{1-6}$ alkyl; (iii) $R^{3a}$ and $R^{3b}$ together are $(CH_2)_f$ so as to form a spiro ring; (iv) $R^{3a}$ is hydrogen and $R^{3b}$ and $R^2$ together are $(CH_2)_n$ so as to form a cyclic ring that includes the adjoining N and C atoms; (v) $R^{3b}$ is hydrogen and $R^{3a}$ and $R^2$ together are $(CH_2)_n$ so as to form a cyclic ring that includes the adjoining N and C atoms, where c is 1 to 6, d is 0 to 2, e is 0 to 3, f is 2 to 5, n is 2 to 4, and where $R^{3'}$ is independently hydrogen or $C_{1-6}$ alkyl and $R^{3''}$ is $-OR'$ or $-N(R^{3'})_2$); (vi) $R^{3a}$ is H and $R^{3b}$ is H, $CH_3$, $CH_2CH_3$, $CH(CH_3)_2$, $CH_2CH(CH_3)_2$, $CH(CH_3)CH_2CH_3$, $CH_2Ph$, $CH_2$-indol-3-yl, $-CH_2CH_2SCH_3$, $CH_2CO_2H$, $CH_2C(O)NH_2$, $CH_2CH_2COOH$, $CH_2CH_2C(O)NH_2$, $CH_2CH_2CH_2CH_2NH_2$, $-CH_2CH_2CH_2NHC(NH)NH_2$, $CH_2$-imidazol-4-yl, $CH_2OH$, $CH(OH)CH_3$, $CH_2((4'-OH)-Ph)$, $CH_2SH$, or lower cycloalkyl; or (vii) $R^{3a}$ is $CH_3$, $-CH_2CH_3$, $CH(CH_3)_2$, $CH_2CH(CH_3)_2$, $CH(CH_3)CH_2CH_3$, $CH_2Ph$, $CH_2$-indol-3-yl, $-CH_2CH_2SCH_3$, $CH_2CO_2H$, $CH_2C(O)NH_2$, $CH_2CH_2COOH$, $CH_2CH_2C(O)NH_2$, $CH_2CH_2CH_2CH_2NH_2$, $-CH_2CH_2CH_2NHC(NH)NH_2$, $CH_2$-imidazol-4-yl, $CH_2OH$, $CH(OH)CH_3$, $CH_2((4'-OH)-Ph)$, $CH_2SH$, or lower cycloalkyl and $R^{3b}$ is H, where $R^{3'}$ is independently hydrogen or alkyl, which includes, but is not limited to, $C_{1-20}$ alkyl, $C_{1-10}$ alkyl, or $C_{1-6}$ alkyl, $R^{3''}$ is $-OR'$ or $-N(R^{3'})_2$);

(d) $R^4$ is hydrogen, $C_{1-10}$ alkyl, $C_{1-10}$ alkyl optionally substituted with a lower alkyl, alkoxy or halogen, $C_{1-10}$ haloalkyl, $C_{3-10}$ cycloalkyl, cycloalkyl alkyl, cycloheteroalkyl, aminoacyl, di(lower alkyl)amino-lower alkyl, aryl, such as phenyl, heteroaryl, such as, pyridinyl, substituted aryl, or substituted heteroaryl;

(e) $R^5$ is H, a lower alkyl, CN, vinyl, O-(lower alkyl), hydroxyl lower alkyl, i.e., $-(CH_2)_pOH$, where p is 1-6, including hydroxyl methyl ($CH_2OH$), $CH_2F$, $N_3$, $CH_2CN$, $CH_2NH_2$, $CH_2NHCH_3$, $CH_2N(CH_3)_2$, alkyne (optionally substituted), or halogen, including F, Cl, Br, or I;

(f) $R^6$ is H, $CH_3$, $CH_2F$, $CHF_2$, $CF_3$, $CH_2CH_3$, F, CN, vinyl, ethynyl;

(g) X is H, OH, OMe, CN, F, Cl, Br, I, $NH_2$, or $N_3$;

(h) Y is OH;

(i) $R^8$ and $R^9$ are independently H, F, Br, I, OH, OR', $NH_2$, NHR', $NR'_2$, nitrogen heterocycle, $CO_2R'$, $CONH_2$, CONHR', $CONR'_2$, $CH=CHCO_2H$, or $CH=CHCO_2R'$;

(j) Z is N or $CR^{10}$; and (k) $R^{10}$ is an H, halogen (including F, Cl, Br, I), OR', $NH_2$, NHR', $NR'_2$, $NO_2$, lower alkyl of $C_1$-$C_6$, $-C\equiv CH$, $CO_2R'$, $CONH_2$, CONHR', $CONR'_2$, $CH=CHCO_2H$, or $CH=CHCO_2R'$;

wherein R' is a lower alkyl, a lower cycloalkyl, a lower alkaryl, or a C(O)(lower alkyl);

A first aspect of the first embodiment is directed to compound I wherein (a) $R^1$ is hydrogen, methyl, ethyl, n-propyl, i-propyl, phenyl, p-tolyl, p-bromo-phenyl, p-chloro-phenyl, p-fluorophenyl;

(b) $R^2$ is hydrogen or $CH_3$;

(c) $R^{3a}$ is H and $R^{3b}$ is H, $CH_3$, $CH(CH_3)_2$, $CH_2CH(CH_3)_2$, $CH(CH_3)CH_2CH_3$, $CH_2Ph$, $CH_2$-indol-3-yl, $-CH_2CH_2SCH_3$, $CH_2CO_2H$, $CH_2C(O)NH_2$, $CH_2CH_2COOH$, $CH_2CH_2C(O)NH_2$, $CH_2CH_2CH_2CH_2NH_2$, $-CH_2CH_2CH_2NHC(NH)NH_2$, $CH_2$-imidazol-4-yl, $CH_2OH$, $CH(OH)CH_3$, $CH_2((4'-OH)-Ph)$, $CH_2SH$, or lower cycloalkyl;

(d) $R^4$ is hydrogen, $CH_3$, Et, $^iPr$, $^nPr$, $^nBu$, 2-butyl, $^tBu$, benzyl, cyclopropyl, cyclobutyl, cyclopentyl, cyclohexyl, N-methyl-aziridin-2-yl, N-methyl-azetidin-3-yl, N-methyl-pyrrolidin-3-yl, N-methyl-pyrrolidin-4-yl, N-methyl-piperidin-4-yl, lower haloalkyl, or di(lower alkyl)amino-lower alkyl;

(e) $R^5$ is H, CN, $CH_3$, $OCH_3$, $CH_2OH$, $CH_2F$, $N_3$, halogen, including F, Cl, Br, or I;

(f) $R^6$ is H, $CH_3$, $CH_2F$, $CHF_2$, $CF_3$, $CH_2CH_3$, F, CN, vinyl, or ethynyl;

(g) X is H, OH, $OCH_3$, CN, F, Cl, Br, I, $NH_2$, or $N_3$;

(h) Y is OH;

(i) $R^8$ and $R^9$ are independently H, F, Br, I, OH, OR', $NH_2$, NHR', $NR'_2$, nitrogen heterocycle, $CO_2R'$, $CONH_2$, CONHR', $CONR'_2$, $CH=CHCO_2H$, or $CH=CHCO_2R'$;

(j) Z is N or $CR^{10}$; and (k) $R^{10}$ is an H, halogen (including F, Cl, Br, I), OR', $NH_2$, NHR', $NR'_2$, $NO_2$, lower alkyl of $C_1$-$C_6$, —C≡CH, $CO_2R'$, $CONH_2$, CONHR', $CONR'_2$, CH=$CHCO_2H$, or CH=$CHCO_2R'$;

wherein R' is a lower alkyl, a lower cycloalkyl, a lower alkyaryl, or a C(O)(lower alkyl).

A second aspect of the first embodiment is directed to compound I
wherein (a) $R^1$ is hydrogen, methyl, ethyl, n-propyl, i-propyl, phenyl, p-tolyl, p-bromo-phenyl, p-chloro-phenyl, or p-fluorophenyl;

(b) $R^2$ is hydrogen or $CH_3$;

(c) $R^{3a}$ is H and $R^{3b}$ is H, $CH_3$, $CH(CH_3)_2$, $CH_2CH(CH_3)_2$, $CH(CH_3)CH_2CH_3$, $CH_2Ph$, or lower cycloalkyl;

(d) $R^4$ is hydrogen, $CH_3$, Et, $^iPr$, $^nPr$, $^nBu$, 2-butyl, $^tBu$, benzyl, cyclopropyl, cyclobutyl, cyclopentyl, cyclohexyl, N-methyl-aziridin-2-yl, N-methyl-azetidin-3-yl, N-methyl-pyrrolidin-3-yl, N-methyl-pyrrolidin-4-yl, N-methyl-piperidin-4-yl, lower haloalkyl, or di(lower alkyl)amino-lower alkyl;

(e) $R^5$ is H, CN, $CH_2F$, $N_3$, F, Cl, Br, or I;

(f) $R^6$ is H, $CH_3$, $CH_2F$, $CHF_2$, $CF_3$, F, vinyl, or ethynyl;

(g) X is H, OH, $OCH_3$, CN, F, Cl, Br, I, $NH_2$ or $N_3$;

(h) Y is OH;

(i) $R^8$ and $R^9$ are independently H, F, Br, I, OH, OR', $NH_2$, NHR', $NR'_2$, nitrogen heterocycle, $CO_2R'$, $CONH_2$, CONHR', $CONR'_2$, CH=$CHCO_2H$, or CH=$CHCO_2R'$;

(j) Z is N or $CR^{10}$; and (k) $R^{10}$ is a H, halogen (including F, Cl, Br, I), OR', $NH_2$, NHR', $NR'_2$, $NO_2$, lower alkyl of $C_1$-$C_6$, —C≡CH, $CO_2R'$, $CONH_2$, CONHR', $CONR'_2$, CH=$CHCO_2H$, or CH=$CHCO_2R'$;

wherein R' is a lower alkyl, a lower cycloalkyl, a lower alkaryl, or a C(O)(lower alkyl).

A third aspect of the first embodiment is directed to compound I,
wherein (a) $R^1$ is hydrogen, methyl, ethyl, n-propyl, i-propyl, phenyl, p-tolyl, p-bromo-phenyl, p-chloro-phenyl, or p-fluorophenyl;

(b) $R^2$ is hydrogen;

(c) $R^{3a}$ is H and $R^{3b}$ is H, $CH_3$, $CH(CH_3)_2$, $CH_2CH(CH_3)_2$, $CH(CH_3)CH_2CH_3$, $CH_2Ph$, or lower cycloalkyl;

(d) $R^4$ is hydrogen, $CH_3$, Et, $^iPr$, $^nPr$, $^nBu$, 2-butyl, $^tBu$, benzyl, cyclopropyl, cyclobutyl, cyclopentyl, cyclohexyl, N-methyl-aziridin-2-yl, N-methyl-azetidin-3-yl, N-methyl-pyrrolidin-3-yl, N-methyl-pyrrolidin-4-yl, N-methyl-piperidin-4-yl, lower haloalkyl, or di(lower alkyl)amino-lower alkyl;

(e) $R^5$ is H or $N_3$;

(f) $R^6$ is H, $CH_3$, $CH_2F$, $CHF_2$, $CF_3$, $CH_2CH_3$, F, vinyl or ethynyl;

(g) X is H, OH, $OCH_3$, CN, F, $NH_2$ or $N_3$;

(h) Y is OH;

(i) $R^8$ and $R^9$ are independently H, F, Br, I, OH, OR', $NH_2$, NHR', $NR'_2$, nitrogen heterocycle, $CO_2R'$, $CONH_2$, CONHR', $CONR'_2$, CH=$CHCO_2H$, or CH=$CHCO_2R'$;

(j) Z is N or $CR^{10}$; and (k) $R^{10}$ is an H, halogen (including F, Cl, Br, I), OR', $NH_2$, NHR', $NR'_2$, $NO_2$, lower alkyl of $C_1$-$C_6$, —C≡CH, $CO_2R'$, $CONH_2$, CONHR', $CONR'_2$, CH=$CHCO_2H$, or CH=$CHCO_2R'$;

wherein R' is a lower alkyl, a lower cycloalkyl, a lower alkyaryl, or a C(O)(lower alkyl).

A fourth aspect of the first embodiment is directed to compound I,
wherein (a) $R^1$ is hydrogen, methyl, phenyl, p-bromo-phenyl, p-chloro-phenyl, or p-fluorophenyl;

(b) $R^2$ is hydrogen;

(c) $R^{3a}$ is H and $R^{3b}$ is H, $CH_3$, $CH(CH_3)_2$, $CH_2CH(CH_3)_2$, $CH(CH_3)CH_2CH_3$, $CH_2Ph$, or lower cycloalkyl;

(d) $R^4$ is hydrogen, $CH_3$, Et, $^iPr$, $^nPr$, $^nBu$, 2-butyl, $^tBu$, benzyl, cyclopropyl, cyclobutyl, cyclopentyl, cyclohexyl, N-methyl-aziridin-2-yl, N-methyl-azetidin-3-yl, N-methyl-pyrrolidin-3-yl, N-methyl-pyrrolidin-4-yl, N-methyl-piperidin-4-yl, lower haloalkyl, or di(lower alkyl)amino-lower alkyl;

(e) $R^5$ is H or $N_3$;

(f) $R^6$ is H, $CH_3$, $CH_2F$, $CHF_2$, $CF_3$, $CH_2CH_3$, F, vinyl, or ethynyl;

(g) X is H, OH, $OCH_3$, CN, F, $NH_2$ or $N_3$;

(h) Y is OH;

(i) $R^8$ and $R^9$ are independently H, F, Br, I, OH, OR', $NH_2$, NHR', $NR'_2$, nitrogen heterocycle, $CO_2R'$, $CONH_2$, CONHR', $CONR'_2$, CH=$CHCO_2H$, or CH=$CHCO_2R'$;

(j) Z is N or $CR^{10}$; and (k) $R^{10}$ is an H, halogen (including F, Cl, Br, I), OR', $NH_2$, NHR', $NR'_2$, $NO_2$, lower alkyl of $C_1$-$C_6$, —C≡CH, $CO_2R'$, $CONH_2$, CONHR', $CONR'_2$, CH=$CHCO_2H$, or CH=$CHCO_2R'$;

wherein R' is a lower alkyl, a lower cycloalkyl, a lower alkyaryl, or a C(O)(lower alkyl).

A fifth aspect of the first embodiment is directed to compound I,
wherein (a) $R^1$ is hydrogen, methyl, phenyl, p-bromo-phenyl, p-chloro-phenyl, or p-fluorophenyl;

(b) $R^2$ is hydrogen;

(c) $R^{3a}$ is H and $R^{3b}$ is H, $CH_3$, $CH(CH_3)_2$, $CH_2CH(CH_3)_2$, $CH(CH_3)CH_2CH_3$, $CH_2Ph$, or lower cycloalkyl;

(d) $R^4$ is hydrogen, $CH_3$, Et, $^iPr$, $^nPr$, $^nBu$, 2-butyl, $^tBu$, benzyl, cyclopropyl, cyclobutyl, cyclopentyl, cyclohexyl, N-methyl-aziridin-2-yl, N-methyl-azetidin-3-yl, N-methyl-pyrrolidin-3-yl, N-methyl-pyrrolidin-4-yl, N-methyl-piperidin-4-yl, lower haloalkyl, or di(lower alkyl)amino-lower alkyl;

(e) $R^5$ is H or $N_3$;

(f) $R^6$ is H, $CH_3$, $CH_2F$, $CHF_2$, $CF_3$, $CH_2CH_3$, F, vinyl, or ethynyl;

(g) X is H, OH, $OCH_3$, CN, F, $NH_2$ or $N_3$;

(h) Y is OH;

(i) $R^8$ and $R^9$ are independently H, F, Br, I, OH, OR', $NH_2$, NHR', $NR'_2$, nitrogen heterocycle, $CO_2R'$, $CONH_2$, CONHR', $CONR'_2$, CH=$CHCO_2H$, or CH=$CHCO_2R'$;

(j) Z is N or $CR^{10}$; and (k) $R^{10}$ is an H, halogen (including F, Cl, Br, I), OR', $NH_2$, NHR', $NR'_2$, $NO_2$, lower alkyl of $C_1$-$C_6$, —C≡CH, $CO_2R'$, $CONH_2$, CONHR', $CONR'_2$, CH=$CHCO_2H$, or CH=$CHCO_2R'$;

wherein R' is a lower alkyl, a lower cycloalkyl, a lower alkyl, or a C(O)(lower alkyl).

A sixth aspect of the first embodiment is directed to compound I,
wherein (a) $R^1$ is hydrogen, phenyl, p-tolyl, p-bromo-phenyl, p-chloro-phenyl, or p-fluorophenyl;

(b) $R^2$ is hydrogen or $CH_3$;

(c) $R^{3a}$ is H and $R^{3b}$ is H, $CH_3$, $CH(CH_3)_2$, $CH_2CH(CH_3)_2$, $CH(CH_3)CH_2CH_3$, $CH_2Ph$, $CH_2OH$, $CH_2((4'-OH)-Ph)$, or lower cycloalkyl;

(d) $R^4$ is hydrogen, $CH_3$, Et, $^iPr$, $^nPr$, $^nBu$, 2-butyl, $^tBu$, benzyl, cyclopropyl, cyclobutyl, cyclopentyl, or cyclohexyl;
(e) $R^5$ is H or $N_3$;
(f) $R^6$ is H, $CH_3$, $CH_2F$, $CHF_2$, $CF_3$, $CH_2CH_3$, F, CN, vinyl or ethynyl;
(g) X is H, OH, $OCH_3$, CN, F, Cl, Br, I, $NH_2$, or $N_3$;
(h) Y is OH;
(i) $R^9$ is $NH_2$ and $R^8$ is H, F, Br, I, OH, OR', $NH_2$, NHR', $NR'_2$, nitrogen heterocycle, $CO_2R'$, $CONH_2$, CONHR', $CONR'_2$, $CH=CHCO_2H$, or $CH=CHCO_2R'$;
(j) Z is N or $CR^{10}$; and
(k) $R^{10}$ is an H, F, Cl, Br, I, OR', $NH_2$, NHR', $NR'_2$, or lower alkyl of $C_1$-$C_6$, or —C≡CH;
wherein R' is a lower alkyl, a lower cycloalkyl, a lower alkaryl, or a C(O)(lower alkyl).

A seventh aspect of the first embodiment is directed to compound I,
wherein
(a) $R^1$ is hydrogen, phenyl, p-tolyl, p-bromo-phenyl, or p-chloro-phenyl;
(b) $R^2$ is hydrogen or $CH_3$;
(c) $R^{3a}$ is H and $R^{3b}$ is H, $CH_3$, $CH(CH_3)_2$, $CH_2CH(CH_3)_2$, $CH(CH_3)CH_2CH_3$, $CH_2OH$, or lower cycloalkyl;
(d) $R^4$ is hydrogen, $CH_3$, Et, $^iPr$, $^nPr$, $^nBu$, 2-butyl, $^tBu$, benzyl, cyclopropyl, cyclobutyl, cyclopentyl, or cyclohexyl;
(e) $R^5$ is H of $N_3$;
(f) $R^6$ is H, $CH_3$, $CH_2F$, $CHF_2$, $CF_3$, $CH_2CH_3$, F, CN, vinyl or ethynyl;
(g) X is H, OH, $OCH_3$, CN, F, Cl, Br, or $N_3$;
(h) Y is OH;
(i) $R^9$ is $NH_2$ and $R^8$ is H, F, OH, O(lower alkyl), O(lower alkyaryl), $NH_2$, NHR', $NR'_2$, or nitrogen heterocycle; and
(j) Z is N;
wherein R' is a lower alkyl, a lower cycloalkyl, a lower alkaryl, or a C(O)(lower alkyl).

An eighth aspect of the first embodiment is directed to compound I,
wherein
(a) $R^1$ is hydrogen, phenyl, p-bromo-phenyl, p-chloro-phenyl, or p-fluorophenyl;
(b) $R^2$ is hydrogen;
(c) $R^{3a}$ is H and $R^{3b}$ is H, $CH_3$, $CH(CH_3)_2$, $CH_2CH(CH_3)_2$, or $CH(CH_3)CH_2CH_3$;
(d) $R^4$ is hydrogen, $CH_3$, Et, $^iPr$, $^nPr$, $^nBu$, 2-butyl, or cyclopentyl;
e) $R^5$ is H or $N_3$;
(f) $R^6$ is H, $CH_3$, $CH_2F$, $CHF_2$, $CF_3$, $CH_2CH_3$, F, CN, vinyl or ethynyl;
(g) X is H, OH, CN, F, or $N_3$;
(h) Y is OH;
(i) $R^9$ is $NH_2$ and $R^8$ is H, F, OH, O(lower alkyl), O(lower alkaryl), $NH_2$, NHR', $NR'_2$, or nitrogen heterocycle; and
(j) Z is N;
wherein R' is a lower alkyl, a lower cycloalkyl, a lower alkaryl, or a C(O)(lower alkyl).

A ninth aspect of the first embodiment is directed to compound I
wherein
(a) $R^1$ is hydrogen, phenyl, p-bromo-phenyl, p-chloro-phenyl, or p-fluorophenyl;
(b) $R^2$ is hydrogen;
(c) $R^{3a}$ is H and $R^{3b}$ is H, $CH_3$, $CH(CH_3)_2$, or $CH_2CH(CH_3)_2$;
(d) $R^4$ is hydrogen, $CH_3$, Et, $^iPr$, $^nPr$, $^nBu$, 2-butyl, or cyclopentyl;
(e) $R^5$ is H;
(f) $R^6$ is H, $CH_3$, $CH_2F$, $CHF_2$, $CF_3$, $CH_2CH_3$, F, CN, vinyl, or ethynyl;
(g) X is H, OH, CN, F, or $N_3$;
(h) Y is OH;
(i) $R^9$ is $NH_2$ and $R^8$ is H, F, OH, O(lower alkyl), O(lower alkaryl), $NH_2$, NHR', $NR'_2$, or nitrogen heterocycle; and
(j) Z is N;
wherein R' is a lower alkyl, a lower cycloalkyl, a lower alkaryl, or a C(O)(lower alkyl).

A tenth aspect of the first embodiment is directed to compound I wherein (a) $R^1$ is hydrogen, phenyl, p-bromo-phenyl, p-chloro-phenyl, or p-fluorophenyl; (b) $R^2$ is hydrogen; (c) $R^{3a}$ is H and $R^{3b}$ is $CH_3$; (d) $R^4$ is hydrogen, $CH_3$, $^iPr$, or cyclopentyl; (e) $R^5$ is H; (f) $R^6$ is $CH_3$; (g) X is F; (h) Y is OH; (i) $R^8$ is independently OH, OMe, OEt, $O^iPr$, OBn, or —N(—$CH_2CH_2CH_2$—) (azetidin-1-yl), and $R^9$ is $NH_2$; (j) Z is N.

An eleventh aspect of the first embodiment is directed to compound I wherein (a) $R^1$ is phenyl; (b) $R^2$ is hydrogen; (c) $R^{3a}$ is H and $R^{3b}$ is $CH_3$; (d) $R^4$ is $^iPr$; (e) $R^5$ is H; (f) $R^6$ is $CH_3$; (g) X is F; (h) Y is OH; $R^8$ is OMe; and (j) Z is N.

A twelfth aspect of the first embodiment is directed to compound I wherein (a) $R^1$ is phenyl; (b) $R^2$ is hydrogen; (c) $R^{3a}$ is H and $R^{3b}$ is $CH_3$; (d) $R^4$ is $^iPr$; (e) $R^5$ is H; (f) $R^6$ is $CH_3$; (g) X is F; (h) Y is OH; $R^8$ is OEt; and (j) Z is N.

A thirteenth aspect of the first embodiment is directed to compound I wherein (a) $R^1$ is phenyl; (b) $R^2$ is hydrogen; (c) $R^{3a}$ is H and $R^{3b}$ is $CH_3$; (d) $R^4$ is $^iPr$; (e) $R^5$ is H; (f) $R^6$ is $CH_3$; (g) X is F; (h) Y is OH; $R^8$ is $O^iPr$; and (j) Z is N.

A fourteenth aspect of the first embodiment is directed to compound I wherein (a) $R^1$ is phenyl; (b) $R^2$ is hydrogen; (c) $R^{3a}$ is H and $R^{3b}$ is $CH_3$; (d) $R^4$ is $CH_3$; (e) $R^5$ is H; (f) $R^6$ is $CH_3$; (g) X is F; (h) Y is OH; $R^8$ is —N(—$CH_2CH_2CH_2$—) (azetidin-1-yl), and $R^9$ is $NH_2$; and (j) Z is N.

A fifteenth aspect of the first embodiment is directed to compound I wherein (a) $R^1$ is phenyl; (b) $R^2$ is hydrogen; (c) $R^{3a}$ is H and $R^{3b}$ is $CH_3$; (d) $R^4$ is cyclopentyl; (e) $R^5$ is H; (f) $R^6$ is $CH_3$; (g) X is F; (h) Y is OH; $R^8$ is independently OBn; and $R^9$ is $NH_2$; and (j) Z is N.

A sixteenth aspect of the first embodiment is directed to compound I wherein (a) $R^1$ is phenyl; (b) $R^2$ is hydrogen; (c) $R^{3a}$ is H and $R^{3b}$ is $CH_3$; (d) $R^4$ is cyclopentyl; (e) $R^5$ is H; (f) $R^6$ is $CH_3$; (g) X is F; (h) Y is OH; $R^8$ is OH and $R^9$ is $NH_2$; and (j) Z is N.

Preferred compounds of the first embodiment include compounds represented by the following structure:

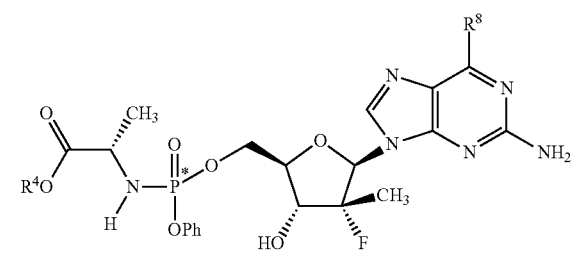

where $R^4$ is a lower alkyl and $R^8$ is a O(lower alkyl). Additionally preferred compounds include:

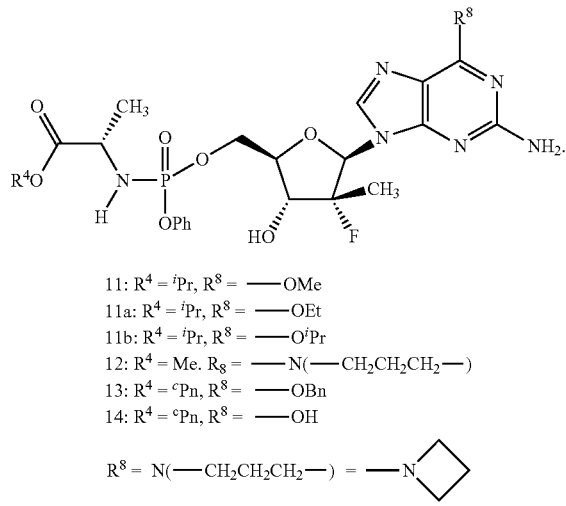

11: $R^4 = {}^iPr$, $R^8 =$ —OMe
11a: $R^4 = {}^iPr$, $R^8 =$ —OEt
11b: $R^4 = {}^iPr$, $R^8 =$ —O$^i$Pr
12: $R^4 = $ Me, $R^8 =$ —N(—CH$_2$CH$_2$CH$_2$—)
13: $R^4 = {}^cPn$, $R^8 =$ —OBn
14: $R^4 = {}^cPn$, $R^8 =$ —OH $R^8 = $ N(—CH$_2$CH$_2$CH$_2$—) = —N☐

Of the preferred compounds, compound 11 is particularly preferred. One of ordinary skill will recognize that 11 comprises a mixture of diastereomers designated $S_P$-11 and $R_P$-11. Contemplated herein is a composition that comprises $S_P$-11, $R_P$-11, or mixtures thereof.

The composition that comprises $S_P$-11, $R_P$-11, or mixtures thereof can also be part of a solvate, a hydrate, or a mixed solvate/hydrate. The solvate is designated as $S_P$-11.nS, $R_P$-11.nS, or 11.nS; while the hydrate is designated as $S_P$-11.mH$_2$O, $R_P$-11.mH$_2$O, or 11.mH$_2$O, where S is a lattice solvent, n varies by an integer or non-integer amount from about 0 to about 3 and m varies by an integer or non-integer amount from about 0 to about 5. The composition that comprises $S_P$-11, $R_P$-11, or mixtures thereof and its salts, solvates, and hydrates thereof is crystalline, crystal-like, or amorphous.

A second embodiment is directed to compound II,
wherein
(a) $R^5$ is H, a lower alkyl, cyano (CN), vinyl, O-(lower alkyl), including OCH$_3$, OCH$_2$CH$_3$, hydroxyl lower alkyl, i.e., —(CH$_2$)$_p$OH, where p is 1-6, including hydroxyl methyl (CH$_2$OH), fluoromethyl (CH$_2$F), azido (N$_3$), CH$_2$CN, CH$_2$N$_3$, CH$_2$NH$_2$, CH$_2$NHCH$_3$, CH$_2$N(CH$_3$)$_2$, F, Cl, Br, or I
(b) $R^6$ is H, CH$_3$, CH$_2$F, CHF$_2$, CF$_3$, CH$_2$CH$_3$, F, vinyl, or ethynyl;
(c) $R^7$ is H, n-alkyl, branched alkyl, cycloalkyl, alkaryl, alkenyl, or aryl, which includes, but is not limited to, phenyl or naphthyl, where phenyl or naphthyl are optionally substituted with at least one of H, F, Cl, Br, I, OH, OR$^{7'}$, SH, SR$^{7'}$, NH$_2$, NHR$^{7'}$, NR$^{7'}_2$, lower alkyl of C$_1$-C$_6$, halogenated (F, Cl, Br, I), halogenated (F, Cl, Br, I) lower alkenyl of C$_2$-C$_6$, lower alkynyl of C$_2$-C$_6$ such as C≡CH, halogenated (F, Cl, Br, I) lower alkynyl of C$_2$-C$_6$, lower alkoxy of C$_1$-C$_6$, halogenated (F, Cl, Br, I) lower alkoxy of C$_1$-C$_6$, CO$_2$H, CO$_2$R$^{7'}$, CONH$_2$, CONHR$^{7'}$, CONR$^{7'}_2$, CH=CHCO$_2$H, or CH=CHCO$_2$R$^{7'}$ wherein R$^{7'}$ is an optionally substituted alkyl, cycloalkyl, alkenyl, alkynyl, or alkoxyalkyl, which includes, but is not limited to, C$_{1-10}$ alkyl, C$_{3-7}$ cycloalkyl, C$_{2-10}$ alkenyl, C$_{2-10}$ alkynyl, or C$_{1-10}$ alkoxyalkyl;
(d) X is H, OH, F, OMe, NH$_2$, or N$_3$;
(e) $R^8$ and $R^9$ are independently H, F, Cl, Br, I, OH, OR', SH, SR', NH$_2$, NHR', NR'$_2$, nitrogen heterocycle, CH$_3$, CH$_{3-q}$X$_q$, where X is F, Cl, Br, or I and q is 1 to 3, vinyl, CO$_2$H, CO$_2$CH$_3$, CONH$_2$, CONHCH$_3$, or CON(CH$_3$)$_2$,
(f) Z is N or CR$^{10}$; and
(g) R$^{10}$ is an H, halogen (including F, Cl, Br, I), OH, OR', SH, SR', NH$_2$, NHR', NR'$_2$, NO$_2$ lower alkyl of C$_1$-C$_6$, halogenated (F, Cl, Br, I) lower alkyl of C$_1$-C$_6$, lower alkenyl of C$_2$-C$_6$, halogenated (F, Cl, Br, I) lower alkenyl of C$_2$-C$_6$, lower alkynyl of C$_2$-C$_6$, halogenated (F, Cl, Br, I) lower alkynyl of C$_2$-C$_6$, lower alkoxy of C$_1$-C$_6$, halogenated (F, Cl, Br, I) lower alkoxy of C$_1$-C$_6$, CO$_2$H, CO$_2$R', CONH$_2$, CONHR', CONR'$_2$, CH=CHCO$_2$H, or CH=CHCO$_2$R'
wherein R' is a C$_{1-20}$ alkyl; a C$_{1-20}$ cycloalkyl; an alkaryl, a C$_2$-C$_6$ alkenyl, a C$_2$-C$_6$ alkynyl.

A first aspect of the second embodiment is directed to compound II,
wherein
(a) $R^5$ is H, a lower alkyl, cyano (CN), vinyl, O-(lower alkyl), including OCH$_3$, OCH$_2$CH$_3$, hydroxyl lower alkyl, i.e., —(CH$_2$)$_p$OH, where p is 1-6, including hydroxyl methyl (CH$_2$OH), fluoromethyl (CH$_2$F), azido (N$_3$), CH$_2$CN, CH$_2$N$_3$, CH$_2$NH$_2$, CH$_2$NHCH$_3$, CH$_2$N(CH$_3$)$_2$, F, Cl, Br, or I
(b) $R^6$ is H, CH$_3$, CH$_2$F, CHF$_2$, CF$_3$, CH$_2$CH$_3$, or F;
(c) $R^7$ is H, n-alkyl, branched alkyl, cycloalkyl, alkaryl, alkenyl, or aryl, which includes, but is not limited to, phenyl or naphthyl, where phenyl or naphthyl are optionally substituted with at least one of H, F, Cl, Br, I, OH, OR$^{7'}$, SH, SR$^{7'}$, NH$_2$, NHR$^{7'}$, NR$^{7'}_2$, lower alkyl of C$_1$-C$_6$, halogenated (F, Cl, Br, I), halogenated (F, Cl, Br, I) lower alkenyl of C$_2$-C$_6$, lower alkynyl of C$_2$-C$_6$ such as C≡CH, halogenated (F, Cl, Br, I) lower alkynyl of C$_2$-C$_6$, lower alkoxy of C$_1$-C$_6$, halogenated (F, Cl, Br, I) lower alkoxy of C$_1$-C$_6$, CO$_2$H, CO$_2$R$^{7'}$, CONH$_2$, CONHR$^{7'}$, CONR$^{7'}_2$, CH=CHCO$_2$H, or CH=CHCO$_2$R$^{7'}$
wherein R$^{7'}$ is an optionally substituted alkyl, cycloalkyl, alkenyl, alkynyl, or alkoxyalkyl, which includes, but is not limited to, C$_{1-10}$ alkyl, C$_{3-7}$ cycloalkyl, C$_{2-10}$ alkenyl, C$_{2-10}$ alkynyl, or C$_{1-10}$ alkoxyalkyl;
(d) X is H, OH, F, OMe, NH$_2$, or N$_3$;
(e) $R^8$ and $R^9$ are independently H, F, Cl, Br, I, OH, OR', SH, SR', NH$_2$, NHR', NR'$_2$, nitrogen heterocycle, CH$_3$, CH$_{3-q}$X$_q$, where X is F, Cl, Br, or I and q is 1 to 3, vinyl, CO$_2$H, CO$_2$CH$_3$, CONH$_2$, CONHCH$_3$, or CON(CH$_3$)$_2$,
(f) Z is N or CR$^{10}$; and
(g) R$^{10}$ is an H, F, OH, OR', NH$_2$, NHR', NR'$_2$, NR''$_2$, lower alkyl of C$_1$-C$_6$, halogenated (F, Cl, Br, I) lower alkyl of C$_1$-C$_6$, or —C≡CH;
wherein R' is a C$_{1-20}$ alkyl; a C$_{1-20}$ cycloalkyl; an alkaryl, a C$_2$-C$_6$ alkenyl, a C$_2$-C$_6$ alkynyl.

A second aspect of the second embodiment is directed to compound II,
wherein
(a) $R^5$ is H, a lower alkyl, cyano (CN), vinyl, O-(lower alkyl), including OCH$_3$, OCH$_2$CH$_3$, hydroxyl lower alkyl, i.e., —(CH$_2$)$_p$OH, where p is 1-6, including hydroxyl methyl (CH$_2$OH), fluoromethyl (CH$_2$F), azido (N$_3$), CH$_2$CN, CH$_2$N$_3$, CH$_2$NH$_2$, CH$_2$NHCH$_3$, CH$_2$N(CH$_3$)$_2$, F, Cl, Br, or I
(b) $R^6$ is H, CH$_3$, CH$_2$F, CHF$_2$, CF$_3$, or CH$_2$CH$_3$;
(c) $R^7$ is H, n-alkyl, branched alkyl, cycloalkyl, alkaryl, alkenyl, or aryl, which includes, but is not limited to, phenyl or naphthyl, where phenyl or naphthyl are optionally substituted with at least one of H, F, Cl, Br, I, OH, OR$^{7'}$, SH, SR$^{7'}$, NH$_2$, NHR$^{7'}$, NR$^{7'}_2$, lower alkyl of C$_1$-C$_6$, halogenated (F, Cl, Br, I), halogenated (F, Cl, Br, I) lower alkenyl of C$_2$-C$_6$, lower alkynyl of C$_2$-C$_6$ such as C≡CH, halogenated (F, Cl, Br, I) lower alkynyl of C$_2$-C$_6$, lower alkoxy of C$_1$-C$_6$, halogenated (F, Cl, Br, I) lower alkoxy of C$_1$-C$_6$, CO$_2$H, CO$_2$R$^{7'}$, CONH$_2$, CONHR$^{7'}$, CONR$^{7'}_2$, CH=CHCO$_2$H, or CH=CHCO$_2$R$^{7'}$
wherein R$^{7'}$ is an optionally substituted alkyl, cycloalkyl, alkenyl, alkynyl, or alkoxyalkyl, which includes, but is not limited to, $C_{1-10}$ alkyl, $C_{3-7}$ cycloalkyl, $C_{2-10}$ alkenyl, $C_{2-10}$ alkynyl, or $C_{1-10}$ alkoxyalkyl;

(d) X is H, OH, F, OMe, $NH_2$, or $N_3$;

(e) $R^8$ and $R^9$ are independently H, F, Br, OH, OR', $NH_2$, NHR', $NR'_2$, nitrogen heterocycle, $CH_3$, $CH_{3-q}X_q$, where X is F, Cl, Br, or I and q is 1 to 3, vinyl, $CO_2CH_3$, $CONH_2$, $CONHCH_3$, $CON(CH_3)_2$;

(f) Z is N or $CR^{10}$; and (g) $R^{10}$ is an H, F, OH, OR', $NH_2$, NHR', $NR'_2$, lower alkyl of $C_1$-$C_6$, halogenated (F, Cl, Br, I) lower alkyl of $C_1$-$C_6$, or —C≡CH;

wherein R' is a $C_{1-20}$ alkyl; a $C_{1-20}$ cycloalkyl; an alkaryl, a $C_2$-$C_6$ alkenyl, a $C_2$-$C_6$ alkynyl.

A third aspect of the second embodiment is directed to compound II,
wherein (a) $R^5$ is H, a lower alkyl, cyano (CN), vinyl, O-(lower alkyl), including $OCH_3$, $OCH_2CH_3$, hydroxyl lower alkyl, i.e., —$(CH_2)_pOH$, where p is 1-6, including hydroxyl methyl ($CH_2OH$), fluoromethyl ($CH_2F$), azido ($N_3$), $CH_2CN$, $CH_2N_3$, $CH_2NH_2$, $CH_2NHCH_3$, $CH_2N(CH_3)_2$, F, Cl, Br, or I (b) $R^6$ is H, $CH_3$, $CH_2F$, $CHF_2$, $CF_3$, or $CH_2CH_3$;

(c) $R^7$ is H, n-alkyl, branched alkyl, cycloalkyl, alkaryl, alkenyl, or aryl, which includes, but is not limited to, phenyl or naphthyl, where phenyl or naphthyl are optionally substituted with at least one of H, F, Cl, Br, I, OH, $OR^{7'}$, SH, $SR^{7'}$, $NH_2$, $NHR^{7'}$, $NR^{7'}_2$, lower alkyl of $C_1$-$C_6$, halogenated (F, Cl, Br, I), halogenated (F, Cl, Br, I) lower alkenyl of $C_2$-$C_6$, lower alkynyl of $C_2$-$C_6$ such as C≡CH, halogenated (F, Cl, Br, I) lower alkynyl of $C_2$-$C_6$, lower alkoxy of $C_1$-$C_6$, halogenated (F, Cl, Br, I) lower alkoxy of $C_1$-$C_6$, $CO_2H$, $CO_2R^{7'}$, $CONH_2$, $CONHR^{7'}$, $CONR^{7'}_2$, CH=$CHCO_2H$, or CH=$CHCO_2R^{7'}$ wherein $R^{7'}$ is an optionally substituted alkyl, cycloalkyl, alkenyl, alkynyl, or alkoxyalkyl, which includes, but is not limited to, $C_{1-10}$ alkyl, $C_{3-7}$ cycloalkyl, $C_{2-10}$ alkenyl, $C_{2-10}$ alkynyl, or $C_{1-10}$ alkoxyalkyl;

(d) X is F;

(e) $R^8$ and $R^9$ are independently H, F, Br, OH, OR', $NH_2$, NHR', $NR'_2$, nitrogen heterocycle, $CH_3$, $CH_{3-q}X_q$, where X is F, Cl, Br, or I and q is 1 to 3, vinyl, $CO_2CH_3$, $CONH_2$, $CONHCH_3$, or $CON(CH_3)_2$;

(f) Z is N or $CR^{10}$; and (g) $R^{10}$ is an H, F, OH, OR', $NH_2$, NHR', $NR'_2$, lower alkyl of $C_1$-$C_6$, halogenated (F, Cl, Br, I) lower alkyl of $C_1$-$C_6$, or —C≡CH;

wherein R' is a lower alkyl; a lower cycloalkyl; a lower alkaryl, a $C_2$-$C_6$ alkenyl, a $C_2$-$C_6$ alkynyl.

A fourth aspect of the second embodiment is directed to compound II,
wherein (a) $R^5$ is H, —$CH_3$, cyano (CN), vinyl, —$OCH_3$, —$CH_2OH$, —$CH_2F$, azido ($N_3$), $CH_2CN$, $CH_2N_3$, $CH_2NH_2$, $CH_2NHCH_3$, $CH_2N(CH_3)_2$, F, Cl, Br, or I (b) $R^6$ is H, $CH_3$, or $CH_2CH_3$;

(c) $R^7$ is H, n-alkyl, branched alkyl, cycloalkyl, alkaryl, alkenyl, or aryl, which includes, but is not limited to, phenyl or naphthyl, where phenyl or naphthyl are optionally substituted with at least one of H, F, Cl, Br, I, OH, $OR^{7'}$, SH, $SR^{7'}$, $NH_2$, $NHR^{7'}$, $NR^{7'}_2$, lower alkyl of $C_1$-$C_6$, halogenated (F, Cl, Br, I), halogenated (F, Cl, Br, I) lower alkenyl of $C_2$-$C_6$, lower alkynyl of $C_2$-$C_6$ such as C≡CH, halogenated (F, Cl, Br, I) lower alkynyl of $C_2$-$C_6$, lower alkoxy of $C_1$-$C_6$, halogenated (F, Cl, Br, I) lower alkoxy of $C_1$-$C_6$, $CO_2H$, $CO_2R^{7'}$, $CONH_2$, $CONHR^{7'}$, $CONR^{7'}_2$, CH=$CHCO_2H$, or CH=$CHCO_2R^{7'}$ wherein $R^{7'}$ is an optionally substituted alkyl, cycloalkyl, alkenyl, alkynyl, or alkoxyalkyl, which includes, but is not limited to, $C_{1-10}$ alkyl, $C_{3-7}$ cycloalkyl, $C_{2-10}$ alkenyl, $C_{2-10}$ alkynyl, or $C_{1-10}$ alkoxyalkyl;

(d) X is F;

(e) $R^8$ and $R^9$ are independently H, F, OH, OR', SH, $SCH_3$, $NH_2$, NHR', $NR'_2$, nitrogen heterocycle, $CH_3$, $CH_{3-q}X_q$, where X is F, Cl, Br, or I and q is 1 to 3, vinyl, $CO_2H$, $CO_2CH_3$, $CONH_2$, $CONHCH_3$, $CON(CH_3)_2$;

(f) Z is N or $CR^{10}$; and (g) $R^{10}$ is an H, F, OH, OR', $NH_2$, NHR', $NR'_2$, lower alkyl of $C_1$-$C_6$, halogenated (F, Cl, Br, I) lower alkyl of $C_1$-$C_6$, or —C≡CH;

wherein R' is a lower alkyl; a lower cycloalkyl; a lower alkaryl, a $C_2$-$C_6$ alkenyl, a $C_2$-$C_6$ alkynyl.

A fifth aspect of the second embodiment is directed to compound II,
wherein (a) $R^5$ is H, —$CH_3$, cyano (CN), vinyl, —$OCH_3$, —$CH_2OH$, —$CH_2F$, azido ($N_3$), $CH_2CN$, $CH_2N_3$, $CH_2NH_2$, $CH_2NHCH_3$, $CH_2N(CH_3)_2$, F, Cl, Br, or I (b) $R^6$ is H or $CH_3$;

(c) $R^7$ is H, lower alkyl, lower alkylaryl, lower cycloalkyl, lower alkenyl, or aryl, which includes, but is not limited to, phenyl or naphthyl, where phenyl or naphthyl are optionally substituted with at least one of H, F, Cl, Br, I, OH, $OR^{7'}$, SH, $SR^{7'}$, $NH_2$, $NHR^{7'}$, $NR^{7'}_2$, lower alkoxy of $C_1$-$C_6$, halogenated (F, Cl, Br, I) lower alkoxy of $C_1$-$C_6$, wherein $R^{7'}$ is an optionally substituted alkyl, cycloalkyl, alkenyl, alkynyl, or alkoxyalkyl, which includes, but is not limited to, $C_{1-10}$ alkyl, $C_{3-7}$ cycloalkyl, $C_{2-10}$ alkenyl, $C_{2-10}$ alkynyl, or $C_{1-10}$ alkoxyalkyl;

(d) X is F;

(e) $R^8$ and $R^9$ are independently H, F, OH, OR', $NH_2$, NHR', $NR'_2$, nitrogen heterocycle, $CH_3$, $CH_{3-q}X_q$, where X is F, Cl, Br, or I and q is 1 to 3, vinyl, $CO_2H$, $CO_2CH_3$, $CONH_2$, $CONHCH_3$, $CON(CH_3)_2$;

(f) Z is N or $CR^{10}$; and (g) $R^{10}$ is an H, F, OH, OR', $NH_2$, NHR', $NR'_2$, lower alkyl of $C_1$-$C_6$, halogenated (F, Cl, Br, I) lower alkyl of $C_1$-$C_6$, or —C≡CH;

wherein R' is a lower alkyl; a lower cycloalkyl; a lower alkaryl, a $C_2$-$C_6$ alkenyl, a $C_2$-$C_6$ alkynyl.

A sixth aspect of the second embodiment is directed to compound II,
wherein (a) $R^5$ is H or $N_3$;

(b) $R^6$ is H, $CH_3$, or $CH_2CH_3$;

(c) $R^7$ is H, lower alkyl, lower alkylaryl, lower cycloalkyl, lower alkenyl, or aryl, which includes, but is not limited to, phenyl or naphthyl, where phenyl or naphthyl are optionally substituted with at least one of H, F, Cl, Br, I, OH, $OR^{7'}$, SH, $SR^{7'}$, $NH_2$, $NHR^{7'}$, $NR^{7'}_2$, lower alkoxy of $C_1$-$C_6$, halogenated (F, Cl, Br, I) lower alkoxy of $C_1$-$C_6$, wherein $R^{7'}$ is an optionally substituted alkyl, cycloalkyl, alkenyl, alkynyl, or alkoxyalkyl, which includes, but is not limited to, $C_{1-10}$ alkyl, $C_{3-7}$ cycloalkyl, $C_{2-10}$ alkenyl, $C_{2-10}$ alkynyl, or $C_{1-10}$ alkoxyalkyl;

(d) X is F;

(e) $R^8$ and $R^9$ are independently H, F, OH, OR', $NH_2$, NHR', $NR'_2$, nitrogen heterocycle, $CH_3$, $CH_{3-q}X_q$, where X is F, Cl, Br, or I and q is 1 to 3, vinyl, $CO_2H$, $CO_2CH_3$, $CONH_2$, $CONHCH_3$, $CON(CH_3)_2$, (f) Z is N or $CR^{10}$; and (g) $R^{10}$ is an H, F, OH, OR', $NH_2$, NHR', $NR'_2$, lower alkyl of $C_1$-$C_6$, halogenated (F, Cl, Br, I) lower alkyl of $C_1$-$C_6$, or —C≡CH;

wherein R' is a lower alkyl; a lower cycloalkyl; a lower alkaryl, a $C_2$-$C_6$ alkenyl, a $C_2$-$C_6$ alkynyl.

A seventh aspect of the second embodiment is directed to compound II, wherein (a) $R^5$ is H; (b) $R^6$ is H, $CH_3$, or $CH_2CH_3$; (c) $R^7$ is lower alkyl or lower cycloalkyl; (d) X is F; (e) $R^8$ and $R^9$ are independently H, F, OH, OR', $NH_2$, NHR', $NR'_2$, nitrogen heterocycle, and (f) Z is N; wherein R' is a lower alkyl; a lower cycloalkyl; a lower alkaryl, a $C_2$-$C_6$ alkenyl, a $C_2$-$C_6$ alkynyl.

An eighth aspect of the second embodiment is directed to compound II, wherein (a) $R^5$ is H; (b) $R^6$ is H, $CH_3$, or $CH_2CH_3$; (c) $R^7$ is lower alkyl or lower cycloalkyl; (d) X is F; (e) $R^9$ is $NH_2$ and $R^8$ OH, OR', or nitrogen heterocycle, and (f) Z is N; wherein R' is a lower alkyl; a lower cycloalkyl; a lower alkaryl, a $C_2$-$C_6$ alkenyl, a $C_2$-$C_6$ alkynyl.

A ninth aspect of the second embodiment is directed to compound II, wherein (a) $R^5$ is H; (b) $R^6$ is H, $CH_3$, or $CH_2CH_3$; (c) $R^7$ is lower alkyl or lower cycloalkyl; (d) X is F; (e) $R^9$ is $NH_2$ and $R^8$ is O(lower alkyl), O(lower cycloalkyl), or nitrogen heterocycle; and (f) Z is N.

A tenth aspect of the second embodiment is directed to compound II, wherein (a) $R^5$ is H; (b) $R^6$ is $CH_3$; (c) $R^7$ is lower alkyl or lower cycloalkyl; (d) X is F; (e) $R^9$ is $NH_2$ and $R^8$ is O(lower alkyl), O(lower cycloalkyl), or nitrogen heterocycle; and (f) Z is N.

An eleventh aspect of the second embodiment is directed to compound II, wherein (a) $R^5$ is H; (b) $R^6$ is $CH_3$; (c) $R^7$ is lower alkyl or lower cycloalkyl; (d) X is F; (e) $R^9$ is $NH_2$ and $R^8$ is O(lower alkyl), O(lower cycloalkyl) or —N(—$CH_2CH_2CH_2$—) (azetidin-1-yl); and (f) Z is N.

A twelfth aspect of the second embodiment is directed to compound II, wherein (a) $R^5$ is H; (b) $R^6$ is $CH_3$; (c) $R^7$ is $CH_3$, $^iPr$, $^cBu$, or $^cPn$; (d) X is F; (e) $R^9$ is $NH_2$ and $R^8$ is O(lower alkyl) or —N(—$CH_2CH_2CH_2$—) (azetidin-1-yl); and (f) Z is N.

A thirteenth aspect of the second embodiment is directed to compound II, wherein (a) $R^5$ is H; (b) $R^6$ is $CH_3$; (c) $R^7$ is $CH_3$, $^iPr$, $^cBu$, or $^cPn$; (d) X is F; (e) $R^9$ is $NH_2$ and $R^8$ is OMe, OEt, $O^iPr$, or —N(—$CH_2CH_2CH_2$—) (azetidin-1-yl); and (f) Z is N.

A fourteenth aspect of the second embodiment is directed to compound II, wherein (a) $R^5$ is H; (b) $R^6$ is $CH_3$; (c) $R^7$ is $CH_3$, $^iPr$, $^cBu$, or $^cPn$; (d) X is F; (e) $R^9$ is $NH_2$ and $R^8$ is OMe, OEt, or $O^iPr$; and (f) Z is N.

A fifteenth aspect of the second embodiment is directed to compound II, wherein (a) $R^5$ is H; (b) $R^6$ is $CH_3$; (c) $R^7$ is $CH_3$, $^iPr$, $^cBu$, or $^cPn$; (d) X is F; (e) $R^8$ is OMe and $R^9$ is $NH_2$; and (f) Z is N.

A sixteenth aspect of the second embodiment is directed to compound II, wherein (a) $R^5$ is H; (b) $R^6$ is $CH_3$; (c) $R^7$ is $CH_3$, $^iPr$, $^cBu$, or $^cPn$; (d) X is F; (e) $R^8$ is OEt and $R^9$ is $NH_2$; and (f) Z is N.

A seventeenth aspect of the second embodiment is directed to compound II, wherein (a) $R^5$ is H; (b) $R^6$ is $CH_3$; (c) $R^7$ is $CH_3$, $^iPr$, $^cBu$, or $^cPn$; (d) X is F; (e) $R^8$ is $O^iPr$ and $R^9$ is $NH_2$; and (f) Z is N.

An eighteenth aspect of the second embodiment is directed to compound II, wherein (a) $R^5$ is H; (b) $R^6$ is $CH_3$; (c) $R^7$ is $CH_3$; (d) X is F; (e) $R^8$ is —N(—$CH_2CH_2CH_2$—) (azetidin-1-yl); and $R^9$ is $NH_2$; and (f) Z is N.

A nineteenth aspect of the second embodiment is directed to compound II, wherein (a) $R^5$ is H; (b) $R^6$ is $CH_3$; (c) $R^7$ is $CH_3$; (d) X is F; (e) $R^8$ is OEt and $R^9$ is $NH_2$; and (f) Z is N.

A twentieth aspect of the second embodiment is directed to compound II, wherein (a) $R^5$ is H; (b) $R^6$ is $CH_3$; (c) $R^7$ is $^iPr$; (d) X is F; (e) $R^8$ is OEt and $R^9$ is $NH_2$; and (f) Z is N.

A twenty-first aspect of the second embodiment is directed to compound II, wherein (a) $R^5$ is H; (b) $R^6$ is $CH_3$; (c) $R^7$ is $^cBu$; (d) X is F; (e) $R^8$ is OMe and $R^9$ is $NH_2$; and (f) Z is N.

A twenty-second aspect of the second embodiment is directed to a compound II wherein (a) $R^5$ is H; (b) $R^6$ is $CH_3$; (c) $R^7$ is $^cPn$; (d) X is F; (e) $R^8$ is OMe and $R^9$ is $NH_2$; and (f) Z is N.

A twenty-third aspect of the second embodiment is directed to compound II, wherein (a) $R^5$ is H; (b) $R^6$ is $CH_3$; (c) $R^7$ is $^cBu$; (d) X is F; (e) $R^8$ is OEt and $R^9$ is $NH_2$; and (f) Z is N.

A twenty-fourth aspect of the second embodiment is directed to compound II, wherein (a) $R^5$ is H; (b) $R^6$ is $CH_3$; (c) $R^7$ is $^cPn$; (d) X is F; (e) $R^8$ is OEt and $R^9$ is $NH_2$; and (f) Z is N.

Preferred compounds to be prepared by way of the second embodiment, or by another suitable process, include compounds represented by the following structure

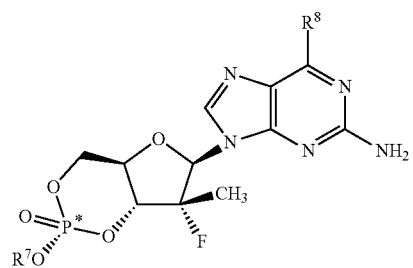

where $R^7$ is a lower alkyl or a lower cycloalkyl and $R^8$ is an O(lower alkyl). Additionally preferred compounds include:

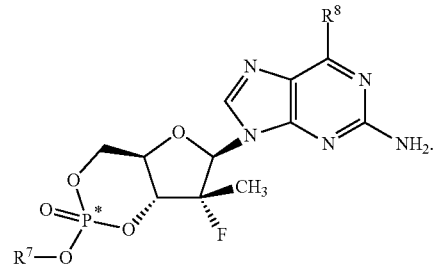

15: $R^7$ = Me, $R^8$ = —N(—$CH_2CH_2CH_2$—)
16: $R^7$ = Me, $R^8$ = —OEt
17: $R^7$ = $^iPr$, $R^8$ = —OEt
23: $R^7$ = $^cBu$, $R^8$ = —OMe
24: $R^7$ = $^cPn$, $R^8$ = —OMe $R^8$ = N(—$CH_2CH_2CH_2$—) = —N◁

Of these preferred compounds, 17 is particularly preferred. One of ordinary skill will recognize that 17 comprises a mixture of diastereomers designated as $R_P$-17 and $S_P$-17. Contemplated herein is a composition that comprises $S_P$-17, $R_P$-17, or mixtures thereof. It is preferred that the composition comprises purified $R_P$-17. It is further preferred that the composition comprises substantially pure $R_P$-17.

The composition that comprises $S_P$-17, $R_P$-17, or mixtures thereof can also be part of a solvate, a hydrate, or a mixed solvate/hydrate. The solvate is designated as $S_P$-17.nS, $R_P$-17.nS, or 17.nS; while the hydrate is designated as $S_P$-17.$mH_2O$, $R_P$-17.$mH_2O$, or 17.$mH_2O$, where S is a lattice solvent, n varies by an integer or non-integer amount from about 0 to about 3 and m varies by an integer or non-integer amount from about 0 to about 5. The composition that comprises $S_P$-17, $R_P$-17, or mixtures thereof and its salts, solvates, and hydrates thereof is crystalline, crystal-like, or amorphous.

A first aspect of the preferred compounds of formula II is directed to crystalline $R_P$-17.

A second aspect of the preferred compounds of formula II directed to crystalline $R_P$-17 having an XRD 2θ-reflections (°) at about 12.2.

A third aspect of the preferred compounds of formula II directed to crystalline R-17 having XRD 2θ-reflections (°) at about 12.2, 14.3, 15.5, and 19.9.

A fourth aspect of the preferred compounds of formula II directed to crystalline $R_P$-17 having XRD 2θ-reflections (°) at about 12.2, 14.3, 15.5, 17.4, 18.1, 19.9, 22.8, 23.6, 24.5, 25.1, and 27.35.

A fifth aspect of the preferred compounds of formula II directed to crystalline $R_P$-17 having an XRD diffraction pattern substantially as that shown in FIG. 1.

A sixth aspect of the preferred compounds of formula II directed to orthorhombic, crystalline $R_P$-17.

A sixth aspect of the preferred compounds of formula II directed to crystalline R-17 having orthorhombic ($P2_12_12_1$) unit cell parameters of a~11.4 Å, b~12.4 Å, and c~14.2 Å.

A seventh aspect of the preferred compounds of formula II directed to crystalline $R_P$-17 having the following FT-IR peaks ($cm^{-1}$): ~1581, ~1295, ~1065, ~999, ~798, and ~79'.

Figure 2:
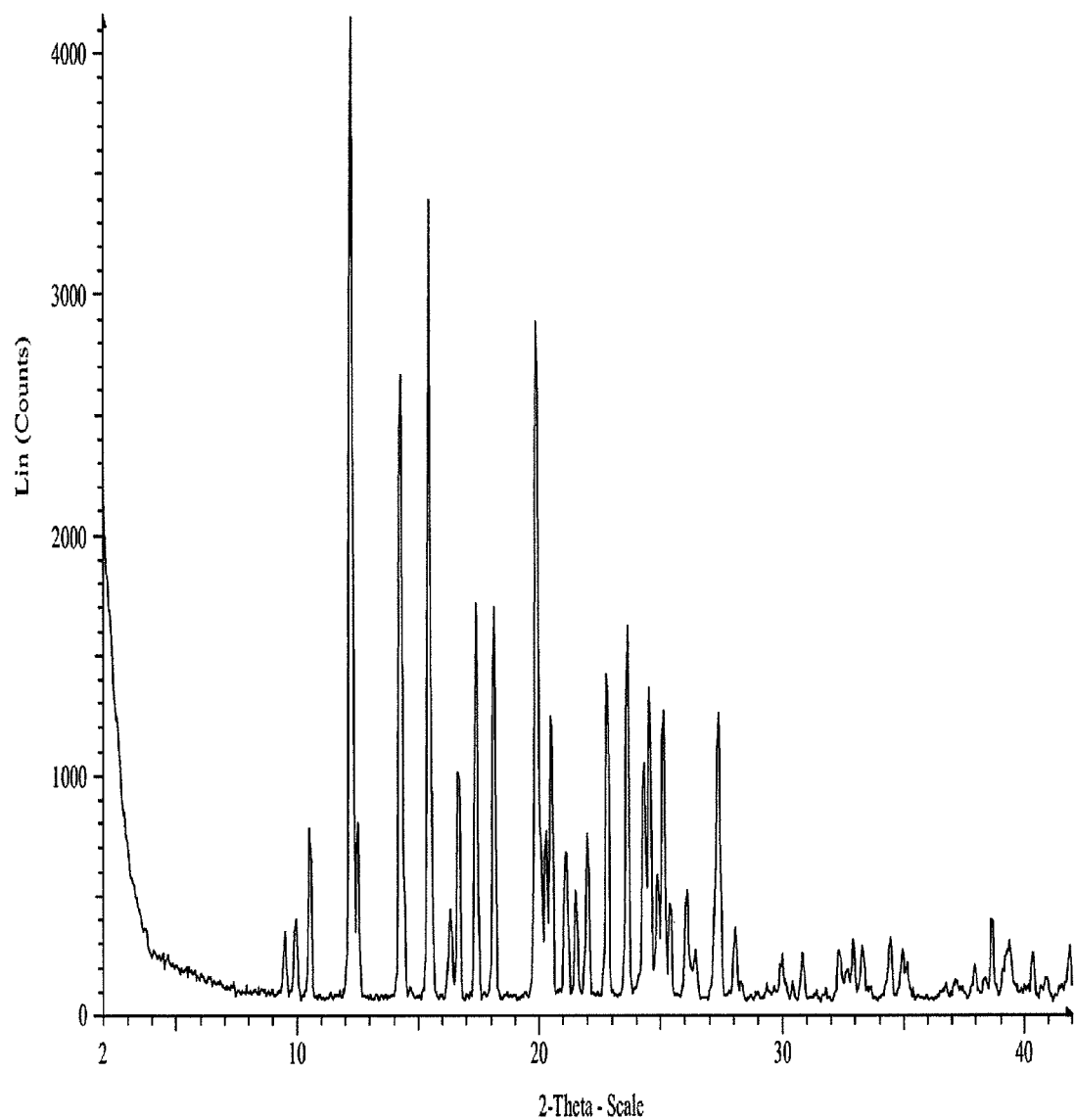
FIG. 2. XRD of $R_P$-17.

An eighth aspect of the preferred compounds of formula II is directed to crystalline $R_P$-17 having an FT-IR spectrum substantially as that shown in FIG. 2.

A ninth aspect of the preferred compounds of formula II is directed to substantially pure $R_P$-17.

A tenth aspect of the preferred compounds of formula II is directed to substantially pure, crystalline $R_P$-17.

An eleventh aspect of the preferred compounds of formula II is directed to substantially pure, crystal-like $R_P$-17.

A twelfth aspect of the preferred compounds of formula II is directed to substantially pure, amorphous $R_P$-17.

A third embodiment is directed to a process for preparing compound I or compound II or any of the compounds recited in any one of the aspects of the first and second embodiments, wherein said process comprises:

(a) stereoselective reduction of a protected ribonolactone III using a hydride reducing agent

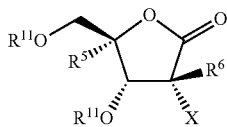

III to provide a beta-lactol derivative IV; and

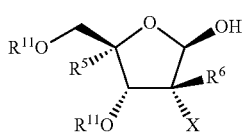

IV (b) stereoselective conversion of the lactol derivative using a reagent to obtain an anomeric alpha-derivative V

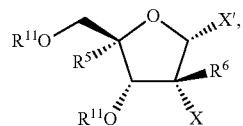

V wherein $R^5$, $R^6$, and X have their meanings as described above, X' is a leaving group, and $R^{11}$ is a protecting group.

A first aspect of the third embodiment directed to a process for preparing a compound I or compound II or any of the compounds recited in any one of the aspects of the first and second embodiments, wherein for the compound III or the compound IV, $R^{11}$ is benzoyl or substituted benzoyl (preferably $R^{11}$ is 4-chloro-benzoyl), $R^5$ is H, $R^6$ is $CH_3$, and X is F. The hydride reducing agent is $(^tBuO)_3AlH$, sodium (bis(2-methoxyethoxy)(2,2,2-trifluoro-ethoxy)aluminum hydride, or Red-Al (sodium bis(2-methoxyethoxy)aluminum hydride). The stereoselective reduction can be performed in a solvent comprising tetrahydrofuran (THF) or diethyl ether, preferably the solvent is THF at a temperature ranging from about (−78° C.) to about 25° C., preferably at a temperature ranging from about (−78° C.) to about 0° C., and most preferably at a temperature from about (−30° C.) to about 0° C.

A second aspect of the third embodiment is directed to a process for preparing a compound I or a compound II or any of the compounds recited in any one of the aspects of the first and second embodiments, said process comprising stereoselective reduction of a protected ribonolactone III using a hydride reducing agent to provide a mixture comprising a beta-lactol derivative IV and an alpha-lactol derivative IV-α:

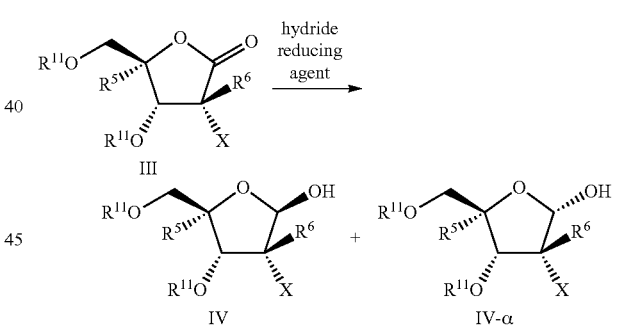

and crystallizing the beta-lactol derivative IV from the mixture comprising the beta-lactol derivative and the alpha-lactol derivative

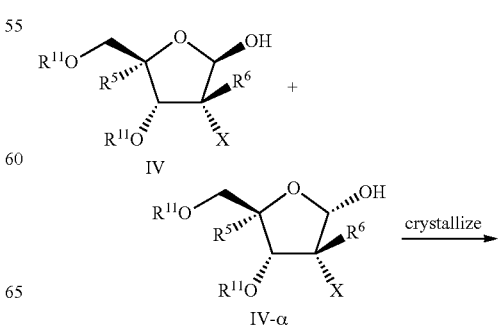

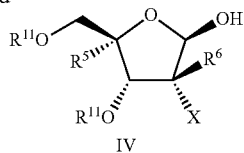

wherein $R^5$, $R^6$, and X have the meanings as defined herein above and $R^{11}$ is a protecting group.

A third aspect of the third embodiment is directed to a process for preparing a compound I or a compound II or any of the compounds recited in any one of the aspects of the first and second embodiments, wherein for the compound III, the compound IV, or the compound IV-α, $R^5$ is H, $R^6$ is $CH_3$, $R^{11}$ is benzoyl or a substituted benzoyl (preferably $R^{11}$ is 4-chloro-benzoyl), and X is F. The hydride reducing agent is ($^t$BuO)$_3$AlH, sodium (bis(2-methoxyethoxy)(2,2,2-trifluoroethoxy)aluminum hydride, or Red-Al (sodium bis(2-methoxyethoxy)aluminum hydride). The stereoselective reduction can be performed in a solvent comprising tetrahydrofuran (THF) or diethyl ether, preferably the solvent is THF at a temperature ranging from about (−78° C.) to about 25° C., preferably at a temperature ranging from about (−78° C.) to about 0° C., and most preferably at a temperature from about (−30° C.) to about 0° C. The crystallization occurs by a process comprising adding to the mixture seed crystals of the beta-lactol derivative and then heating the mixture comprising the seed crystals of the beta-lactol derivative at a temperature that ranges from about 25° C. to about 80° C., preferably about 50° C. with (about 0.2 mmHg) or without applied vacuum.

A fourth aspect of the third embodiment is directed to a process for preparing a compound I or a compound II or any of the compounds recited in any one of the aspects of the first and second embodiments, comprising stereoselective conversion of a lactol derivative IV using a reagent to obtain an anomeric alpha-derivative V

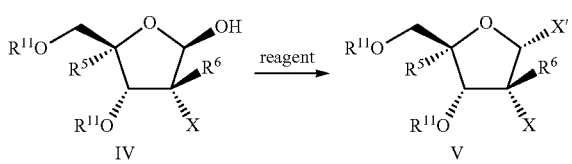

wherein $R^5$, $R^6$, and X, have the meanings as defined herein above, $R^{11}$ is a protecting group and X' is a leaving group.

A fifth aspect of the third embodiment is directed to a process for preparing a compound I or a compound II or any of the compounds recited in any one of the aspects of the first and second embodiments, wherein for the compound IV or the compound V, $R^5$ is H, $R^6$ is $CH_3$, $R^{11}$ is benzoyl or a substituted benzoyl (preferably $R^{11}$ is 4-chloro-benzoyl), X is F, and X" is Br. The reagent is defined as above. Preferably, the reagent is at least one of Ph$_3$P/CBr$_4$, Ph$_3$P/CHBr$_3$, Ph$_3$P/CHBr$_3$/imidazole, Ph$_3$P/Br$_2$, Ph$_3$P/Br$_2$/imidazole, N-bromosuccinimide/Ph$_3$P, HBr in acetic acid, PBr$_3$/DMF, PBr$_3$/sodium bicarbonate, PBr$_3$/imidazole, PBr$_5$/DMF, PBr$_5$/sodium bicarbonate, PBr$_5$/imidazole, and POBr$_3$/imidazole. More preferably, the reagent is Ph$_3$P/CBr$_4$. The stereoselective conversion can be performed in the presence of certain solvents, which include, but are not limited to, CH$_2$Cl$_2$, 1,2-dichloroethane, toluene, chlorobenzene, tetrahydrofuran, dioxane, diethyl ether, dimethylformamide, acetonitrile, N-methylpyrrolidine, dimethoxyethane, preferably the solvent used is CH$_2$Cl$_2$. The stereoselective conversion can be performed at a temperature that ranges from about (−78° C.) to about 0° C. Preferably, the temperature ranges from about (−78° C.) to about (−10° C.). Most preferably, the temperature ranges from about (−30° C.) to about (−10° C.).

A fourth embodiment is directed to a compound IV.

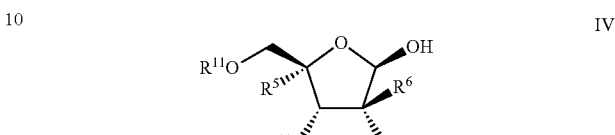

wherein $R^5$, $R^6$, and X have the meanings as defined herein above and $R^{11}$ is a protecting group. Preferably, $R^5$ is H, $R^6$ is $CH_3$, $R^{11}$ is a protecting group, preferably $R^{11}$ is benzoyl or a substituted benzoyl and more preferably $R^{11}$ is 4-chloro-benzoyl, and X is F, preferably $R^{11}$ is 4-chloro-benzoyl. The compound IV can be purified or unpurified. The compound IV is useful for preparing compound I and compound II.

A fifth embodiment is directed to a compound V.

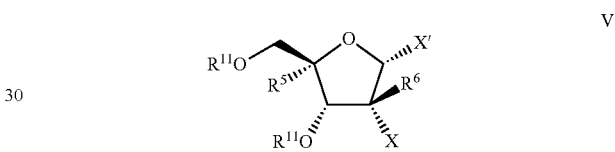

wherein $R^5$, $R^6$, $R^{11}$, X, and X' have the meanings set forth above. Preferably, $R^5$ is H, $R^6$ is $CH_3$, $R^{11}$ is a protecting group, preferably $R^{11}$ is benzoyl or a substituted benzoyl and more preferably $R^{11}$ is 4-chloro-benzoyl, X is F, and X' is Cl, Br, or I (most preferably X' is Br). The compound V can be purified or unpurified. The compound V is useful for preparing a compound I and a compound II.

An sixth embodiment is directed to a process for preparing a compound I or a compound II or any of the compounds recited in any one of the aspects of the first and second embodiments, comprising stereoselective coupling of an alpha-derivative V with a purine or a derivatized purine base using a basic reagent to produce a beta-nucleoside VI

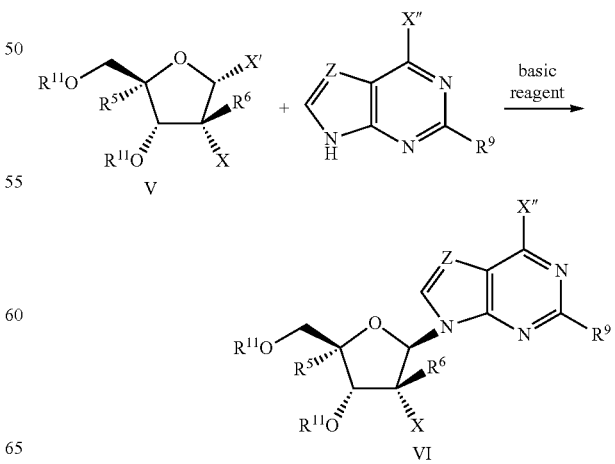

wherein $R^5$, $R^6$, $R^9$ X, and Z have the meanings as defined herein above $R^{11}$ is a protecting group, X' and X" independent of each other are leaving groups.

A first aspect of the sixth embodiment is directed to a process for preparing a compound I or a compound II or any of the compounds recited in any one of the aspects of the first and second embodiments, wherein for the compound V or the compound VI, $R^5$ is H, $R^6$ is $CH_3$, $R^9$ is $NH_2$, $R''$ is a protecting group, preferably $R''$ is benzoyl or a substituted benzoyl and more preferably $R^{11}$ is 4-chloro-benzoyl, X is F, X' is Br, X" is Cl, and Z is N. The basic reagent is as defined above. Preferably, the basic reagent comprises a (lower alk)oxide ((lower alkyl)OM) and an alcoholic solvent. Preferably, the basic reagent is MeONa/MeOH, EtONa/EtOH, or $^t$Bu OK/$^t$BuOH. Most preferably, the basic reagent is $^t$Bu OK/$^t$BuOH. The stereoselective coupling can be performed in a solvent comprising at least one of a polar aprotic solvent, a non-polar solvent, and a polar solvent. Examples of polar aprotic solvents include, but are not limited to, acetonitrile, dimethylsulfoxide, N,N-dimethylformamide, hexamethylphosphoramide, etc. The stereoselective coupling can be performed at a temperature that ranges from about 0° C. up to about the reflux temperature of the solvent. Preferably, the temperature ranges from about 25° C. to about 75° C. More preferably, the temperature ranges from about 40° C. to about 60° C. Most preferably, the temperature is about 50° C.

A seventh embodiment is directed to a compound VI.

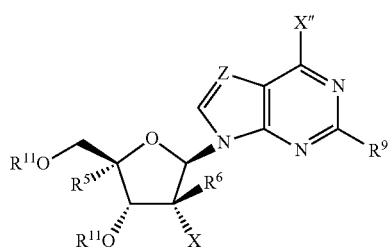

VI wherein $R^5$, $R^6$, $R^9$ X, and Z have the meanings as defined herein above $R^{11}$ is a protecting group, X" is a leaving group. Preferably, $R^{11}$ is benzoyl or a substituted benzoyl, more preferably $R^{11}$ is 4-chloro-benzoyl, $R^5$ is H, $R^6$ is $CH_3$, X is F, X" Is $C^1$, $R^9$ is $NH_2$, and Z is N. Compound VI can be purified or unpurified. Compound VI is useful for preparing compound I and compound II.

A first aspect of the seventh embodiment is directed to a process for preparing compound VI, wherein said process comprises:

(a) stereoselective reduction of a protected ribonolactone III using a hydride reducing agent to provide a beta-lactol derivative IV; and

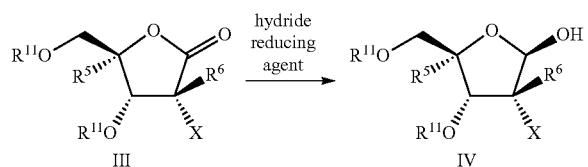

III    IV (b) stereoselective conversion of the lactol derivative using a reagent to obtain an anomeric alpha-derivative V

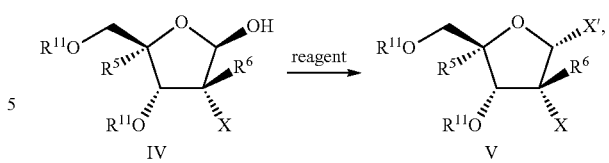

IV    V and (c) stereoselective coupling of an alpha-derivative V with a purine or a derivatized purine base using a basic reagent to produce a beta-nucleoside VI

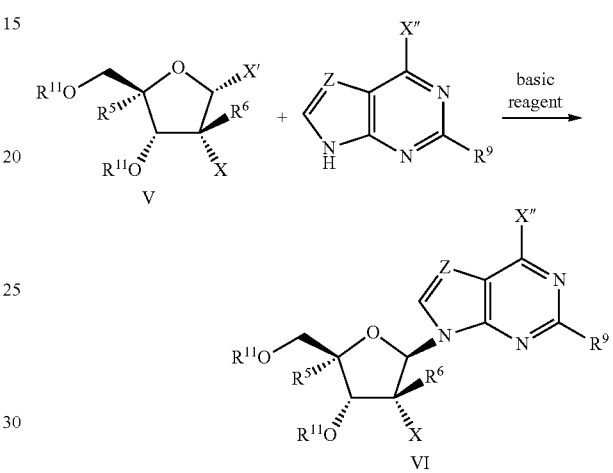

VI wherein $R^5$, $R^6$, $R^9$, and Z have the meanings as defined above, each of X' and X" independent of each other is a leaving group, and $R^{11}$ is a protecting group.

A second aspect of the seventh embodiment is directed to a process for preparing compound VI, where $R^5$ is H, $R^6$ is $CH_3$, $R^9$ is $NH_2$, $R^{11}$ is a protecting group, preferably $R^{11}$ is benzoyl or a substituted benzoyl and more preferably $R^{11}$ is 4-chloro-benzoyl, X is F, X' is Br, X" is Cl, and Z is N. The stereoselective reduction can be performed in a solvent comprising tetrahydrofuran (THF) or diethyl ether, preferably the solvent is THF at a temperature ranging from about (−78° C.) to about 25° C., preferably at a temperature ranging from about (−78° C.) to about 0° C., and most preferably at a temperature from about (−30° C.) to about 0° C. The hydride reducing agent is ($^t$BuO)$_3$AlH, sodium (bis(2-methoxyethoxy)(2,2,2-trifluoroethoxy)aluminum hydride, or Red-Al (sodium bis(2-methoxyethoxy)aluminum hydride). The stereoselective coupling can be performed in a solvent comprising at least one of a polar aprotic solvent, a non-polar solvent, and a polar solvent. Examples of polar aprotic solvents include, but are not limited to, acetonitrile, dimethylsulfoxide, N,N-dimethylformamide, hexamethylphosphoramide, etc. The stereoselective coupling can be performed at a temperature that ranges from about 0° C. up to about the reflux temperature of the solvent. Preferably, the temperature ranges from about 25° C. to about 75° C. More preferably, the temperature ranges from about 40° C. to about 60° C. Most preferably, the temperature is about 50° C. The basic reagent is as defined above. Preferably, the basic reagent comprises a (lower alk)oxide ((lower alkyl)OM) and an alcoholic solvent. Preferably, the basic reagent is MeONa/MeOH, EtONa/EtOH, EtOK/EtOH, $^i$PrONa/$^i$PrOH, $^i$PrOK/PrOH, or $^t$BuOK/$^t$BuOH. Most preferably, the basic reagent is $^t$BuOK/$^t$BuOH.

A third aspect of the seventh embodiment is directed to a process for preparing compound VI said process comprising:

(a) stereoselective reduction of a protected ribonolactone III using a hydride reducing agent to provide a mixture comprising a beta-lactol derivative IV and an alpha-lactol derivative IV-α:

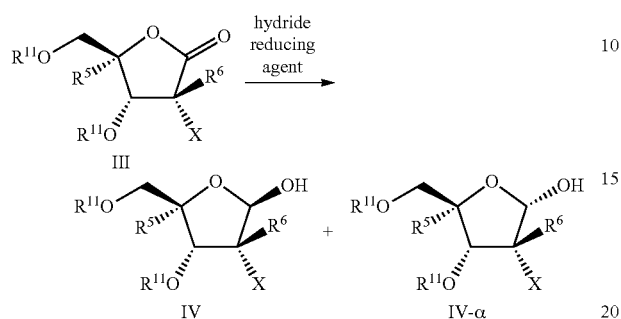

(b) crystallizing the beta-lactol derivative IV from the mixture comprising the beta-lactol derivative and the alpha-lactol derivative;

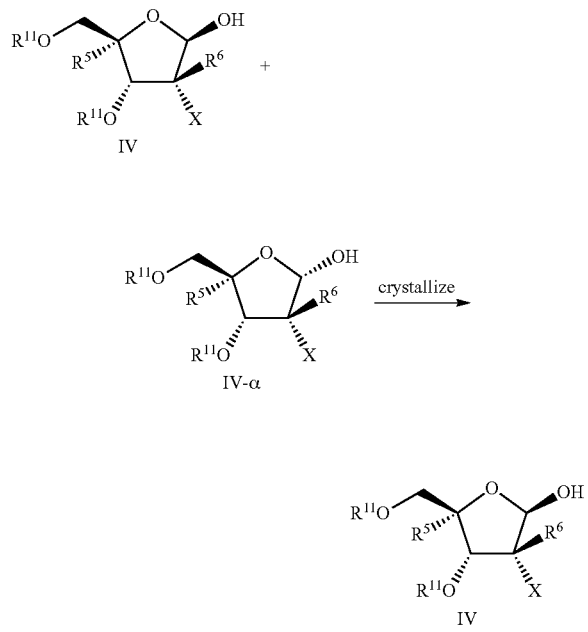

(c) stereoselective conversion of the lactol derivative IV using a reagent to obtain an anomeric alpha-derivative V

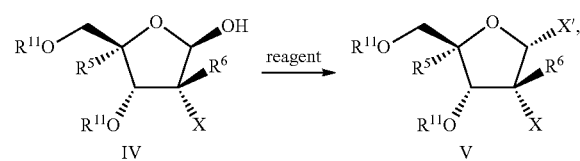

and (c) stereoselective coupling of an alpha-derivative V with a purine or a derivatized purine base using a basic reagent to produce a beta-nucleoside VI

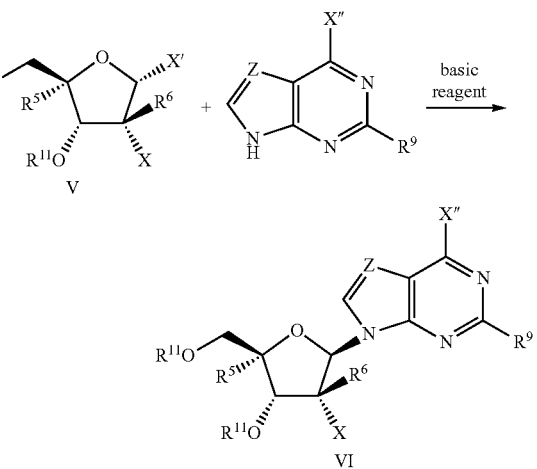

wherein $R^5$, $R^6$, $R^9$, X, and Z have the meanings as defined above, each of X' and X" independent of each other is a leaving group, and $R^{11}$ is a protecting group. Preferably, $R^5$ is H, $R^6$ is $CH_3$, $R^{11}$ is benzoyl or a substituted benzoyl (preferably $R^{11}$ is 4-chlorobenzoyl), X is F, X' is Br, X" is Cl, Z is N, and $R^9$ is $NH_2$. The hydride reducing agent is $(^tBuO)_3AlH$, sodium (bis(2-methoxyethoxy)(2,2,2-trifluoro-ethoxy)aluminum hydride, or Red-Al (sodium bis(2-methoxyethoxy) aluminum hydride). The stereoselective reduction can be performed in a solvent comprising tetrahydrofuran (THF) or diethyl ether, preferably the solvent is THF at a temperature ranging from about (−78° C.) to about 25° C., preferably at a temperature ranging from about (−78° C.) to about 0° C., and most preferably at a temperature from about (−30° C.) to about 0° C. The crystallization occurs by a process comprising adding to the mixture seed crystals of the beta-lactol derivative and then heating the mixture comprising the seed crystals of the beta-lactol derivative at a temperature that ranges from about 25° C. to about 80° C., preferably about 50° C. with (about 0.2 mmHg) or without applied vacuum. The stereoselective coupling can be performed in a solvent comprising at least one of a polar aprotic solvent, a non-polar solvent, and a polar solvent. Examples of polar aprotic solvents include, but are not limited to, acetonitrile, dimethylsulfoxide, N,N-dimethylformamide, hexamethylphosphoramide, etc. The stereoselective coupling can be performed at a temperature that ranges from about 0° C. up to about the reflux temperature of the solvent. Preferably, the temperature ranges from about 25° C. to about 75° C. More preferably, the temperature ranges from about 40° C. to about 60° C. Most preferably, the temperature is about 50° C. The basic reagent is as defined above. Preferably, the basic reagent comprises a (lower alk)oxide ((lower alkyl)OM) and an alcoholic solvent. Preferably, the basic reagent is MeONa/MeOH, EtONa/EtOH, EtOK/EtOH, $^iPrONa/^iPrOH$, $^iPrOK/^iPrOH$, or $^tBuOK/^tBuOH$. Most preferably, the basic reagent is $^tBuOK/^tBuOH$.

An eight embodiment is directed to a process for preparing a compound I or a compound II or any of the compounds recited in any one of the aspects of the first and second embodiments, comprising reacting a beta-nucleoside derivative VI with a nucleophilic reagent to produce a 6-substituted nucleoside VII;

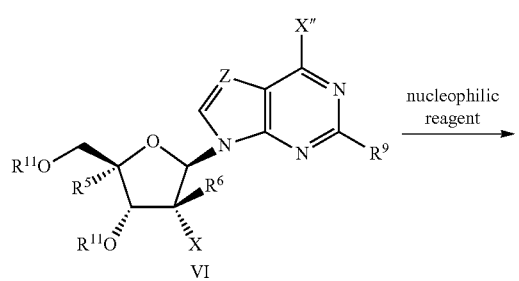

VI

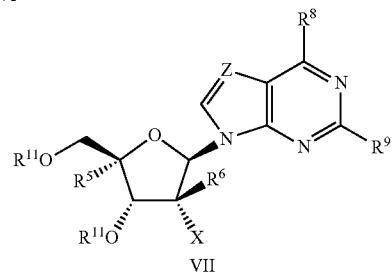

VII deprotecting the 6-substituted nucleoside VII to produce a free purine nucleoside derivative VIII;

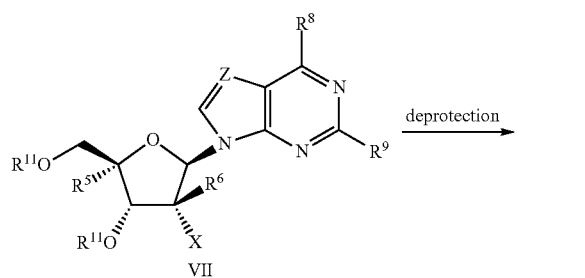

VII

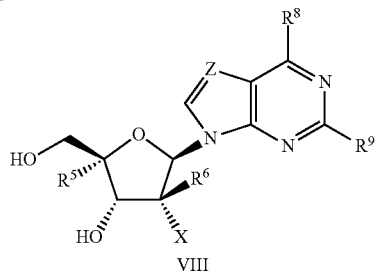

VIII wherein $R^5$, $R^6$, $R^8$, $R^9$, X, Z have the meanings as defined herein above, $R^{11}$ is a protecting group, and X″ is a leaving group.

A first aspect of the eighth embodiment is directed to a process for preparing a compound I or a compound II, wherein for the compound VI, the compound VII, or the compound VIII, $R^5$ is H, $R^6$ is $CH_3$, $R^8$ is any one —OMe, —OEt, O$^i$Pr, —N(—CH$_2$CH$_2$CH$_2$—) (azetidin-1-yl), and —OBn, $R^9$ is $NH_2$, $R^{11}$ is a protecting group (preferably benzoyl or substituted benzoyl, more preferably 4-chlor-benzoyl), X is F, X″ is Cl, and Z is N. The nucleophilic reagent is as defined above. Preferably, the nucleophilic reagent is one that provides for $R^8$ which is any one —OMe, —OEt, —O$^i$Pr, —N(—CH$_2$CH$_2$CH$_2$—) (azetidin-1-yl), and —OBn. The reacting can be performed in at least one solvent comprising at least one of a polar aprotic solvent, a non-polar solvent, and a polar solvent. Examples of polar solvents include, but are not limited to, methanol, ethanol, t-butanol, benzyl alcohol. Examples of polar aprotic solvents include, but are not limited to, acetonitrile, dimethylsulfoxide, N,N-dimethylformamide, hexamethylphosphoramide, etc. The reacting can be performed at a temperature that ranges from about 0° C. up to about the reflux temperature of the at least one solvent. Preferably, the temperature ranges from about 25° C. to about 75° C. More preferably, the temperature ranges from about 40° C. to about 60° C. Most preferably, the temperature is about 50° C. The deprotecting can occur as described herein.

A second aspect of the eight embodiment is directed to a process for preparing a compound I or a compound II, comprising reacting a beta-nucleoside derivative VI with a nucleophilic reagent to produce a 6-substituted nucleoside VII;

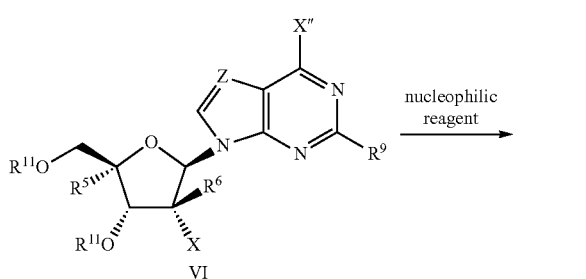

VI

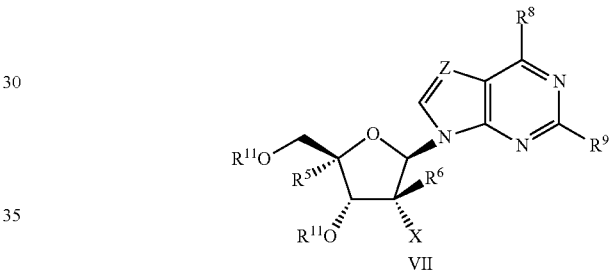

VII deprotecting the 6-substituted nucleoside VII to produce a free purine nucleoside derivative VIII;

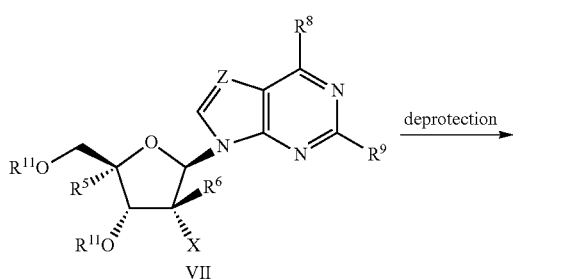

VII

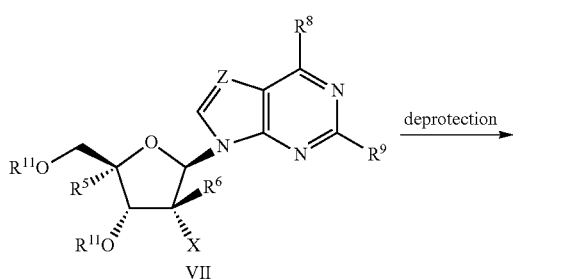

VIII wherein for the compound VI, the compound VII, or the compound VIII, $R^5$ is H, $R^6$ is $CH_3$, $R^8$ is —OMe, $R^9$ is $NH_2$, $R^{11}$ is a protecting group (preferably benzoyl or substituted benzoyl), X is F, X" is Cl, and Z is N (see compound (7) below). The nucleophilic reagent is MeONa/MeOH. The reacting can be performed in a solvent comprising methanol. The reacting can be performed at a temperature that ranges from about 0° C. up to about 65° C. Preferably, the temperature ranges from about 25° C. to about 65° C. or alternatively from a temperature above room temperature to the boiling point of the alcoholic solvent/reagent. More preferably, the temperature ranges from about 40° C. to about 60° C. Most preferably, the temperature is about 50° C. The deprotecting can occur as described herein.

A third aspect of the eighth embodiment is directed to a process for preparing a compound I or a compound II, comprising reacting a beta-nucleoside derivative VI with a nucleophilic reagent to produce a 6-substituted nucleoside VII;

$R^{11}$ is a protecting group (preferably benzoyl or substituted benzoyl), X is F, X" is Cl, and Z is N (see compound (10) below). The nucleophilic reagent is as defined above. In the instance where the nucleophilic reagent is KOEt/EtOH, the nucleophilic reagent can be prepared in situ by reacting EtOH a base, such as potassium carbonate. The reacting can be performed in ethanol and at a temperature that ranges from about 0° C. up to about 78° C. Preferably, the temperature ranges from about 25° C. to about 78° C. More preferably, the temperature ranges from about 40° C. to about 60° C. Most preferably, the temperature is about 50° C. The deprotecting can occur as described herein.

A fourth aspect of the eighth embodiment is directed to a process for preparing a compound I or a compound II comprising reacting a beta-nucleoside derivative VI with a nucleophilic reagent to produce a 6-substituted nucleoside VII;

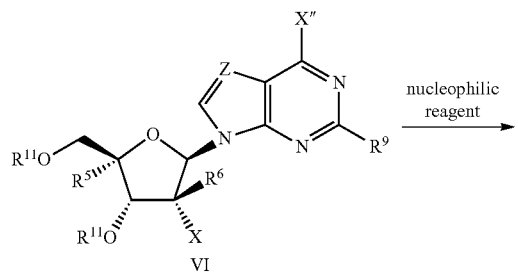

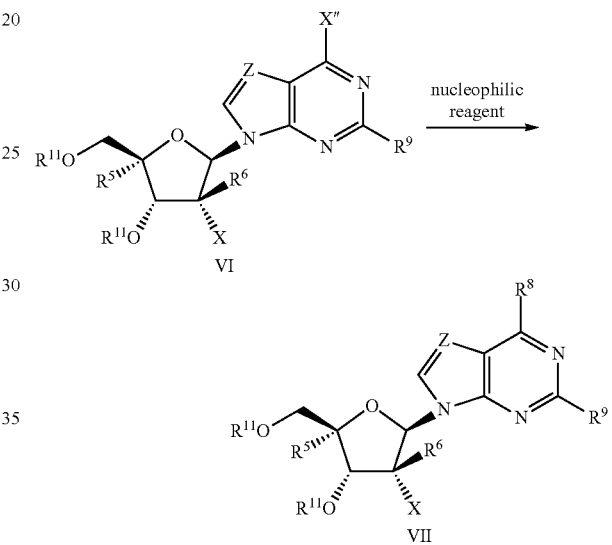

deprotecting the 6-substituted nucleoside VII to produce a free purine nucleoside derivative VIII;

deprotecting the 6-substituted nucleoside VII to produce a free purine nucleoside derivative VIII;

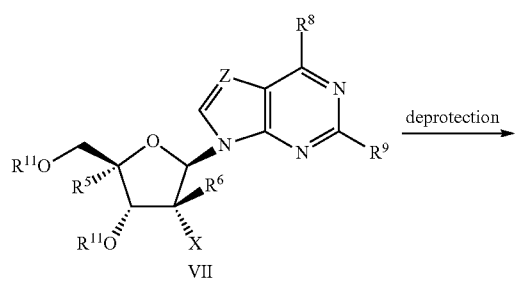

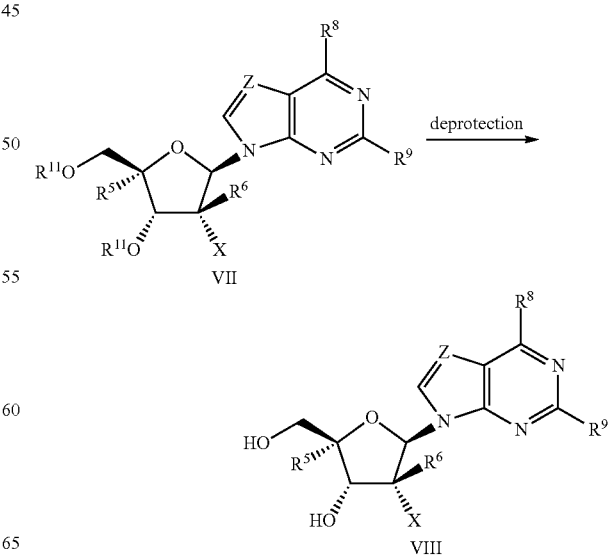

wherein for the compound VI, the compound VII, or the compound VIII, $R^5$ is H, $R^6$ is $CH_3$, $R^8$ is —OEt, $R^9$ is $NH_2$, wherein for the compound VI, the compound VII, or the compound VIII, $R^5$ is H, $R^6$ is $CH_3$, $R^8$ is —OBn, $R^{11}$ is a protecting group (preferably benzoyl or substituted benzoyl), X is F, X" is Cl, and Z is N (see compound (9) below). The nucleophilic reagent is BnONa/BnOH, wherein BnONa is obtained by a process comprising reacting benzyl alcohol with sodium hydride in a N,N-dimethylformamide solution at a temperature achieved using an ice bath (about 0° C.). The reacting can be performed in a solvent comprising benzyl alcohol. The reacting can be performed at a temperature that ranges from about 0° C. up to about 75° C. Preferably, the temperature ranges from about 25° C. to about 65° C. More preferably, the temperature ranges from about 40° C. to about 60° C. Most preferably, the temperature is about 50° C. The deprotecting can occur as described herein.

A fifth aspect of the eighth embodiment is directed to a process for preparing a compound I or a compound II comprising reacting a beta-nucleoside derivative VI with a nucleophilic reagent to produce a 6-substituted nucleoside VII;

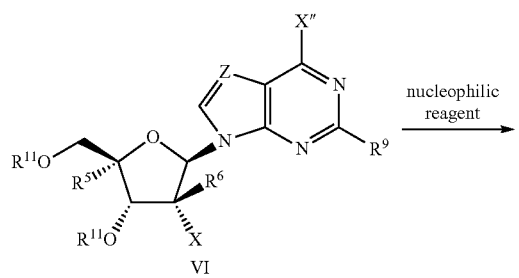

VI deprotecting the 6-substituted nucleoside VII to produce a free purine nucleoside derivative VIII;

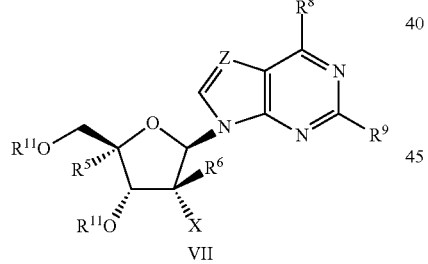

VII

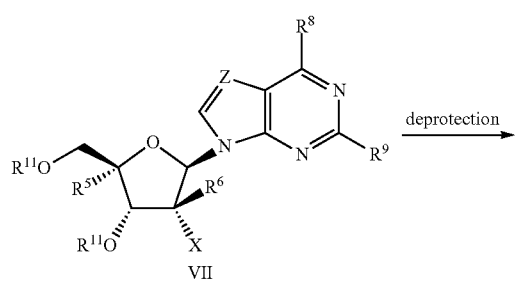

VII

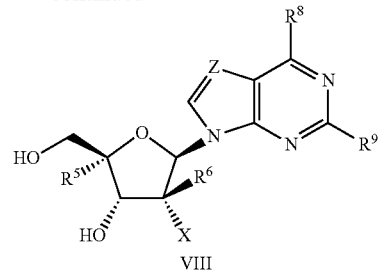

VIII wherein for the compound VI, the compound VII, or the compound VIII, $R^5$ is H, $R^6$ is $CH_3$, $R^8$ is —N(—$CH_2CH_2CH_2$—) (azetidin-1-yl), $R^9$ is $NH_2$, $R^{11}$ is a protecting group (preferably benzoyl or substituted benzoyl), X is F, X" is Cl, and Z is N (see compound (8) below). The nucleophilic reagent is azetidine/triethyl amine. The reacting can be performed in a solvent comprising ethanol. The reacting can be performed at a temperature that ranges from about 0° C. up to about 78° C. Preferably, the temperature ranges from about 25° C. to about 75° C. More preferably, the temperature ranges from about 40° C. to about 60° C. Most preferably, the temperature is about 50° C. The deprotecting can occur as described herein.

A ninth embodiment is directed to a compound VIII.

wherein for the compound VIII, $R^5$, $R^6$, X, $R^8$, $R^9$, and Z have the meanings as defined herein above. Preferably, $R^5$ is H, $R^6$ is $CH_3$, X is F, $R^8$ is a —O(lower alkyl), —O(lower cycloalkyl), —O(lower alkaryl), or nitrogen heterocycle, $R^9$ is $NH_2$, and Z is N. More preferably, $R^5$ is H, $R^6$ is $CH_3$, X is F, $R^8$ is any one of OMe, OEt, $O^iPr$, OBn, and N(—$CH_2CH_2CH_2$—) (azetidin-1-yl), $R^9$ is $NH_2$, and Z is N. The compound VIII can be purified or unpurified. Preferably the compound VIII is purified.

A preferred compound VIII is represented by one of compounds 7, 8, 9, and 10 (see below).

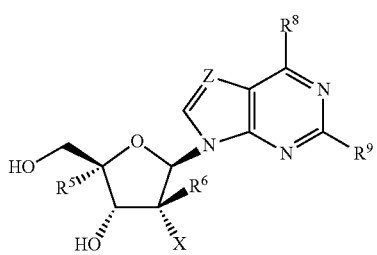

7, $R^8 =$ —OMe
7a, $R^8 =$ —$O^iPr$
8, $R^8 =$ —N(—$CH_2CH_2CH_2$—)
9, $R^8 =$ —OBn
10, $R^8 =$ —OEt wherein, $R^5$ is H, $R^6$ is $CH_3$, X is F, Z is N, and $R^9$ is $NH_2$. The compound VIII is useful for preparing a compound I and a compound II.

A tenth embodiment of is directed to a process comprising converting a free purine nucleoside derivative VIII to compound I or converting the free purine nucleoside derivative to compound II. Procedures for converting a free purine nucleoside derivative VIII to compound I are disclosed herein, as well as U.S. patent application Ser. No. 12/053,015, filed Mar. 21, 2008 (see also WO 2008/121634). Procedures for converting a free purine nucleoside derivative VIII to compound II are disclosed herein and U.S. Provisional Patent Application No. 61/060,683, filed Jun. 11, 2008.

A first aspect of the tenth embodiment related to preparing compound II is directed to a process which comprises reacting the free purine nucleoside derivative VIII with either a P(III)-reagent or a P(V)-reagent.

A second aspect of the tenth embodiment related to preparing the compound II is directed to a process which comprises reacting the free purine nucleoside derivative VIII with a P(III)-reagent to obtain a phosphite derivative of II, wherein the phosphite derivative of II comprises a mixture of isomers.

A third aspect of the tenth embodiment related to preparing the compound II is directed to a process which comprises reacting the free purine nucleoside derivative VIII with a P(III)-reagent in the presence of an activator reagent to obtain a phosphite derivative of II, wherein the phosphite derivative of II comprises a mixture of isomers.

A fourth aspect of the tenth embodiment related to preparing the compound II is directed to a process which comprises reacting the free purine nucleoside derivative VIII with a P(III)-reagent in the presence of an activator reagent to obtain a phosphite derivative of II, wherein the phosphite derivative of II comprises a mixture of isomers; and equilibrating the phosphite derivative of II to provide an equilibrium mixture of phosphite isomer derivatives of II.

A fifth aspect of the tenth embodiment related to preparing the 3',5'-cyclic phosphate derivative II is directed to a process which comprises reacting the free purine nucleoside derivative VIII with a $R^7OP[N(^iPr)_2]_2$ in the presence of 4,5-dicyanoimidazole to obtain a phosphite derivative of II

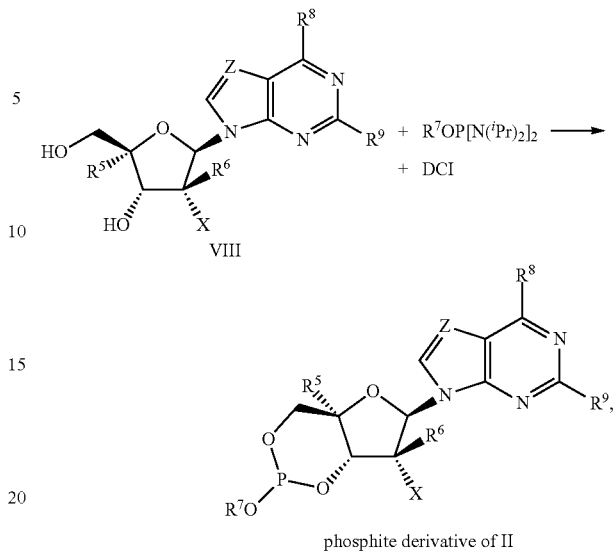

phosphite derivative of II wherein the phosphite derivative of II comprises a mixture of isomers and $R^5$, $R^6$, $R^7$, $R^8$, $R^9$, X and Z are defined herein;

and equilibrating the phosphite derivative of II to obtain an equilibrium mixture of phosphite isomer derivatives of II.

A sixth aspect of the tenth embodiment is related to the fifth aspect further comprising oxidizing the equilibrium mixture of phosphite isomer derivatives of II to obtain the 3',5'-cyclic phosphate derivative II

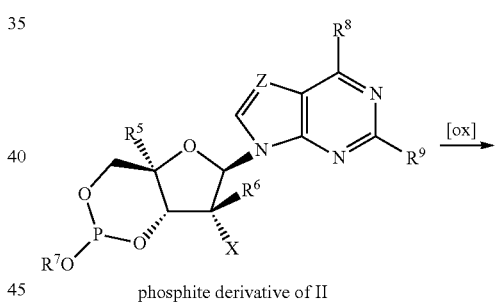

phosphite derivative of II

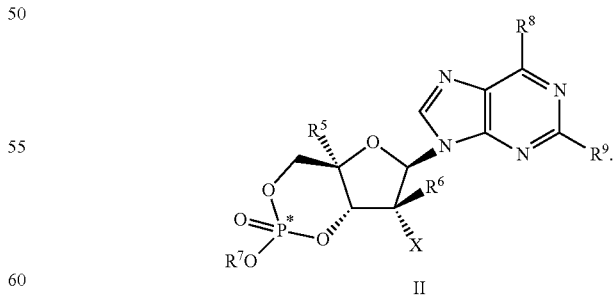

II

A seventh aspect of the tenth embodiment related to preparing the 3',5'-cyclic phosphate derivative II is directed to a process which comprises reacting the free purine nucleoside derivative VIII with a $R^7OP[N(^iPr)_2]_2$ in the presence of 4,5-dicyanoimidazole to obtain a phosphite derivative of II

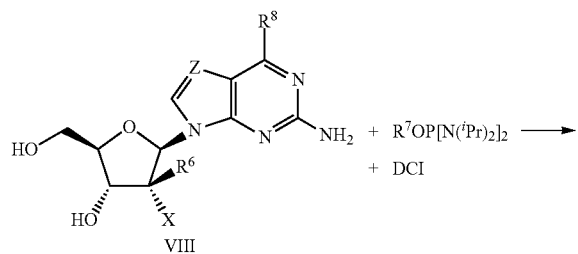

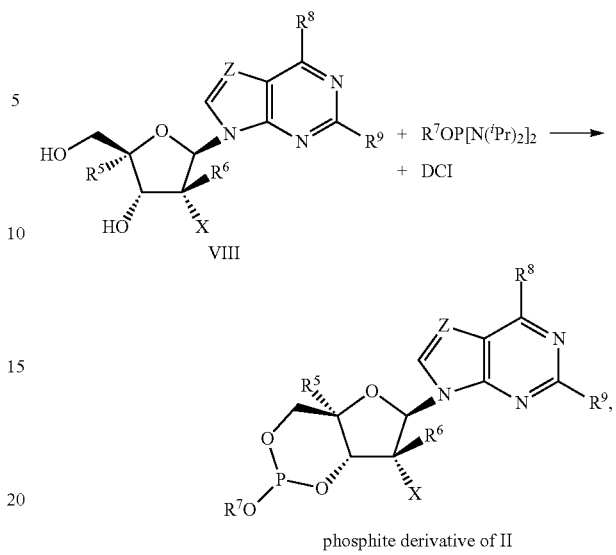

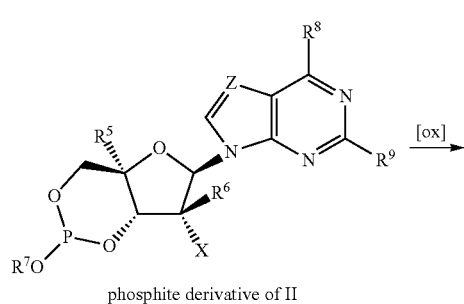

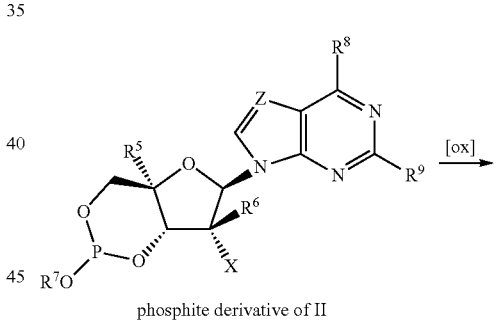

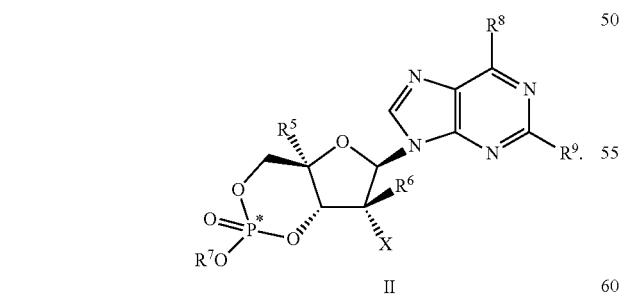

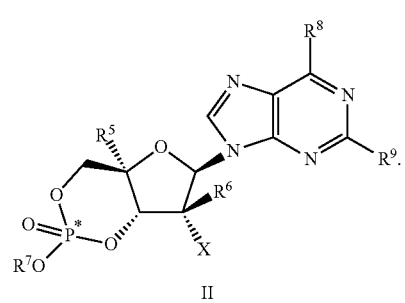

wherein the phosphite derivative of II comprises a mixture of isomers, $R^5$ is H, $R^6$ is $CH_3$, X is F, Z is N, and $R^9$ is $NH_2$, while $R^7$ and $R^8$ are defined herein;

and equilibrating the phosphite derivative of II to obtain an equilibrium mixture of phosphite isomer derivatives of II.

An eighth aspect of the tenth embodiment is related to the seventh aspect further comprising oxidizing the equilibrium mixture of phosphite isomer derivatives of II to obtain the 3',5'-cyclic phosphate derivative II A ninth aspect of the tenth embodiment related to preparing the 3',5'-cyclic phosphate derivative II is directed to a process which comprises reacting the free purine nucleoside derivative VIII with a $R^7OP[N(^iPr)_2]_2$ in the presence of 4,5-dicyanoimidazole to obtain a phosphite derivative of II wherein the phosphite derivative of II comprises a mixture of isomers and $R^5$ is H, $R^6$ is $CH_3$, $R^7$ is Me, $^iPr$, $^cBu$, or $^cPn$, $R^8$ is OMe, OEt, or $O^iPr$, $R^9$ is $NH_2$, X is F, and Z is N.

and equilibrating the phosphite derivative of II to obtain an equilibrium mixture of phosphite isomer derivatives of II.

A tenth aspect of the tenth embodiment is related to the ninth aspect further comprising oxidizing the equilibrium mixture of phosphite isomer derivatives of II to obtain the 3',5'-cyclic phosphate derivative II An eleventh aspect of the tenth embodiment related to preparing the 3',5'-cyclic phosphate derivative II is directed to a process which comprises reacting the free purine nucleoside derivative VIII with a $^iPrOP[N(^iPr)_2]_2$ in the presence of 4,5-dicyanoimidazole to obtain a phosphite derivative of II

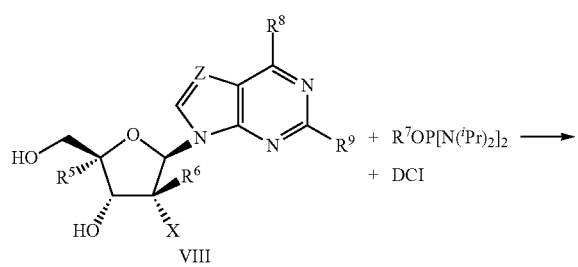
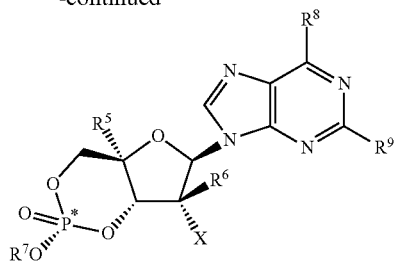

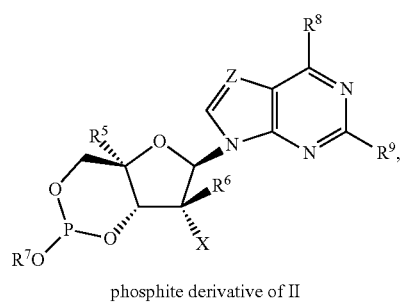

phosphite derivative of II wherein the phosphite derivative of II comprises a mixture of isomers and $R^5$ is H, $R^6$ is $CH_3$, $R^7$ is Me, $^iPr$, $^cBu$, or $^cPn$, $R^8$ is OMe, OEt, or $O^iPr$, $R^9$ is $NH_2$, X is F, and Z is N;

and equilibrating the phosphite derivative of II to obtain an equilibrium mixture of phosphite isomer derivatives of II.

A twelfth aspect of the tenth embodiment is related to the eleventh aspect further comprising oxidizing the equilibrium mixture of phosphite isomer derivatives of II to obtain a disasteromeric mixture of the 3',5'-cyclic phosphate derivatives s shown below.

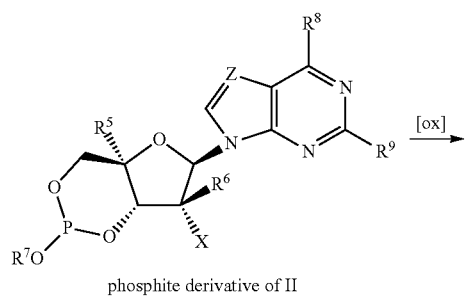

phosphite derivative of II

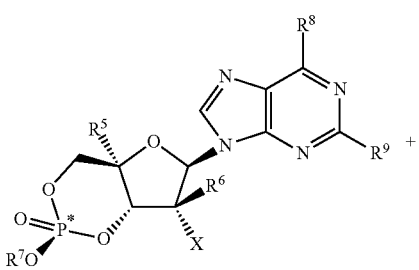

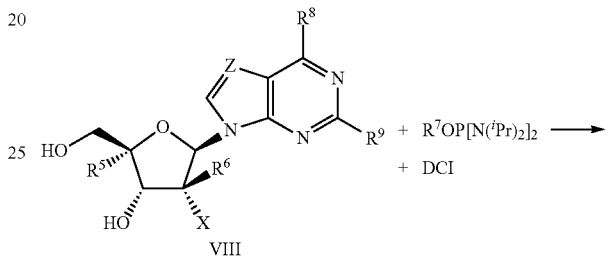

A thirteenth aspect of the tenth embodiment related to preparing the 3',5'-cyclic phosphate derivative II is directed to a process which comprises reacting the free purine nucleoside derivative VIII with a $^iPrOP[N(^iPr)_2]_2$ in the presence of 4,5-dicyanoimidazole to obtain a phosphite derivative of II

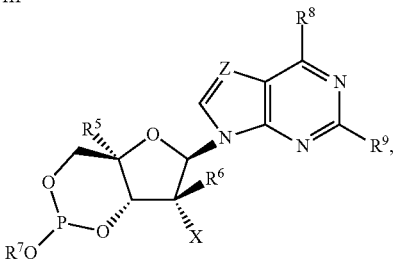

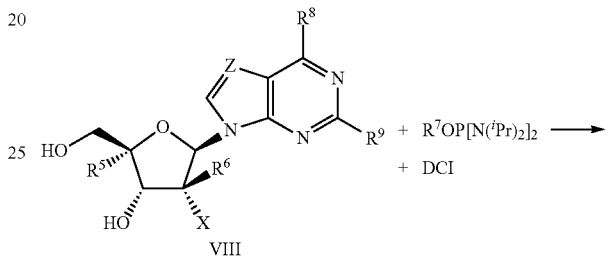

phosphite derivative of II wherein the phosphite derivative of II comprises a mixture of isomers and $R^5$ is H, $R^6$ is $CH_3$, $R^7$ is Me, $^iPr$, $^cBu$, or $^cPn$, $R^8$ is OMe, OEt, or $O^iPr$, $R^9$ is $NH_2$, X is F, and Z is N;

and equilibrating the phosphite derivative of II in a solution at a temperature to obtain an equilibrium mixture of phosphite isomer derivatives of II. The above-noted solution comprises a polar solvent, a non-polar solvent, and mixtures thereof. Examples of polar solvents include, but are not limited to, water, dimethylsulfoxide, N,N-dimethylformamide, hexamethylphosphoramidate, acetonitrile, ethyl acetate, tetrahydrofuran, etc. and mixtures thereof. Examples of non-polar solvents include, but are not limited to, hexane, heptane, benzene, toluene, methylene chloride, chloroform, etc., and mixtures thereof. The temperature can range over the entire available temperature range for the solution, which entails a temperature range where the solution does not solidify due to freezing, the solution does not evaporate due to boiling, or the solution components do not decompose. The solution temperature is determined experimentally based on the equilibrium position of the mixture of isomers of the phosphite derivative of II. For instance, if the cis isomer is desired, then the desirable temperature or temperature range is one where the mole (or molar) ratio of the cis-isomer to the trans-isomer is at an acceptable maximum.

A fourteenth aspect of the tenth embodiment is related to the eleventh aspect further comprising optionally isolating the equilibrium mixture as a solid and contacting an oxidizing agent and the equilibrium mixture of phosphite isomer derivatives of II in a solution comprising an organic solvent to obtain the 3',5'-cyclic phosphate derivatives s shown below.

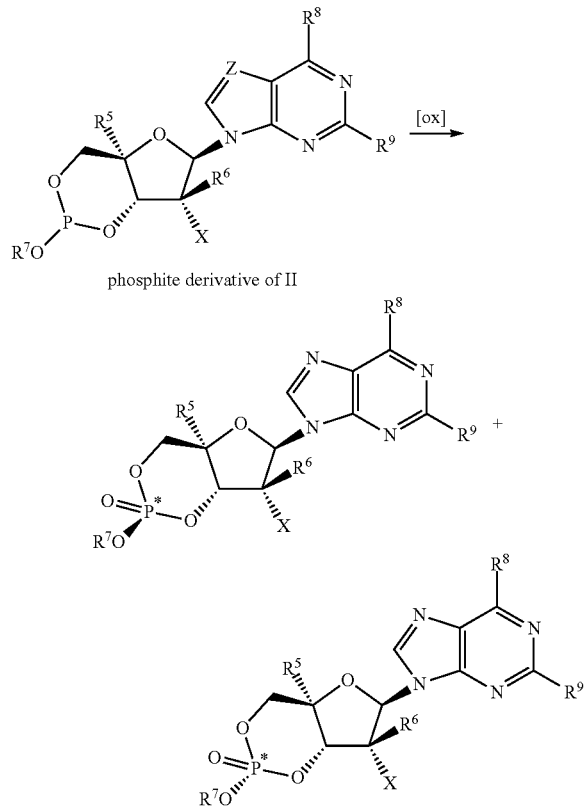

phosphite derivative of II

In a preferred aspect, the mole ratio of oxidizing agent to the phosphite derivative II ranges from about 0.9 to about 1.5, preferably from about 0.9 to about 1.2, more preferably from about 0.9 to about 1.1, most preferably the mole ratio of oxidizing agent to the phosphite derivative II is about 1. In a preferred aspect, the solution comprises tetrahydrofuran ("THF"), and the oxidizing agent comprises iodine ($I_2$). In a first preferred aspect, the solution comprises THF, pyridine ("pyr"), and water in at least about one-molar equivalent relative to the phosphite derivative of II. In a second preferred aspect, the solution comprises about 60 v/v % to about 80 v/v % of THF and about 39 v/v % to about 17 v/v % of pyr, and about 1 v/v % to about 3 v/v % of water, with the proviso that the amount of water is at least about one-molar equivalent relative to the phosphite derivative of II. In a second preferred aspect, the solution comprises about 65 v/v % to about 75 v/v % of THF and about 34 v/v % to about 22 v/v % of pyr, and about 1 v/v % to about 3 v/v % of water, with the proviso that the amount of water is at least about one-molar equivalent relative to the phosphite derivative of II. In a third preferred aspect, the solution comprises about 70 v/v % of THF, about 28 v/v % of pyr, and about 2 v/v % of water, with the proviso that the amount of water is at least about one-molar equivalent relative to the phosphite derivative of II.

A fifteenth aspect of the tenth embodiment related to preparing the compound II is directed to a process which comprises reacting the free purine nucleoside derivative VIII with a P(V)-reagent.

A sixteenth aspect of the tenth embodiment related to preparing the compound II is directed to a process which comprises reacting the free purine nucleoside derivative VIII with a P(V)-reagent and an amine reagent.

A seventeenth aspect of the tenth embodiment related to preparing the compound II is directed to a process which comprises reacting the free purine nucleoside derivative VIII with a P(V)-reagent selected from among $P(O)(Lv)_3$, $R^7OP(O)(Lv)_2$, $R^7OP(O)(Lv)(N(C_{1-6}\ alkyl)_2)$, $R^7OP(O)[N(C_{1-6}\ alkyl)_2]_2$ and an amine reagent.

An eighteenth aspect of the tenth embodiment related to preparing the compound II is directed to a process which comprises reacting the free purine nucleoside derivative VIII with a $R^7OP(O)(Lv)_2$ and an amine reagent.

A nineteenth aspect of the tenth embodiment related to preparing the compound II is directed to a process which comprises reacting the free purine nucleoside derivative VIII with a $R^7OP(O)(Lv)_2$ and an amine reagent, wherein $R^5$ is H, $R^6$ is $CH_3$, $R^7$ is Me, $^iPr$, $^cBu$, or $^cPn$, $R^8$ is OMe, OEt, or $O^iPr$, $R^9$ is $NH_2$, X is F, and Z is N.

A twentieth aspect of the tenth embodiment related to preparing the 3',5'-cyclic phosphate derivative II is directed to a process which comprises reacting the free purine nucleoside derivative VIII with a $R^7OP(O)(Lv)_2$ and an amine reagent, wherein $R^5$ is H, $R^6$ is $CH_3$, $R^7$ is Me, $^iPr$, $^cBu$, or $^cPn$, $R^8$ is OMe, OEt, $O^iPr$, $R^9$ is $NH_2$, X is F, and Z is N, Lv is Cl, and the amine reagent comprises triethyl amine and N-methylimidazole.

A tenth embodiment is directed to a phosphite derivative of II represented by the following formula:

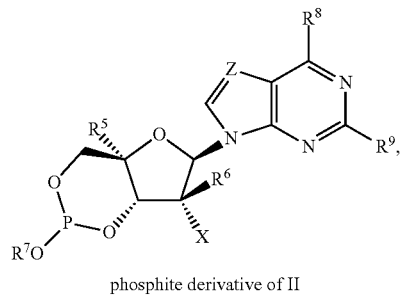

phosphite derivative of II wherein the phosphite derivative of II where $R^5$, $R^6$, $R^7$, $R^8$, $R^9$, X, and Z are as defined herein. In a preferred aspect, the phosphite derivative of II has $R^5$ is H, $R^6$ is $CH_3$, $R^7$ is lower alkyl or lower cycloalkyl, $R^8$ is a —O(lower alkyl), —O(lower cycloalkyl), or —OBn, $R^9$ is $NH_2$, X is F, and Z is N. In an additionally preferred aspect, the phosphite derivative of II has $R^5$ is H, $R^6$ is $CH_3$, $R^7$ is Me, $^iPr$, $^cBu$, or $^cPn$, $R^8$ is OMe, OEt, or $O^iPr$, $R^9$ is $NH_2$, X is F, and Z is N.

An eleventh embodiment is directed to a process for preparing the compound I or the compound II, where for both $R^8$ is OH, said process comprising reacting a beta-nucleoside derivative VI with a nucleophilic reagent to produce a 6-X'''-substituted nucleoside VII';

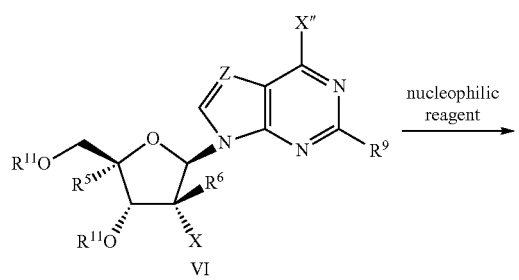

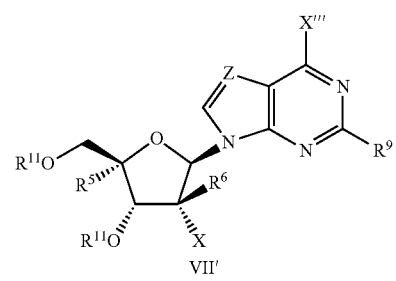

deprotecting the 6-X'''-substituted nucleoside VII' to produce a 6-X'''-substituted nucleoside IX;

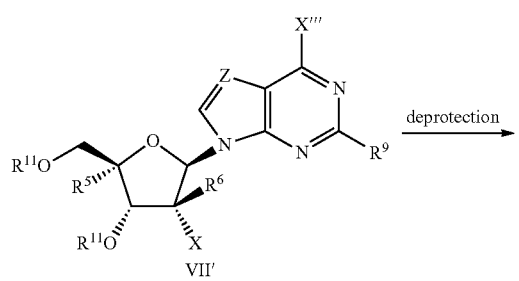

converting the 6-X'''-substituted nucleoside IX to obtain a 6-X'''-phosphoramidate nucleoside I' or a 6-X'''-cyclic phosphate nucleotide II'

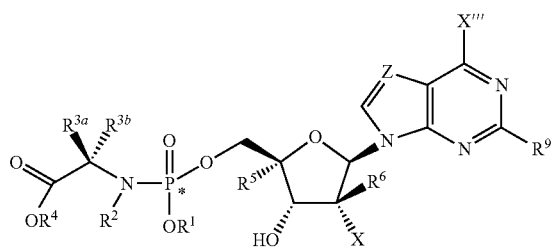

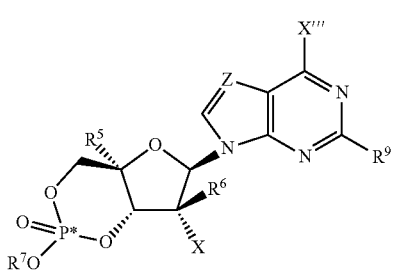

converting the 6-X'''-phosphoramidate nucleoside I' or the 6-X'''-cyclic phosphate nucleotide II' to the phosphoramidate nucleoside I (where $R^8$=OH) or the cyclic phosphate nucleotide II (where $R^8$=OH), wherein for the compounds VI, VII', IX, I', or II', $R^1$, $R^2$, $R^{3a}$, $R^{3b}$, $R^4$, $R^5$, $R^6$, $R^7$, $R^9$, X and Z are as defined herein above, $R^{11}$ is a protecting group (preferably benzoyl or 4-chloro-benzoyl, and more preferably 4-chloro-benzoyl), X'' is a leaving group, and X''' is a group capable of being converted to OH.

A first aspect of the eleventh embodiment is directed to a process for preparing a compound I, where $R^8$ is OH, said process comprising reacting the beta-nucleoside derivative VI with a nucleophilic reagent to produce a 6-X'''-substituted nucleoside VII';

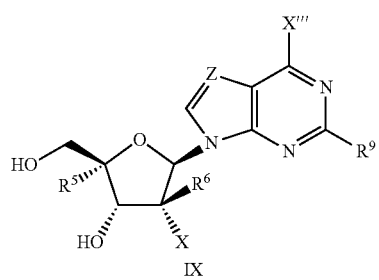

deprotecting a 6-X'''-substituted nucleoside VII' to produce a 6-X'''-substituted nucleoside IX;

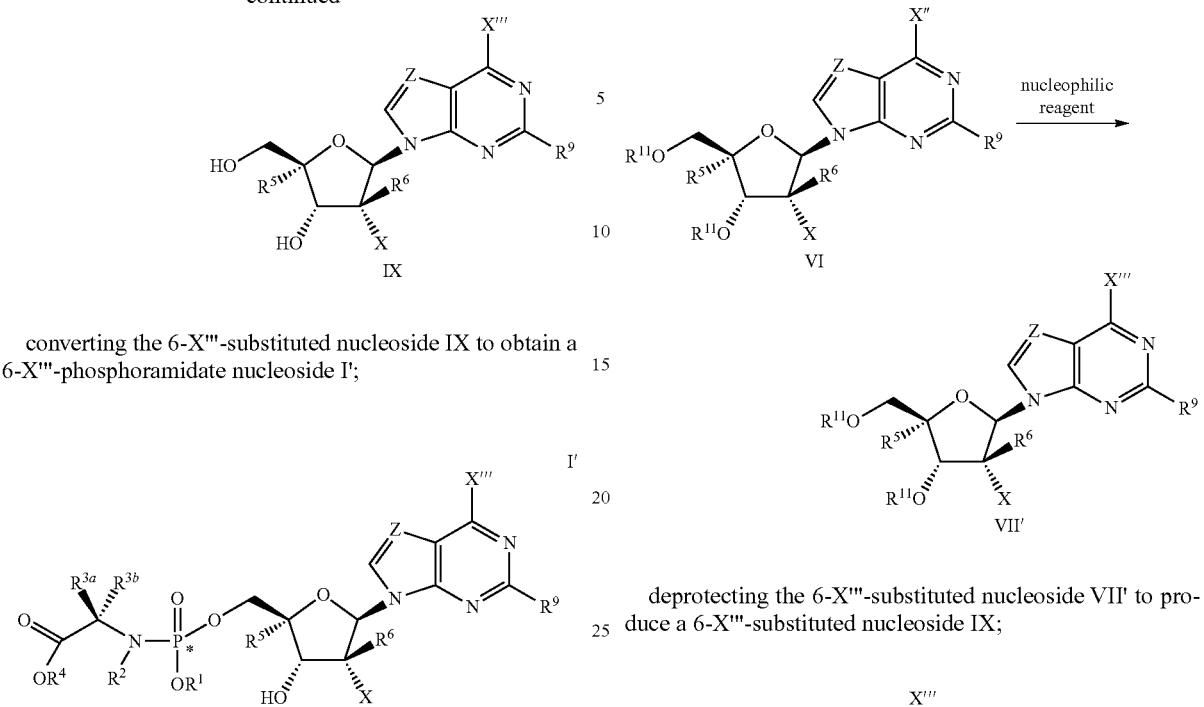

converting the 6-X'''-substituted nucleoside IX to obtain a 6-X'''-phosphoramidate nucleoside I';

converting the 6-X'''-phosphoramidate nucleoside I' to the phosphoramidate nucleoside I (where $R^8$=OH);

wherein for the compounds VI, VII', IX, I', or II', $R^1$, $R^2$, $R^{3a}$, $R^{3b}$, $R^4$, $R^5$, $R^6$, $R^7$, $R^9$, X and Z are as defined herein above, $R^{11}$ is a protecting group (preferably benzoyl or 4-chloro-benzoyl, and more preferably 4-chloro-benzoyl), X" is a leaving group, and X"" is a group capable of being converted to OH;

wherein the reacting can be performed in a solvent comprising ethanol and at a temperature that ranges from about 0° C. up to about 78° C. Preferably, the temperature ranges from about 25° C. to about 75° C. More preferably, the temperature ranges from about 40° C. to about 60° C. Most preferably, the temperature is about 50° C. The deprotecting can occur as described herein.

A second aspect of the eleventh embodiment is directed to a process for preparing a compound I, where $R^8$ is OH, said process comprising reacting a beta-nucleoside derivative VI with a nucleophilic reagent to produce a 6-X'''-substituted nucleoside VII';

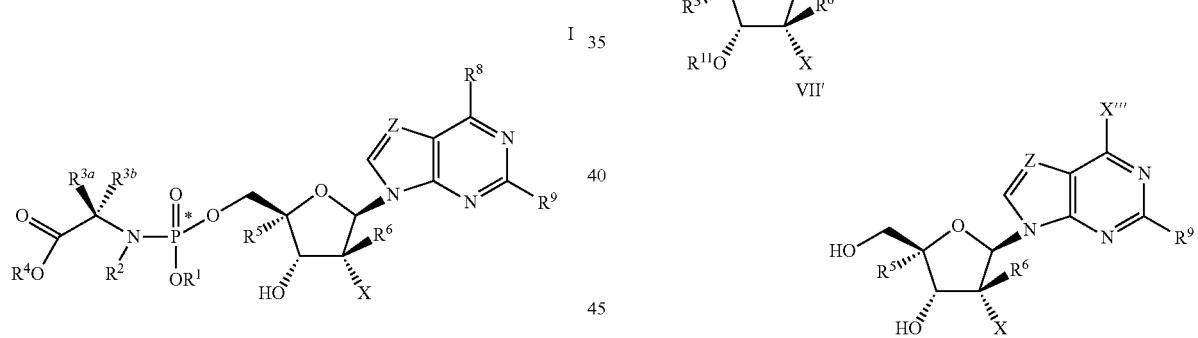

deprotecting the 6-X'''-substituted nucleoside VII' to produce a 6-X'''-substituted nucleoside IX;

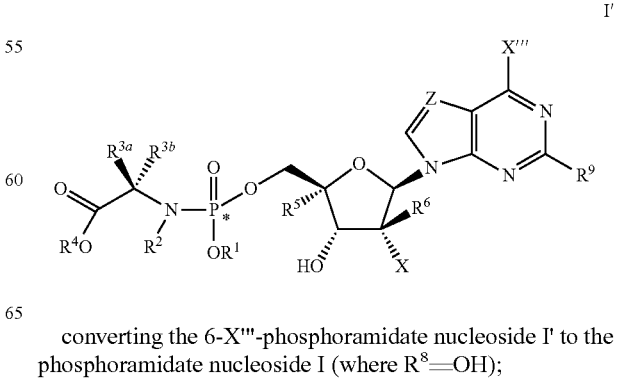

converting the 6-X'''-substituted nucleoside IX to obtain a 6-X'''-phosphoramidate nucleoside I';

converting the 6-X'''-phosphoramidate nucleoside I' to the phosphoramidate nucleoside I (where $R^8$=OH);

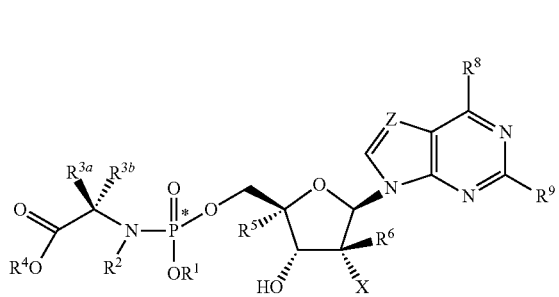

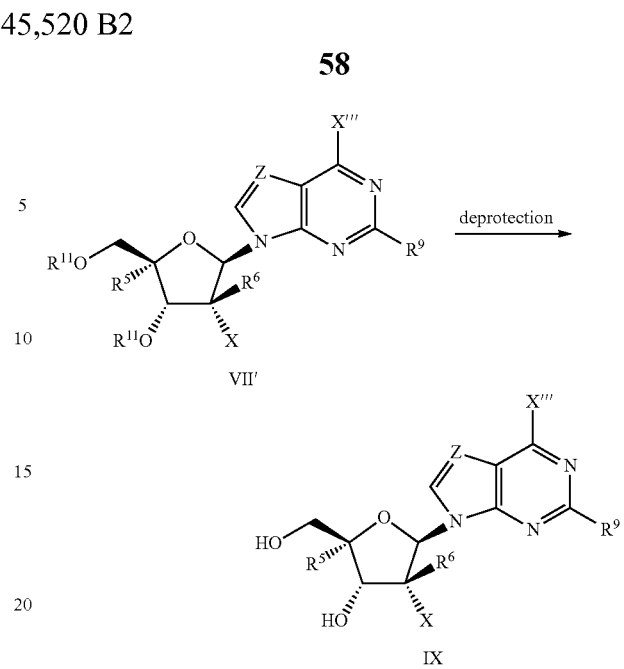

wherein for the compounds VI, VII', IX, I', or II', $R^1$, $R^2$, $R^{3a}$, $R^{3b}$, $R^4$, $R^5$, $R^6$, $R^7$, $R^9$, X and Z are as defined herein above, $R^{11}$ is a protecting group (preferably benzoyl or 4-chloro-benzoyl, and more preferably 4-chloro-benzoyl), X" is a leaving group, and X''' is a group capable of being converted to OH;

wherein the reacting can be performed in a solvent comprising ethanol and at a temperature that ranges from about 0° C. up to about 78° C. Preferably, the temperature ranges from about 25° C. to about 75° C. More preferably, the temperature ranges from about 40° C. to about 60° C. Most preferably, the temperature is about 50° C. The group capable of being converted to OH (X''') is —OBn, an —O-silyl, or an —O-allyl. The deprotecting can occur as described herein.

A third aspect of the eleventh embodiment is directed to a process for preparing a compound I, where $R^8$ is OH, said process comprising reacting a beta-nucleoside derivative VI with a nucleophilic reagent to produce a 6-X'''-substituted nucleoside VII';

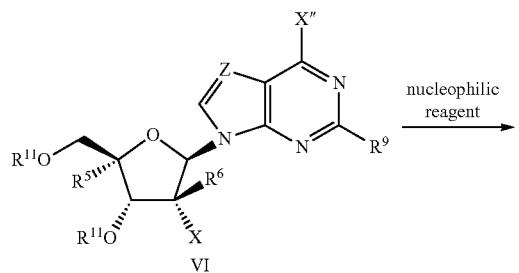

deprotecting the 6-X'''-substituted nucleoside VII' to produce a 6-X'''-substituted nucleoside IX;

converting the 6-X'''-substituted nucleoside IX to obtain a 6-X'''-phosphoramidate nucleoside I';

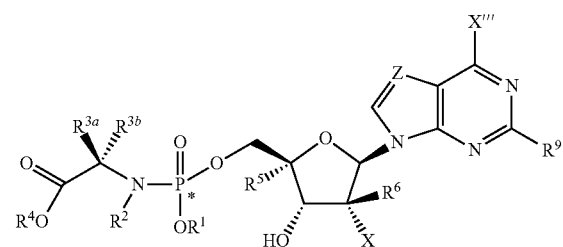

converting the 6-X'''-phosphoramidate nucleoside I' to the phosphoramidate nucleoside I (where $R^8$=OH);

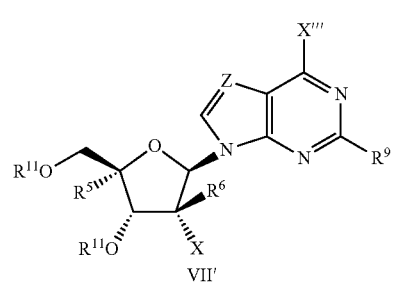

wherein for the compounds represented by formulas VI, VII', IX, I', or II', $R^1$ is phenyl, $R^2$ is hydrogen, $R^{3a}$ is hydrogen, $R^{3b}$ is $CH_3$, $R^4$ is -lower alkyl or -lower cycloalkyl, $R^5$ is H, $R^6$ is $CH_3$, $R^9$ is $NH_2$, $R^{11}$ is a protecting group (preferably benzoyl or 4-chloro benzoyl), X is F, X" is Cl, X''' is —OBn, —O-silyl, or —O-allyl, and Z is N;

wherein the reacting can be performed in a solvent comprising ethanol and at a temperature that ranges from about 0° C. up to about 78° C. Preferably, the temperature ranges from about 25° C. to about 75° C. More preferably, the temperature ranges from about 40° C. to about 60° C. Most preferably, the temperature is about 50° C. The group capable of being converted to OH (X''') is —OBn, an —O-silyl, or an —O-allyl. The deprotecting can occur as described herein.

A fourth aspect of the eleventh embodiment is directed to a process for preparing a compound I, where $R^8$ is OH, said process comprising reacting a beta-nucleoside derivative VI with a nucleophilic reagent to produce a 6-X'''-substituted nucleoside VII';

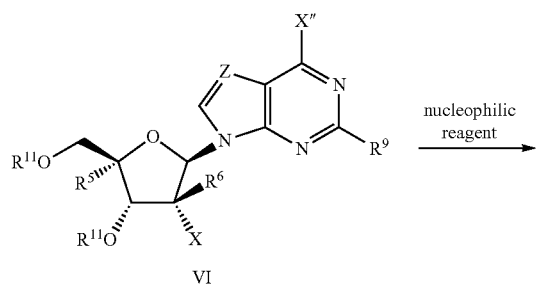

VI wherein X''' is a group capable of being converted to OH;

deprotecting the 6-X'''-substituted nucleoside VII' to produce a 6-X'''-substituted nucleoside IX;

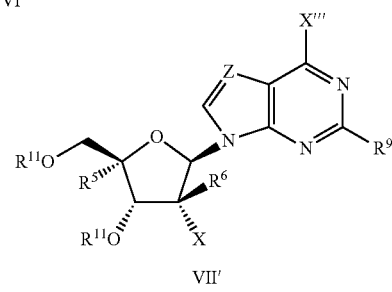

VII'

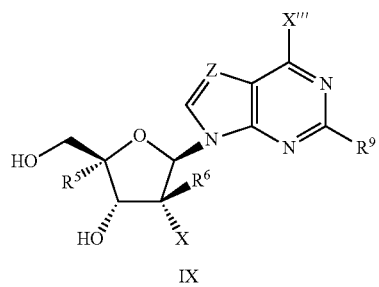

IX converting the 6-X'''-substituted nucleoside IX to obtain a 6-X'''-phosphoramidate nucleoside I';

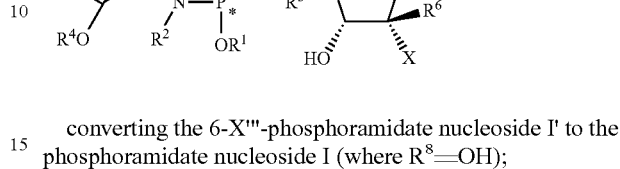

I' converting the 6-X'''-phosphoramidate nucleoside I' to the phosphoramidate nucleoside I (where $R^8$=OH);

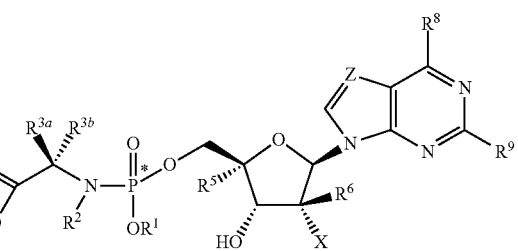

I wherein for the compounds represented by formulas VI, VII', IX, I', or II', $R^1$ is phenyl, $R^2$ is hydrogen, $R^{3a}$ is hydrogen, $R^{3b}$ is $CH_3$, $R^4$ is -lower alkyl or -lower cycloalkyl, $R^5$ is H, $R^6$ is $CH_3$, $R^9$ is $NH_2$, $R^{11}$ is a protecting group (preferably benzoyl or 4-chloro-benzoyl), X is F, X'' is Cl, X''' is —OBn or —O-allyl, and Z is N;

wherein the reacting can be performed in a solvent comprising ethanol and at a temperature that ranges from about 0° C. up to about 78° C. Preferably, the temperature ranges from about 25° C. to about 75° C. More preferably, the temperature ranges from about 40° C. to about 60° C. Most preferably, the temperature is about 50° C. The deprotecting can occur as described herein.

A fifth aspect of the eleventh embodiment is directed to a process for preparing a compound I, where $R^8$ is OH, said process comprising reacting a beta-nucleoside derivative VI with a nucleophilic reagent to produce a 6-X'''-substituted nucleoside VII';

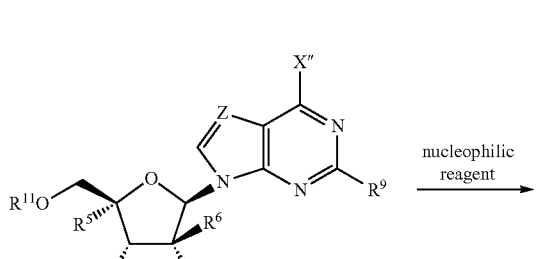

VI

-continued

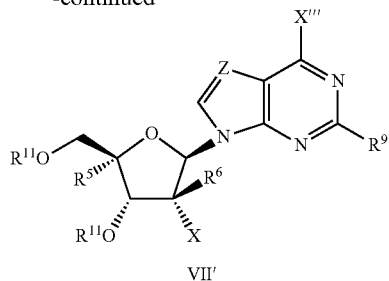

VII' wherein X''' is a group capable of being converted to OH; deprotecting the 6-X'''-substituted nucleoside VII' to produce a 6-X'''-substituted nucleoside IX;

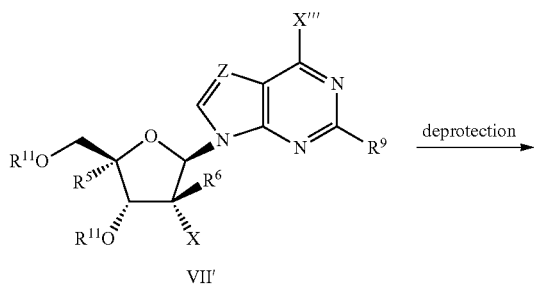

VII' converting the 6-X'''-substituted nucleoside IX to obtain a 6-X'''-phosphoramidate nucleoside I';

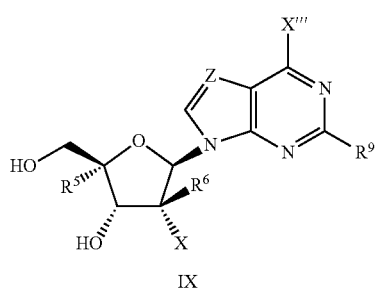

I' converting the 6-X'''-phosphoramidate nucleoside I' to the phosphoramidate nucleoside I (where $R^8$=OH);

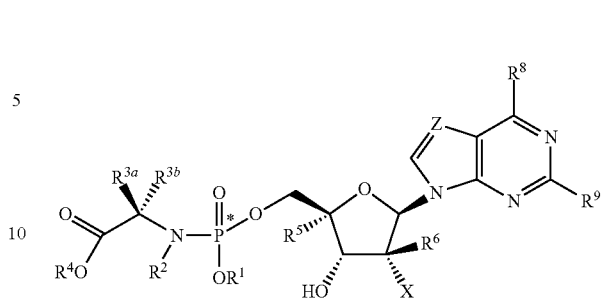

I wherein for the compounds represented by formulas VI, VII', IX, I', or II', $R^1$ is phenyl, $R^2$ is hydrogen, $R^{3a}$ is hydrogen, $R^{3b}$ is $CH_3$, $R^4$ is -Me, -Et, -$^nPr$, -$^iPr$, -$^cPn$, or -$^cHx$, $R^5$ is H, $R^6$ is $CH_3$, $R^9$ is $NH_2$, $R^{11}$ is a protecting group (preferably benzoyl or substituted benzoyl), X is F, X'' is Cl, X''' is —OBn or —O-allyl, and Z is N;

wherein the reacting can be performed in a solvent comprising ethanol and at a temperature that ranges from about 0° C. up to about 78° C. Preferably, the temperature ranges from about 25° C. to about 75° C. More preferably, the temperature ranges from about 40° C. to about 60° C. Most preferably, the temperature is about 50° C. The deprotecting can occur as described herein.

A twelfth embodiment is directed to a process for preparing a compound I or compound II: said process comprising:

(a-1) stereoselective reduction of a protected ribonolactone III using a hydride reducing agent

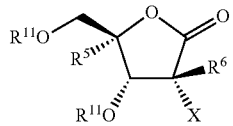

III to provide a beta-lactol derivative of IV;

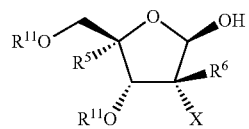

IV (b-1) stereoselective conversion of the lactol derivative using a reagent to obtain an anomeric alpha-derivative V;

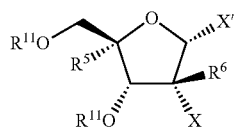

V (c-1) stereoselective coupling of the anomeric alpha-derivative with a purine base or a derivatized purine base using a basic reagent to produce a beta-nucleoside derivative VI;

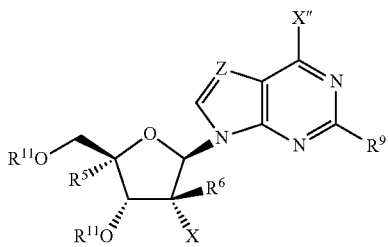

VI (d-1) reacting the beta-nucleoside derivative with a nucleophilic reagent to produce a 6-substituted nucleoside VII;

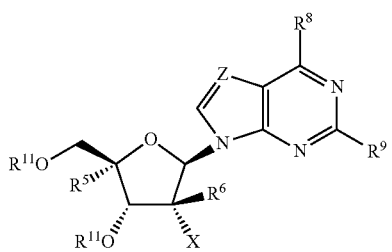

VII (e-1) deprotecting the 6-substituted nucleoside to produce a free purine nucleoside derivative VIII

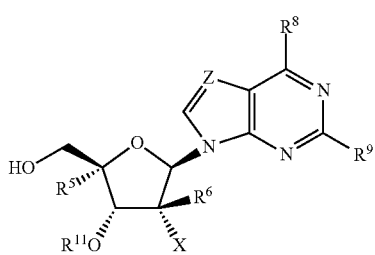

VIII (f-1) converting the free purine nucleoside derivative to its corresponding 5'-phosphoramidate derivative I or (g-1) converting the free purine nucleoside derivative to its corresponding 3',5'-cyclic phosphate derivative II; or (d-2) reacting the beta-nucleoside derivative with a nucleophilic reagent to produce a free purine nucleoside derivative VIII;

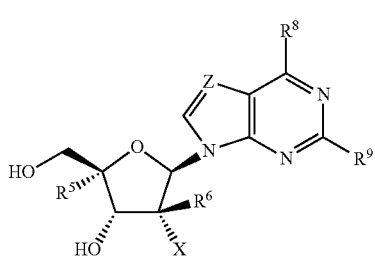

VIII (f-2) converting the free purine nucleoside derivative to its corresponding 5'-phosphoramidate derivative I or (g-2) converting the free purine nucleoside derivative to its corresponding 3',5'-cyclic phosphate derivative II; or in the alternative for the preparation of the compound I or the compound II, where for both $R^8$ is OH, (d-3) reacting the beta-nucleoside derivative VI with a nucleophilic reagent to produce a 6-X'''-substituted nucleoside VII';

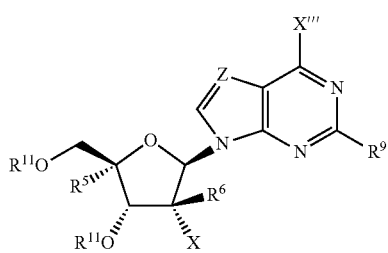

VII'

(h-3) deprotecting the 6-X'''-substituted nucleoside VII' to produce a 6-X'''-substituted nucleoside VIII';

wherein X''' is a group capable of being converted to OH;

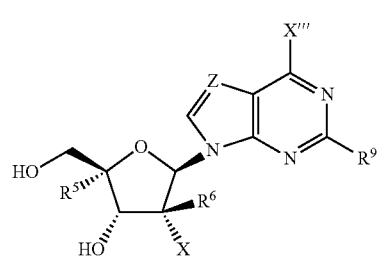

VIII'

(i-3) converting the 6-X'''-substituted nucleoside VIII' to obtain a 6-X'''-phosphoramidate nucleoside I' or a 6-X'''-cyclic phosphate nucleotide II'

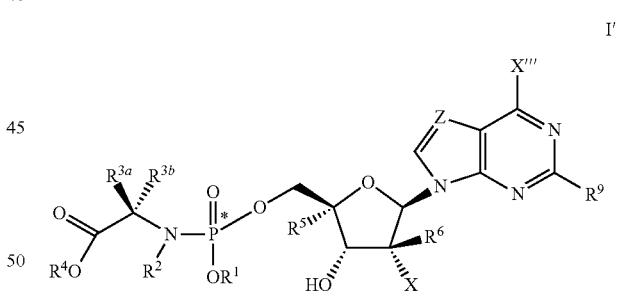

I'

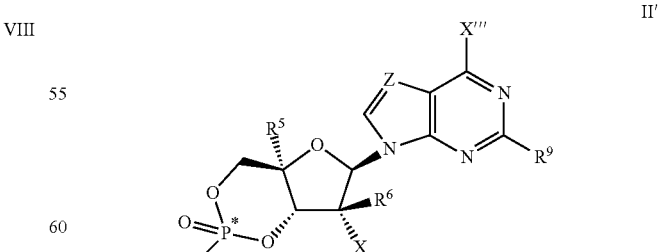

II'

(j-3) converting the 6-X'''-phosphoramidate nucleoside I' or the 6-X'''-cyclic phosphate nucleotide II' to the phosphoramidate nucleoside I (where $R^8$=OH) or the cyclic phosphate nucleotide II (where $R^8$=OH), wherein X' is a leaving group;
wherein X" is a leaving group;
wherein $R^{11}$ is a protecting group; and
X''' is a group capable of being converted to —OH.

Utility

Compounds prepared by the processes disclosed herein are useful for the treatment of any condition the result of an infection by any one of the following viral agents: hepatitis C virus, West Nile virus, yellow fever virus, dengue virus, rhinovirus, polio virus, hepatitis A virus, bovine viral diarrhea virus and Japanese encephalitis virus.

Dosage, Administration, and Use

In a thirteenth embodiment, the invention is related to a composition for the treatment and/or prophylaxis of any of the viral agents using compound I or II. Possible viral agents include, but are not limited to: hepatitis C virus, hepatitis B virus, Hepatitis A virus, West Nile virus, yellow fever virus, dengue virus, rhinovirus, polio virus, bovine viral diarrhea virus, Japanese encephalitis virus, or those viruses belonging to the groups of Pestiviruses, hepaciviruses, or flavaviruses. In the fourteenth embodiment, a preferred compound of formula I is represented by compound 11, while a preferred compound of formula II is represented by compound 17, more preferably $R_P$-17.

An aspect of this embodiment is directed to a composition for the treatment of any of the viral agents disclosed herein said composition comprising a pharmaceutically acceptable medium selected from among an excipient, carrier, diluent, and equivalent medium and compound I or II.

The compound I or II may be independently formulated in a wide variety of oral administration dosage forms and carriers. Oral administration can be in the form of tablets, coated tablets, hard and soft gelatin capsules, solutions, emulsions, syrups, or suspensions. The compound I or II is efficacious when administered by suppository administration, among other routes of administration. The most convenient manner of administration is generally oral using a convenient daily dosing regimen which can be adjusted according to the severity of the disease and the patient's response to the antiviral medication.

The compound I or II, as well as their pharmaceutically acceptable salts, together with one or more conventional excipients, carriers, or diluents, may be placed into the form of pharmaceutical compositions and unit dosages. The pharmaceutical compositions and unit dosage forms may be comprised of conventional ingredients in conventional proportions, with or without additional active compounds and the unit dosage forms may contain any suitable effective amount of the active ingredient commensurate with the intended daily dosage range to be employed. The pharmaceutical compositions may be employed as solids, such as tablets or filled capsules, semisolids, powders, sustained release formulations, or liquids such as suspensions, emulsions, or filled capsules for oral use; or in the form of suppositories for rectal or vaginal administration. A typical preparation will contain from about 5% to about 95% active compound or compounds (w/w).

The compound I or II can be administered alone but will generally be administered in admixture with one or more suitable pharmaceutical excipients, diluents or carriers selected with regard to the intended route of administration and standard pharmaceutical practice.

A pharmaceutically acceptable salt form of an active ingredient may also initially confer a desirable pharmacokinetic property on the active ingredient which were absent in the non-salt form, and may even positively affect the pharmacodynamics of the active ingredient with respect to its therapeutic activity in the body.

Solid form preparations include, for example, powders, tablets, pills, capsules, suppositories, and dispersible granules. A solid carrier may be one or more substances which may also act as diluents, flavoring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. Suitable carriers include but are not limited to magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. Solid form preparations may contain, in addition to the active component, colorants, flavors, stabilizers, buffers, artificial and natural sweeteners, dispersants, thickeners, solubilizing agents, and the like. Examples of solid formulations are exemplified in EP 0524579; U.S. Pat. No. 6,635,278; US 2007/0099902; U.S. Pat. No. 7,060,294; US 2006/0188570; US 2007/0077295; US 2004/0224917; U.S. Pat. No. 7,462,608; US 2006/0057196; U.S. Pat. No. 6,267,985; U.S. Pat. No. 6,294,192; U.S. Pat. No. 6,569,463; U.S. Pat. No. 6,923,988; US 2006/0034937; U.S. Pat. No. 6,383,471; U.S. Pat. No. 6,395,300; U.S. Pat. No. 6,645,528; U.S. Pat. No. 6,932,983; US 2002/0142050; US 2005/0048116; US 2005/0058710; US 2007/0026073; US 2007/0059360; and US 2008/0014228, each of which is incorporated by reference.

Liquid formulations also are suitable for oral administration include liquid formulation including emulsions, syrups, elixirs and aqueous suspensions. These include solid form preparations which are intended to be converted to liquid form preparations shortly before use. Examples of liquid formulation are exemplified in U.S. Pat. Nos. 3,994,974; 5,695,784; and 6,977,257. Emulsions may be prepared in solutions, for example, in aqueous propylene glycol solutions or may contain emulsifying agents such as lecithin, sorbitan monooleate, or acacia. Aqueous suspensions can be prepared by dispersing the finely divided active component in water with viscous material, such as natural or synthetic gums, resins, methylcellulose, sodium carboxymethylcellulose, and other well known suspending agents.

The compound I or II may be independently formulated for administration as suppositories. A low melting wax, such as a mixture of fatty acid glycerides or cocoa butter is first melted and the active component is dispersed homogeneously, for example, by stirring. The molten homogeneous mixture is then poured into convenient sized molds, allowed to cool, and to solidify.

The compound I or II may be independently formulated for vaginal administration. Pessaries, tampons, creams, gels, pastes, foams or sprays containing in addition to the active ingredient such carriers as are known in the art to be appropriate. Certain of these formulations may also be used in conjunction with a condom with or without a spermicidal agent.

Suitable formulations along with pharmaceutical carriers, diluents and excipients are described in *Remington: The Science and Practice of Pharmacy* 1995, edited by E. W. Martin, Mack Publishing Company, 19th edition, Easton, Pa., which is hereby incorporated by reference. A skilled formulation scientist may modify the formulations within the teachings of the specification to provide numerous formulations for a particular route of administration without rendering the compositions unstable or compromising their therapeutic activity.

Additionally, the purified compound I or II may be independently formulated in conjunction with liposomes or micelles. As to liposomes, it is contemplated that the purified compounds can be formulated in a manner as disclosed in U.S. Pat. No. 5,013,556; U.S. Pat. Nos. 5,213,804; 5,225,212; 5,891,468; 6,224,903; 6,180,134; 5,192,549; 5,316,771; 4,797,285; 5,376,380; 6,060,080; 6,132,763; 6,653,455; 6,680,068; 7,060,689; 7,070,801; 5,077,057; 5,277,914; 5,549,910; 5,567,434; 5,077,056; 5,154,930; 5,736,155; 5,827,533; 5,882,679; 6,143,321; 6,200,598; 6,296,870; 6,726,925; and 6,214,375, each of which is incorporated by reference. As to micelles, it is contemplated that the purified compounds can be formulated in a manner as disclosed in U.S. Pat. Nos. 5,145,684 and 5,091,188, both of which are incorporated by reference.

The fourteenth embodiment is directed to a use compound I or II in the manufacture of a medicament for the treatment of any condition the result of an infection by any one of the following viral agents: hepatitis C virus, West Nile virus, yellow fever virus, dengue virus, rhinovirus, polio virus, hepatitis A virus, bovine viral diarrhea virus and Japanese encephalitis virus. In the fourteenth embodiment, a preferred compound of formula I is represented by compound 11, while a preferred compound of formula II is represented by compound 17, more preferably $R_P$-17.

The term "medicament" means a substance used in a method of treatment and/or prophylaxis of a subject in need thereof, wherein the substance includes, but is not limited to, a composition, a formulation, a dosage form, and the like, comprising compound I or II. It is contemplated that the use of any of compound I or II in the manufacture of a medicament, for the treatment of any of the antiviral conditions disclosed herein, either alone or in combination with another compound. A medicament includes, but is not limited to, any one of the compositions contemplated by the thirteenth embodiment.

A fifteenth embodiment is directed to a method of treatment and/or prophylaxis in a subject in need thereof said method comprises administering a therapeutically effective amount of any of compound I or II to the subject. In the fifteenth embodiment, a preferred compound of formula I is represented by compound 11, while a preferred compound of formula II is represented by compound 17, more preferably $R_P$-17.

It is intended that a subject in need thereof is one that has any condition the result of an infection by any of the viral agents disclosed herein, which includes, but is not limited to, hepatitis C virus, West Nile virus, yellow fever virus, dengue virus, rhinovirus, polio virus, hepatitis A virus, bovine viral diarrhea virus or Japanese encephalitis virus, flaviviridae viruses or pestiviruses or hepaciviruses or a viral agent causing symptoms equivalent or comparable to any of the above-listed viruses.

The term "subject" means a mammal, which includes, but is not limited to, cattle, pigs, sheep, chicken, turkey, buffalo, llama, ostrich, dogs, cats, and humans, preferably the subject is a human. It is contemplated that in the method of treating a subject thereof of the fifteenth embodiment can be any of the compounds contemplated herein, either alone or in combination with another compound.

The term "therapeutically effective amount" as used herein means an amount required to reduce symptoms of the disease in an individual. The dose will be adjusted to the individual requirements in each particular case. That dosage can vary within wide limits depending upon numerous factors such as the severity of the disease to be treated, the age and general health condition of the patient, other medicaments with which the patient is being treated, the route and form of administration and the preferences and experience of the medical practitioner involved. For oral administration, a daily dosage of between about 0.001 and about 10 g, including all values in between, such as 0.001, 0.0025, 0.005, 0.0075, 0.01, 0.025, 0.050, 0.075, 0.1, 0.125, 0.150, 0.175, 0.2, 0.25, 0.5, 0.75, 1, 1.5, 2, 2.5, 3, 3.5, 4, 4.5, 5, 5.5, 6, 6.5, 7, 7.5, 8, 8.5, 9, and 9.5, per day should be appropriate in monotherapy and/or in combination therapy. A particular daily dosage is between about 0.01 and about 1 g per day, including all incremental values of 0.01 g (i.e., 10 mg) in between, a preferred daily dosage about 0.01 and about 0.8 g per day, more preferably about 0.01 and about 0.6 g per day, and most preferably about 0.01 and about 0.25 g per day, each of which including all incremental values of 0.01 g in between. Generally, treatment is initiated with a large initial "loading dose" to rapidly reduce or eliminate the virus following by a decreasing the dose to a level sufficient to prevent resurgence of the infection. One of ordinary skill in treating diseases described herein will be able, without undue experimentation and in reliance on personal knowledge, experience and the disclosures of this application, to ascertain a therapeutically effective amount of the compound I or salt thereof or the compound II or salt thereof for a given disease and patient.

Therapeutic efficacy can be ascertained from tests of liver function including, but not limited to protein levels such as serum proteins (e.g., albumin, clotting factors, alkaline phosphatase, aminotransferases (e.g., alanine transaminase, aspartate transaminase), 5'-nucleosidase, γ-glutaminyl-transpeptidase, etc.), synthesis of bilirubin, synthesis of cholesterol, and synthesis of bile acids; a liver metabolic function, including, but not limited to, carbohydrate metabolism, amino acid and ammonia metabolism. Alternatively the therapeutic effectiveness may be monitored by measuring HCV-RNA. The results of these tests will allow the dose to be optimized.

A first aspect of the fifteenth embodiment is directed to a method of treatment and/or prophylaxis in a subject in need thereof said method comprises administering to the subject a therapeutically effective amount of a compound represented by any of compound I (preferably compound 11) or II (preferably compound 17, more preferably $R_P$-17) and a therapeutically effective amount of another antiviral agent; wherein the administration is concurrent or alternative. It is understood that the time between alternative administration can range between 1-24 hours, which includes any sub-range in between including, 2, 3, 4, 5, 6, 7, 8, 9, 10, 11, 12, 13, 14, 15, 16, 17, 18, 19, 20, 21, 22, and 23 hours.

Examples of "another antiviral agent" include, but are not limited to: HCV NS3 protease inhibitors (see WO 2008010921, WO 2008010921, EP 1881001, WO 2007015824, WO 2007014925, WO 2007014926, WO 2007014921, WO 2007014920, WO 2007014922, US 2005267018, WO 2005095403, WO 2005037214, WO 2004094452, US 2003187018, WO 200364456, WO 2005028502, and WO 2003006490); HCV NS5B Inhibitors (see US 2007275947, US20072759300, WO2007095269, WO 2007092000, WO 2007076034, WO 200702602, US 2005-98125, WO 2006093801, US 2006166964, WO 2006065590, WO 2006065335, US 2006040927, US 2006040890, WO 2006020082, WO 2006012078, WO 2005123087, US 2005154056, US 2004229840, WO 2004065367, WO 2004003138, WO 2004002977, WO 2004002944, WO 2004002940, WO 2004000858, WO 2003105770, WO 2003010141, WO 2002057425, WO 2002057287, WO 2005021568, WO 2004041201, US 20060293306, US 20060194749, US 20060241064, U.S. Pat. No. 6,784,166, WO 2007088148, WO 2007039142, WO 2005103045, WO 2007039145, WO 2004096210, and WO 2003037895); HCV NS4 Inhibitors (see WO 2007070556 and WO 2005067900); HCV NS5a Inhibitors (see US 2006276511, WO 2006120252, WO 2006120251, WO 2006100310, WO 2006035061); Toll-like receptor agonists (seeWO 2007093901); and other inhibitors (see WO 2004035571, WO 2004014852, WO 2004014313, WO 2004009020, WO 2003101993, WO 2000006529); and compounds disclosed in U.S. patent application Ser. No. 12/053, 015, filed Mar. 21, 2008 (the contents of which are incorporated by reference), interferon-α, interferon-β, pegylated interferon-α, ribavirin, levovirin, viramidine, another nucleoside HCV polymerase inhibitor, a HCV non-nucleoside polymerase inhibitor, a HCV protease inhibitor, a HCV helicase inhibitor or a HCV fusion inhibitor.

When compound I or II is administered in combination with another antiviral agent the activity may be increased over the parent compound. When the treatment is combination therapy, such administration may be concurrent or sequential with respect to that of the nucleoside derivatives. "Concurrent administration" as used herein thus includes administration of the agents at the same time or at different times. Administration of two or more agents at the same time can be achieved by a single formulation containing two or more active ingredients or by substantially simultaneous administration of two or more dosage forms with a single active agent.

It will be understood that references herein to treatment extend to prophylaxis as well as to the treatment of existing conditions. Furthermore, the term "treatment" of a HCV infection, as used herein, also includes treatment or prophylaxis of a disease or a condition associated with or mediated by HCV infection, or the clinical symptoms thereof.

EXAMPLES

A further understanding of the disclosed embodiments will be appreciated by consideration of the following examples, which are only meant to be illustrative, and not limit the disclosed invention.

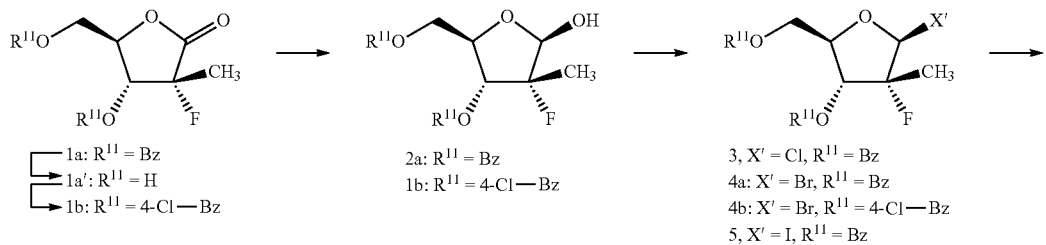

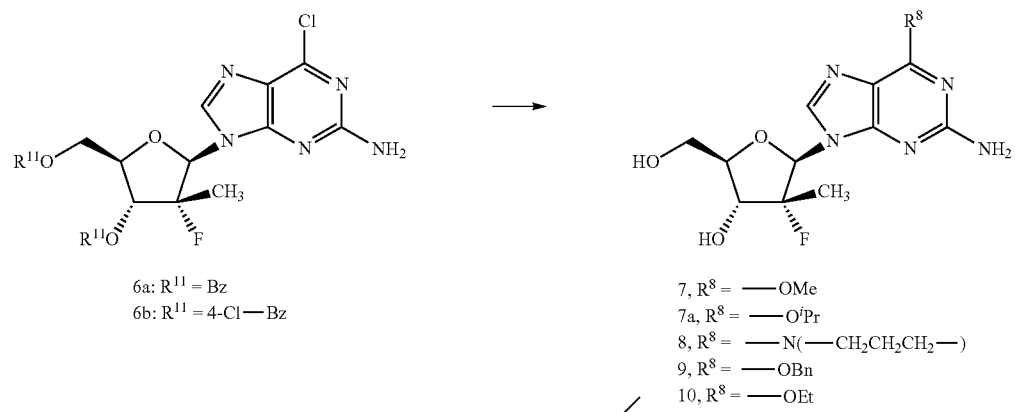

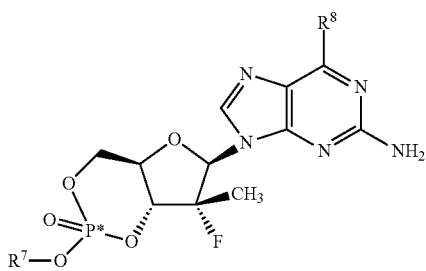
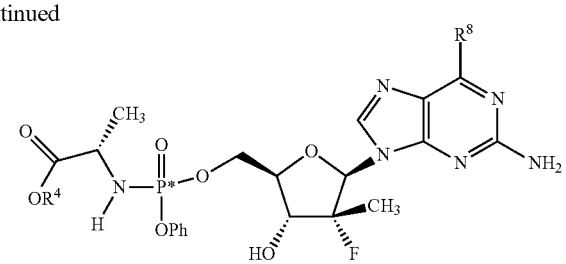

15: $R^7$ = Me, $R^8$ = —N(—CH$_2$CH$_2$CH$_2$—)
16: $R^7$ = Me, $R^8$ = —OEt
17: $R^7$ = $^i$Pr, $R^8$ = —OEt
23: $R^7$ = $^c$Bu, $R^8$ = —OMe
24: $R^7$ = $^c$Pn, $R^8$ = —OMe

11: $R^4$ = $^i$Pr, $R^8$ = —OMe
11a: $R^4$ = $^i$Pr, $R^8$ = —OEt
11b: $R^4$ = $^i$Pr, $R^8$ = —O$^i$Pr
12: $R^4$ = Me, $R^8$ = —N(—CH$_2$CH$_2$CH$_2$—)
13: $R^4$ = $^c$Pn, $R^8$ = —OBn
14: $R^4$ = $^c$Pn, $R^8$ = —OH

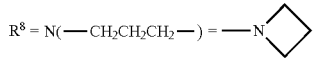

The use of the convergent glycosylation route to prepare 2'-deoxy-2'-fluoro-2'-C-methyl purine nucleosides and their corresponding nucleotide phosphoramidates came about with the development of the synthesis of 3,5-di-O-benzoyl-2-deoxy-2-fluoro-2-C-methylribonolactone (1a) (Chun, K.; Wang, P. Intl. Pat. Appl. WO 2006/031725). An alternative common intermediate is the 4-chlorobenzoyl analog 1a, which can be produced either by debenzoylation of 1a to form the intermediate lactone diol, 1a', followed by 4-chlorobenzoylation, or by substituting 4-chlorobenzoyl chloride directly to react with 1a'. An unexpected feature of the 3,5-di(4-chloro-benzoylated) intermediates is that they tend to have better crystalline properties, compared to the 3,5-di(benzoylated) intermediates, and so provides for an alternative means of purification in addition to chromatography.

After several attempts using Vorbrueggen-type Lewis acid mediated coupling and the ribonolactol 1-O-acetate of 3,5-di-O-benzoyl-2-deoxy-2-fluoro-2-C-methylribonolactone, we observed very low coupling yields and the undesired α-anomer was the major product. Mitsunobu coupling with the ribonolactol (2a/2b) did give the desired product but with no stereoselectivity and very difficult chromatographic separation resulting in isolated yields of 6-10% for this step alone and the method was not scaleable.

The preferred approach became the $S_N2$ type reaction using a halo-sugar and a salt of the purine base. Again, the challenge of this approach was how to obtain an α halo-sugar stereospecifically in high yield to take advantage the inversion of configuration expected with $S_N2$ type reactions. A typical method treats an anomeric mixture of the 1-O-acetate of a sugar with HCl or HBr in acetic acid. However, this method resulted in production of unfavorable anomeric mixtures. Reducing the lactone (e.g., with LiAlH(t-BuO)$_3$ or Red-Al) initially generates at 2:1 ratio of β/α anomers but after initial purification through a silica gel filtration column, the resulting oil slowly anomerizes to form pure crystalline β-anomer of the lactol (2a/2b). This can be accelerated from several days at ambient temperature to 5-17 h at 50° C. with seeding β-crystals. We observed that once the lactol is in solution, it slowly anomerizes back towards the 2:1 equilibrium in solvents such as dichloromethane or chloroform at ambient temperature. This process can be slowed considerable by chilling the solution (e.g. −20° C.).

Chlorination through an $S_N2$ mechanism with N-chlorosuccinimide (NCS) produced an α-chlorosugar (3) in a stereospecific manner in almost quantitative yield.

To obtain an α-bromosugar (4a), many bromination conditions were tried including N-bromosuccinimide (NBS) and HBr in acetic acid. Among them, we followed a general bromination reaction using a combination of triphenylphosphine (PPh$_3$) and carbon tetrabromide (CBr$_4$) (e.g. Hooz et al, Can. J. Chem., 1968, 46, 86-87). Under the conditions of using methylene chloride as the solvent and maintaining a low temperature (−10 to −20° C.) we obtained the best result where the desired α/β isomer ratio was greater than 10:1, in a yield of greater than 80%. Applicants believe that there are no literature precedents describing this level of stereoselectivity for this reaction type. Another practical observation was that by conducting the bromination under sub-ambient temperature conditions, such as, most preferably about −20° C.) and exposing the cold reaction solution to silica gel as soon as possible after the completion of the reaction minimizes anomerization of the bromosugar. The bromosugar can be purified through a silica gel filtration column. Once treated with silica gel, the bromosugar it is practically stable even at elevated temperatures.

The iodosugar (5a) was prepared in a similar manner, which can be coupled with the purine to produce a key intermediate (6a).

Following the general purine coupling method of Bauta et al (Intl. Pat. Appl. WO 2003/011877), we coupled the α-bromosugar (4a) with the potassium salt of 6-chloro-2-aminopurine in t-butanol in acetonitrile. The reaction took over a week at ambient temperatures. The reaction was optimized to go to completion in 24 h at 50° C. After partial purification through a silica gel filtration column, the anomeric mixture was isolated in 63% yield in a ratio of 14:1 β/α. The β-anomer (6a) could be selectively crystallized out from a methanolic solution to give the pure desired β-anomer (6a) in 55% yield from the bromosugar (4a).

With a key intermediate 6a in hand, conversion to unprotected 2-amino-6-substituted purines (e.g., 7-10) was accomplished. Further conversion to the phosphoramidate derivatives (e.g., 11-14) proceeded by an adaptation of the method of Lehsten et al., Org. Proc. Res. Dev., 2002, 6, 819-822 or as disclosed in U.S. patent application Ser. No. 12/053,015, filed Mar. 21, 2008, pp. 651-675. Cyclic phosphate derivatives (e.g., 15-17) were prepared as described in Can J. Chem., 1993, 71, 855 or as disclosed in U.S. Provisional Patent Application No. 61/060,683, filed Jun. 11, 2008, pp. 79-89. As the phosphoramidate group can also react to a minor extent on the secondary 3' hydroxyl, the potential exists for 3' monophosphoramidate and 3',5' bis-phosphoramidate impurities. The 3' isomer would be expected to have similar physical properties to the desired 5' isomer making purification by chromatography difficult. This is ameliorated by further reacting the crude product mixture with sub-stoichiometric amounts of protecting groups which are selective for primary hydroxyls over secondary hydroxyls such as t-butyldimethylsilyl chloride, t-butyldiphenylsilyl chloride or 4,4'-dimethoxytrityl chloride in the presence of pyridine or similar base to generate 5' protected 3' phosphoramidate. The resulting product and the bis substituted phosphoramidate are less polar than the desired 5' phosphoramidate and can be separated readily by chromatography.

Compound (1a) can be obtained by a process disclosed at page 5 in U.S. Published Application No. 2008/0139802 (which corresponds to WO 2008/045419), at pages 11-13 in WO 2006/012440, and at pages 20-22 and 30-31 in WO 2006/031725, each of which is hereby incorporated by reference. Alternatively, the 4-chlorobenzoyl lactone analog (1b) can be produced either by debenzoylation of 1a to form the intermediate lactone diaol, 1a', followed by 4-chlorobenzoylation, or by substituting 4-chlorobenzoyl chloride directly to react with 1a'.

Example 1

((2R,3R,4R)-3-(4-chlorobenzoyloxy)-4-fluoro-4-methyl-5-oxotetrahydrofuran-2-yl)methyl 4-chlorobenzoate (1b)

((2R,3R,4R)-3-(benzoyloxy)-4-fluoro-4-methyl-5-oxotetrahydrofuran-2-yl)methyl benzoate (1a, 44.50 g, 119.5 mmol) was suspended in anhydrous methanol (240 mL). A catalytic amount of 25 wt. % sodium methoxide in methanol (2.3 mL, 10 mmol, 8.3 mol %) was added at room temperature. After 2 h, the reaction was complete as shown by TLC (20% EtOAc in hexanes). After concentration of the solvent under reduced pressure, the residue was triturated with a mixture of ethyl ether and hexanes (1:2 v/v) (200 mL) to afford crude intermediate lactone, a. The solid was collected via filtration and rinsed with hexanes (3×40 mL). To a dry 1 L of round flask was loaded the crude intermediate and it was dissolved in anhydrous THF (500 mL). 4-Chlorobenzoyl chloride (46 mL, 358 mmol) was added at room temperature. The mixture was cooled in an ice-water bath and then triethylamine (100 mL, 717 mmol) was added. The cloudy mixture was stirred at room temperature for overnight. The reaction was quenched via addition of water (60 mL) and then the solution was concentrated under reduced pressure. The residue was diluted with ethyl acetate (200 mL) and washed with water, brine (2×100 mL each). The organic layer was concentrated under reduced pressure and the residue was purified by column chromatography (20% EtOAc in hexanes) to afford the product as a light yellow fluffy solid. The product was dried under (0.2 mmHg, 50° C., 2 h) to afford 24.3 g (46%), mp: 138-141° C. $^1$H NMR (CDCl$_3$): δ 7.99 (m, 2H, arom.), 7.91 (m, 2H, arom.), 7.45 (m, 2H, arom.), 7.39 (m, 2H, arom.), 5.45 (dd, 1H, J=17.6 Hz, J=7.2 Hz, C3-H), 4.97 (m, 1H, C4-H), 4.73 (m, 1H, C5-Ha), 4.58 (m, 1H, C5-Hb), 1.73 (d, 3H, CH$_3$).

Example 2

((2R,3R,4R,5R)-3-(benzoyloxy)-4-fluoro-5-hydroxy-4-methyltetrahydrofuran-2-yl)methyl benzoate (2a)

To a 5 L of dry three-neck round-bottomed flask fit with a mechanical stirrer, addition funnel and thermometer was charged the lactone ((2R,3R,4R)-3-(benzoyloxy)-4-fluoro-4-methyl-5-oxotetrahydrofuran-2-yl)methyl benzoate) (1a, 379 g, 1.018 mol). The solid was dissolved in anhydrous THF (1.75 L) and cooled to −30° C. under a nitrogen atmosphere. A solution of lithium tri-tert-butoxyaluminohydride (1.0 M in THF, 1.527 L) was added to the lactone solution while stirring over 1 h and maintaining the −30° C. temperature. After finishing the addition, the temperature was slowly increased and the reaction was followed by TLC (lactol R$_f$ 0.4, 30% EtOAc in hexanes). The reaction was complete after 1 h 15 min (temperature reached −10° C.). The reaction was quenched by addition of Ethyl acetate (900 mL) via addition funnel. Sat. NH$_4$Cl (40 mL) was added at 0° C. The cloudy mixture was decanted into a 10 L round-bottomed flask. The solid residue left behind was filtered and washed with ethyl acetate (2×200 mL). The filtrate was combined with the decanted solution and the combined solution was concentrated under reduced pressure. The oily residue was dissolved in ethyl acetate (2 L) and washed with 3 N HCl (600 mL). The aqueous layer was back-extracted with ethyl acetate (3×400 mL). The combined organic layer was washed with water (3×800 mL), sat. NaHCO$_3$ (400 mL) and brine (400 mL). The organic solution was dried over MgSO$_4$, filtered and concentrated under reduced pressure to afford a light brown oily residue. The residue was purified by plug column (2.2 kg of 40-63 micron silica gel, packed in a 6 L sintered glass funnel, 22 cm length of silica gel, diameter 15 cm) using suction and a step-gradient of 5%, 10%, 20%, and 30% ethyl acetate in hexanes—ca 5 L of each). The product containing fractions were combined and concentrated under reduced pressure to a colorless, very thick liquid (310.4 g).

The liquid slowly solidified after adding crystalline beta product as seeds (ca 100 mg spread out) under vacuum (0.2 mmHg) at 50° C. The process of solidification was complete in 20 hours at 50° C. with or without vacuum. The white solid thus collected (293.8 g, 77%) has amp of 79-80° C. and ratio of β/α is 20:1 based on NMR.

$^1$H-NMR (DMSO-d$_6$) β-isomer, δ=5.20 (dd, 1H, OH); α-isomer, δ=5.40 (dd, 1H, OH). (β-lactol). (DMSO-d$_6$): δ 7.99 (m, 2H, arom.), 7.93 (m, 2H, arom.), 7.70 (m, 1H, arom.), 7.61 (m, 1H, arom.), 7.55 (m, 2H, arom.), 7.42 (m, 2H, arom.), 7.32 (dd, 1H, C1-H), 5.54 (dd, 1H, C3-H), 5.20 (dd, 1H, OH), 4.55-4.50 (m, 1H, C5-Ha), 4.46-4.40 (m, 2H, C5-Hb and C4-H), 1.42 (d, 3H, CH$_3$).

Example 3

((2R,3R,4R,5R)-3-(4-chlorobenzoyloxy)-4-fluoro-5-hydroxy-4-methyltetrahydrofuran-2-yl)methyl 4-chlorobenzoate (2b)

To a 1 liter dry round-bottomed flask was loaded ((2R,3R,4R)-3-(4-chlorobenzoyloxy)-4-fluoro-4-methyl-5-oxotetrahydrofuran-2-yl)methyl 4-chlorobenzoate (1b, 50.0 g, 113 mmol) and the solid was dissolved in anhydrous THF (200 mL). The solution was cooled to −20° C. Lithium tri-tert-butoxyaluminohydride (1.0 M in THF) (170 mL, 170 mmol) was added via an addition funnel over 20 min and the resulting mixture was stirred for an additional one hour at −20° C.

Ethyl acetate (120 mL) was added and the mixture was allowed to warm up slowly to 0° C. Sat. aq ammonium chloride (4.5 mL) was added. The mixture was concentrated under reduced pressure and then diluted with EtOAc (500 mL). Aqueous HCl (3 N, 300 mL) was added to dissolve all solids. After separation, the organic layer was washed with water (2×200 mL), brine (100 mL), and dried over sodium sulfate. The organic layer was concentrated under reduced pressure to furnish an amorphous solid. The solid was dissolved in methanol (169 mL) heated to reflux. After cooling to room temperature, water was added portionwise (37 mL total) until a slightly turbid mixture formed. After standing, the precipitated β-lactol product was filtered and washed with methanol (2×20 mL) and dried (0.2 mmHg, 50° C., 17 h) to 30.5 g (61%) of an off-white solid with an anomeric ratio of β/α>35:1. $^1$NMR (DMSO-$d_6$): δ 7.95 (m, 2H, arom.), 7.90 (m, 2H, arom.), 7.61 (m, 2H, arom.), 7.51 (m, 2H, arom.), 7.31 (dd, 1H, C1-H, J=5.2 Hz, J=0.8 Hz), 5.50 (dd, 1H, C3-H, J=24 Hz, J=7.2 Hz), 5.19 (dd, 1H, C4-H, J=10.8 Hz, J=5.6 Hz), 4.56 (m, 1H, C5-Ha), 4.42 (m, 2H, C5-Hb and OH), 1.42 (d, 3H, $CH_3$, J=22.8 Hz).

Example 4

((2R,3R,4R,5R)-3-(benzoyloxy)-5-chloro-4-fluoro-4-methyltetrahydrofuran-2-yl)methyl benzoate (3)

To a solution of mixture of compound 2a (1.0 g, 2.67 mmol) and $PPh_3$ (1.4 g, 5.34 mmol) in $CH_2Cl_2$ (15 mL) was added NCS (1.07 g, 8.01 mmol) portionwise at 0° C. Then the resulting mixture was stirred at rt for 1 h and poured into a silica gel column and eluted with EtOAc-hexanes (1:4) using pressure. The collected right fractions were combined, concentrated, and co-evaporated with $CH_2Cl_2$ several times and used next step (1.0 g, 95%).
$^1$H-NMR ($CDCl_3$) δ=8.13-8.02 (m, 4H, aromatic), 7.78-7.50 (m, aromatic, 2H), 7.53-7.43 (m, 4H, aromatic), 6.01 (s, 1H, H-1), 5.28 (dd, 1H, J=3.2, 5.6 Hz, H-3), 4.88 (m, 1H, H—H-4), 4.77 (dd, 1H, J=3.2, 12.4 Hz, H-5), 4.61 (dd, 1H, J=4.0, 12.4 Hz, H-5'), 1.73 (d, 3H, J=21.6 Hz, $CH_3$).

Example 5

((2R,3R,4R,5R)-3-(benzoyloxy)-5-bromo-4-fluoro-4-methyltetrahydrofuran-2-yl)methyl benzoate (4a)

Anhydrous dichloromethane (5.6 L) was charged into a reactor and cooled to −22° C. or below. Triphenylphosphine (205.4 g, 0.783 mol) was added to the cold solvent and the suspension was stirred to form a solution. The lactol (2a, 209.4 g, 0.559 mol) in solid form was added to the cold solution and stirred for 15 mins. Carbon tetrabromide (278.2 g, 0.839 mol) was added portion-wise while maintaining the temperature of the solution between −22° C. to −20° C. under a flow of nitrogen gas (approx. 30 min). After finishing the addition of $CBr_4$, the temperature was slowly raised to −17° C. over 20 mins. The reaction was judged to be >95% complete by TLC ($R_f$s 0.61 (α), 0.72 (β), 0.36 lactol; 20% EtOAc in hexanes). The reaction solution was immediately transferred to a vessel containing 230 g of flash chromatography grade silica gel (40-63 microns). The stirred mixture was immediately passed through a pad of silica gel (680 g) in a 2.5 L sintered glass Buchner funnel. The filtrate was concentrated under reduced pressure to about 800 mL and the ratio of α/β isomers of the crude product was 10:1 as determined by $^1$H-NMR. ($CDCl_3$) δ=6.35, (s, αC1-H), 6.43, (d, βC1-H). The residue was purified by plug column chromatography using 2.1 kg of silica gel in a 6 L sintered glass Buchner funnel and eluted (via suction) with a stepwise gradient elution of 1%, 5%, 8% 12% EtOAc in hexane (ca 4 L each) to remove non-polar impurities followed by 12%, 25% EtOAc in hexane (6 L total) to elute the product. The product containing fractions were combined into two fractions, concentrated under reduced pressure, dried under vacuum (0.1 mmHg, ambient temp., 20 h) to colorless oils. Main fraction (197 g, 89% α/β=20:1). The alpha isomer crystallized from a small portion of the oil upon standing at 0° C. for several weeks to give large, thin plates, mp 59-61° C. The pure beta isomer crystallized from a mixture of alpha and beta product oil from an earlier less selective run to give needles, mp 77-79° C.
$^1$H-NMR (β-bromide) ($CDCl_3$): δ=8.08 (m, 2H, arom.), 8.04 (m, 2H, arom.), 7.62 (m, 1H, arom.), 7.54-7.45 (m, 3H, arom.), 7.35 (m, 2H, arom.), 6.43 (d, 1H, C1-H), 6.04 (dd, 1H, C3-H), 4.78-4.73 (m, 2H, C4-H and C5-Ha), 4.63-4.58 (m, 1H, C5-Hb), 1.76 (d, 3H, $CH_3$). α-bromide, α/β=20:1) ($CDCl_3$): δ 8.13 (m, 2H, arom.), 8.02 (m, 2H, arom.), 7.63-7.56 (m, 2H, arom.), 7.50-7.42 (m, 4H, arom.), 6.34 (s, 1H, C1-H), 5.29 (dd, 1H, C3-H), 4.88 (m, 1H, C4-H), 4.78 (dd, 1H, C5-Ha), 4.63 (dd, 1H, C5-Hb), 1.72 (d, 3H, $CH_3$).

Example 6

(2R,3R,4R,5R)-5-bromo-2-((4-chlorobenzoyloxy)methyl)-4-fluoro-4-methyltetrahydrofuran-3-yl 4-chlorobenzoate (4b)

Anhydrous dichloromethane (530 mL) was added to a 1 L of dry round-bottomed flask and cooled to −22° C. Triphenylphosphine (19.5 g, 74 mmol) was added and then added the β-lactol (2b, 23.5 g, 53 mmol). To that solution, carbon tetrabromide (26.3 g, 79.5 mmol, solid) was added portionwise over 5 min. at −22° C. The reaction was slowly warmed up to room temperature and once reaction was complete, the solution was passed through a short pad of silica gel (148 g in a 600 mL of fritted disc Buchner funnel) to remove any brown color polar impurities. The colorless filtrate was concentrated to dryness under reduced pressure and the solid residue was dissolved in ethyl ether (170 mL). Hexanes (50 mL) was added slowly until a precipitate started to form. The product was collected as a light yellow solid via filtration and dried (0.2 mm Hg, 25° C., 17 h) to afford 21.23 g, (79%) with an anomeric ratio of α/β>65:1. The product was contaminated with 3-4% of triphenylphosphine oxide which had no effect on the next reaction step. $^1$H NMR ($CDCl_3$): δ 8.05 (m, 2H, arom.), 7.95 (m, 2H, arom.), 7.47-7.40 (m, 4H, arom.), 6.33 (s, 1H, C1-H), 5.22 (m, 1H, C3-H), 4.84 (m, 1H, C4-H), 4.76 (m, 1H, C5-Ha), 4.62 (m, 1H, C5-Hb), 1.69 (d, 3H, $CH_3$, J=21.6 Hz).

Example 7

((2R,3R,4R,5R)-3-(benzoyloxy)-4-fluoro-5-iodo-4-methyltetrahydrofuran-2-yl)methyl benzoate (5)

To a solution of compound 2 (1 g, 2.67 mmol), triphenylphosphine (700 mg, 2.67 mmol), and imidazole (180 mg, 2.67 mmol) in anhydrous $CH_2Cl_2$ (10 mL) iodine (680 mg, 2.68 mmol) was added. The resulting mixture was stirred for 30 min and poured into a silica gel column and eluted with EtOAc-hexanes (1:4) to give a syrupy product (1.3 g, quantitative) and used in next reaction without further characterization.

Example 8

(2R,3R,4R,5R)-5-(2-amino-6-chloro-9H-purin-9-yl)-2-(benzoyloxymethyl)-4-fluoro-4-methyltetrahydrofuran-3-yl benzoate (6a)

To a 12 L of three-neck round-bottomed flask was charged 6-chloro-2-aminopurine (225.4 g, 1.329 mol). Anhydrous tert-BuOH (4.5 L) was added and the solution was stirred with a mechanical stirrer at ambient temperature. Potassium tert-butoxide (solid, 151.6 g, 1.35 mol) was added portion-wise under a flow of nitrogen gas while stirring. The mixture was stirred at RT for an additional 30 min. To a 5 L round-bottomed flask was loaded the α-bromide (4a, 197 g, 0.451 mol) and 3 L of anhydrous acetonitrile at ambient temperature. The bromide solution was added to the purine base suspension over 1 min at ambient temperature. The 5 L flask was rinsed with acetonitrile (2×1 L) to transfer bromide completely to the reaction mixture. The mixture was heated gradually to 50° C. over 2 h with a heating mantle and controller, and stirred for 20 h. The reaction was almost complete as shown by TLC beta ($R_f$ 0.28, 30% EtOAc in hexanes). The reaction was quenched by the addition of sat. $NH_4Cl$ (200 mL) to form a suspension. The suspended solid[1] was removed by filtration through a 3 cm pad of Celite in a 2.5 L porcelain Buchner funnel. The solid was washed with toluene (3×100 mL). The combined filtrate was neutralized by adding 6 N HCl solution until pH 7 (approx 220 mL). The mixture was concentrated under reduced pressure. When the volume of mixture was reduced to about one-third volume, additional precipitated solid was removed by filtration in a similar manner. The filtrate was further concentrated to a volume of about 800 mL. The residue was loaded onto a plug column (1.6 kg flash grade silica gel in a 6 L sintered glass Buchner funnel) and eluted (via suction) with a gradient of 10% ethyl acetate in hexanes (6 L) to remove non-polar impurities, 30% ethyl acetate in hexanes to afford a small amount of lactol (6 L), and then 40%~45% ethyl acetate in hexanes (4 L) to elute the main amount of product. The product containing fractions were combined, concentrated under reduced pressure and dried under vacuum (0.2 mmHg, 24 h, ambient temp.) to a white foam solid (150.7 g, β/α=14:1 by NMR.

$^1$H-NMR. ($CDCl_3$) beta: δ=1.33 (d, 22.4 Hz, 2'-C—$CH_3$), alpha: 1.55 (d, 22 Hz, 2'-C—$CH_3$).

The product mixture foam was dissolved in methanol (700 mL) at ambient temperature. Upon standing, a solid slowly formed over 2 h. The suspension was cooled in a freezer to −5° C. for 17 h. The resulting white solid was collected by filtration and washed with cold MeOH (−5° C., 3×60 mL) and ethyl ether (3×100 mL). The solid was dried under vacuum (0.2 mmHg, 24 h, ambient temp.) to afford 110.5 g of β-product with excellent de (β/α 99.8:1 by HPLC). The filtrate was partially concentrated (ca. 400 mL) and then diluted with more MeOH (400 mL) while heating to 60° C. The solution was cooled down to ambient temperature, seeded and the cooled to −5° C. The second crop was collected, washed and dried in a similar manner to give more product as a white solid (12.26 g) with similar diastereomeric purity. The mother liquor was concentrated to dryness under reduced pressure (ca. 25 g). The residue was a mixture of β and α-isomers. It was subjected to automated silica gel column chromatography (Analogix, 240 g cartridge, 40% to 50% ethyl acetate in hexanes) to afford 14.52 g of product foam which was recrystallized from MeOH, washed and dried in a similar manner to afford an additional 8.46 g of product in high purity.

The three solids were judged to be of similar purity and they were combined to give 131.2 g of white crystalline product 6a, (55% from bromosugar, 49% from lactol). Mp 160.5-162.0° C. HPLC purity 99.5% including 0.20% alpha.

$^1$H-NMR (pure β-anomer, $CDCl_3$): δ=8.03 (m, 2H, arom.), 7.93 (m, 2H, arom.), 7.88 (s, 1H, C8-H), 7.60 (m, 1H, arom.), 7.50 (m, 1H, arom.), 7.44 (m, 2H, arom.), 7.33 (m, 2H, arom.), 6.44 (dd, 1H, C1'-H), 6.12 (d, 1H, C3'-H), 5.35 (s, 2H, $NH_2$), 5.00 (dd, 1H, C5'-Ha), 4.76 (m, 1H, C4'-H), 4.59 (dd, 1H, C5'-Hb), 1.33 (d, 3H, $CH_3$).

$^1$H-NMR (α-isomer, $CDCl_3$): δ=8.11-8.09 (m, 3H, arom. and C8-H), 8.01 (m, 2H, arom.), 7.63 (m, 1H, arom.), 7.55 (m, 1H, arom.), 7.48 (m, 2H, arom.), 7.39 (m, 2H, arom.), 6.35 (d, 1H, C1'-H), 5.76 (dd, 1H, C3'-H), 5.18 (s, 2H, $NH_2$), 4.93-4.89 (m, 1H, C4'-H), 4.75-4.71 (m, 1H, C5'-Ha), 4.58-4.54 (m, 1H, C5'-Hb), 1.55 (d, 3H, $CH_3$).

Example 9

(2R,3R,4R,5R)-5-(2-amino-6-chloro-9H-purin-9-yl)-2-((4-chlorobenzoyloxy)methyl)-4-fluoro-4-methyltetrahydrofuran-3-yl-4-chlorobenzoate (6b)

To a 250 mL of dry round-bottomed flask was charged 2-amino-6-chloropurine (2.57 g, 15.1 mmol, 2.95 eq). Anhydrous tert-BuOH (51 mL) was added, followed by potassium tert-butoxide (1.73 g, 15.4 mmol). The suspension was stirred at room temperature for 30 min. and then added to a solution of the bromide (4b, 2.60 g, 5.14 mmol) in anhydrous acetonitrile (86 mL). The mixture was heated at 50° C. for 43 hours. The reaction was quenched by the addition of aq. sat'd ammonium chloride (3 mL). A precipitated solid consisting mostly of excess starting purine base was removed by filtration and the product containing filtrate was concentrated under reduced pressure. The resulting solid residue was triturated with ethyl acetate (110 mL). After removal of the remaining solid by filtration, the filtrate was washed with water (3×40 mL), brine (1×40 mL) and dried over sodium sulfate. The organic solution was concentrated under reduced pressure to afford 2.96 g of crude products with an anomeric ratio of β/α about 10:1. The crude product was purified through column chromatography (25% ethyl acetate in hexanes) to give 1.98 g (65%) of product as an oil. A portion was dissolved in methanol (8 ml/g) to furnish crystalline white solid (β/α=26:1) mp shrinks 155, melts 167-175° C. $^1$H NMR ($CDCl_3$): δ 7.91 (m, 2H, arom.), 7.84 (m, 2H, arom.), 7.84 (s, 1H, C8-H), 7.40 (m, 2H, arom.), 7.28 (m, 2H, arom.), 6.48 (dd, 1H, C3'-H, J=22.8 Hz, J=9.2 Hz), 6.09 (d, 1H, C1'-H, J=18 Hz), 5.39 (s, 2H, $NH_2$), 5.06 (m, 1H, C5'-Ha), 4.73 (m, 1H, C4'-H), 4.56 (m, 1H, C5'-Hb), 1.32 (d, 3H, $CH_3$, J=22.4 Hz).

Example 10

(2R,3R,4R,5R)-5-(2-amino-6-chloro-9H-purin-9-yl)-2-(benzoyloxymethyl)-4-fluoro-4-methyltetrahydrofuran-3-yl benzoate (6a) from compound 3

To a solution of compound 3 (450 mg, 2.68 mmol) in chlorobenzene (1.5 mL) were added potassium salt of the base (1.37 g, 8.05 mmol) in t-butanol (5 mL) and subsequently anhydrous acetonitrile (5 mL) at rt. The resulting mixture was stirred at 80-140° C. in a sealed tube for 7 days and concentrated in vacuo after neutralization with HCl. The residue was purified by silica gel column chromatography (hexanes:EtOAc=2:1) to give compound 6a (90 mg, 15%) as a white foam.

Example 11

(2R,3R,4R,5R)-5-(2-amino-6-chloro-9H-purin-9-yl)-2-(benzoyloxymethyl)-4-fluoro-4-methyltetrahydrofuran-3-yl benzoate (6a) from compound 5

To a solution of compound 5 (1.3 g, 2.68 mmol) in t-butanol (10 mL) was added sodium salt of the base (1.37 g, 8.05 mmol) in DMF (10 mL) at ambient temperature. The resulting mixture was stirred for 15 h and concentrated in vacuo. The residue was purified by silica gel column chromatography (hexanes:EtOAc=2:1) to give compound 6 (220 mg, 16%) as a white foam.

Example 12

(2R,3R,4R,5R)-5-(2-amino-6-methoxy-9H-purin-9-yl)-4-fluoro-2-(hydroxymethyl)-4-methyltetrahydrofuran-3-ol (7) from 6a To a 250 mL dry round-bottomed flask was charged (2R,3R,4R,5R)-5-(2-amino-6-chloro-9H-purin-9-yl)-2-(benzoyloxymethyl)-4-fluoro-4-methyltetrahydrofuran-3-yl benzoate (6a, 7.50 g, 14.26 mmol) Anhydrous methanol (30 mL) was added and a white suspension was formed. At 50° C., a solution of sodium methoxide in methanol (25%, 19.7 mL, 64.17 mmol) was added via a dry syringe under a nitrogen atmosphere. A white cloudy reaction mixture was formed. After 3.5 h at 50° C., the reaction was complete with no starting material left as shown by TLC test. The mixture was cooled down to room temperature and neutralized by addition of glacial acetic acid (3 mL). A white solid was filtered out and washed with methanol (3×5 mL). The filtrate was mixed with 20 g of silica gel and concentrated to dryness. The mixture was loaded in line with a silica gel cartridge and separated via column chromatography using a gradient of methanol in dichloromethane 0 to 15% MeOH. The product eluted out at 12% methanol in dichloromethane. The product containing fractions were combined, concentrated under reduced pressure and dried under vacuum (0.2 mmHg, 50° C., 24 h) to a white powder solid (4.45 g, 98% yield), mp 199-202° C.

$^1$H-NMR (DMSO-$d_6$): δ=8.18 (1H, s, C8-H), 6.61 (2H, s, NH$_2$), 6.05 (1H, d, C1'-H), 5.68 (1H, d, 3'-OH), 5.26 (1H, m, 5'-OH), 4.23-4.13 (1H, m, C3'-H), 3.96 (3H, s, OCH$_3$), 3.92-3.83 (2H, m, C4'-H and C5'-H$_a$), 3.70-3.67 (1H, m, C5'-H$_b$), 1.06 (3H, d, C2'-CH$_3$).

Example 13

(2R,3R,4R,5R)-5-(2-amino-6-methoxy-9H-purin-9-yl)-4-fluoro-2-(hydroxymethyl)-4-methyltetrahydrofuran-3-ol (7) from 6b To a dry 5 L three-necked round flask fitted with a mechanical stirrer and an addition funnel was loaded (2R,3R,4R,5R)-5-(2-amino-6-chloro-9H-purin-9-yl)-2-(((4-chlorobenzoyl)oxy)methyl)-4-fluoro-4-methyltetrahydrofuran-3-yl 4-chlorobenzoate (6b, 313.2 g, 526.5 mmol). The solid was suspended in anhydrous methanol (2.1 L) and cooled in an ice-water bath under an atmosphere of nitrogen. A solution of sodium 25 wt. % methoxide in methanol (361 mL, 1.58 mol) was added via an additional funnel over 20 min to give a clear solution. The reaction was allowed to warm to room temperature for 6 hours to form a turbid solution. The completion of the reaction was confirmed by LC/MS by the lack of any remaining 6-chloro deprotected nucleoside. The reaction solution was acidified with con. HCl (132 mL, 1.58 mol). After standing at room temperature (1 h), the solution was filtered to remove a white precipitate. The precipitate was washed with methanol (3×50 mL). The combined filtrate was concentrated under reduced pressure to afford a sticky solid residue. The residue was mixed with 420 mL of 2 N HCl (420 mL) and dichloromethane (1 L). The organic layer was separated and the aqueous layer was extracted with additional dichloromethane (3×500 mL). To the aqueous layer, ethyl acetate (1.4 L) was added and solid sodium carbonate (86 g) was added portion-wise to neutralize the aqueous layer to ca pH 8 (caution: foaming). After separation of the organic layer, the solid in aqueous layer was dissolved by adding more water (200 mL). The aqueous layer was extracted with ethyl acetate (3×700 mL and 400 mL). The combined organic layer was dried over sodium sulfate and concentrated under reduced pressure to a light yellow color solid that was redissolved in acetone (820 mL) at 50° C. and stirred until new solid formation initiated. The saturated solution was cooled in a freezer and product was collected by filtration. The white solid was rinsed with acetone (2×150 mL) and ethyl ether (3×80 mL) and dried (0.2 mm Hg, 50° C., 4H) to a white crystalline solid, 151.6 g (92%) of material with NMR and HPLC matching material purified by chromatography.

Compound (7a) is prepared in a manner analogous to either Examples 12-13 for the preparation of compound (7).

Example 14

(2S)-isopropyl 2-((((2R,3R,4R,5R)-5-(2-amino-6-methoxy-9H-purin-9-yl)-4-fluoro-3-hydroxy-4-methyltetrahydrofuran-2-yl)methoxy) (phenoxy) phosphorylamino)propanoate (11)

To a 250 mL dry round-bottomed flask were loaded phenyl dichlorophosphate (2.66 g, 12.61 mmol) and anhydrous dichloromethane (40 mL). The amino ester salt (2.60 g, 15.53 mmol) was added to the solution and the mixture was cooled to −5° C. N-Methyl imidazole (7.7 mL, 97 mmol) was then added quickly via a dry syringe at −5° C. and the solution was stirred at −5° C. for 1 h. The nucleoside (7, 3.04 g, 9.7 mmol) was added from a vial in one portion at −5° C. and the solid was slowly dissolved in 20 minutes. The reaction temperature was allowed to rise to ambient temperature over 2 h. After 17 h, the reaction was not complete. More chemical reagents were made (as described above from phosphate (2.66 g), aminoester (2.60 g), and NMI (3.8 mL, 48 mmol)) and added to the reaction mixture at −5° C. The reaction was stirred at room temperature for 2 more hours. The reaction was almost complete as shown by TLC result and diluted with 70 mL of dichloromethane.HCl solution (1 N, 70 mL) was added. The aqueous layer was separated and extracted with dichloromethane. The organic layer was washed with saturated NaHCO$_3$, water, brine and dried over MgSO$_4$. After removal of the solvent under reduced pressure, the sticky residue was purified through automated column chromatography using a 240 g cartridge and a gradient of 0-8% 2-PrOH in dichloromethane to afford product as a foam solid (4.16 g, 7.14 mmol, 73% yield). HPLC purity 97.4%. NMR spectra of product showed it is a mixture of two diastereoisomers with a ratio of 1.2:1.

$^1$H-NMR (DMSO-$d_6$): δ=7.98 (1H, s, 8-H of one isomer), 7.95 (1H, s, 8-H of another isomer), 7.37-7.32 (2H, m, arom-H), 7.22-7.15 (3H, m, arom-H), 6.6 (2H, s, NH$_2$), 6.11 (1H, d, C1'-H of one isomer), 6.09 (1H, d, C1'-H of another isomer), 6.09-5.98 (1H, m, amide NH), 5.88 (1H, d, 3'-OH of one isomer), 5.81 (1H, d, 3'-H of another isomer), 4.85-4.75 (1H, hepta, methine H of iso-propyl), 4.46-4.27 (2H, m, C4'-H, α-H of amino ester), 4.15-4.07 (1H, m, C3'-H), 3.96 (3H, s, OCH$_3$), 3.82-3.72 (2H, m, C5'-H$_a$ and C5'-H$_b$), 1.23-1.06 (9H, m, CH$_3$'s of amino ester), 1.03 (3H, d, C2'-CH$_3$).

$^{31}$P-NMR (DMSO-d$_6$): δ=4.91 (one isomer), 4.72 (another isomer).

An alternate purification method is to chemically alter the minor 3' phosphoramidate by-product in order to simplify the chromatographic separation. The crude phosphoramidate product is dissolved in anhydrous pyridine (5 mL/g), and is treated with 0.5 molar equivalents of t-butyldimethylsilyl chloride at ambient temperature to react selectively with the free 5' primary hydroxyl of the 3' isomer impurity. Reaction progress can be monitored by LC/MS. Once the 3' isomer is converted to a 5'-tBDMS-3'-phosphoramidate derivative, the reaction is quenched with methanol (3 eq), concentrated under reduced pressure, partitioned between ethyl acetate and 5% citric acid and then the organic layer is concentrated. The residue is then subjected to chromatography which can now be done with a higher loading and a faster gradient and achieve a higher purity.

Compounds (11a) and (11b) are prepared by an analogous method as Example 14 using compounds (10) and (7a) as starting reagents.

Example 15

(2R,3R,4R,5R)-5-(2-amino-6-(azetidin-1-yl)-9H-purin-9-yl)-4-fluoro-2-(hydroxymethyl)-4-methyltetrahydrofuran-3-ol (8)

To a 350 mL of dry seal pressure flask (Chemglass) were added (2R,3R,4R,5R)-5-(2-amino-6-chloro-9H-purin-9-yl)-2-(benzoyloxymethyl)-4-fluoro-4-methyltetrahydrofuran-3-yl benzoate (6a, 3.6 g, 6.85 mmol) and 150 mL of absolute ethanol. Azetidine hydrochloride (2.56 g, 27.4 mmol) was added and then followed by triethylamine (4.16 g, 41.1 mmol). The suspension was stirred and heated to 70° C. while sealed for 5 hours. All the starting material was consumed but the benzoyl groups remained as shown by TLC. Sodium methoxide (7.8 mL, 34.3 mmol, 25% solution in methanol) was added to the mixture and heated at 50° C. The reaction was complete after 3.5 h. The reaction mixture was allowed to cool to room temperature and neutralized by addition of glacial acetic acid (0.41 g, 6.85 mmol). The mixture was concentrated under reduced pressure and then the residue was triturated with ethyl acetate. The resulting solid was removed by filtration and the solid was washed with EtOAc (2×15 mL). The filtrate was concentrated under reduced pressure and the residue was purified via column chromatography (Analogix, 120 g cartridge, gradient of 0 to 15% MeOH in DCM). The pure product containing fractions were combined, concentrated under reduced pressure and dried (50° C., 0.2 mmHg, 17 h) to a light pink colored foam solid (2.15 g, 6.35 mmol, 93%).

$^1$H-NMR (DMSO-d$_6$) δ=8.00 (s, 1H, C8-H), 6.03 (s, 2H, NH$_2$), 6.00 (d, 1H, C1'-H), 5.64 (d, 1H, 3'-OH), 5.24 (t, 1H, 5'-OH), 4.24-4.10 (m, 5H, N—CH$_2$ of azetidine, C3'-H), 3.90-3.81 (m, 2H, C4'-H and C5'-H$_a$), 3.69-3.64 (m, 1H, C5'-H$_b$), 2.37 (penta, 2H, center CH$_2$ of azetidine), 1.05 (d, 3H, C2'-CH$_3$).

Example 16

(2S)-methyl 2-((((2R,3R,4R,5R)-5-(2-amino-6-(azetidin-1-yl)-9H-purin-9-yl)-4-fluoro-3-hydroxy-4-methyltetrahydrofuran-2-yl)methoxy)(phenoxy)phosphorylamino)propanoate (12)

To a 100 mL dry round-bottomed flask were added phenyl dichlorophosphate (1.72 g, 8.15 mmol) and anhydrous dichloromethane (17 mL). The amino ester (1.42 g, 10.2 mmol) was added and the suspension was cooled to −5° C. N-Methylimidazole (3.34 g, 40.7 mmol) was added via a syringe in one portion and the solution was stirred at −5° C. for 1 h under a nitrogen atmosphere. The nucleoside (8, 1.38 g, 4.07 mmol) (foam solid) was then added in one portion and the solution was allowed to warm up over 1 h to ambient temperature. After 4 h at ambient temperature, TLC (5% MeOH in DCM) indicated an incomplete reaction (about 30% SM remained) but also a growing less polar impurity. The reaction was quenched by the addition of sat NH$_4$Cl (20 mL) and diluted with dichloromethane (20 mL). The organic layer was separated and washed with water (5×30 mL), brine (20 mL) and dried over Na$_2$SO$_4$. The product containing solution was filtered and concentrated under reduced pressure to a crude oily residue, 3.26 g. This was purified by column chromatography (Analogix, 40 g cartridge, gradient of MeOH in DCM from 0% to 10%). The product eluted at 4% MeOH in DCM. The pure product containing fractions were combined, concentrated under reduced pressure and dried (50° C., 0.2 mmHg, 17 h) to a white foam solid (1.322 g, 2.28 mmol, 56%). HPLC purity 99.25%. NMR spectra of product showed it is a mixture of two diastereoisomers with a ratio of 55:45.

$^1$H-NMR (DMSO-d$_6$) δ=7.80 (s, 1H, 8-H of one isomer), 7.80 (s, 1H, 8-H of another isomer), 7.38-7.33 (m, 2H, arom-H), 7.22-7.14 (m, 3H, arom-H), 6.09 (s, 2H, NH$_2$), 6.12-6.02 (m, 2H, C1'-H and NH), 5.83 (d, 1H, 3'-OH of one isomer), 5.77 (d, 1H, 3'-OH of another isomer), 4.46-4.05 (m, 8H, NCH$_2$ of azetidine, α-H of aminoester, C3'-H, C4'-H, C5'-H$_a$), 3.89-3.79 (m, 1H, C5'-H$_b$), 3.56 (s, 3H, OCH$_3$ of aminoester in one isomer), 3.54 (s, 3H, OCH$_3$ of aminoester in another isomer), 2.37 (penta, 2H, center CH$_2$ of azetidine), 1.21 (d, 3H, α-CH$_3$ of aminoester in one isomer), 1.19 (d, 3H, α-CH$_3$ of aminoester in another isomer), 1.08 (d, 3H, C2'-CH$_3$).

$^{31}$P NMR (DMSO-d$_6$): δ 4.85 (one isomer), 4.77 (other isomer).

Example 17

(2R,3R,4R,5R)-5-(2-amino-6-(benzyloxy)-9H-purin-9-yl)-4-fluoro-2-(hydroxymethyl)-4-methyltetrahydrofuran-3-ol (9)

To a 500 mL of dry round-bottomed flask were added (2R,3R,4R,5R)-5-(2-amino-6-chloro-9H-purin-9-yl)-2-(benzoyloxymethyl)-4-fluoro-4-methyltetrahydrofuran-3-yl benzoate (6a, 8.0 g, 15.2 mmol) and anhydrous benzyl alcohol (128 mL). To another 250 mL of dry round-bottomed flask were charged NaH (60% in mineral oil, 2.44 g, 60.8 mmol) and anhydrous DMF (40 mL). The suspension was stirred at 0° C. in an ice-water bath. Benzyl alcohol (27 mL) was added drop-wise via a syringe. A solution was slowly formed and it was transferred to the nucleoside suspension quickly under a nitrogen atmosphere at room temperature. The mixture was heated to 50° C. and stirred. The reaction was complete after 3 h and cooled to ambient temperature. It was neutralized by the addition of 4 N HCl to ca. pH=7 (12 mL). The solution was concentrated under reduced pressure (4 mbar, 90° C. bath). The cloudy residue was diluted with dichloromethane (100 mL) and washed with water (3×30 mL), brine (30 mL) and dried over Na$_2$SO$_4$. The suspension was filtered and the filtrate was concentrated under reduced pressure to an oily residue. This was purified by column chromatography (Analogix, 0 to 8% gradient of MeOH in DCM). The product eluted at 4% MeOH in DCM. The product containing fractions were combined, concentrated under reduced pressure and dried (50° C., 0.2 mmHg, 17 h) to a white foam solid (4.57 g, 11.7 mmol, 77.2%).

$^1$H-NMR (DMSO-d$_6$) δ=8.18 (s, 1H, 8-H), 7.53-7.51 (m, 2H, arom-H), 7.43-7.34 (m, 3H, arom-H), 6.66 (s, 2H, NH$_2$), 6.05 (d, 1H, C1'-H), 5.67 (d, 1H, 3'-OH), 5.48 (dd, 2H, CH$_2$ of Benzyl), 5.25 (t, 1H, 5'-OH), 4.18 (dt, 1H, C3'-H), 3.92-3.82 (m, 2H, C4'-H and C5'-H$_a$), 3.71-3.66 (m, 1H, C5'-H$_b$), 1.07 (d, 3H, C2'-CH$_3$).

Example 18

(2S)-cyclopentyl 2-((((2R,3R,4R,5R)-5-(2-amino-6-(benzyloxy)-9H-purin-9-yl)-4-fluoro-3-hydroxy-4-methyltetrahydrofuran-2-yl)methoxy)(phenoxy)phosphorylamino)propanoate (13)

To a 100 mL of dry round-bottomed flask were charged phenyl dichlorophosphate (3.29 g, 15.58 mmol) and anhydrous dichloromethane (24 mL). The aminoester tosylate (white powder) was added and the solution was cooled to −5° C. under nitrogen. N-Methylimidazole (4.92 g, 59.94 mmol) was added via a dry syringe in one portion and the resulted colorless clear solution was stirred at −5° C. for one hour. Then the nucleoside (9) solid was added (2.334 g, 5.99 mmol) to the solution under nitrogen in one portion and the mixture was allowed to warm to ambient temperature to give a colorless solution. Reaction progress was monitored by TLC (5% methanol in dichloromethane). TLC indicated an incomplete reaction after 20 h (about 30% starting material left). The reaction was still quenched by the addition of dichloromethane (30 mL) and 1 N HCl (60 mL). The organic layer was separated and the aqueous layer was extracted with dichloromethane (2×20 mL). The combined organic layer was washed with water (2×40 mL), sat NaHCO$_3$ (30 mL), water, and brine. The organic layer was dried over Na$_2$SO$_4$. After removal of solid by filtration, the filtrate was concentrated under reduced pressure to a gummy residue (7.28 g). The residue was purified via column chromatography (Analogix, 80 g cartridge, gradient of 0 to 10% MeOH in DCM). The product eluted at 2% MeOH in DCM. The product containing fractions were combined, concentrated under reduced pressure and dried (50° C., 0.2 mmHg, 17 h) to a white foam solid (2.249 g, a mixture of two isomers, 60:40). A portion of the starting nucleoside (0.257 g) was also recovered. Yield is 62% based on consumed starting material.

$^1$H-NMR (DMSO-d$_6$): δ=7.98 (s, 1H, 8-H of one isomer), 7.96 (s, 1H, 8-H of another isomer), 7.52-7.50 (m, 2H, arom-H), 7.42-7.31 (m, 5H, arom-H), 7.21-7.12 (m, 3H, arom-H), 6.68 (s, 2H, NH$_2$), 6.12 (d, 1H, C1'-H of one isomer), 6.10 (d, 1H, C1'-H of another isomer), 6.04-5.96 (m, 1H, NH), 5.87 (d, 1H, 3'-OH of one isomer), 5.81 (d, 1H, 3'-OH of another isomer), 5.48 (dd, 2H, CH$_2$ of Benzyl), 4.99-4.93 (m, 1H, α-H of aminoester), 4.46-4.27 (m, 3H, C3'-H, C4'-H, OCH of aminoester), 4.15-4.06 (m, 1H, C5'-H$_a$), 3.81-3.71 (m, 1H, C5'-H$_b$), 1.74-1.43 (m, 8H, methylene CH$_2$ of c-pentyl), 1.18 (d, 3H, α-CH$_3$ of aminoester), 1.09 (d, 3H, C2'-CH$_3$ of one isomer), 1.08 (d, 3H, C2'-CH$_3$ of another isomer).

$^{31}$P NMR (DMSO-d$_6$): δ=4.91 (one isomer), 4.73 (other isomer).

Example 19

(2S)-cyclopentyl 2-((((2R,3R,4R,5R)-5-(2-amino-6-hydroxy-9H-purin-9-yl)-4-fluoro-3-hydroxy-4-methyltetrahydrofuran-2-yl)methoxy)(phenoxy)phosphorylamino)propanoate (14)

To a 250 mL of dry round-bottomed flask with starting material (13, 1.92 g, 2.8 mmol) was added anhydrous absolute ethanol (50 mL). Palladium on charcoal (10%, 120 mg) was added. The atmosphere in the flask was exchanged with hydrogen and the mixture was stirred under 1 atm of hydrogen gas for 3.5 h at room temperature. The reaction was judged complete by TLC and the Pd on charcoal was removed by filtration and washed with ethanol (2×10 mL). The filtrate was concentrated under reduced pressure to a solid residue. The solid was mixed with silica gel (10 g) and purified by column chromatography (Analogix, 40 g cartridge, gradient of 1% to 16% MeOH in DCM). The product containing fractions were combined, concentrated under reduced pressure and dried (50° C., 0.2 mmHg, 17 h) to a white powder (1.43 g, 86%). HPLC purity 99.55%. NMR spectra of product showed it is a mixture of two diastereoisomers with a ratio of 60:40. Mp=133-150° C.

$^1$H-NMR (DMSO-d$_6$): δ=10.70 (s, 1H, NH of imide), 7.81 (s, 1H, 8-H of one isomer), 7.79 (s, 1H, 8-H of another isomer), 7.38-7.33 (m, 2H, arom-H), 7.22-7.14 (m, 3H, arom-H), 6.62 (s, 2H, NH$_2$), 6.08-5.97 (m, 2H, C1'-H and NH of aminoester), 5.88 (b, 1H, 3'-OH of one isomer), 5.82 (b, 1H, 3'-OH of another isomer), 5.01-4.94 (m, 1H, α-H of aminoester), 4.44-4.25 (m, 3H, C3'-H, C4'-H, OCH of aminoester), 4.12-4.04 (m, 1H, C5'-H$_a$), 3.82-3.72 (m, 1H, C5'-H$_b$), 1.77-1.46 (m, 8H, methylene CH$_2$ of c-pentyl), 1.21-1.19 (m, 3H, α-CH$_3$ of aminoester), 1.09 (d, 3H, C2'-CH$_3$ of one isomer), 1.08 (d, 3H, C2'-CH$_3$ of another isomer).

$^{31}$P-NMR (DMSO-d$_6$): δ=4.95 (one isomer), 4.72 (another isomer).

Example 20

(2R,3R,4R,5R)-5-(2-amino-6-ethoxy-9H-purin-9-yl)-4-fluoro-2-(hydroxymethyl)-4-methyltetrahydrofuran-3-ol (10) from 6a To a 500 mL of dry round-bottomed flask was loaded (6a, 11 g, 20.92 mmol). Anhydrous absolute ethanol (210 mL) was added and followed by anhydrous K$_2$CO$_3$ (28.91 g, 209.2 mmol). The suspension was stirred and heated at 75° C. under nitrogen for 5.5 h. All the starting material was consumed at that time by TLC test. The mixture was cooled to room temperature and solid was filtered out. The filtrate was neutralized by addition of glacial acetic acid (2.52 g) to pH~7 and concentrated under reduced pressure. The residue was dissolved in methanol and mixed with silica gel (15 g). The dried mixture of crude product and silica gel was transferred to an empty cartridge and separated through column chromatography (Analogix 220 g, gradient of 0 to 15% MeOH in DCM) to afford product (5% MeOH in DCM) as a white foam solid (3.73 g, 54.5%). A second white solid was isolated from column (10% MeOH in DCM, 1.44 g) and it is a mixture of two dimers of nucleoside. A more polar, third white solid was collected from column (15% MeOH in DCM, 0.47 g) and it is a mixture of trimers of nucleoside. HPLC purity of product 99.94%.

$^1$H-NMR (DMSO-d$_6$): δ 8.16 (s, 1H, 8-H), 6.55 (s, 2H, NH$_2$), 6.04 (d, 1H, C1'-H), 5.66 (d, 1H, 3'-OH), 5.24 (m, 1H, 5'-OH), 4.44 (q, 2H, 6-OCH$_2$), 4.23-4.08 (m, 1H, C3'-H), 3.91-3.82 (m, 2H, C4'-H and C5'-H$_a$), 3.71-3.66 (m, 1H, C5'-H$_b$), 1.36 (t, 3H, CH$_3$ of ethyl), 1.06 (d, 3H, C2'-CH$_3$).

Example 21

(2R,3R,4R,5R)-5-(2-amino-6-ethoxy-9H-purin-9-yl)-4-fluoro-2-(hydroxymethyl)-4-methyltetrahydrofuran-3-ol (10) from 6b (2R,3R,4R,5R)-5-(2-amino-6-chloro-9H-purin-9-yl)-2-(((benzoyl)oxy)methyl)-4-fluoro-4-methyltetrahydrofuran- 3-yl benzoate (6b, 9.66 g, 18.4 mmol) was coevaporated with abs. ethanol (50 mL) under reduced pressure to remove any traces of methanol. Sodium ethoxide solution was prepared by adding sodium hydride (60 wt. % in mineral oil, 2.21 g, 55.2 mmol) in small portions to abs. ethanol (50 mL) cooled in an ice bath under a nitrogen atmosphere (caution, hydrogen gas evolution). This was added to the starting material and the resulting mixture was heated to reflux for one hour and then neutralized by addition of concentrated HCl at 5° C. The solution was concentrated under reduced pressure and to the residue was added was added 1N HCl (18 mL) and dichloromethane (18 mL). The layers were separated and the aqueous layer was washed with dichloromethane (2×10 mL). To the aqueous solution, ethyl acetate was added and sat. sodium carbonate solution was added to adjust the pH of aqueous layer to ca 8. The organic layer was separated and the aqueous layer was extracted with EtOAc (4×10 mL). The combined organic layer was dried over sodium sulfate and concentrated under reduced pressure to a light yellow foam solid. The crude mixture was purified by crystallization from acetone (10 mL) to give pure product in two crops. The combined solid product was dried (50° C., 0.2 mmHg, 24 h) to 5.04 g (84%) of material with NMR and HPLC matching material purified by chromatography.

Example 22

$N^6,N^6$-Diethyl-9-((4aR,6R,7R,7aR)-7-fluoro-2-methoxy-7-methyl-tetrahydro-furo[3,2-d][1,3,2]dioxaphosphinin-6-yl)-9H-purine-2,6-diamine (phosphite precursor to 15)

(2R,3R,4R,5R)-5-(2-Amino-6-azetidin-1-yl-purin-9-yl)-4-fluoro-2-hydroxymethyl-4-methyl-tetrahydro-furan-3-ol (8,340 mg, 1.0 mmol) was dissolved in anhydrous pyridine (6 ml) at ambient temperature. A solution of 0.45 M 1H-tetrazole in acetonitrile (5.5 mL, 2.5 mmol) was added followed by bis(N,N-diisopropylamino)methylphosphoramidite (317 μL, 1.1 mmol). The mixture was stirred at ambient temperature for 17 h. The solvent was concentrated under reduced pressure and the residue was triturated with ethyl acetate (20 mL). The resulting precipitant of salts was removed by filtration and the filtrate was concentrated under reduced pressure. The residue was purified by silica gel column chromatography using a gradient of ethyl acetate in hexanes (40-80%). The product containing fractions were combined and concentrated to a white solid, 47 mg (12% yield).

Example 23

6-Azetidin-1-yl-9-((4aR,6R,7R,7aR)-7-fluoro-2-methoxy-7-methyl-2-oxo-tetrahydrofuro[3,2-d][1,3,2]dioxaphosphinin-6-yl)-9H-purin-2-ylamine (15)

To a stirred solution of the cyclic phosphite (47 mg, 0.12 mmol) in dichloromethane (2 mL) was added 77% mCPBA (32 mg, 0.14 mmol) at ambient temperature. After 5 min, the solution was concentrated under reduced pressure the residue was purified by silica gel column chromatography (4 g) using a gradient of ethyl acetate in hexanes (80-100%). The pure product fractions were combined and concentrated under reduced pressure to a white solid, 21 mg (43%).

$^1$H-NMR (400 MHz, CDCl$_3$): δ=7.45 and 7.44 (two s, 1H), 5.45 (d, J=20 Hz, 1H), 4.89-4.41 (m, 10H), 3.93 (app. t, J=13.0 Hz, 3H), 2.49 (bs, 2H), 1.39 (overlapping d, J=22.4 Hz, 3H); MS (ESI) m/z 415 (M+H)$^+$.
$^{31}$P-NMR (162 MHz, CDCl$_3$): δ=−1.26, −3.58;

Example 24

6-Ethoxy-9-((4aR,6R,7R,7aR)-7-fluoro-2-methoxy-7-methyl-2-oxo-tetrahydro-2,5-furo[3,2-d][1,3,2]dioxaphosphinin-6-yl)-9H-purin-2-ylamine (16)

(2R,3R,4R,5R)-5-(2-Amino-6-ethoxy-purin-9-yl)-4-fluoro-2-hydroxymethyl-4-methyl-tetrahydro-furan-3-ol (10, 150 mg, 0.46 mmol) was dissolved in anhydrous pyridine (2 ml) at 0° C. A solution of 0.45 M 1H-tetrazole in acetonitrile (2.55 mL) was added followed by bis(N,N-diisopropylamino)methylphosphoramidite (0.16 mL, 0.55 mmol). The mixture was allowed to slowly warm to ambient temperature over 5 h. TLC indicated a complete reaction. The reaction was quenched upon the addition of water (0.1 mL). The reaction solution was concentrated under reduced pressure and then the residue was triturated with ethyl acetate (5 mL). The resulting white precipitate was removed by filtration and the filtrate was concentrated under reduced pressure. The resulting intermediate cyclic phosphite residue was dissolved in acetonitrile (2 mL) and then treated with t-butyl hydroperoxide (70% in water, 0.25 mL) for 17 at ambient temperature. TLC indicated a complete reaction. The reaction solution was concentrated under reduced pressure and the residue was purified by column chromatography (Analogix using a gradient of 0 to 10% IPA in DCM). The product containing fractions were combined and concentrated under reduced pressure to a white solid, 80 mg (34% yield) as a mixture of two diastereomers ~2:1.

$^1$H-NMR (400 MHz, DMSO-d$_6$): δ=8.16 (s, 1.5H), 6.65 (s, 2H), 6.55 (bs, 1H), 6.28 (d, J=20.8 Hz, 1.5H), 4.78-4.60 (m, 4.5H), 4.45 (q, J=6.8 Hz, 1H), 4.44 (q, J=6.8 Hz, 2H), 4.28-4.22 (m, 1.5H), 3.83 (d, J=11.6 Hz, 1.5H), 3.76 (d, J=11.6 Hz, 3H), 1.36 (t, J=7.2 Hz, 1.5H), 1.36 (t, J=7.2 Hz, 3H), 2.46 (d, J=22.4 Hz, 1.5H), 2.44 (d, J=22.8 Hz, 3H).
$^{31}$P-NMR (162 MHz, DMSO-d$_6$): δ −3.25, −4.16; t$_R$=0.86 (35.0%), 0.89 (64.4%).
LRMS (ESI): [M+H]$^+$calculated for $C_{14}H_{20}FN_5O_6P$ 404.3. found 404.3.

Example 25

6-Ethoxy-9-((4aR,6R,7R,7aR)-7-fluoro-2-isopropoxy-7-methyl-2-oxo-tetrahydro-2,5-furo[3,2-d][1,3,2]dioxaphosphinin-6-yl)-9H-purin-2-yl amine (17)

(2R,3R,4R,5R)-5-(2-Amino-6-ethoxy-purin-9-yl)-4-fluoro-2-hydroxymethyl-4-methyl-tetrahydro-furan-3-ol (10, 150 mg, 0.46 mmol) was dissolved in anhydrous pyridine (2 ml) at 0° C. A solution of 0.45 M 1H-tetrazole in acetonitrile (2.55 mL) was added followed by bis(N,N-diisopropylamino)isopropylphosphoramidite (0.16 mL, 0.55 mmol, 1.2 eq). The mixture was allowed to slowly warm to ambient temperature over 3 h. TLC indicated a complete reaction. The reaction was quenched upon the addition of water (0.1 mL). The reaction solution was concentrated under reduced pressure and then the residue was triturated with ethyl acetate (5 mL). The resulting white precipitate was removed by filtration and the filtrate was concentrated under reduced pressure. The resulting intermediate cyclic phosphite residue was dissolved in acetonitrile (2 mL) and then treated with t-butyl hydroperoxide (70% in water, 0.19 mL) for 5 h at ambient temperature. TLC indicated a complete reaction. The reaction solution was concentrated under reduced pressure and the residue was purified by column chromatography (Analogix using a gradient of 0 to 5% IPA in DCM). The two diastereomers were separable. Fractions containing each diastereomer were separately combined and concentrated under reduced pressure to white solids to give 20 mg of each diastereomer (combined yield 20%).

$R_P$-17: $^1$H-NMR (400 MHz, CDCl$_3$) δ 7.60 (s, 1H, C8-H), 6.02 (br d, 1H, J=19.6 Hz, C1'H), 5.46 (br s, 1H, 3'-H), 4.90 (sept, 1H, J=6.4 Hz, CH(CH$_3$)$_2$), 4.84 (br s, 2H, NH$_2$), 4.69-4.42 (m, 4H, 5'-Ha and Hb, CH$_2$CH$_3$), 4.40-4.37 (m, 1H, 4'-H), 1.48-1.33 (m, 9H, CH(CH$_3$)$_2$) and CH$_2$CH$_3$), 1.35 (d, 3H, J=22 Hz, 2'-C—CH$_3$). $^{31}$P-NMR (162 MHz, CDCl$_3$ with respect to an external standard of triphenylphosphate in CDCl$_3$ set to −17.80): δ −7.18 (s). LRMS (ESI) [M+H]$^+$ calculated for C$_{16}$H$_{24}$FN$_5$O$_6$P 432.4. found 432.4. Optical rotation [α]$^{25}_D$ −80.3 (c 1.00, methanol). Elemental analysis: Calcd: C, 44.15; H, 5.37; N, 16.24. Fd: C, 44.21; H, 5.21; N, 15.90. Mp 193.5-197.0 (melt with decomp.)

$S_P$-17: $^1$H-NMR (400 MHz, CDCl$_3$) δ 7.58 (s, 1H, C8-H), 5.98 (br d, 1H, J=20.0 Hz, C1'-H), 5.78 (br s, 1H, 3'-H), 5.10 (br s, 2H, NH$_2$), 4.83 (sept, 1H, J=6.4 Hz, CH(CH$_3$)$_2$), 4.63-4.48 (m, 4H, 5'-Ha and Hb, CH$_2$CH$_3$), 4.45-4.38 (m, 1H, 4'-H), 1.47-1.21 (m, 12H, CH(CH$_3$)$_2$), CH$_2$CH$_3$ and 2'-C—CH$_3$). $^{31}$P-NMR (162 MHz, CDCl$_3$ with respect to an external standard of triphenylphosphate in CDCl$_3$ set to −17.80) δ −3.74 (s). LRMS (ESI) [M+H]$^+$ calculated for C$_{16}$H$_{24}$FN$_5$O$_6$P 432.4. found 432.4.

Alternative Synthetic Process for Cyclic Phosphate Nucleotide, 17. (Scheme 2.)

We have found that the cyclic phosphate nucleotide, such as 17, can be prepared using either P(III)- or P(V)-reagents, as evidenced by the following discussion and accompanying schemes.

The P(III)-reagent cyclization reaction incorporating nucleoside 10 and a P(III)-reagent, such as 18 using 1H-tetrazole as the activator initially gives an approximately equimolar mixture of cyclic phosphite diastereomers, but with elevated reaction temperature (50-60° C.) for 6-24 hours, the mixture equilibrates predominantly to the cis isomer as reported in the literature. We have found that 4,5-dicyanoimidazole, DCI, accelerates this conversion rate and drives the equilibrium from initially approximately 80% to greater than 95% cis at 40-60° C. after 6 h. The cis-phosphite diastereomer leads to $R_P$-17 upon oxidation and also doubles the effective yield of this diastereomer and also simplifies the purification away from $S_P$-17. We have found it more efficient to oxidize the crude cyclic phosphite esters directly, but it is possible to isolate them as well. The cyclic phosphate esters do not equilibrate under the reaction conditions.

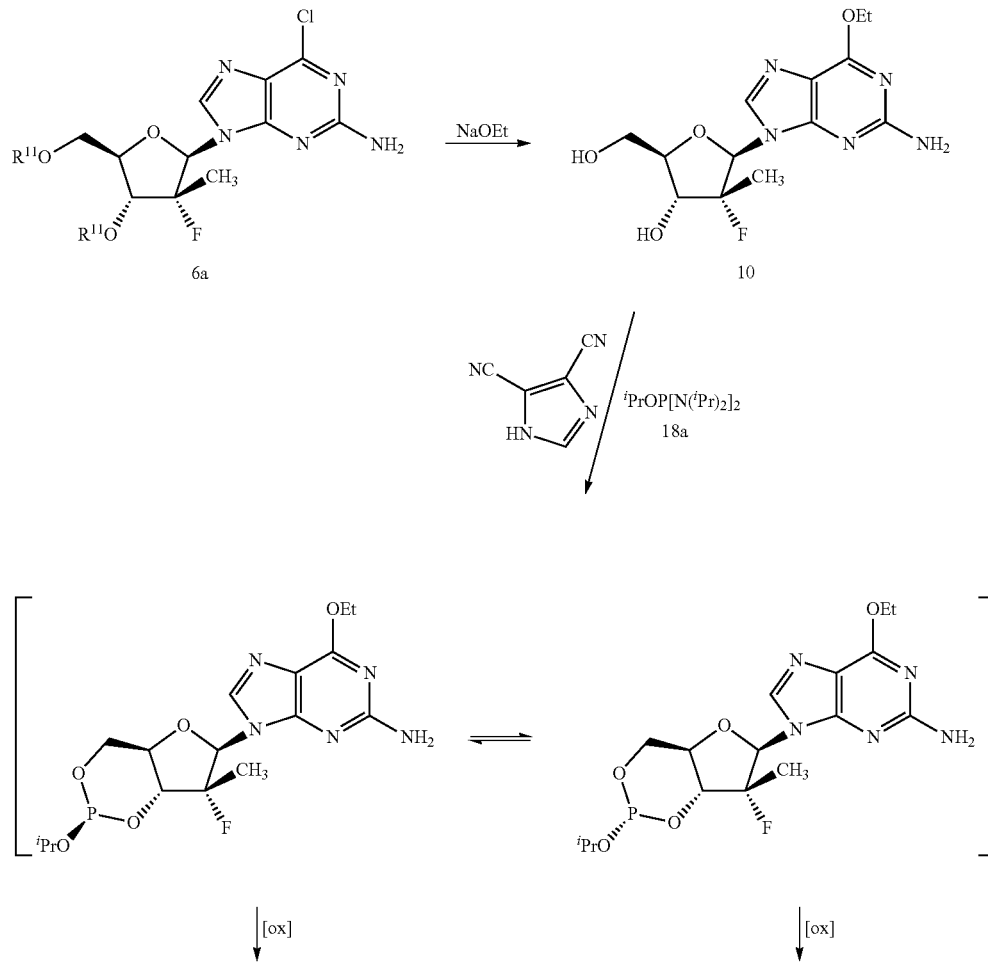

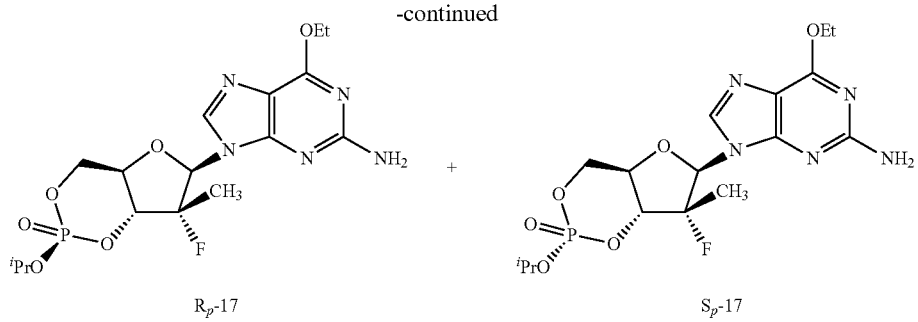

R_p-17      S_p-17

Oxidation [ox] of the phosphite esters to the phosphate esters can be accomplished in many ways. Peroxides such as m-chloroperbenzoic acid, t-butylhydroperoxide, hydrogen peroxide work well but are potentially explosive. Urea hydrogen peroxide is a safer peroxide form that works well for this conversion. One can envision using potassium persulfate, bleach and air-oxidation with or without catalysts such as TEMPO. We have chosen to use an iodine-THF-pyridine-water based oxidation reagent commonly used in automated oligonucleotide synthesis. The reaction is nearly instantaneous and can be monitored colorimetrically based on the brown color of iodine.

Alternatively, the diastereomers, $R_P$-17 and $S_p$-17, can be prepared directly from compound (10) by using an appropriate P(V)-reagent, as illustrated in Scheme 3.

For P(V)-reagent-based chemistry, one can start with phosphorus oxychloride and monsubstitute one chloride with isopropanol. The resulting dichlorophosphate isopropanoate reagent 22 (Grunze et al., U.S. Pat. No. 2,960,527) can be purified by vacuum distillation and can then be reacted with nucleoside 10 to form $R_P$-17 directly in approximately 50-70% isolated yield. Using the described conditions with triethylamine and N-methylimidazole, only traces of $S_P$-17 can be observed. The resulting crude product after an aqueous workup is also more amenable to direct crystallization without pre-purification by chromatography.

Purification of $R_P$-17 from $S_p$-17 and other by-products such as ring opened phosphates can be accomplished through washing an organic solution of the crude product with dilute base to remove free phosphates and the activating reagents

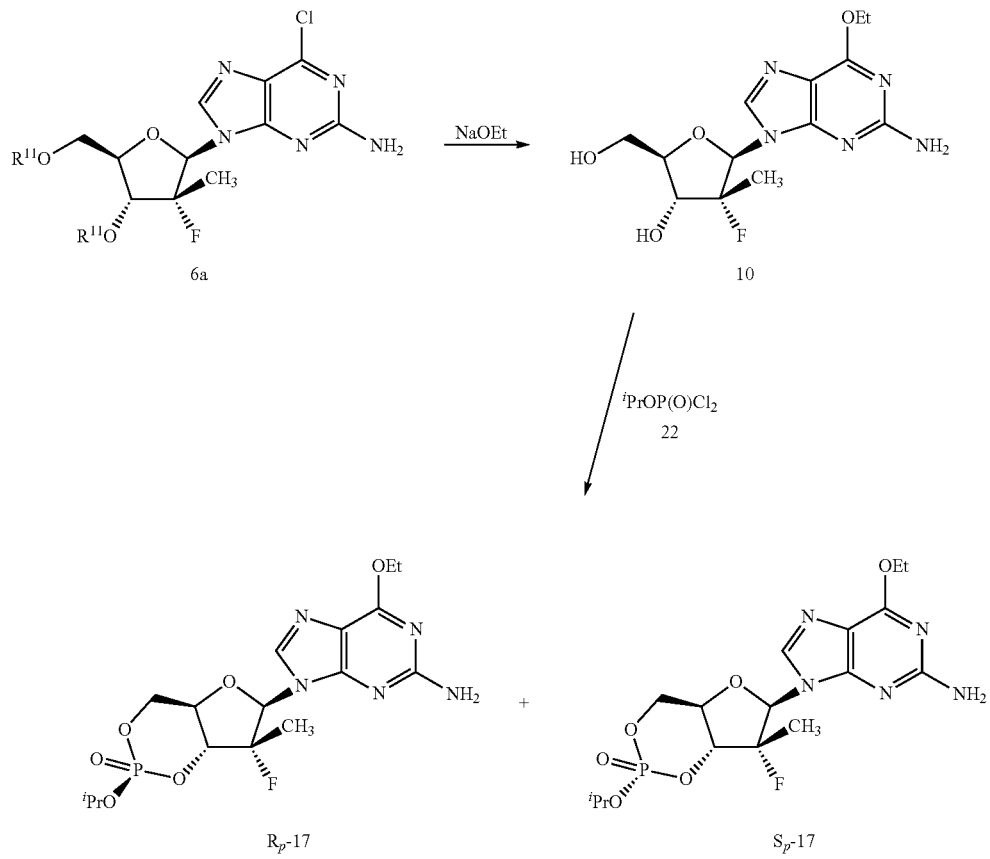

Scheme 3. Cyclic Phosphate Nucleotide By P(V)-Reagent followed by silica gel chromatography or crystallization or by a combination of both. As noted earlier, the desired product R$_P$-17 crystallizes readily from several solvents that include ethyl acetate, acetone and isopropanol. Although the gross form of the crystals vary, an XPRD study of crystals from the three solvents showed a single polymorph which is the same as could be mathematically predicted from the single crystal x-ray from ethyl acetate.

The synthesis of the cyclic phosphate ester can be done either through P(III)- or P(V)-reagents. Chemistry involving the use of the P(III)-reagent requires an oxidation step for the intermediate cyclic phosphite esters as shown in Scheme 2. For the P(III)-reagent chemistry, the preferred route is to make the phosphorus reagent, isopropyl-N,N,N',N'-tetraisopropylphosphorodiamidite (18), which is not commercially available, but can be prepared readily by reacting commercially available chloro-N,N,N',N'-tetraisopropylphosphorodiamidite (19) with isopropanol in the presence of a tertiary amine base as described below. Reagent 18 can be used as crude or it can be purified by vacuum distillation. Based on an analogous compound known in the literature, 2-cyanoethyl-N,N,N',N'-tetraisopropylphosphorodiamidite commonly used in oligonucleotide chemistry, one can envision also synthesizing 18 by reacting isopropanol or its trimethylsilyl ether with phosphorus trichloride to form the dichloro intermediate 20 which could then be converted to 18 or the monoamine reagent 21. Intermediate 20 can be reacted directly with the nucleoside in pyridine to make the intermediate cyclic phosphite esters although in a poor yield. The diisopropylamine groups in 18 can be activated for displacement by acidic and/or nucleophilic reagents. This method is well-documented in the literature for automated synthesis of oligonucleotides and their nucleoside phosphoramidite precursor reagents. 1H-tetrazole is the most commonly used activator reagent historically, but this activator reagent is no longer readily available in the US due to hazardous shipping regulations of a potentially explosive compound. We have found that non-explosive known activator reagent DCI gives superior yields for our cyclic phosphate ester derivatives. Other known activators such as 5-ethylthiotetrazole and imidazolium triflate also work as well as 1H-tetrazole.

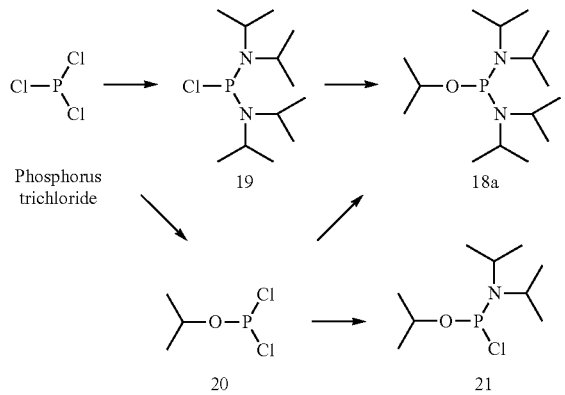

Scheme 4. Synthesis of Selected P(III)- and P(V) Reagents

Example 26

Isopropyl-N,N,N',N'-tetraisopropylphosphorodiamidite (18a)

Bis(diisopropylamino)chlorophosphine (19, 250.1 g, 937 mmol) was dissolved in anhydrous ethyl ether (3.6 L) and triethylamine (190 g, 1.87 mol) was introduced. The turbid mixture was cooled at 0° C. and a solution of 2-propanol (225 g, 287 mL) in ether (200 mL) was added via a funnel. The resulting cloudy mixture was stirred at room temperature for 5.5 hours. The reaction was complete by checking with $^{31}$P NMR (δ=116.10 ppm, S). White solid (triethylamine HCl salt) was removed by filtration. The filtrate was concentrated to furnish a pale brown liquid (272 g, quantitative) and used for next step without further purification. Note that the P(III)-reagent can be purified by vacuum distillation (bp 84-86° C., 5 mm Hg) if desired to furnish a colorless clear oil. $^1$H NMR (CDCl$_3$): δ 3.91 (m, 1H), 3.51 (m, 4H), 1.19 (d, 6H, J=6 Hz), 1.16 (24H, m). $^{31}$P NMR (CDCl$_3$): δ 116.1.

Example 27

6-Ethoxy-9-((2R,4aR,6R,7R,7aR)-7-fluoro-2-isopropoxy-7-methyl-2-oxo-tetrahydro-R$^5$-furo[3,2-d][1,3,2]dioxaphosphinin-6-yl)-9H-purin-2-ylamine (17-R$_P$) and 6-Ethoxy-9-((2S,4aR,6R,7R,7aR)-7-fluoro-2-isopropoxy-7-methyl-2-oxo-tetrahydro-R$^5$-furo[3,2-d][1,3,2]dioxaphosphinin-6-yl)-9H-purin-2-ylamine (S$_P$-17)

To a stirred suspension of (2R,3R,4R,5R)-5-(2-amino-6-ethoxy-9H-purin-9-yl)-4-fluoro-2-(hydroxymethyl)-4-methyltetrahydrofuran-3-ol (10, 65.0 g, 0.199 mol) and 4,5-dicyanoimidazole (59 g, 496 mol) in acetonitrile (1000 mL) at 0-5° C. was added P(III)-reagent 18 (62.35 mL, 0.199 mol), drop-wise over a period of 20 min. The solid was dissolved after the completion of the addition of the P(III)-reagent and a clear solution was observed. After 30 min, the solution was warmed to room temperature and stirred for 3 h. The reaction mixture was then heated at 50° C. (bath) for 6 h. (A small aliquot of the reaction was solution was diluted with an equal volume of CDCl$_3$ and tested by P-NMR to show less than 5% of the minor trans isomer at δ 127.91 ppm. The solvent was evaporated to dryness and the residue was stirred with EtOAc (500 mL) to form a white solid suspension of the DCI salt. The solid was removed by filtration and washed with EtOAc (250 mL). The combined filtrate was concentrated to dryness. To the residue was added a 0.1M solution of iodine in 70:28:2 (each in v/v %) THF:Pyridine:H$_2$O (2 L) over a period of 30 min at 5-10° C. After 2 h, more white DCI salt solid was collected by filtration and the filtrate was concentrated under reduced pressure. The residue was dissolved in ethyl acetate (1 L), washed with a 10% aqueous sodium thiosulfate (200 mL) and then saturated aq.NaHCO$_3$ (3×250 mL) until DCI was mostly removed as judged by TLC. The organic layer was washed with water (250 mL). (Also note that saturated sodium carbonate solution can remove DCI more efficiently). The organic layer was dried over anhydrous sodium sulfate, filtered and concentrated to give 86 g of foam. This was combined with similar material from two additional runs totaling 259 mmol of starting nucleoside. The combined crude foams were dissolved in a minimum of dichloromethane and subjected to silica gel chromatography using 3 L of silica gel in a 6 L sintered glass Buchner funnel with a step gradient of 30-75% EtOAc/hexanes to give 83 g of purified product as a foam as the primary fraction and 16 g of a secondary partially purified fraction. The primary fraction was suspended in ethyl ether (250 mL) which immediately gave a fine granular solid. The solid was collected by filtration and dried (40° C., 0.2 mmHg, 17 h) to 73.5 g of slightly off white powder containing 20 mole % of ethyl ether. The solid was co-evaporated with acetone (200 mL) and re-dried in a similar manner to 71.5 g of white solid with 2 mole % of acetone, and HPLC purity of 98.5%. The secondary contaminated fractions were purified by chromatography to afford an additional 9.0 g for a total recovery of 80.5 g (41%) of pure product. Portions of the desired R$_P$-17 solid could be re-crystallized into large irregular prisms by slow evaporation of product solutions in ethyl acetate, isopropanol and acetone. A small portion of the lower isomer (S$_P$-17 250 mg) was also isolated as an amorphous white foam solid.

R$_P$-17: $^1$H-NMR (400 MHz, CDCl$_3$) δ 7.60 (s, 1H, C8-H), 6.02 (br d, 1H, J=19.6 Hz, C1'-H), 5.46 (br s, 1H, 3'-H), 4.90 (sept, 1H, J=6.4 Hz, CH(CH$_3$)$_2$), 4.84 (br s, 2H, NH$_2$), 4.69-4.42 (m, 4H, 5'-Ha and Hb, CH$_2$CH$_3$), 4.40-4.37 (m, 1H, 4'-H), 1.48-1.33 (m, 9H, CH(CH$_3$)$_2$ and CH$_2$CH$_3$), 1.35 (d, 3H, J=22 Hz, 2'-C—CH$_3$). $^{31}$P-NMR (162 MHz, CDCl$_3$ with respect to an external standard of triphenylphosphate in CDCl$_3$ set to −17.80) δ −7.18 (s). LRMS (ESI) [M+H]$^+$ calculated for C$_{16}$H$_{24}$FN$_5$O$_6$P 432.4. found 432.4. Optical rotation [α]$^{25}_D$ −80.3 (c 1.00, methanol). Elemental analysis: Calcd: C, 44.15; H, 5.37; N, 16.24. Fd: C, 44.21; H, 5.21; N, 15.90. Mp 193.5-197.0 (melt with decomp.)

S$_P$-17: $^1$H-NMR (400 MHz, CDCl$_3$) δ 7.58 (s, 1H, C8-H), 5.98 (br d, 1H, J=20.0 Hz, C1'H), 5.78 (br s, 1H, 3'-H), 5.10 (br s, 2H, NH$_2$), 4.83 (sept, 1H, J=6.4 Hz, CH(CH$_3$)$_2$), 4.63-4.48 (m, 4H, 5'-Ha and Hb, CH$_2$CH$_3$), 4.45-4.38 (m, 1H, 4'-H), 1.47-1.21 (m, 12H, CH(CH$_3$)$_2$, CH$_2$CH$_3$ and 2'-C—CH$_3$). $^{31}$P-NMR (162 MHz, CDCl$_3$ with respect to an external standard of triphenylphosphate in CDCl$_3$ set to −17.80) δ −3.74 (s). LRMS (ESI) [M+H]$^+$ calculated for C$_{16}$H$_{24}$FN$_5$O$_6$P 432.4. found 432.4

Alternate Synthesis of 17 via P(V)-Reagent Chemistry

Example 28

Synthesis of Isopropyl Phoshorodichloridate (22)

A solution of isopropyl alcohol (38.6 mL, 0.50 mol) and triethylamine (69.83 mL, 0.50 mol) in dichloromethane (250 mL) was added to a stirred solution of POCl$_3$ (50.45 mL, 0.551 mmol) in DCM (250 mL), drop-wise over a period of 25 min at −5° C. After stirring the mixture for 1 h the solvent was evaporated and the residue was suspended in diethyl ether (400 mL). The triethylamine hydrochloride salt was filtered and washed with ether (100 mL). The filtrate was concentrated and the residue was distilled under high vacuum (~10 mmHg) with a cow-head (bath temperature slowly raised to 85° C. in 30 min). The required product was collected at 42-48° C. (distillation head temperature) as a colorless liquid (82.0 g, 93% yield).

Scheme 5: Preparation of Selected Cyclophosphate Nucleotides

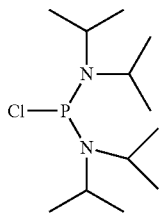

19

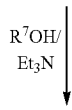

R$^7$OH/ Et$_3$N

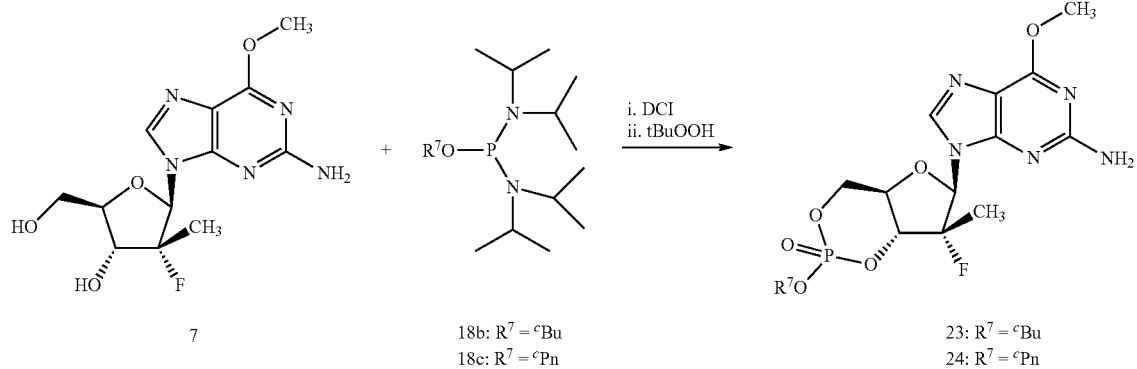

18b: R⁷ = ᶜBu
18c: R⁷ = ᶜPn

23: R⁷ = ᶜBu
24: R⁷ = ᶜPn

Example 29

Cyclobutyl-N,N,N',N'-tetraisopropylphosphorodiamidite (18b) and Cyclopentyl-N,N,N',N'-tetraisopropylphosphorodiamidite (18c)

To a solution of alcohol (R⁷OH, 10 mmol) in dry ethyl ether (20 mL) was added Et₃N (10 mmol) followed by chloride 1 (10 mmol) and the mixture was stirred at room temperature for 16 h. Solid was removed by filtration. Solvent was evaporated to give reagents 18b (for ᶜBuOH) and 18c (for ᶜPnOH) that were used for the next reaction without further purification.

Example 30

6-Methoxy-9-((2R,4aR,6R,7R,7aR)-7-fluoro-2-cyclobutoxy-7-methyl-2-oxo-tetrahydro-2λ⁵-furo[3,2-d][1,3,2]dioxaphosphinin-6-yl)-9H-purin-2-ylamine (23)

Preparation of cyclophosphates 23. To a solution of 7 (0.63 g, 2.00 mmol) in dry acetonitrile (30 mL) were added dicyanoimidazole (DCI, 0.59 g, 5 mmol) then reagent 18b (0.58 g, 2.00 mmol), and the mixture was stirred at room temperature for 30 min then at 45° C. for 1 h. To the mixture was added additional reagent 18b (1 mmol) and dicyanoimidazole (1.25 mmol). The resulting solution was stirred at 45° C. for 4 h. Solvent was evaporated and the residue was dissolved in CH₂Cl₂ (30 mL). To the solution was added t-BuOOH (70%, 1 mL) followed by Na₂SO₄ to dry the solution. The mixture was stirred at room temperature for 1 h. Toluene (20 mL) was added and the solvents were evaporated and the residue was dissolved in EtOAc (150 mL). The solution was washed with aq. K₂CO₃ to remove dicyanoimidazole and dried over Na₂SO₄. Solvent was evaporated and the residue was purified by silica gel column chromatography (0-100% EtOAc in hexanes) to give compound 23 was white solid (0.19 g, 22%). $\delta_H$ (400 MHz, CDCl₃): 7.59 (s, 1H), 6.01 (d, J=19.2 Hz, 1H), 5.50 (br. s, 1H), 4.89 (m, 3H), 4.36-4.67 (m, 3H), 4.08 (s, 3H), 2.23-2.50 (m, 4H), 1.67, 1.83 (m, 2H), 1.34 (d, J=22.0 Hz, 3H). MS (ESI): 430 (M+H⁺). ³¹P (CDCl₃): −6.98.

Example 31

6-Methoxy-9-((2R,4aR,6R,7R,7aR)-7-fluoro-2-cyclopentoxy-7-methyl-2-oxo-tetrahydro-R⁵-furo[3,2-d][1,3,2]dioxaphosphinin-6-yl)-9H-purin-2-ylamine (24)

Preparation of cyclophosphate 24. The above procedure was applied for the preparation of compound 24 except that 18c was used instead of 18b obtaining a 21% yield of crystalline 24. $\delta_H$ (400 MHz, CDCl₃): 7.59 (s, 1H), 6.02 (d, J=19.4 Hz, 1H), 5.30 (br. s, 1H), 5.08 (m, 1H), 4.85 (br.s, 2H), 4.35-4.66 (m, 3H), 4.07 (s, 3H), 1.65-1.99 (m, 8H), 1.34 (d, J=22.0 Hz, 3H). MS (ESI): 444 (M+H). ³¹P (CDCl₃): −6.00.

Example 32

6-Ethoxy-9-((2R,4aR,6R,7R,7aR)-7-fluoro-2-isopropoxy-7-methyl-2-oxo-tetrahydro-2λ⁵-furo[3,2-d][1,3,2]dioxaphosphinin-6-yl)-9H-purin-2-ylamine ($R_P$-17)

To a stirred suspension of (2R,3R,4R,5R)-5-(2-amino-6-ethoxy-9H-purin-9-yl)-4-fluoro-2-(hydroxymethyl)-4-methyltetrahydrofuran-3-ol (10, 5.00 g, 15.28 mmol) in dichloromethane (75 mL) was added triethylamine (8.52 mL, 61.1 mmol) at room temperature. The reaction mixture was cooled to −30° C. and then was added isopropyl phosphorodichloridate (22), drop-wise over a period of 5 min. The mixture was stirred at this temperature for 15 min and then was added NMI (2.54 mL, 32.1 mmol), drop-wise over a period of 5 min. The mixture was stirred between −25° C. and −15 for 1 h and then slowly warmed to room temperature in 20 h. The solvent was evaporated and the residue was triturated with EtOAc (500 mL). The off-white solid was filtered and washed with ethyl acetate (100 mL). Only a trace (<2%) of the other isomer $S_P$-17 was visible in the crude reaction. The filtrate was evaporated and the residue was chromatographed using 20-85% ethyl acetate/hexanes gradient to give pure $R_P$-17 as a white solid (4.65 g, 70.6% yield).

As an alternative non-chromatographic isolation method, the crude reaction mixture from a same scale reaction was diluted with dichloromethane (100 mL) and washed with 1 N HCl(2×100 mL) and water (2×50 mL). The organic layer was dried over sodium sulfate, filtered and concentrated under reduced pressure followed by high vacuum for 2 h to give 5.1 g of crude $R_P$-17. One portion of the crude (750 mg) was dissolved in ethyl acetate (2.0 mL) and heated to reflux with stirring for 6 h. The resulting suspension was cooled to ambient temperature and stirred for 20 h. The solid was collected by filtration and dried under high vacuum to give 482 mg (50% yield from 10) $R_P$-17 as a white solid, HPLC purity 99.03%. A second portion (1.0 g) was treated in a similar manner with isopropanol (2 mL) to afford 671 mg (52% from 10) of $R_P$-17 as a white solid, HPLC purity 98.64%.

Example 33

X-Ray Crystallography of $R_P$-17

$R_P$-17, crystallized from ethyl acetate through slow partial evaporation at ambient temperature starting at 20 mL/g, ($C_{16}H_{23}N_5PO_6F$) crystallizes in the orthorhombic space group (systematic absences 0k0: k=odd, and h01: 1=odd) with a=11.3544(13)Å, b=12.4153(14)Å, c=14.1622(15)Å, V=1996.4(4)Å$^3$, Z=4, and $d_{calc}$=1.435 g/cm$^3$ X-ray intensity data were collected on a Rigaku Mercury CCD area detector employing graphite-monochromated Mo-Kα radiation (λ=0.71073 Å) at a temperature of 150(1)K. Preliminary indexing was performed from a series of twelve 0.5° rotation images with exposures of 30 seconds. A total of 860 rotation images were collected with a crystal to detector distance of 35 mm, a 2θ swing angle of −10°, rotation widths of 0.5° and exposures of 5 seconds: scan no. 1 was a ϕ-scan from 0° to 310° at ω=10° and χ=20°; scan no. 2 was an ω-scan from −20° to 20° at χ=−90° and ϕ=0°; scan no. 3 was an ω-scan from −20° to 20° at χ=−90° and ϕ=90°; scan no. 4 was an ω-scan from −20° to 20° at χ=−90° and ϕ=135°. Rotation images were processed using CrystalClear (CrystalClear: Rigaku Corporation, 1999), producing a listing of unaveraged F$^2$ and σ(F$^2$) values which were then passed to the CrystalStructure program package for further processing and structure solution on a Dell Pentium 4 computer (CrystalStructure: Crystal Structure Analysis Package, Rigaku Corp. Rigaku/MSC (2002)). A total of 23016 reflections were measured over the ranges 2.82≤θ≤25.02°, −13≤h≤13, −14≤k≤14, −16≤l≤16 yielding 3520 unique reflections (Rint=0.0292). The intensity data were corrected for Lorentz and polarization effects and for absorption using REQAB (minimum and maximum transmission 0.8833, 1.0000).

The structure was solved by direct methods (SIR97) (SIR97: Altomare, A., M. Burla, M. Camalli, G. Cascarano, C. Giacovazzo, A. Guagliardi, A. Moliterni, G. Polidori & R. Spagna (1999). J. Appl. Cryst., 32, 115-119). Refinement was by full-matrix least squares based on F$^2$ using SHELXL-97 (SHELXL-97: Sheldrick, G. M. (2008) Acta Cryst., A64, 112-122). All reflections were used during refinement. The weighting scheme used was w=1/[σ$^2$(F$_o^2$)+0.0500P$^2$+1.0836 P=(F$_o^2$+2F$_c^2$)/3. Non-hydrogen atoms were refined anisotropically and hydrogen atoms were refined using a riding model. Refinement converged to R1=0.0417 and wR2=0.0994 for 3376 observed reflections for which F>4σ(F) and R$^1$=0.0440 and wR2=0.1020 and GOF=1.063 for all 3520 unique, non-zero reflections and 268 variables (R1=Σ||F$_o$|−|F$_c$||/Σ|F$_o$|; wR2=[Σw(F$_o^2$−F$_c^2$)2/Σw(F$_o^2$)$^2$]$^{1/2}$; GOF=[Σw(F$_o^2$−F$_c^2$)$^2$/(n−p)]$^{1/2}$; where n=the number of reflections and p=the number of parameters refined.). The maximum Δ/σ in the final cycle of least squares was 0.009 and the two most prominent peaks in the final difference Fourier were +0.487 and −0.291 e/Å$^3$.

Table 1 lists cell information, data collection parameters, and refinement data. Final positional and equivalent isotropic thermal parameters are given in Table 2. FIG. 1 is an ORTEP representation of R$_P$-17 with 30% probability thermal ellipsoids displayed (ORTEP-II: A Fortran Thermal Ellipsoid Plot Program for Crystal Structure Illustrations". C. K. Johnson (1976) ORNL-5138).

TABLE 1

Summary of Structure Determination of Compound R$_P$-17.

| | |
|---|---|
| Empirical formula | $C_{16}H_{23}N_5PO_6F$ |
| Formula weight | 431.36 |
| Temperature | 150(1) K |
| Wavelength | 0.71073 Å |
| Crystal system | orthorhombic |
| Space group | $P2_12_12_1$ |

TABLE 1-continued

Summary of Structure Determination of Compound R$_P$-17.

| | |
|---|---|
| Cell constants: | |
| a | 11.3544(13) Å |
| b | 12.4153(14) Å |
| c | 14.1622(15) Å |
| Volume | 1996.4(4) Å$^3$ |
| Z | 4 |
| Density (calculated) | 1.435 Mg/m$^3$ |
| Absorption coefficient | 0.191 mm$^{-1}$ |
| F(000) | 904 |
| Crystal size | 0.42 × 0.30 × 0.25 mm$^3$ |
| Theta range for data collection | 2.82 to 25.02° |
| Index ranges | −13 ≤ h ≤ 13, −14 ≤ k ≤ 14, −16 ≤ l ≤ 16 |
| Reflections collected | 23016 |
| Independent reflections | 3520 [R(int) = 0.0292] |
| Completeness to theta = 25.02° | 99.7% |
| Absorption correction | Semi-empirical from equivalents |
| Max. and min. transmission | 1.0000 and 0.8833 |
| Refinement method | Full-matrix least-squares on F$^2$ |
| Data/restraints/parameters | 3520/0/268 |
| Goodness-of-fit on F$^2$ | 1.063 |
| Final R indices [I > 2σ(I)] | R1 = 0.0417, wR2 = 0.0994 |
| R indices (all data) | R1 = 0.0440, wR2 = 0.1020 |
| Absolute structure parameter | 0.00(12) |
| Largest diff. peak and hole | 0.487 and −0.291 e · Å$^{-3}$ |

TABLE 2

Refined Positional Parameters for Compound R$_P$-17

| Atom | x | y | z | $U_{eq}$, Å$^2$ |
|---|---|---|---|---|
| C1 | 0.2555(2) | 0.83827(19) | 0.78326(17) | 0.0272(5) |
| C2 | 0.1938(2) | 0.9120(2) | 0.64894(17) | 0.0301(5) |
| C3 | 0.2700(2) | 1.0255(2) | 0.76243(18) | 0.0322(6) |
| C4 | 0.2878(2) | 0.93680(19) | 0.82096(17) | 0.0302(6) |
| C5 | 0.3333(2) | 0.82033(19) | 0.92511(17) | 0.0332(6) |
| H5 | 0.3610 | 0.7881 | 0.9801 | 0.044 |
| H5a | 0.1295 | 0.8410 | 0.5396 | 0.058 |
| H5b | 0.1386 | 0.9599 | 0.5274 | 0.058 |
| C6 | 0.2826(3) | 1.2144(2) | 0.7297(2) | 0.0412(7) |
| H6a | 0.2744 | 1.2798 | 0.7666 | 0.055 |
| H6b | 0.2103 | 1.2039 | 0.6944 | 0.055 |
| C7 | 0.3837(3) | 1.2265(2) | 0.6621(2) | 0.0493(8) |
| H7a | 0.4558 | 1.2338 | 0.6970 | 0.074 |
| H7b | 0.3718 | 1.2894 | 0.6239 | 0.074 |
| H7c | 0.3881 | 1.1641 | 0.6223 | 0.074 |
| C8 | 0.2857(2) | 0.64618(18) | 0.84428(17) | 0.0291(5) |
| H8 | 0.3230 | 0.6174 | 0.9013 | 0.039 |
| C9 | 0.1647(2) | 0.59037(19) | 0.83228(17) | 0.0300(5) |
| C10 | 0.1676(2) | 0.56883(18) | 0.72778(16) | 0.0271(5) |
| H10 | 0.1524 | 0.6364 | 0.6941 | 0.036 |
| C11 | 0.3245(3) | 0.5338(2) | 0.6094(2) | 0.0429(7) |
| H11a | 0.3123 | 0.6037 | 0.5803 | 0.057 |
| H11b | 0.4058 | 0.5123 | 0.6002 | 0.057 |
| C12 | 0.2940(2) | 0.5370(2) | 0.71253(17) | 0.0304(5) |
| H12 | 0.3080 | 0.4660 | 0.7406 | 0.040 |
| C13 | 0.0594(3) | 0.6481(3) | 0.8722(2) | 0.0466(7) |
| H13a | −0.0097 | 0.6046 | 0.8635 | 0.070 |
| H13b | 0.0494 | 0.7157 | 0.8403 | 0.070 |
| H13c | 0.0714 | 0.6608 | 0.9384 | 0.070 |
| C14 | −0.0316(3) | 0.6077(3) | 0.4951(2) | 0.0465(7) |
| H14 | −0.0835 | 0.5450 | 0.4886 | 0.062 |
| C15 | −0.0061(4) | 0.6550(4) | 0.4010(3) | 0.0822(14) |
| H15a | 0.0552 | 0.7078 | 0.4069 | 0.123 |
| H15b | −0.0760 | 0.6886 | 0.3766 | 0.123 |
| H15c | 0.0189 | 0.5992 | 0.3586 | 0.123 |
| C16 | −0.0817(4) | 0.6858(4) | 0.5660(4) | 0.0911(15) |
| H16a | −0.0922 | 0.6500 | 0.6255 | 0.137 |
| H16b | −0.1563 | 0.7120 | 0.5439 | 0.137 |
| H16c | −0.0284 | 0.7452 | 0.5737 | 0.137 |
| N1 | 0.28432(18) | 0.76254(15) | 0.85124(14) | 0.0283(5) |
| N2 | 0.20704(19) | 0.82043(16) | 0.69836(14) | 0.0292(5) |

TABLE 2-continued

Refined Positional Parameters for Compound $R_P$-17

| Atom | x | y | z | $U_{eq}$, Å$^2$ |
|---|---|---|---|---|
| N3 | 0.22347(19) | 1.01316(16) | 0.67699(14) | 0.0321(5) |
| N4 | 0.3370(2) | 0.92399(17) | 0.91070(15) | 0.0353(5) |
| N5 | 0.1485(2) | 0.90323(19) | 0.56147(16) | 0.0433(6) |
| O1 | 0.30100(19) | 1.12352(13) | 0.79270(13) | 0.0396(5) |
| O2 | 0.08771(16) | 0.48743(14) | 0.69318(11) | 0.0322(4) |
| O3 | 0.24398(19) | 0.45382(16) | 0.57040(13) | 0.0452(5) |
| O4 | 0.35659(15) | 0.61669(14) | 0.76480(12) | 0.0330(4) |
| O5 | 0.0411(2) | 0.37249(17) | 0.55075(14) | 0.0509(6) |
| O6 | 0.0849(2) | 0.57405(18) | 0.53123(15) | 0.0519(6) |
| F1 | 0.17654(15) | 0.48997(12) | 0.87802(10) | 0.0419(4) |
| P1 | 0.10640(7) | 0.46627(6) | 0.58365(5) | 0.0394(2) |

$U_{eq} = \frac{1}{3}[U_{11}(aa^*)^2 + U_{22}(bb^*)^2 + U_{33}(cc^*)^2 + 2U_{12}aa^*bb^*\cos\gamma + 2U_{13}aa^*cc^*\cos\beta + 2U_{23}bb^*cc^*\cos\alpha]$

Example 34

X-Ray Powder Diffraction of $R_P$-17

Samples of $R_P$-17 were analyzed by X-Ray Powder Diffraction (XRD) under the following regimen.

a. Bruker AXS/Siemens D5000

X-Ray Powder Diffraction patterns were collected on a Siemens D5000 diffractometer using Cu Kα radiation (40 kV, 40 mA), θ-θ goniometer, divergence of V20 and receiving slits, a graphite secondary monochromator and a scintillation counter. The instrument is performance checked using a certified Corundum standard (NIST 1976). The software used for data collection was Diffrac Plus XRD Commander v2.3.1 and the data were analyzed and presented using Diffrac Plus EVA v 11.0.0.2 or v 13.0.0.2.

Ambient Conditions

Samples run under ambient conditions were prepared as flat plate specimens using powder as received. Approximately 35 mg of the sample was gently packed into a cavity cut into polished, zero-background (510) silicon wafer. The sample was rotated in its own plane during analysis. The details of the data collection are: angular range: 2 to 42°2θ; step size: 0.05°2θ; and collection time: 4 s.step$^{-1}$.

b. Bruker AXS C2 GADDS

X-Ray Powder Diffraction patterns were collected on a Bruker AXS C2 GADDS diffractometer using Cu Kα radiation (40 kV, 40 mA), automated XYZ stage, laser video microscope for auto-sample positioning and a HiStar 2-dimensional area detector. X-ray optics consists of a single Gael multilayer mirror coupled with a pinhole collimator of 0.3 mm.

FIG. 2 shows an XRD Diffractogram for $R_P$-17.

Table 3 provides a tabulation of XRD diffractogram peaks for $R_P$-17.

TABLE 3

| Angle 2-Theta (°) | Relative Intensity % |
|---|---|
| 9.45 | 8.1 |
| 9.9 | 9.5 |
| 10.53 | 18.5 |
| 12.2 | 100 |
| 12.47 | 20.2 |
| 14.25 | 64 |
| 15.46 | 81.7 |
| 16.29 | 10.4 |
| 16.64 | 24.1 |
| 17.4 | 41.1 |
| 18.12 | 40.8 |
| 19.92 | 69.4 |
| 20.28 | 21.5 |
| 20.47 | 29.8 |
| 21.14 | 16.2 |
| 21.48 | 12.3 |
| 21.96 | 18.1 |
| 22.84 | 34 |
| 23.63 | 38.9 |
| 24.24 | 22.4 |
| 24.51 | 32.6 |
| 24.87 | 15.3 |
| 25.08 | 30.3 |
| 25.41 | 12 |
| 26.09 | 12.3 |
| 26.49 | 6.3 |
| 27.35 | 30.1 |
| 28.06 | 8.6 |
| 29.94 | 5.7 |
| 30.04 | 6.6 |
| 30.87 | 6.1 |
| 32.37 | 6.2 |
| 32.69 | 5.7 |
| 32.94 | 7.3 |
| 33.32 | 6.7 |
| 34.45 | 7.6 |
| 35.04 | 6.5 |
| 35.19 | 5.7 |
| 36.71 | 2.9 |
| 37.2 | 3.4 |
| 38.67 | 9.5 |
| 39.38 | 7.2 |
| 40.38 | 6 |
| 41.91 | 7.2 |

Example 35

Fourier Transform-Infrared (FT-IR) Spectrometry

Data for $R_P$-17 were collected on a Perkin-Elmer Spectrum One fitted with a universal Attenuated Total Reflectance (ATR) sampling accessory. The data were collected and analyzed using Spectrum v5.0.1 software.

Figure 3:
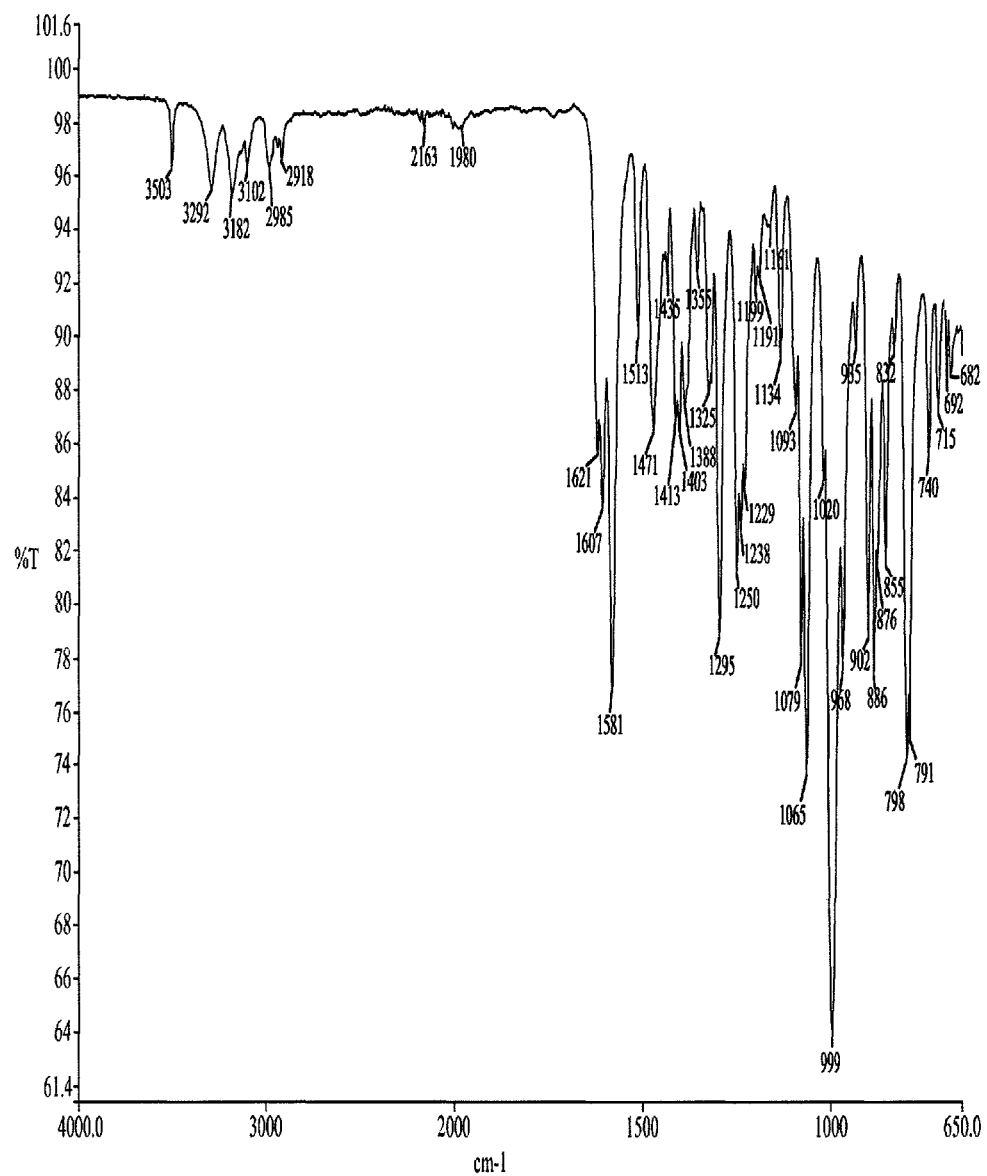
FIG. 3. FT-IR spectrum of $R_P$-17.

The FT-IR spectrum obtained for $R_P$-17 is shown in FIG. 3. Selected peaks, in wave-numbers (cm$^{-1}$) are recited below:

~1607, ~1581, ~1295, ~1250, ~1238, ~1229, ~1079, ~1065, ~999, ~968, ~902, ~886, ~876, ~855, ~798, and ~791

Scheme 6. Preparation of Selected Isotopically Enriched Purine Analogs

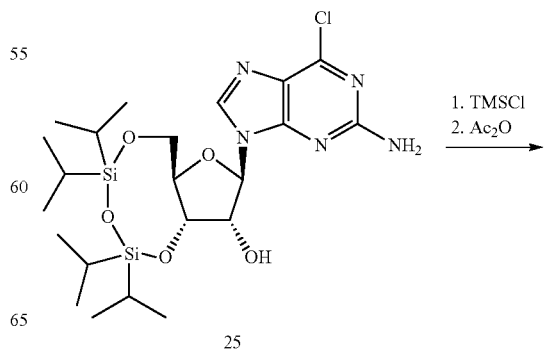

25

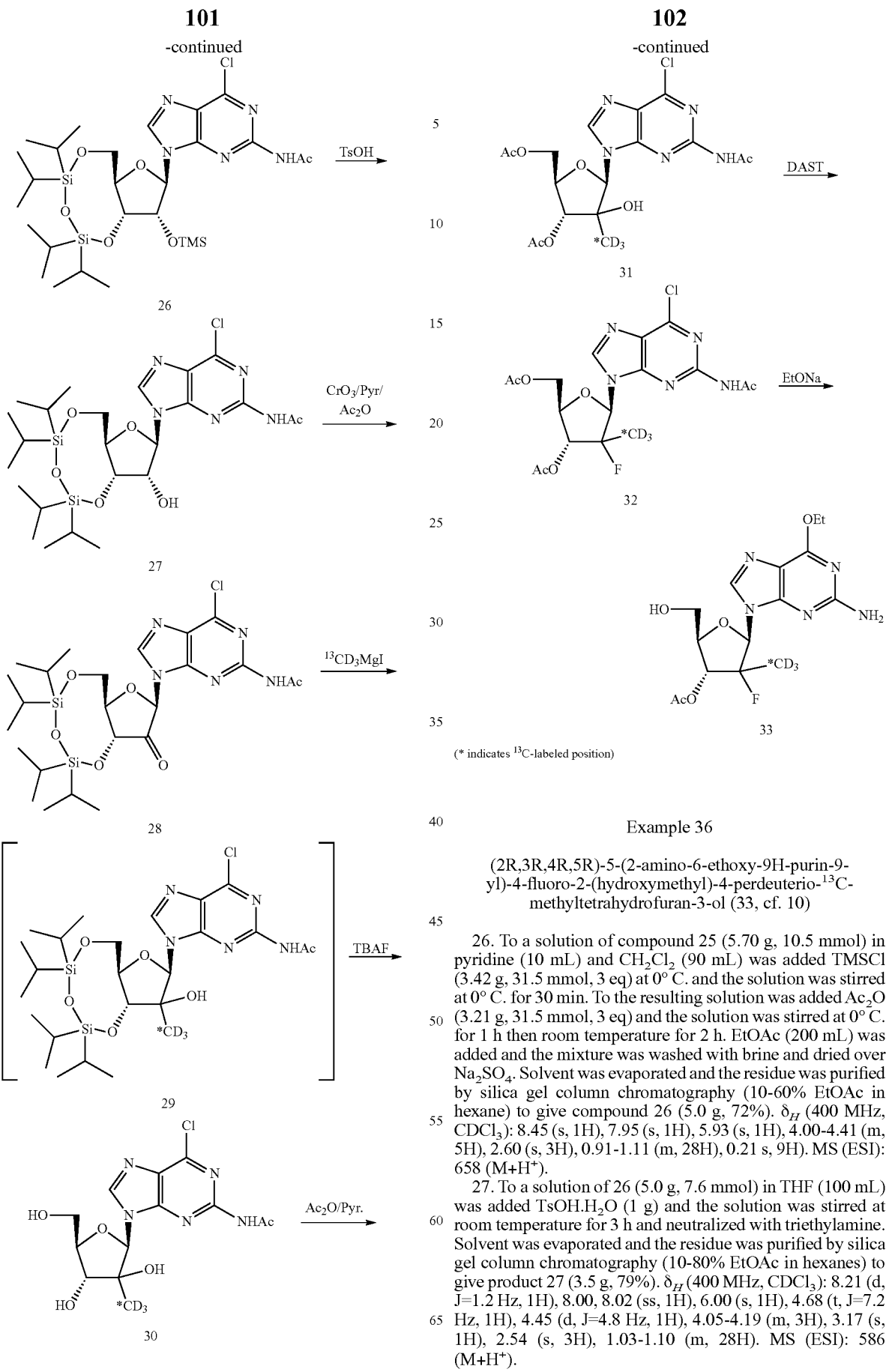

Example 36

(2R,3R,4R,5R)-5-(2-amino-6-ethoxy-9H-purin-9-yl)-4-fluoro-2-(hydroxymethyl)-4-perdeuterio-$^{13}$C-methyltetrahydrofuran-3-ol (33, cf. 10)

26. To a solution of compound 25 (5.70 g, 10.5 mmol) in pyridine (10 mL) and CH$_2$Cl$_2$ (90 mL) was added TMSCl (3.42 g, 31.5 mmol, 3 eq) at 0° C. and the solution was stirred at 0° C. for 30 min. To the resulting solution was added Ac$_2$O (3.21 g, 31.5 mmol, 3 eq) and the solution was stirred at 0° C. for 1 h then room temperature for 2 h. EtOAc (200 mL) was added and the mixture was washed with brine and dried over Na$_2$SO$_4$. Solvent was evaporated and the residue was purified by silica gel column chromatography (10-60% EtOAc in hexane) to give compound 26 (5.0 g, 72%). $\delta_H$ (400 MHz, CDCl$_3$): 8.45 (s, 1H), 7.95 (s, 1H), 5.93 (s, 1H), 4.00-4.41 (m, 5H), 2.60 (s, 3H), 0.91-1.11 (m, 28H), 0.21 s, 9H). MS (ESI): 658 (M+H$^+$).

27. To a solution of 26 (5.0 g, 7.6 mmol) in THF (100 mL) was added TsOH.H$_2$O (1 g) and the solution was stirred at room temperature for 3 h and neutralized with triethylamine. Solvent was evaporated and the residue was purified by silica gel column chromatography (10-80% EtOAc in hexanes) to give product 27 (3.5 g, 79%). $\delta_H$ (400 MHz, CDCl$_3$): 8.21 (d, J=1.2 Hz, 1H), 8.00, 8.02 (ss, 1H), 6.00 (s, 1H), 4.68 (t, J=7.2 Hz, 1H), 4.45 (d, J=4.8 Hz, 1H), 4.05-4.19 (m, 3H), 3.17 (s, 1H), 2.54 (s, 3H), 1.03-1.10 (m, 28H). MS (ESI): 586 (M+H$^+$).

28. To a mixture of CrO$_3$ (2.2 g, 21.99 mmol, 3 mol eq) in CH$_2$Cl$_2$ (30 mL) were added pyridine (1.74 g, 22.0 mmol, 3 eq) then Ac$_2$O (2.24 g, 22 mmol, 3 eq). To the resulting mixture was added a solution of 27 (4.3 g, 7.33 mmol) in CH$_2$Cl$_2$ (10 mL) and the mixture was stirred at room temperature for 30 min. To the mixture was added EtOAc (200 mL) slowly and the mixture was stirred at room temperature for 1 h. The solid was filtered off through silica gel pad. The filtrate was concentrated to dryness and the residue was co-evaporated with toluene. EtOAc (100 mL) was added and the mixture was filtered through silica gel pad. The filtrate was evaporated. The residue was co-evaporated with toluene to give white solid. The residue was purified by silica gel column chromatography (5-80% EtOAc in hexane) to give a syrup. The syrup (hydrated) was co-evaporated with toluene (2×50 mL) to give compound 28 which was dried under vacuum overnight (free ketone, 3.65 g, 85%). δ$_H$ (400 MHz, CDCl$_3$): 8.00 (s, 1H), 7.86 (s, 1H), 5.77 (s, 1H), 5.25 (d, J=9.2 Hz, 1H), 4.07-4.28 (m, 3H), 2.41 (s, 3H), 1.06-1.16 (m, 28H).

31. To a mixture of Mg (1.68 g, 69.14 mmom) in dry ethyl ether (40 mL) was added ⅓ of $^{13}$CD$_3$I (8.70 g, 60.00 mmol) and the mixture was stirred at room temperature until reflux. To the mixture was added the rest of $^{13}$CD$_3$I at the rate that kept the reaction under gentle reflux. After cooled down to room temperature, the solution was transferred to another flask in ice-bath. To the solution of the reagent was added AlCl$_3$ (2.67 g, 20.00 mmol) and the mixture was stirred at 0° C. for 1 h. Ether was evaporated at room temperature to obtain syrup. To the syrup was added CH$_2$Cl$_2$ (100 mL). To the mixture was added a solution of compound 28 (5.84 g, 10.00 mmol) in CH$_2$Cl$_2$ (30 mL) slowly at 0° C. The solution was stirred at 0° C. for 3 h. The reaction was quenched by addition of saturated NH$_4$Cl (10 mL). EtOAc (300 mL) was added and the mixture was stirred at room temperature for 10 min. Solid was removed by filtration. The filtrate was washed with brine and dried over Na$_2$SO$_4$. Solvent was evaporated and the residue was dissolved in THF (100 mL). To the mixture was added TBAF (30 mmol, 1M in THF) and the solution was stirred at room temperature for 2 h. Solvent was evaporated and the residue was purified by silica gel column (0-15% MeOH in CH$_2$Cl$_2$) to give nucleoside 30 which was dissolved in pyridine (30 mL) and CH$_2$Cl$_2$ (100 mL). To the solution was added Ac$_2$O (3 mL, excess) and the mixture was stirred at 0° C. for 16 h. Water (10 mL) was added and the mixture was stirred at room temperature for 10 min. EtOAc (200 mL) was added and the solution was washed with water, brine and dried over Na$_2$SO$_4$. Solvent was evaporated and the residue was purified by silica gel column chromatography (0-8% MeOH in CH$_2$Cl$_2$) to give compound 31 as white solid 1.33 g, 29.9%). δ$_H$ (400 MHz, CDCl$_3$): 8.28 (s, 1H), 8.10 (s, 1H), 6.03 (d, J=2.4 Hz, 1H), 5.22 (d, J=3.2 Hz, 1H), 4.50 (m, 2H), 4.24 (m, 1H), 4.00 (s, 1H), 2.45 (s, 3H), 2.20, 2.12 (ss, 2×3H). MS (ESI): 446 (M+H$^+$).

32. To a solution of 31 (0.68 g, 1.53 mmol) in CH$_2$Cl$_2$ (68 mL) precooled at −78° C. was added DAST (0.74 g, 4.59 mmol) within 20 min and the solution was stirred at the same temperature for 30 min then at room temperature for 1 h. EtOAc (200 mL) was added and the solution was washed with aq. NaHCO$_3$, brine and dried over Na$_2$SO$_4$. Solvent was evaporated and the residue was purified by silica gel column chromatography (0-90% EtOAc in hexanes) to give compound 32 (0.21 g, 30.6%) as white solid. δ$_H$ (400 MHz, CDCl$_3$): 8.26 (s, 1H), 8.11 (s, 1H), 6.23 (d, J=17.2 Hz, 1H), 5.75 (m, 1H), 4.39, 4.56 (m, 3H), 2.21, 2.17 (ss, 2×3H). MS (ESI): 448 (M+H$^+$).

33. To dry EtOH (25 mL) was added EtONa in EtOH (3.1 mL, 21%, 0.53 g, 7.83 mmol). To the solution was added a solution of compound 32 (0.35 g, 0.78 mmol) in EtOH (11 mL) and the solution was stirred at room temperature for 20 h. The reaction was quenched with AcOH to pH7. Solvent was evaporated and the residue was purified by silica gel column chromatography (0-10% MeOH in CH$_2$Cl$_2$) to give compound 33 (0.21 g, 81%). δ$_H$ (400 MHz, CD$_3$OD): 8.22 (s, 1H), 6.15 (d, J=18.0 Hz, 1H), 4.52 (q, J=6.8 Hz, 2H), 4.38 (dd, J=5.8, 23.6 Hz, 1H), 4.03 (m, 2H), 3.86 (m, 1H). MS (ESI): 332 (M+H$^+$).

Example 37

Synthesis of R$_P$-6-Ethoxy-9-((4aR,6R,7R,7aR)-7-fluoro-2-isopropoxy-7-methyl-$^{13}$CD$_3$-2-oxo-tetrahydro-2,5-furo[3,2-d][1,3,2]dioxaphosphinin-6-yl)-9H-purin-2-yl amine (34)

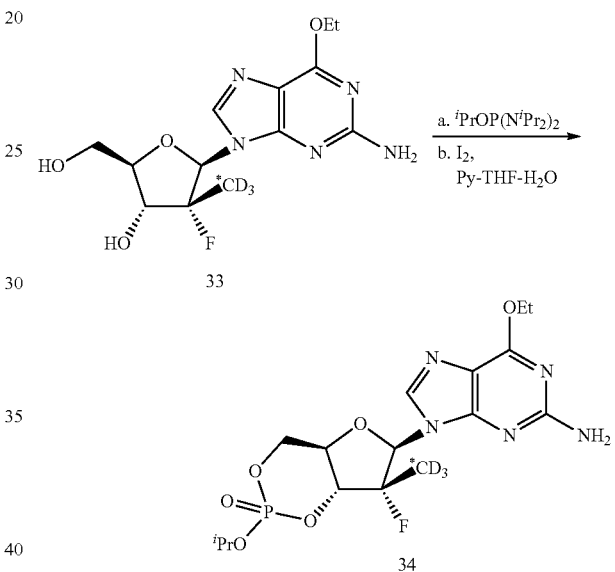

To a dry 50 mL round-bottomed flask was charged 205 mg of the nucleoside 33. Anhydrous acetonitrile (4 mL) was added and the suspension was cooled in an ice bath. To the mixture 4,5-dicyanoimidazole (183 mg) was added and followed by isopropyl tetraisopropylphosphorodiamidite (209 mg). The resulted clear solution was then heated at 45° C. for 6 hrs. The reaction mixture was concentrated and residue was triturated with 20 mL of ethyl acetate. White solid was removed by passing the supernatant through a short pad of cotton in a pipette. The flask and pipette were rinsed with ethyl acetate (4×5 mL). The combined solution was concentrated and the flask with the residue was cooled in an ice bath. A solution of iodine (ca. 0.1 M in a mixture of THF, pyridine and water, ~8 mL) was added and the brown solution was stirred at room temperature for 5 mins. An aqueous solution of sodium thiosulphate (10%) was added dropwise until a light brown solution was formed. After removal of solvents, the residue was triturated with ethyl acetate (20 mL) and solid was removed by passing the solution through a pad of cotton in a pipette and rinsed the flask and pipette with ethyl acetate (4×5 mL). The combined organic solution was washed with sat. sodium bicarbonate (2×15 mL) and sat sodium carbonate (15 mL). The combined aqueous layer was extracted with ethyl acetate (4×20 mL). The combined organic layer was washed with brine (5 mL) and dried over Na$_2$SO$_4$. Solvent was removed and residue was purified by column chromatography (silica gel, 40% EtOAc in hexanes) to afford 98.7 mg of product 34 as a white solid with a yield of 34%. HPLC purity of product: 98.23%. $^1$H NMR (CDCl$_3$): δ 7.59 (s, 1H, 8-H), 6.01 (d, 1H, C1'-H), 5.41 (br, 1H, C3'-H), 4.88 (s, 2H, NH$_2$), 4.85 (m, 1H, CH of ester), 4.64-4.46 (m, 4H, 6-OCH$_2$, C4'-H and C5'-H$_a$), 4.38-4.32 (m, 1H, C5'-H$_b$), 1.45-1.41 (m, 9H, CH$_3$s). $^{31}$P NMR (CDCl$_3$): δ −5.96.

Example 38

(2S)-isopropyl-2-(((((2R,3R,4R,5R)-5-(2-amino-6-methoxy-9H-purin-9-yl)-4-fluoro-3-hydroxy-4-methyltetrahydrofuran-2-yl)methoxy) (phenoxy)phosphorylamino)-2-deuterio-propanoate-d$_3$ (36)

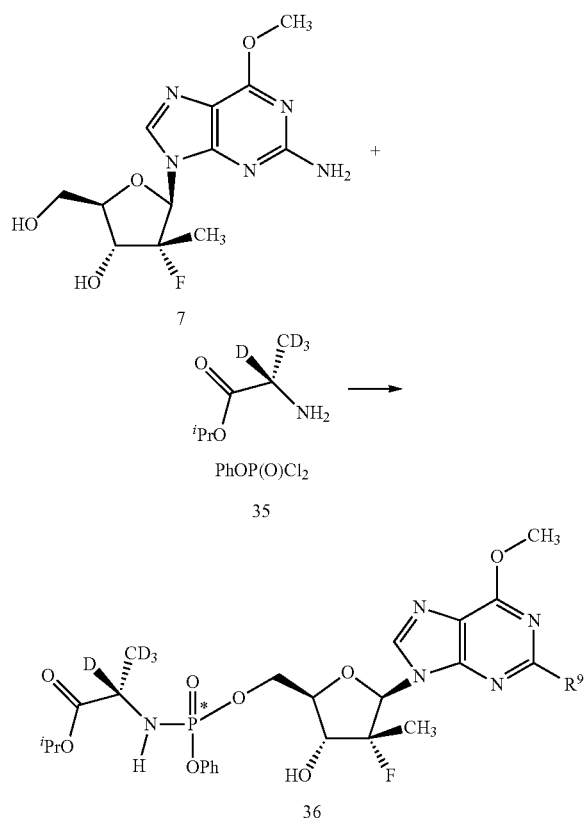

Isopropyl 2,3,3,3-d$_4$ L-alaninate, 35. 2,3,3,3-d$_4$ L-alanine (Aldrich, 7.19 g, 77.2 mmol) was added to anhydrous isopropanol (50 mL) and stirred under a nitrogen atmosphere. Thionyl chloride (9.19 g, 77.2 mmol) was dropped in over 15 min and the warm reaction mixture was heated to reflux for 17 h. The reaction was concentrated under reduced pressure and then coevaporated with acetonitrile (40 mL) and then dried (25° C., 0.1 mm) for 17 h. Upon standing for 3 days, a portion crystallized. Ethyl ether (50 mL) was added and the mixture was stirred for 2 h to break up into a fine suspension. The solid was collected by filtration and washed with ether (50 mL) and dried (50° C., 0.1 mm) to give 6.3 g g (48%) of product as white, shiny plates. The product was used as is in the next step.

36. To a 100 mL dry round-bottomed flask was loaded phenyl dichlorophosphate (1.4 eq. 0.47 g, 2.24 mmol) and anhydrous dichloromethane (20 ml). The labeled-amino acid isopropyl ester salt of L-alanine (1.8 eq., 0.492 g, 2.88 mmol) was added to the solution and the mixture was cooled to −5° C. A solution of N-Methyl imidazole (10. eq., 1.26 mL, 15.9 mmol) in anhydrous dichloromethane (5 ml) was then added quickly via a dry syringe at −5° C. and the solution was stirred at −5° C. for 1 h. The nucleoside (7, 0.5 g, 1.6 mmol) was added from a vial in one portion at −5° C. and the solid was slowly dissolved in 20 minutes. The reaction temperature was allowed to rise to ambient temperature over 1 h and stirred overnight. After 18 h, the reaction was almost complete as shown by TLC result and diluted with 25 mL of dichloromethane. HCl solution (1 N, 20 mL) was added. The aqueous layer was separated and extracted with dichloromethane. The organic layer was washed with sat NaHCO$_3$, water, brine and dried over MgSO$_4$. After removal of the solvent under reduced pressure, the off-white foam was purified through automated column chromatography using a 40 g cartridge and a gradient of 0-3% methanol in dichloromethane to afford product as a white foam solid (62% yield). HPLC purity 99.6%. NMR spectra of product showed it is a mixture of two diastereoisomers with a ratio of 1:3. $^1$H NMR (DMSO D$_6$): δ 7.97 (1H, s), 7.95 (1H, s) 7.37-7.31 (2H, m), 7.29-7.20 (3H, m), 6.62 (2H, s), 6.11 (1H, d), 6.06 (1H, d), 6.05-5.97 (1H, m), 5.80 (1H, d), 5.81 (1H, d), 4.87-4.76 (1H, hept), 4.45-4.28 (2H, m), 4.10-4.00 (1H, m), 3.95 (3H, s), 3.82-3.72 (2H, m), 1.13-1.09 (6H, m), 1.03 (3H, d). $^{31}$P NMR (CDCl$_3$): δ 5.55, 4.71 (1:3); MS, m/e 587 (M+1)$^+$.

Example 39

Biological Data

HCV replicon assay. HCV replicon RNA-containing Huh7 cells (clone A cells; Apath, LLC, St. Louis, Mo.) were kept at exponential growth in Dulbecco's modified Eagle's medium (high glucose) containing 10% fetal bovine serum, 4 mM L-glutamine and 1 mM sodium pyruvate, 1× nonessential amino acids, and G418 (1,000 μg/ml). Antiviral assays were performed in the same medium without G418. Cells were seeded in a 96-well plate at 1,500 cells per well, and test compounds were added immediately after seeding. Incubation time 4 days. At the end of the incubation step, total cellular RNA was isolated (RNeasy 96 kit; Qiagen). Replicon RNA and an internal control (TaqMan rRNA control reagents; Applied Biosystems) were amplified in a single-step multiplex RT-PCR protocol as recommended by the manufacturer. The HCV primers and probe were designed with Primer Express software (Applied Biosystems) and covered highly conserved 5'-untranslated region (UTR) sequences (sense, 5'-AGCCATGGCGTTAGTA(T)GAGTGT-3', and antisense, 5'-TTCCGCAGACCAC-TATGG-3'; probe, 5'-FAM-CCTCCAGGAC-CCCCCTCCC-TAMRA-3').

To express the antiviral effectiveness of a compound, the threshold RT-PCR cycle of the test compound was subtracted from the average threshold RT-PCR cycle of the no-drug control (ΔCt$_{HCV}$). A ΔCt of 3.3 equals a 1-log 10 reduction (equal to the 90% effective concentration [EC$_{90}$]) in replicon RNA levels. The cytotoxicity of the test compound could also be expressed by calculating the ΔCt$_{rRNA}$ values. The ΔΔCt specificity parameter could then be introduced (ΔCt$_{HCV}$−ΔCt$_{rRNA}$), in which the levels of HCV RNA are normalized for the rRNA levels and calibrated against the no-drug control.

Compounds 11, 12, 14, 15, 16, and 17, represented by the following structure(s),

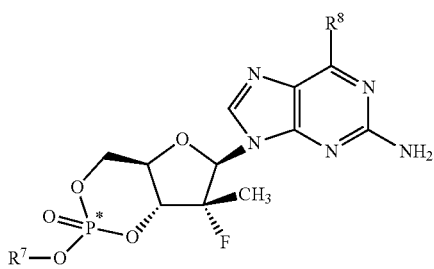

15: $R^7$ = Me, $R^8$ = —N(—CH₂CH₂CH₂—)
16: $R^7$ = Me, $R^8$ = —OEt
17: $R^7$ = $^i$Pr, $R^8$ = —OEt
23: $R^7$ = $^c$Bu, $R^8$ = —OMe
24: $R^7$ = $^c$Pn, $R^8$ = —OMe

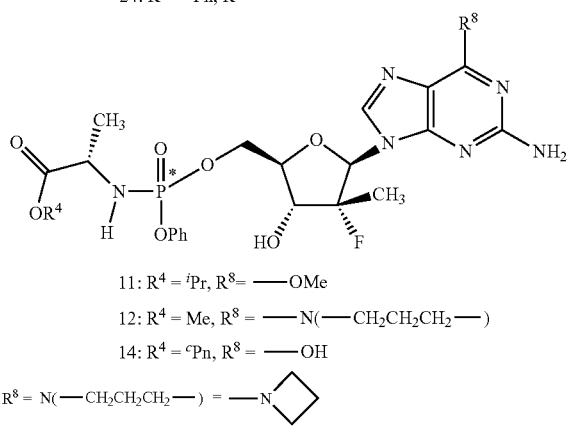

11: $R^4$ = $^i$Pr, $R^8$ = —OMe
12: $R^4$ = Me, $R^8$ = —N(—CH₂CH₂CH₂—)
14: $R^4$ = $^c$Pn, $R^8$ = —OH $R^8$ = N(—CH₂CH₂CH₂—) = —N⟨azetidine⟩ were tested for their biological properties based on the preceding assay. The results of these tests are disclosed in the Table 4.

TABLE 4

Activity of Selected Compounds

| Compd. No. | CloneA $EC_{90}$ (µM) |
|---|---|
| 11 | 0.02 |
| 12 | 0.07 |
| 14 | 0.13 |
| 15 | 0.71 |
| 16 | 0.48 |
| 17 | 0.60 |
| 23 | 0.13 |
| 24 | 0.037 |

The contents of U.S. patent application Ser. No. 12/053,015, filed Mar. 21, 2008 (see also WO 2008/121634), U.S. patent application Ser. No. 12/479,075, filed Jun. 5, 2009, and U.S. Provisional Patent Application Nos. 61/060,683, filed Jun. 11, 2008, 61/140,423, 61/140,441, 61/140,317, and 61/140,369, each of which being filed Dec. 23, 2008 are hereby incorporated by reference in their entirety. Moreover, the patent and non-patent references disclosed herein are incorporated by reference. In the event that the incorporated subject matter contains a term that conflicts with a term disclosed in the present application text, the meaning of the term contained in the present application controls provided that the overall meaning of the incorporated subject matter is not lost.

The invention claimed is:

1. A compound of formula IV:

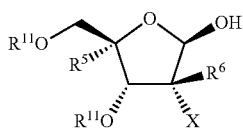

or a salt thereof, wherein:
$R^5$ is H or $N_3$;
$R^6$ is $CH_3$;
$R^{11}$ is a protecting group; and
X is F.

2. A compound of formula V:

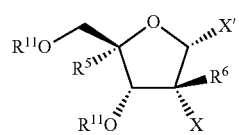

or a salt thereof, wherein:
$R^5$ is $N_3$;
$R^6$ is $CH_3$;
$R^{11}$ is a protecting group;
X is F; and
X' is Cl, Br, or I.

3. The compound of claim 1, wherein $R^5$ is H.

4. A process for preparing a compound of formula IV, wherein said process comprises:
(a) stereoselective reduction of a compound of formula III using a hydride reducing agent to provide a mixture comprising a compound of formula IV and a compound of formula IV-α:

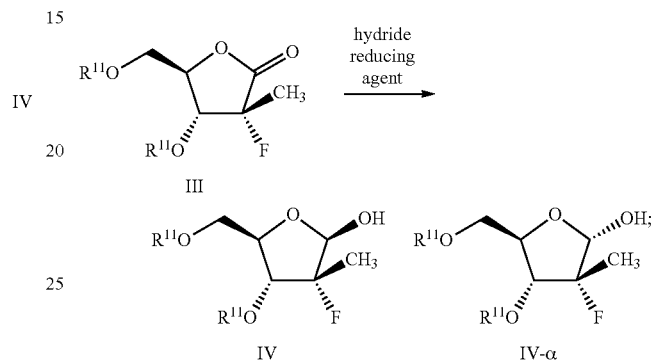

and (b) crystallizing the compound of formula IV from the mixture comprising the compounds of formula IV and formula IV-α:

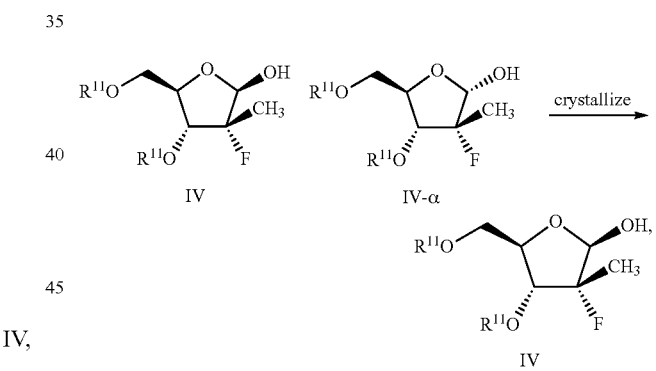

wherein $R^{11}$ is a protecting group.

* * * * *

SEQUENCE LISTING

```
<160> NUMBER OF SEQ ID NOS: 3

<210> SEQ ID NO 1
<211> LENGTH: 23
<212> TYPE: DNA
<213> ORGANISM: Artificial Sequence
<220> FEATURE:
<223> OTHER INFORMATION: HCV Sense Primer

<400> SEQUENCE: 1
agccatggcg ttagtatgag tgt                                          23

<210> SEQ ID NO 2
<211> LENGTH: 18
<212> TYPE: DNA
<213> ORGANISM: Artificial Sequence
<220> FEATURE:
<223> OTHER INFORMATION: HCV Antisense Primer

<400> SEQUENCE: 2
ttccgcagac cactatgg                                                18

<210> SEQ ID NO 3
<211> LENGTH: 20
<212> TYPE: DNA
<213> ORGANISM: Artificial Sequence
<220> FEATURE:
<223> OTHER INFORMATION: HCV Probe with 5'-FAM Label and 3'-TAMRA Label
<220> FEATURE:
```

```
<221> NAME/KEY: misc_feature
<222> LOCATION: (1)..(1)
<223> OTHER INFORMATION: 5'-FAM-LABEL
<220> FEATURE:
<221> NAME/KEY: misc_feature
<222> LOCATION: (20)..(20)
<223> OTHER INFORMATION: 3'-TAMRA-LABEL

<400> SEQUENCE: 3
cctccaggac cccccctccc                                            20
```